(12) United States Patent
Blum et al.

(10) Patent No.: US 7,662,830 B2
(45) Date of Patent: Feb. 16, 2010

(54) SUBSTITUTED BIARYL PIPERAZINYL-PYRIDINE ANALOGUES

(75) Inventors: Charles A. Blum, Westbrook, CT (US);
Harry Brielmann, Guilford, CT (US);
Bertrand L. Chenard, Waterford, CT (US); Xiaozhang Zheng, Branford, CT (US)

(73) Assignee: Neurogen Corporation, Branford, CT (US)

( * ) Notice: Subject to any disclaimer, the term of this patent is extended or adjusted under 35 U.S.C. 154(b) by 513 days.

(21) Appl. No.: 11/204,202

(22) Filed: Aug. 13, 2005

(65) Prior Publication Data

US 2006/0122394 A1 Jun. 8, 2006

Related U.S. Application Data

(60) Provisional application No. 60/601,721, filed on Aug. 13, 2004, provisional application No. 60/641,796, filed on Jan. 5, 2005.

(51) Int. Cl.
C07D 401/14 (2006.01)
C07D 403/14 (2006.01)
A61K 31/506 (2006.01)
A61P 19/02 (2006.01)
A61K 31/53 (2006.01)

(52) U.S. Cl. ........... 514/275; 544/326; 544/328; 544/330; 544/331; 544/194; 514/246

(58) Field of Classification Search ............... 544/326, 544/328, 330, 331; 514/275
See application file for complete search history.

(56) References Cited

U.S. PATENT DOCUMENTS

| | | | |
|---|---|---|---|
| 4,260,621 A | 4/1981 | Roch et al. | |
| 4,824,846 A | 4/1989 | Kampe et al. | |
| 5,589,477 A | 12/1996 | Chokai et al. | |
| 5,962,453 A | 10/1999 | Ueda et al. | |
| 6,414,149 B1 | 7/2002 | Chu-Moyer et al. | |
| 6,417,185 B1 | 7/2002 | Goff et al. | |
| 6,660,740 B1 | 12/2003 | Chu-Moyer et al. | |
| 6,710,058 B2 | 3/2004 | Jacobson et al. | |
| 6,894,047 B2 | 5/2005 | Mylari | |
| 2002/0132807 A1 | 9/2002 | Wang et al. | |
| 2003/0060466 A1 | 3/2003 | Binggeli et al. | |
| 2007/0027155 A1 | 2/2007 | Bakthavatchalam et al. | |
| 2007/0043049 A1 | 2/2007 | Bakthavatchalam et al. | |
| 2007/0161637 A1 | 7/2007 | Bakthavatchalam et al. | |
| 2008/0045525 A1 | 2/2008 | Bakthavatchalam et al. | |

FOREIGN PATENT DOCUMENTS

| | | |
|---|---|---|
| EP | 0459830 A1 | 12/1991 |
| EP | 0 775 487 | 5/1997 |
| EP | 1 136 483 A1 | 9/2001 |
| EP | 1 136 483 A2 | 9/2001 |
| EP | 1 247 809 | 10/2002 |
| FR | 2 262 512 | 9/1975 |
| JP | 49 021148 B | 5/1974 |
| WO | WO-98/24782 | 6/1998 |
| WO | WO-00/09496 A2 | 2/2000 |
| WO | WO-01/70728 | 9/2001 |
| WO | WO-02/02539 | 1/2002 |
| WO | WO-02/08221 | 1/2002 |
| WO | WO-04/000820 A2 | 12/2003 |
| WO | WO-2004/048365 A2 | 6/2004 |
| WO | WO-2005/007648 | 1/2005 |

OTHER PUBLICATIONS

Johansen, M.E. et al., "TRPV1 Antagonists Elevate Cell Surface Populations of Receptor Protein and Exacerbate TRPV1-Mediated Toxicities in Human Lung Epithelial Cells", *Toxicological Sciences* 89(1), 278-286 (2006) (Advance Access publication Aug. 24, 2005).

Thomas, Karen C. et al., "Transient Receptor Potential Vanilloid 1 Agonists Cause Endoplasmic Reticulum Stress and Cell Death in Human Lung Cells," *The Journal of Pharmacology and Experimental Therapeutics* 321(3), 830-838 (2007).

Bolcskei, Kata et al., "Investigation of the role of TRPV1 receptors in acute and chronic nociceptive processes using gene-deficient mice," *Pain* 117, 368-376 (2005).

Helyes, Zsuzsanna et al., "Role of transient receptor potential vanilloid 1 receptors in endotoxin-induced airway inflammation in the mouse," *Am J Physiol Lung Cell Mol Physiol.* 292(5):L1173-81 (2007).

(Continued)

*Primary Examiner*—Venkataraman Balasubramanian
(74) *Attorney, Agent, or Firm*—Edwards Angell Palmer & Dodge LLP; Peter F. Corless; Mark D. Russett

(57) ABSTRACT

Substituted biaryl piperazinyl-pyridine analogues are provided, of the Formula:

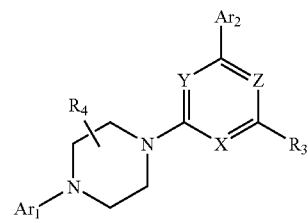

wherein variables are as described herein. Such compounds are ligands that may be used to modulate specific receptors activity in vivo or in vitro, and are particularly useful in the treatment of conditions associated with pathological receptor activation in humans, domesticated companion animals and livestock animals. Pharmaceutical compositions and methods for using such compounds to treat such disorders are provided, as are methods for using such ligands for receptor localization studies.

6 Claims, No Drawings

OTHER PUBLICATIONS

Banvolgyi, Agnes et al., "Evidence for a novel protective role of the vanilloid TRPV1 receptor in a cutaneous contact allergic dermatitis model," *J Neuroimmunol*. 169, 86-96 (2005).

U.S. Appl. No. 11/795,651, filed Jul. 19, 2007, Charles Blum.

Luo et al., "Microwave-assisted synthesis of aminopyrimidines," Tetrahedron Letters 43:5739-5742 (2002).

Ojea et al., "Synthesis of Pyrazino[1,2-a:4,5-a']D1[1,8]Naphthyridine and Pyrazino[1,2-a][1,8]Naphthyridines," Heterocycles 36:1337-1349 (1993).

Ram et al., "Synthesis of Pyrimidines and Fused Pyrimidines as Leishmanicides," Journal fuer Praktische Chemie 331:957-963 (1989).

Agarwal et al., "A diversity oriented synthesis of highly functionalized unsymmetrical biaryls through carbanion induced ring transformation of 2H-oyran-2-ones," Tetrahedron 58:8793-8798 (2002).

Ram et al., "One-pot synthesis of unsymmetrical biaryls from suitably functionalized 2H-pyran-2-ones through carbanion-induced ring-transformation reactions," J. Chem. Soc. Perkin Trans. 16:1953-1959 (2001).

Chu-Moyer et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," J. Med. Chem. 45:511-528 (2002).

Xia et al., "Substituted 1,3,5-Triazines as Cholesteryl Ester Transfer Protein Inhibitors," Bioorganic & Medical Chemistry Letters 6:919-922 (1996).

Farhanullah et al., "Synthesis of Aminonicotinonitriles and Diaminopyridines through Base-Catalyzed Ring Transformation of 2H-Pyran-2-ones," J. Org. Chem. 68:2983-2985 (2003).

Ram et al., "Synthesis of *-Deficient Pyrimidines as Leishmanicides," Arch. Pharm. 324:837-839 (1991).

Vishwakarma et al., "Reactions of Polarized Keten S,N-Acetals with Guanidine: A Facile General Route to Novel 5,6-Substituted 2-Amino-4-N-alkyl/aryl/N-azacycloalkylaminopyrimidines," Indian Journal of Chemistry 24B:466-471 (1985).

SciFinder Report for CAS Registry No. 477866-20-9, Apr. 30, 2003.
SciFinder Report for CAS Registry No. 380546-69-0, Apr. 29, 2003.
SciFinder Report for CAS Registry No. 339279-02-6, Apr. 30, 2003.
SciFinder Report for CAS Registry No. 477866-17-4, Jan. 1, 2004.
SciFinder Report for CAS Registry No. 667895-91-2, Jul. 7, 2004.
SciFinder Report for CAS Registry No. 477863-89-1, Jan. 1, 2004.
SciFinder Report for CAS Registry No. 552286-80-3, Apr. 30, 2003.
SciFinder Report for CAS Registry No. 330981-81-2, Apr. 30, 2003.

Wang et al., "Amino-substituted heterocycles as isosteres of *trans*-cinnamides: design and synthesis of heterocyclic biaryl sulfides as potent antagonists of LFA-1/ICAM-1 binding", Bioorganic & Medicinal Chemistry Letters 15 (2005) pp. 195-201.

The Extended European Search Report dated Apr. 6, 2009, from corresponding EPO application No. 05810146.0.

SUBSTITUTED BIARYL PIPERAZINYL-PYRIDINE ANALOGUES

CROSS-REFERENCE TO RELATED APPLICATION(S)

This application claims priority from U.S. Provisional Application Ser. No. 60/601,721 filed Aug. 13, 2004 and of U.S. Provisional Application Ser. No. 60/641,796 filed Jan. 5, 2005, each of which is incorporated by reference.

FIELD OF THE INVENTION

This invention relates generally to substituted biaryl piperazinyl-pyridine analogues that have useful pharmacological properties. The invention further relates to the use of such compounds for treating conditions related to capsaicin receptor activation, for identifying other agents that bind to capsaicin receptor, and as probes for the detection and localization of capsaicin receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Topical treatment with capsaicin has been used to treat chronic and acute pain, including neuropathic pain. Capsaicin is a pungent substance derived from the plants of the Solanaceae family (which includes hot chili peppers) and appears to act selectively on the small diameter afferent nerve fibers (A-delta and C fibers) that are believed to mediate pain. The response to capsaicin is characterized by persistent activation of nociceptors in peripheral tissues, followed by eventual desensitization of peripheral nociceptors to one or more stimuli. From studies in animals, capsaicin appears to trigger C fiber membrane depolarization by opening cation selective channels for calcium and sodium.

Similar responses are also evoked by structural analogues of capsaicin that share a common vanilloid moiety. One such analogue is resiniferatoxin (RTX), a natural product of *Euphorbia* plants. The term vanilloid receptor (VR) was coined to describe the neuronal membrane recognition site for capsaicin and such related irritant compounds. The capsaicin response is competitively inhibited (and thereby antagonized) by another capsaicin analog, capsazepine, and is also inhibited by the non-selective cation channel blocker ruthenium red, which binds to VR with no more than moderate affinity (typically with a $K_i$ value of no lower than 140 µM).

Rat and human vanilloid receptors have been cloned from dorsal root ganglion cells. The first type of vanilloid receptor to be identified is known as vanilloid receptor type 1 (VR1), and the terms "VR1" and "capsaicin receptor" are used interchangeably herein to refer to rat and/or human receptors of this type, as well as mammalian homologues. The role of VR1 in pain sensation has been confirmed using mice lacking this receptor, which exhibit no vanilloid-evoked pain behavior and impaired responses to heat and inflammation. VR1 is a nonselective cation channel with a threshold for opening that is lowered in response to elevated temperatures, low pH, and capsaicin receptor agonists. Opening of the capsaicin receptor channel is generally followed by the release of inflammatory peptides from neurons expressing the receptor and other nearby neurons, increasing the pain response. After initial activation by capsaicin, the capsaicin receptor undergoes a rapid desensitization via phosphorylation by cAMP-dependent protein kinase.

Because of their ability to desensitize nociceptors in peripheral tissues, VR1 agonist vanilloid compounds have been used as topical anesthetics. However, agonist application may itself cause burning pain, which limits this therapeutic use. Recently, it has been reported that VR1 antagonists, including certain nonvanilloid compounds, are also useful for the treatment of pain (see, e.g., PCT International Application Publication Numbers WO 02/08221, WO 03/062209, WO 04/054582, WO 04/055003, WO 04/055004, WO 04/056774, WO 05/007646, WO 05/007648, WO 05/007652, WO 05/009977, WO 05/009980 and WO 05/009982).

Thus, compounds that interact with VR1, but do not elicit the initial painful sensation of VR1 agonist vanilloid compounds, are desirable for the treatment of chronic and acute pain, including neuropathic pain, as well as other conditions that are responsive to capsaicin receptor modulation. The present invention fulfills this need, and provides further related advantages.

SUMMARY OF THE INVENTION

The present invention provides compounds of Formula I:

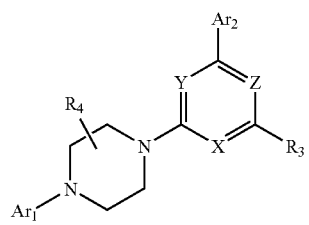

Formula I as well as pharmaceutically acceptable salts of such compounds. Within Formula I:

$Ar_1$ is phenyl or a 6-membered aromatic heterocycle, each of which is substituted with $R_{10}$ and with from 0 to 4 additional substituents (e.g., independently chosen from $R_1$);

$Ar_2$ is phenyl or a 6-membered aromatic heterocycle, each of which is optionally substituted, (e.g., with from 0 to 4 substituents independently chosen from $R_2$);

X, Y and Z are independently optionally substituted carbon (e.g., $CR_x$) or N, such that at least one of X, Y and Z is N;

$R_x$ is independently chosen at each occurrence from hydrogen, halogen, $C_1$-$C_4$alkyl, amino, cyano and mono- and di-($C_1$-$C_4$alkyl)amino;

Each $R_1$ is independently chosen from:
(a) halogen, cyano and nitro;
(b) groups of the formula -Q-M-$R_y$; and
(c) groups that are taken together with $R_{10}$ to form a fused 5- to 7-membered carbocyclic or heterocyclic ring that is optionally substituted (e.g., with from 0 to 4 substituents independently chosen from halogen, cyano, nitro and groups of the formula -Q-M-$R_y$);

$R_{10}$ represents one substituent chosen from:
(a) nitro;
(b) groups of the formula -Q-M-$R_y$; and
(c) groups that are taken together with a substituent represented by $R_1$ to form a fused, optionally substituted 5- to 7-membered carbocyclic or heterocyclic ring;

such that, in certain aspects, $R_{10}$ is not hydroxy, amino or an unsubstituted group chosen from $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)aminosulfonyl or mono- or di-($C_1$-$C_6$alkyl) aminocarbonyl;

Each Q is independently chosen from $C_0$-$C_4$alkylene;
Each M is independently absent or selected from

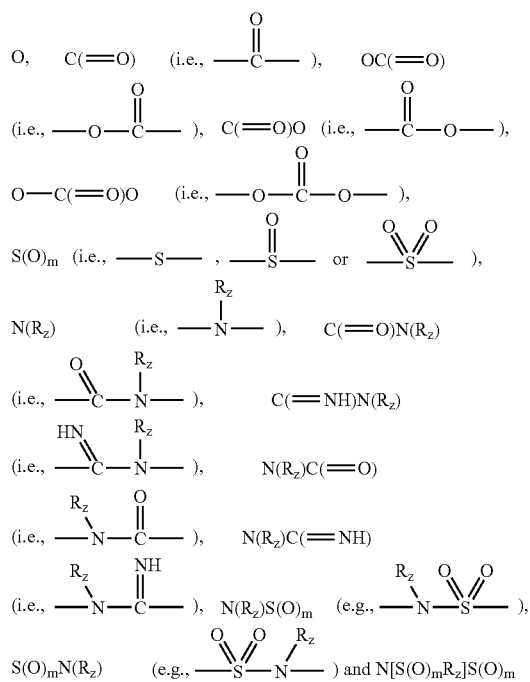

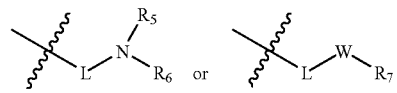

wherein m is independently selected at each occurrence from 0, 1 and 2; and $R_z$ is independently selected at each occurrence from hydrogen, $C_1$-$C_8$alkyl and groups that are taken together with $R_y$ to form an optionally substituted 4- to 7-membered heterocycle;

Each $R_y$ is independently hydrogen, $C_1$-$C_8$haloalkyl, optionally substituted $C_1$-$C_8$alkyl, optionally substituted $C_2$-$C_8$alkenyl, optionally substituted ($C_3$-$C_8$carbocycle)$C_0$-$C_4$alkyl, optionally substituted (4- to 7-membered heterocycle)$C_0$-$C_4$alkyl, or taken together with $R_z$ to form an optionally substituted 4- to 7-membered heterocycle (e.g., in certain embodiments each alkyl, carbocycle and heterocycle is substituted with from 0 to 4 substituents independently selected from hydroxy, halogen, amino, cyano, nitro, oxo, —COOH, aminocarbonyl, aminosulfonyl, $C_1$-$C_6$alkyl, $C_3$-$C_7$cycloalkyl, $C_2$-$C_6$alkyl ether, $C_1$-$C_6$alkanoyl, $C_1$-$C_6$alkylsulfonyl, $C_1$-$C_8$alkoxy, $C_1$-$C_8$hydroxyalkyl, $C_1$-$C_8$alkylthio, mono- and di-($C_1$-$C_6$alkyl)aminocarbonyl, $C_1$-$C_6$alkanoylamino, mono- and di-($C_1$-$C_6$alkyl)aminosulfonyl, mono and di-($C_1$-$C_6$alkyl) amino and phenyl); such that $R_y$ is not hydrogen if Q is a single covalent bond (i.e., $C_0$alkyl) and M is absent;

Each $R_2$ is:
(a) independently chosen from (i) hydroxy, amino, cyano, halogen, —COOH, aminosulfonyl, nitro and aminocarbonyl; and (ii) $C_1$-$C_6$alkyl, ($C_3$-$C_8$cycloalkyl)$C_0$-$C_4$alkyl, $C_1$-$C_6$haloalkyl, $C_1$-$C_6$alkoxy, $C_1$-$C_6$alkylthio, $C_2$-$C_6$alkyl ether, $C_2$-$C_6$alkanoyl, $C_1$-$C_6$alkoxycarbonyl, $C_2$-$C_6$alkanoyloxy, $C_3$-$C_6$alkanone, mono- and di-($C_1$-$C_8$alkyl)amino$C_0$-$C_6$alkyl, (4- to 7-membered heterocycle)$C_0$-$C_4$alkyl, $C_1$-$C_6$alkylsulfonyl, mono- and di-($C_1$-$C_6$alkyl)aminosulfonyl, and mono- and di-($C_1$-$C_6$alkyl)aminocarbonyl, each of which is optionally substituted, (e.g., with from 0 to 4 substituents independently chosen from halogen, hydroxy, cyano, amino, aminocarbonyl, aminosulfonyl, —COOH and oxo); or
(b) taken together with an adjacent $R_2$ to form a fused 5- to 13-membered carbocyclic or heterocyclic group that is optionally substituted (e.g., with from 0 to 3 substituents independently chosen from halogen, oxo and $C_1$-$C_6$alkyl);

$R_3$ is selected from:
(i) hydrogen and halogen;
(ii) $C_1$-$C_6$alkyl, ($C_3$-$C_8$cycloalkyl)$C_0$-$C_2$alkyl, $C_1$-$C_6$haloalkyl and phenyl $C_0$-$C_2$alkyl; and
(iii) groups of the formula:

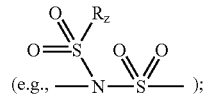

wherein:
L is $C_0$-$C_6$alkylene or $C_1$-$C_6$alkylene that is taken together with $R_5$, $R_6$ or $R_7$ to form a 4- to 7-membered heterocycle;
W is O, CO, S, SO or $SO_2$;

$R_5$ and $R_6$ are:
  (a) independently chosen from hydrogen, $C_1$-$C_{12}$alkyl, $C_2$-$C_{12}$alkenyl, ($C_3$-$C_8$cycloalkyl)$C_0$-$C_4$alkyl, $C_2$-$C_6$alkanoyl, $C_1$-$C_6$alkylsulfonyl, phenyl$C_0$-$C_6$alkyl, (4- to 7-membered heterocycle)$C_0$-$C_6$alkyl and groups that are joined to L to form a 4- to 7-membered heterocycle; or
  (b) joined to form a 4- to 12-membered heterocycle; and $R_7$ is hydrogen, $C_1$-$C_{12}$alkyl, $C_2$-$C_{12}$alkenyl, ($C_3$-$C_8$cycloalkyl)$C_0$-$C_4$alkyl, $C_2$-$C_6$alkanoyl, phenyl$C_0$-$C_6$alkyl, (4- to 7-membered heterocycle)$C_0$-$C_6$alkyl or a group that is joined to L to form a 4- to 7-membered heterocycle;

wherein each of (ii) and (iii) is optionally substituted (e.g., with from 0 to 4 substituents independently chosen from:
  (1) halogen, hydroxy, amino, cyano, nitro, —COOH, aminosulfonyl, aminocarbonyl and oxo; and
  (2) $C_1$-$C_6$alkyl, ($C_3$-$C_8$cycloalkyl)$C_0$-$C_2$alkyl, $C_1$-$C_6$haloalkyl, $C_1$-$C_6$alkoxy, $C_1$-$C_6$alkanoyl, $C_1$-$C_6$alkoxycarbonyl, $C_2$-$C_6$alkanoylamino, mono- and di-($C_1$-$C_6$alkyl)amino$C_0$-$C_4$alkyl, $C_1$-$C_6$alkylsulfonyl, mono- and di-($C_1$-$C_6$alkyl)aminosulfonyl, mono- and di-($C_1$-$C_6$alkyl)aminocarbonyl$C_0$-$C_4$alkyl, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_1$-$C_4$alkyl, $C_1$-$C_4$alkoxy and $C_1$-$C_4$haloalkyl); and $R_4$ represents from 0 to 2 substituents (e.g., substituents that are independently chosen from $C_1$-$C_3$alkyl, $C_1$-$C_3$haloalkyl and oxo).

Within certain aspects, substituted biaryl piperazinyl-pyridine analogues provided herein are VR1 modulators and exhibit a $K_i$ of no greater than 1 micromolar, 500 nanomolar, 100 nanomolar, 50 nanomolar, 10 nanomolar or 1 nanomolar in a capsaicin receptor binding assay and/or have an $EC_{50}$ or $IC_{50}$ value of no greater than 1 micromolar, 500 nanomolar, 100 nanomolar, 50 nanomolar, 10 nanomolar or 1 nanomolar in an in vitro assay for determination of capsaicin receptor agonist or antagonist activity. In certain embodiments, such VR1 modulators are VR1 antagonists and exhibit no detectable agonist activity in an in vitro assay of capsaicin receptor activation at a concentration equal to the $IC_{50}$, 10 times the $IC_{50}$ or 100 times the $IC_{50}$.

Within certain aspects, compounds as described herein are labeled with a detectable marker (e.g., radiolabeled or fluorescein conjugated).

The present invention further provides, within other aspects, pharmaceutical compositions comprising at least one substituted biaryl piperazinyl-pyridine analogue provided herein in combination with a physiologically acceptable carrier or excipient.

Within further aspects, methods are provided for reducing calcium conductance of a cellular capsaicin receptor, comprising contacting a cell (e.g., neuronal) expressing a capsaicin receptor with at least one VR1 modulator as described herein. Such contact may occur in vivo or in vitro.

Methods are further provided for inhibiting binding of vanilloid ligand to a capsaicin receptor. Within certain such aspects, the inhibition takes place in vitro. Such methods comprise contacting a capsaicin receptor with at least one VR1 modulator as described herein, under conditions and in an amount or concentration sufficient to detectably inhibit vanilloid ligand binding to the capsaicin receptor. Within other such aspects, the capsaicin receptor is in a patient. Such methods comprise contacting cells expressing a capsaicin receptor in a patient with at least one VR1 modulator as described herein in an amount or concentration that would be sufficient to detectably inhibit vanilloid ligand binding to cells expressing a cloned capsaicin receptor in vitro, and thereby inhibiting binding of vanilloid ligand to the capsaicin receptor in the patient.

The present invention further provides methods for treating a condition responsive to capsaicin receptor modulation in a patient, comprising administering to the patient a therapeutically effective amount of at least one VR1 modulator as described herein.

Within other aspects, methods are provided for treating pain in a patient, comprising administering to a patient suffering from pain a therapeutically effective amount of at least one substituted biaryl piperazinyl-pyridine analogue.

Methods are further provided for treating itch, urinary incontinence, overactive bladder, cough and/or hiccup in a patient, comprising administering to a patient suffering from one or more of the foregoing conditions a therapeutically effective amount of at least one substituted biaryl piperazinyl-pyridine analogue.

The present invention further provides methods for promoting weight loss in an obese patient, comprising administering to an obese patient a therapeutically effective amount of at least one substituted biaryl piperazinyl-pyridine analogue.

Methods are further provided for identifying an agent that binds to capsaicin receptor, comprising: (a) contacting capsaicin receptor with a labeled compound as described herein under conditions that permit binding of the compound to capsaicin receptor, thereby generating bound, labeled compound; (b) detecting a signal that corresponds to the amount of bound, labeled compound in the absence of test agent; (c) contacting the bound, labeled compound with a test agent; (d) detecting a signal that corresponds to the amount of bound labeled compound in, the presence of test agent; and (e) detecting a decrease in signal detected in step (d), as compared to the signal detected in step (b).

Within further aspects, the present invention provides methods for determining the presence or absence of capsaicin receptor in a sample, comprising: (a) contacting a sample with a compound as described herein under conditions that permit binding of the compound to capsaicin receptor; and (b) detecting a signal indicative of a level of the compound bound to capsaicin receptor.

The present invention also provides packaged pharmaceutical preparations, comprising: (a) a pharmaceutical composition as described herein in a container; and (b) instructions for using the composition to treat one or more conditions responsive to capsaicin receptor modulation, such as pain, itch, urinary incontinence, overactive bladder, cough, hiccup and/or obesity.

In yet another aspect, the present invention provides methods for preparing the compounds disclosed herein, including the intermediates.

These and other aspects of the invention will become apparent upon reference to the following detailed description.

DETAILED DESCRIPTION

As noted above, the present invention provides substituted biaryl piperazinyl-pyridine analogues. Such compounds may be used in vitro or in vivo, to modulate capsaicin receptor activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_3$, $Ar_1$, Z). Unless otherwise specified, each variable within such a formula is defined independently of any other variable, and any variable that occurs more than one time in a formula is defined independently at each occurrence.

The term "substituted biaryl piperazinyl-pyridine analogues," as used herein, encompasses all compounds of Formula I (including compounds of other Formulas provided herein, as well as any enantiomers, racemates and stereoisomers) and pharmaceutically acceptable salts of such compounds. Compounds in which the core ring

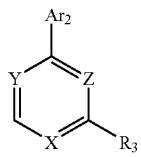

is pyridyl, pyrimidyl or triazinyl (e.g., 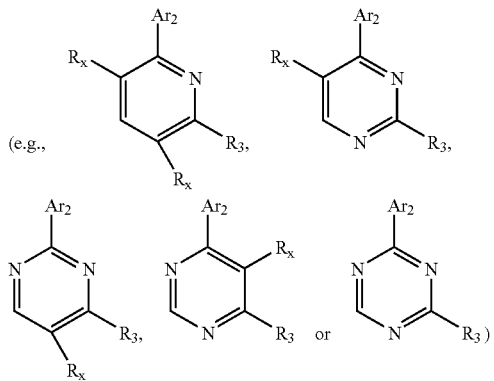 )

are specifically included within the definition of substituted biaryl piperazinyl-pyridine analogues.

A "pharmaceutically acceptable salt" of a compound recited herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound of Formula I may, but need not, be formulated as a hydrate, solvate or non-covalent complex. In addition, the various crystal forms and polymorphs are within the scope of the present invention, as are prodrugs of the compounds of Formula I. A "prodrug" is a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein (except when used in the terms "alkylamino" and "alkylaminoalkyl," as discussed below), the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_n$alkyl" refers to a single covalent bond ($C_0$) or an alkyl group having from 1 to n carbon atoms; for example "$C_0$-$C_4$alkyl" refers to ga single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group linked via a single covalent bond or a $C_1$-$C_4$alkylene group.

By "alkoxy," as used herein, is meant an alkyl group as described above attached via an oxygen bridge. Alkoxy groups include $C_1$-$C_6$alkoxy and $C_1$-$C_4$alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups. Similarly, "alkylthio" refers to an alkyl group as described above attached via a sulfur bridge.

The term "oxo," as used herein, refers to a keto group (C=O). An oxo group that is a substituent of a nonaromatic carbon atom results in a conversion of —$CH_2$— to —C(=O)—.

Similarly, an "imino" is a group of the formula C=N. The term "iminoalkyl" refers to an alkyl group as described above substituted with an imine (e.g., a group of the formula

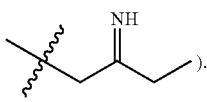

).

The term "alkanoyl" refers to an acyl group (e.g., —C=O)-alkyl), in which carbon atoms are in a linear or branched alkyl arrangement and where attachment is through the carbon of the keto group. Alkanoyl groups have the indicated number of carbon atoms, with the carbon of the keto group being included in the numbered carbon atoms. For example a $C_2$alkanoyl group is an acetyl group having the formula —(C=O)$CH_3$. Alkanoyl groups include, for example, $C_2$-$C_8$alkanoyl, $C_2$-$C_6$alkanoyl and $C_2$-$C_4$alkanoyl groups, which have from 2 to 8, from 2 to 6 or from 2 to 4 carbon atoms, respectively. "$C_1$alkanoyl" refers to —(C=O)H, which (along with $C_2$-$C_8$alkanoyl) is encompassed by the term "$C_1$-$C_8$alkanoyl."

An "alkanone" is a ketone group in which carbon atoms are in a linear or branched alkyl arrangement. "$C_3$-$C_8$alkanone," "$C_3$-$C_6$alkanone" and "$C_3$-$C_4$alkanone" refer to an alkanone having from 3 to 8, 6 or 4 carbon atoms, respectively. A $C_3$ alkanone has the structure —$CH_2$—C(=O)—$CH_3$.

Similarly, "alkyl ether" refers to a linear or branched ether substituent (ie., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$ alkyl ether has the structure —$CH_2$—O—$CH_3$.

The term "alkoxycarbonyl" refers to an alkoxy group attached through a keto (—(C=O)—) bridge (i.e., a group having the general structure —C(=O—O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group (i.e., the carbon of the keto bridge is not included in the indicated number of carbon atoms). "$C_1$alkoxycarbonyl" refers to —C(=O)—O—$CH_3$; $C_3$alkoxycarbonyl indicates —C(=O)—O—$(CH_2)_2CH_3$ or —C(=O)—O—$(CH)(CH_3)_2$.

"Alkanoyloxy," as used herein, refers to an alkanoyl group linked via an oxygen bridge (i.e., a group having the general structure —O—C(=O)alkyl). Alkanoyloxy groups include $C_2$-$C_8$, $C_2$-$C_6$ and $C_2$-$C_4$alkanoyloxy groups, which have from 2 to 8, 6 or 4 carbon atoms. "$C_2$alkanoyloxy" refers to —O—C(=O)—$C_3$.

"Alkanoylamino," as used herein, refers to an alkanoyl group attached through an amino linker (i.e., a group having the general structure —N(R)—C(=O)alkyl), in which R is hydrogen or $C_1$-$C_6$alkyl. Alkanoylamino groups include $C_2$-$C_8$, $C_2$-$C_6$ and $C_2$-$C_4$alkanoylamino groups, which have from 2 to 8, 6 or 4 carbon atoms, respectively.

"Alkylsulfonyl" refers to groups of the formula —($SO_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or from 1 to 4 carbon atoms, respectively. Methylsulfonyl is one representative alkylsulfonyl group. "$C_1$-$C_4$haloalkylsulfonyl" is an alkylsulfonyl group of from 1 to 4 carbon atoms that is substituted with at least one halogen (e.g., trifluoromethylsulfonyl).

"Alkylsulfonylamino" refers to groups of the formula —N(R)—($SO_2$)-alkyl, in which R is hydrogen or $C_1$-$C_6$alkyl and the nitrogen atom is the point of attachment. Alkylsulfonylamino groups include $C_1$-$C_6$alkylsulfonylamino and $C_1$-$C_4$alkylsulfonylamino groups, which have from 1 to 6 or 1 to 4 carbon atoms, respectively. Methylsulfonylamino is a representative alkylsulfonylamino group.

"Aminosulfonyl" refers to groups of the formula —($SO_2$)—$NH_2$, in which the sulfur atom is the point of attachment. The term "mono- or di-($C_1$-$C_6$alkyl)aminosulfonyl" refers to groups that satisfy the formula —($SO_2$)—$NR_2$, in which the sulfur atom is the point of attachment, and in which one R is $C_1$-$C_8$alkyl and the other R is hydrogen or an independently chosen $C_1$-$C_6$alkyl.

"Alkylamino" refers to a secondary or tertiary amine of the formula —NH-alkyl or —N(alkyl)(alkyl), wherein each alkyl may be the same or different. In this context, each alkyl may be linear, branched or cyclic (including ($C_3$-$C_8$cycloalkyl)$C_0$-$C_4$alkyl). Such groups include, for example, mono- and di-($C_1$-$C_8$alkyl)amino groups, in which each $C_1$-$C_8$alkyl may be the same or different, as well as mono- and di-($C_1$-$C_6$alkyl) amino groups and mono- and di-($C_1$-$C_4$alkyl)amino groups.

"Alkylaminoalkyl" refers to an alkylamino group linked via an alkylene group (i.e., a group having the general structure-alkylene-NH-alkyl or -alkylene-N(alkyl)(alkyl)) in which each alkyl is selected independently from alkyl, cycloalkyl and (cycloalkyl)alkyl groups. Alkylaminoalkyl groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_6$alkyl)amino$C_1$-$C_4$alkyl. "Mono- or di-($C_1$-$C_6$alkyl)amino$C_0$-$C_8$alkyl" refers to a mono- or di- ($C_1$-$C_6$alkyl)amino group linked via a single covalent bond or a $C_1$-$C_8$alkylene group. The following are representative alkylaminoalkyl groups:

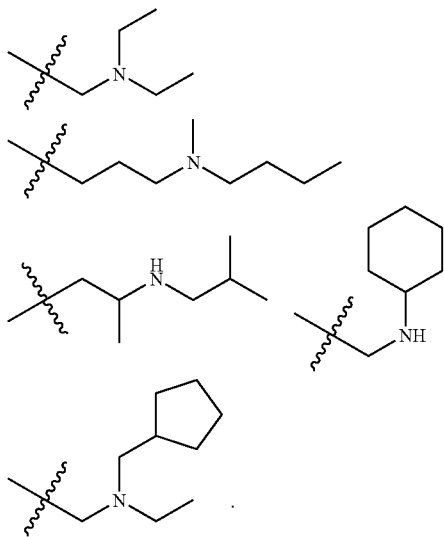

It will be apparent that the definition of "alkyl" as used in the terms "alkylamino" and "alkylaminoalkyl" differs from the definition of "alkyl" used for all other alkyl-containing groups, in the inclusion of cycloalkyl and (cycloalkyl)alkyl groups (e.g., ($C_3$-$C_8$cycloalkyl)$C_0$-$C_4$alkyl).

Similarly, "alkylaminoalkoxy" refers to an alkylamino group linked via an alkoxy group (i.e., a group having the general structure —O-alkyl-NH-alkyl or —O-alkyl-N(alkyl)(alkyl)) in which each alkyl is selected independently. Such groups include, for example, mono- and di-($C_1$-$C_6$alkyl)amino$C_1$-$C_4$alkoxy groups, such as

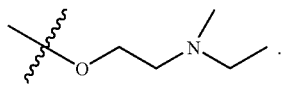

The term "aminocarbonyl" refers to an amide group (i.e., —(C=O)NH$_2$). "Mono- or di-($C_1$-$C_6$alkyl) aminocarbonyl$C_0$-$C_4$alkyl" is an aminocarbonyl group in which one or both of the hydrogen atoms is replaced with $C_1$-$C_6$alkyl, and which is linked via a single covalent bond (i.e., mono- or di-($C_1$-$C_6$alkyl)aminocarbonyl) or a $C_1$-$C_4$alkylene group (i.e., —($C_0$-$C_4$alkyl)-(C=O)N($C_1$-$C_8$alkyl)$_2$). If both hydrogen atoms are so replaced, the $C_1$-$C_6$alkyl groups may be the same or different.

The term "halogen" refers to fluorine, chlorine, bromine or iodine.

A "haloalkyl" is an alkyl group that is substituted with 1 or more independently chosen halogens (e.g., "$C_1$-$C_8$haloalkyl" groups have from 1 to 8 carbon atoms; "$C_1$-$C_6$haloalkyl" groups have from 1 to 6 carbon atoms). Examples of haloalkyl groups include, but are not limited to, mono-, di- or trifluoromethyl; mono-, di- or tri-chloromethyl; mono-, di-, tri-, tetra- or penta-fluoroethyl; mono-, di-, tri-, tetra- or pentachloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above attached via an oxygen bridge. "$C_1$-$C_8$haloalkoxy" groups have 1 to 8 carbon atoms.

A dash ("—") that is not between two letters or symbols is used to indicate a point of attachment for a substituent. For example, —CONH$_2$ is attached through the carbon atom.

A "carbocycle" or "carbocyclic group" comprises at least one ring formed entirely by carbon-carbon bonds (referred to herein as a carbocyclic ring), and does not contain a heterocycle. Unless otherwise specified, each ring within a carbocycle may be independently saturated, partially saturated or aromatic, and is optionally substituted as indicated. A carbocycle generally has from 1 to 3 fused, pendant or spiro rings; carbocycles within certain embodiments have one ring or two fused rings. Typically, each ring contains from 3 to 8 ring members (ie., $C_3$-$C_8$); $C_5$-$C_7$ rings are recited in certain embodiments. Carbocycles comprising fused, pendant or spiro rings typically contain from 9 to 14 ring members. Certain representative, carbocycles are cycloalkyl as described above. Other carbocycles are aryl (ie., contain at least one aromatic carbocyclic ring, with or without one or more additional aromatic and/or cycloalkyl rings). Such aryl carbocycles include, for example, phenyl, naphthyl (e.g., 1-naphthyl and 2-naphthyl), fluorenyl, indanyl and 1,2,3,4-tetrahydro-naphthyl.

Certain carbocycles recited herein are $C_6$-$C_{10}$aryl$C_0$-$C_8$alkyl groups (ie., groups in which a 6- to 10-membered carbocyclic group comprising at least one aromatic ring is linked via a single covalent bond or a $C_1$-$C_8$alkylene group). Such groups include, for example, phenyl and indanyl, as well as groups in which either of the foregoing is linked via $C_1$-$C_8$alkylene, preferably via $C_1$-$C_4$alkylene. Phenyl groups linked via a single covalent bond or $C_1$-$C_6$alkylene group are designated phenyl$C_0$-$C_6$alkyl (e.g., benzyl, 1-phenyl-ethyl, 1-phenyl-propyl and 2-phenyl-ethyl).

A "heterocycle" or "heterocyclic group" has from 1 to 3 fused, pendant or spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or SO$_2$. Heterocycles may be optionally substituted with a variety of substituents, as indicated. Unless otherwise specified, a heterocycle may be a heterocycloalkyl group (ie., each ring is saturated or partially saturated) or a heteroaryl group (ie., at least one ring within the group is aromatic), such as a 5- to 10-membered heteroaryl (which may be monocyclic or bicyclic) or a 6-membered heteroaryl (e.g., pyridyl or pyrimidyl). N-linked heterocyclic groups are linked via a component nitrogen atom.

Heterocyclic groups include, for example, azepanyl, azocinyl, benzimidazolyl, benzimidazolinyl, benzisothiazolyl, benzisoxazolyl, benzofuranyl, benzothiofuranyl, benzoxazolyl, benzothiazolyl, benztetrazolyl, chromanyl, chromenyl, cinnolinyl, decahydroquinolinyl, dihydrofuro[2,3-b]tetrahydrofuranyl, dihydroisoquinolinyl, dihydrotetrahydrofuranyl, 1,4-dioxa-8-aza-spiro[4.5]decyl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phthalazinyl, piperazinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thiazolyl, thienothiazolyl, thienooxazolyl, thienoimidazolyl, thienyl, thiophenyl, thiomorpholinyl and variants thereof in which the sulfur atom is oxidized, triazinyl, and any of the foregoing that are substituted with from 1 to 4 substituents as described above.

A "heterocycle$C_0$-$C_8$alkyl" is a heterocyclic group linked via a single covalent bond or $C_1$-$C_8$alkylene group. A (4- to 7-membered heterocycle)$C_0$-$C_8$alkyl is a heterocyclic group (e.g., monocyclic or bicyclic) having from 4 to 7 ring members linked via a single covalent bond or an alkylene group having from 1 to 8 carbon atoms. A "(6-membered heteroaryl)$C_0$-$C_6$alkyl" refers to a heteroaryl group linked via a direct bond or $C_1$-$C_6$alkyl group.

Certain heterocycles are 4- to 12-membered, 5- to 10-membered, 3- to 7-membered, 4- to 7-membered or 5- to 7-membered groups that contain 1 heterocyclic ring or 2 fused, pendant or spiro rings, optionally substituted. 4- to 10-membered heterocycloalkyl groups include, for example, piperidinyl, piperazinyl, pyrrolidinyl, azepanyl, 1,4-dioxa-8-aza-spiro[4.5]dec-8-yl, morpholino, thiomorpholino and 1,1-dioxo-thiomorpholin-4-yl. Such groups may be substituted as indicated. Representative aromatic heterocycles are azocinyl, pyridyl, pyrimidyl, imidazolyl, tetrazolyl and 3,4-dihydro-1H-isoquinolin-2-yl.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (ie., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

The terms "VR1" and "capsaicin receptor" are used interchangeably herein to refer to a type 1 vanilloid receptor. Unless otherwise specified, these terms encompass both rat and human VR1 receptors (e.g., GenBank Accession Numbers AF327067, AJ277028 and NM_018727; sequences of certain human VR1 cDNAs and the encoded amino acid sequences are provided in U.S. Pat. No. 6,482,611), as well as homologues thereof found in other species.

A "VR1 modulator," also referred to herein as a "modulator," is a compound that modulates VR1 activation and/or VR1-mediated signal transduction. VR1 modulators specifically provided herein are compounds of Formula I and pharmaceutically acceptable salts thereof. Certain preferred VR1 modulators are not vanilloids. A VR1 modulator may be a VR1 agonist or antagonist. A modulator binds with high affinity if the $K_i$ at VR1 is less than 1 micromolar, preferably less than 500 nanomolar, 100 nanomolar, 10 nanomolar or 1 nanomolar. A representative assay for determining $K_i$ at VR1 is provided in Example 5, herein.

A modulator is considered an "antagonist" if it detectably inhibits vanilloid ligand binding to VR1 and/or VR1-mediated signal transduction (using, for example, the representative assay provided in Example 6); in general, such an antagonist inhibits VR1 activation with a $IC_{50}$ value of less than 1 micromolar, preferably less than 500 nanomolar, and more preferably less than 100 nanomolar, 10 nanomolar or 1 nanomolar within the assay provided in Example 6. VR1 antagonists include neutral antagonists and inverse agonists.

A "neutral antagonist" of VR1 is a compound that inhibits the activity of vanilloid ligand at VR1, but does not significantly change the basal activity of the receptor (ie., within a calcium mobilization assay as described in Example 6 performed in the absence of vanilloid ligand, VR1 activity is reduced by no more than 10%, more preferably by no more than 5%, and even more preferably by no more than 2%; most preferably, there is no detectable reduction in activity). Neutral antagonists of VR1 may also inhibit the binding of vanilloid ligand to VR1.

An "inverse agonist" of VR1 is a compound that reduces the activity of VR1 below its basal activity level in the absence of added vanilloid ligand. Inverse agonists of VR1 may also inhibit the activity of vanilloid ligand at VR1 and/or binding of vanilloid ligand to VR1. The basal activity of VR1, as well as the reduction in VR1 activity due to the presence of VR1 antagonist, may be determined from a calcium mobilization assay, as described in Example 6.

As used herein a "capsaicin receptor agonist" or "VR1 agonist" is a compound that elevates the activity of the receptor above the basal activity level (i.e., enhances VR1 activation and/or VR1-mediated signal transduction). Capsaicin receptor agonist activity may be identified using the representative assay provided in Example 6. In general, such an agonist has an $EC_{50}$ value of less than 1 micromolar, preferably less than 500 nanomolar, and more preferably less than 100 nanomolar or 10 nanomolar within the assay provided in Example 6.

A "vanilloid" is capsaicin or any capsaicin analogue that comprises a phenyl ring with two oxygen atoms bound to adjacent ring carbon atoms (one of which carbon atom is located para to the point of attachment of a third moiety that is bound to the phenyl ring). A vanilloid is a "vanilloid ligand" if it binds to VR1 with a $K_i$ (determined as described herein) that is no greater than 10 μM. Vanilloid ligand agonists include capsaicin, olvanil, N-arachidonoyl-dopamine and resiniferatoxin (RTX). Vanilloid ligand antagonists include capsazepine and iodo-resiniferatoxin.

A "therapeutically effective amount" (or dose) is an amount that, upon administration to a patient, results in a discernible patient benefit (e.g., provides detectable relief from a condition being treated). Such relief may be detected using any appropriate criteria, including alleviation of one or more symptoms such as pain. A therapeutically effective amount or dose generally results in a concentration of compound in a body fluid (such as blood, plasma, serum, CSF, synovial fluid, lymph, cellular interstitial fluid, tears or urine) that is sufficient to alter the binding of vanilloid ligand to VR1 in vitro (using the assay provided in Example 5) and/or VR1- mediated signal transduction (using an assay provided in Example 6). It will be apparent that the discernible patient benefit may be apparent after administration of a single dose, or may become apparent following repeated administration of the therapeutically effective dose according to a predetermined regimen, depending upon the indication for which the compound is administered.

A "patient" is any individual treated with a compound provided herein. Patients include humans, as well as other animals such as companion animals (e.g., dogs and cats) and livestock. Patients may be experiencing one or more symptoms of a condition responsive to capsaicin receptor modulation (e.g., pain, exposure to vanilloid ligand, itch, urinary incontinence, overactive bladder, respiratory disorders, cough and/or hiccup), or may be free of such symptom(s) (ie., treatment may be prophylactic in a patient considered at risk for the development of such symptoms).

Substituted Biaryl Piperazinyl-Pyridine Analogues

As noted above, the present invention provides substituted biaryl piperazinyl-pyridine analogues that may be used in a variety of contexts, including in the treatment of pain (e.g., neuropathic or peripheral nerve-mediated pain); exposure to capsaicin; exposure to acid, heat, light, tear gas, air pollutants (such as, for example, tobacco smoke), infectious agents (including viruses, bacteria and yeast), pepper spray or related agents; respiratory conditions such as asthma or chronic obstructive pulmonary disease; itch; urinary incontinence or overactive bladder; cough or hiccup; and/or obesity. Such compounds may also be used within in vitro assays (e.g., assays for receptor activity), as probes for detection and localization of VR1 and as standards in ligand binding and VR1-mediated signal transduction assays.

Certain compounds provided herein detectably modulate the binding of capsaicin to VR1 at nanomolar (i.e., submicromolar) concentrations, at subnanomolar concentrations, or at concentrations below 100 picomolar, 20 picomolar, 10 picomolar or 5 picomolar. Such modulators are preferably not vanilloids. Certain modulators are VR1 antagonists and have no detectable agonist activity in the assay described in Example 6. Preferred VR1 modulators further bind with high affinity to VR1.

In certain embodiments, substituted biaryl piperazinyl-pyridine analogues further satisfy Formula II:

Formula II wherein:

D, K, J and F are independently N, CH or carbon substituted with a substituent represented by $R_1$ or $R_{10}$;

$R_1$ represents from 0 to 3 substituents independently chosen from:
(a) halogen, cyano and nitro;
(b) groups of the formula Q-M-$R_y$; and
(c) groups that are taken together with $R_{10}$ to form a fused 5- to 7-membered carbocyclic or heterocyclic ring that is substituted with from 0 to 4 substituents independently chosen from halogen, cyano, nitro and groups of the formula Q-M-$R_y$;

$R_{10}$ represents one substituent chosen from:
(a) groups of the formula Q-M-$R_y$; and
(b) groups that are taken together with a $R_1$ to form a fused, optionally substituted 5- to 7-membered carbocyclic or heterocyclic ring;

such that $R_{10}$ is not hydroxy, amino or an unsubstituted group chosen from $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone; $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)aminosulfonyl or mono- or di-($C_1$-$C_6$alkyl)aminocarbonyl;

and the remaining variables are as described above for Formula I.

In certain embodiments, substituted biaryl piperazinyl-pyridine analogues of Formula I satisfy one or more of Formulas IIa-IIf, in which variables are as indicated for Formula II, except as defined below:

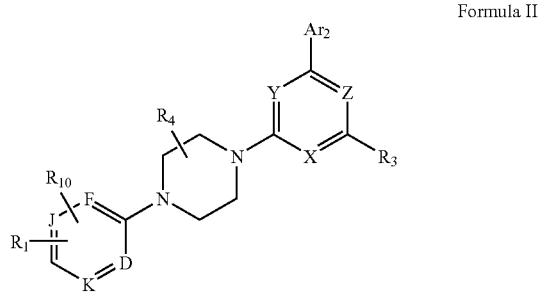

Formula IIa

Formula IIb

Formula IIc

-continued

Formula IId
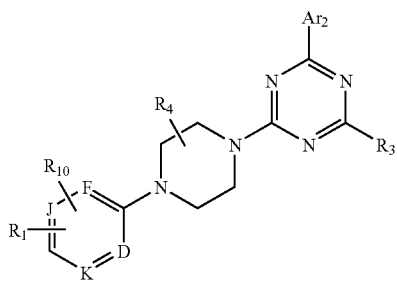

Formula IIe
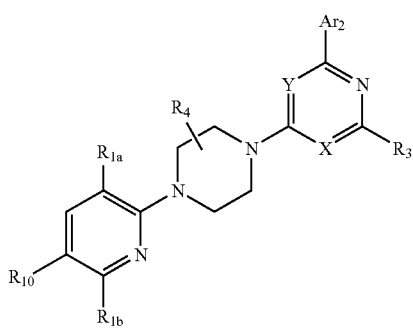

Formula IIf
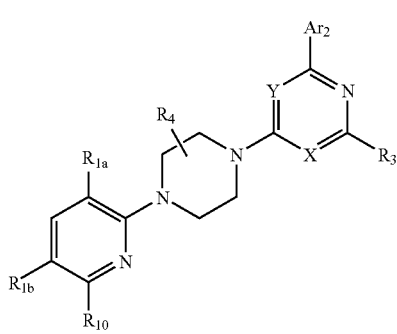

Within Formula IIe and Formula IIf:
$R_{1a}$ and $R_{1b}$ are independently hydrogen, halogen, amino, cyano, $C_1$-$C_6$alkyl, $C_1$-$C_6$haloalkyl, $C_1$-$C_6$alkoxy, $C_1$-$C_6$alkylsulfonyl, mono- or di-($C_1$-$C_6$alkyl)aminosulfonyl, ($C_3$-$C_8$cycloalkyl)aminocarbonyl or a group of the formula:

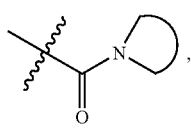, wherein

represents a 4- to 7-membered, N-linked heterocycloalkyl; and
$R_{10}$ is:
(a) —COOH, aminocarbonyl, imino, $C_1$-$C_6$alkoxycarbonyl or $C_2$-$C_6$alkanoyl;

(b) $C_1$-$C_6$alkyl, $C_2$-$C_6$alkyl ether, $C_1$-$C_6$alkoxy, $C_1$-$C_6$alkylamino or mono- or di-($C_1$-$C_4$alkyl)aminocarbonyl, each of which is substituted with from 1 to 4 substituents independently chosen from:
  (i) halogen, hydroxy, —COOH, cyano, amino and aminocarbonyl; and
  (ii) $C_1$-$C_6$alkoxy, $C_3$-$C_8$cycloalkyl, $C_1$-$C_6$alkylsulfonyl, $C_1$-$C_6$alkoxycarbonyl, $C_2$-$C_4$alkanoyl, mono- and di-($C_1$-$C_8$alkyl)amino, phenyl and 4- to 7-membered heterocycles, each of which is substituted with from 0 to 4 substituents independently chosen from halogen, $C_1$-$C_4$alkyl and $C_1$-$C_6$alkoxy; or
(c) ($C_3$-$C_8$cycloalkyl)aminocarbonyl or a group of the formula:

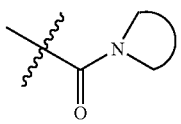

wherein

represents a 4- to 7-membered, N-linked heterocycloalkyl, each of which is substituted with from 0 to 4 substituents independently chosen from hydroxy, —COOH, cyano, amino, aminocarbonyl, $C_1$-$C_6$alkyl, $C_2$-$C_6$alkyl ether, $C_3$-$C_8$cycloalkyl, $C_1$-$C_6$alkoxy, $C_1$-$C_6$alkylsulfonyl, $C_1$-$C_6$alkoxycarbonyl, $C_2$-$C_4$alkanoyl, $C_2$-$C_4$alkanoylamino and mono- and di-($C_1$-$C_4$alkyl)amino.

Within certain embodiments of Formulas IIa-IIf, $Ar_2$ is phenyl, pyridyl or pyrimidyl, each of which is substituted with from 1 to 3 substituents independently chosen from amino, cyano, halogen, $C_1$-$C_4$alkyl, $C_1$-$C_4$haloalkyl, $C_1$-$C_4$aminoalkyl, $C_1$-$C_4$alkoxy, $C_1$-$C_4$haloalkoxy, $C_1$-$C_4$alkylthio, and mono- and di-($C_1$-$C_4$alkyl)amino$C_0$-$C_4$alkyl; and $R_4$ represents 0 substituents or one methyl substituent.

In further embodiments, substituted biaryl piperazinyl-pyridine analogues of Formula I further satisfy Formula III:

Formula III
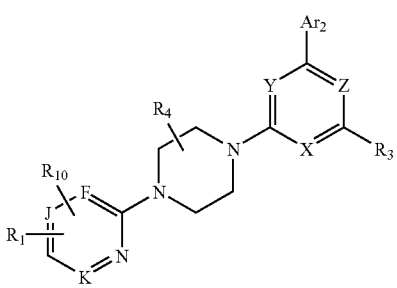

wherein R₁, K, J and F are as described for Formula II and the remaining variables are as described above for Formula I.

In certain embodiments, substituted biaryl piperazinyl-pyridine analogues of Formula III further satisfy one or more of Formulas IIIa-IIId, in which variables are as indicated for Formula III:

Formula IIIa
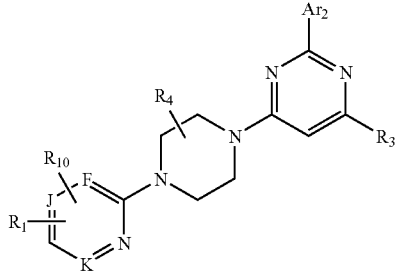

Formula IIIb
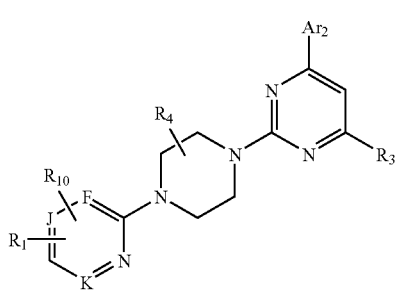

Formula IIIc
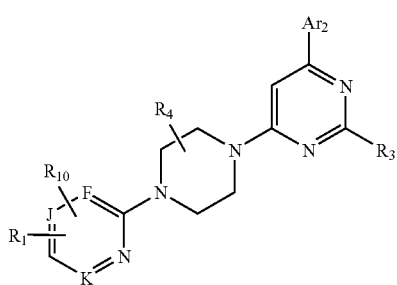

Formula IIId
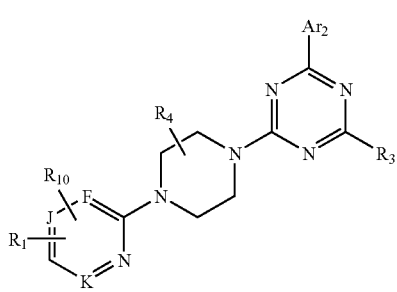

Certain substituted biaryl piperazinyl-pyridine analogues of Formula III further satisfy Formula IIIe or IIIf:

Formula IIIe
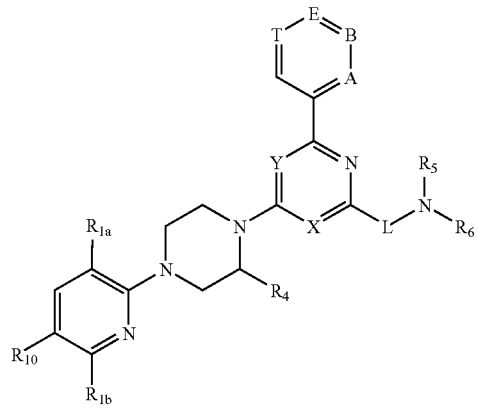

Formula IIIf
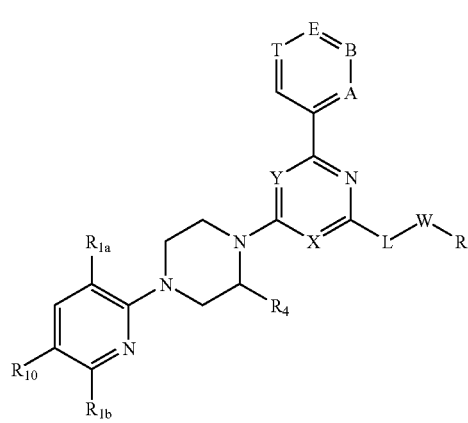

wherein:

A, B, F and T are independently nitrogen or $CR_{2a}$;

$R_{1a}$ and $R_{1b}$ are independently hydrogen, halogen, amino, cyano, $C_1$-$C_6$alkyl, $C_1$-$C_6$haloalkyl, $C_1$-$C_6$alkoxy, $C_1$-$C_6$alkylsulfonyl, mono- or di-($C_1$-$C_6$alkyl)aminosulfonyl, ($C_3$-$C_8$cycloalkyl)aminocarbonyl or a group of the formula:

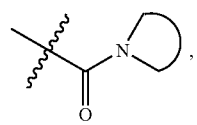

wherein

represents a 4- to 7-membered, N-linked heterocycloalkyl;

Each $R_{2a}$ is independently chosen from hydrogen, hydroxy, amino, cyano, halogen, aminosulfonyl, aminocarbonyl, —COOR, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_8$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- or di-($C_1$-$C_4$alkyl)aminosulfonyl, such that at least one $R_{2a}$ is not hydrogen;

$R_4$ is hydrogen, methyl, ethyl or oxo;

$R_{10}$ is:
 (a) nitro, —COOH, aminocarbonyl, imino, $C_1$-$C_6$alkoxycarbonyl or $C_2$-$C_6$alkanoyl;
 (b) $C_1$-$C_6$alkyl, $C_2$-$C_6$alkyl ether, $C_1$-$C_6$alkoxy, Cl-$C_6$alkylamino or mono- or di-($C_1$-$C_4$alkyl)aminocarbonyl, each of which is substituted with from 1 to 4 substituents independently chosen from:
  (i) halogen, hydroxy, —COOH, cyano, amino and aminocarbonyl; and
  (ii) $C_1$-$C_6$alkoxy, $C_3$-$C_8$cycloalkyl, $C_1$-$C_6$alkylsulfonyl, $C_1$-$C_6$alkoxycarbonyl, $C_2$-$C_4$alkanoyl, mono- and di-($C_1$-$C_8$alkyl)amino, phenyl and 4- to 7-membered heterocycles, each of which is substituted with from 0 to 4 substituents independently chosen from halogen, $C_1$-$C_4$alkyl and $C_1$-$C_6$alkoxy; or
 (c) ($C_3$-$C_8$cycloalkyl)aminocarbonyl or a group of the formula:

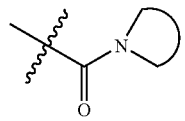

wherein

represents a 4- to 7-membered, N-linked heterocycloalkyl, each of which is substituted with from 0 to 4 substituents independently chosen from hydroxy, —COOH, cyano, amino, aminocarbonyl, $C_1$-$C_6$alkyl, $C_2$-$C_6$alkyl ether, $C_3$-$C_8$cycloalkyl, $C_1$-$C_6$alkoxy, $C_1$-$C_6$alkylsulfonyl, $C_1$-$C_6$alkoxycarbonyl, $C_2$-$C_4$alkanoyl, $C_2$-$C_4$alkanoylamino and mono- and di-($C_1$-$C_4$alkyl)amino;

$R_x$ is independently selected at each occurrence from hydrogen, methyl, amino and cyano;

and the remaining variables are as described for Formula III.

Certain substituted biaryl piperazinyl-pyridine analogues of Formula IIIe further satisfy Formula IIIg, in which $R_4$ is hydrogen or methyl and the remaining variables are as described for Formula IIIe:

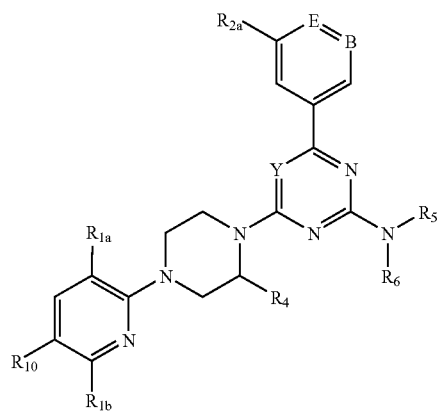

Formula IIIg

Within certain embodiments of Formulas IIIe, IIIf and IIIg:
$R_{1a}$ is halogen, cyano, methyl or trifluoromethyl;
$R_{1b}$ is hydrogen, halogen, amino, $C_1$-$C_3$alkyl, $C_1$-$C_3$alkoxy, mono- or di-($C_1$-$C_4$alkyl)amino, mono- or di-($C_1$-$C_4$alkyl)aminocarbonyl, $C_1$-$C_3$alkylsulfonyl, or mono- or di-($C_1$-$C_4$alkyl)aminosulfonyl; and
each $R_{2a}$ is independently chosen from hydrogen, halogen, cyano, amino, $C_1$-$C_4$alkyl, $C_1$-$C_4$alkoxy, and $C_1$-$C_4$haloalkyl.

Within certain embodiments of Formulas IIIe and IIIg, $R_5$ and $R_6$ are independently chosen from:
 (i) hydrogen; and
 (ii) $C_1$-$C_6$alkyl, $C_2$-$C_6$alkenyl, ($C_5$-$C_7$cycloalkyl)$C_0$-$C_2$alkyl and groups that are joined to L to form a 4- to 7-membered heterocycle; each of which is substituted with from 0 to 2 substituents independently chosen from halogen, hydroxy, oxo, —COOH, aminocarbonyl, aminosulfonyl, $C_1$-$C_4$alkyl, $C_1$-$C_4$haloalkyl, $C_1$-$C_4$alkoxy, $C_1$-$C_4$alkoxycarbonyl, $C_1$-$C_4$alkylsulfonyl and mono- and di-($C_1$-$C_6$alkyl)amino;
or $R_5$ and $R_6$, together with the N to which they are bound, form a 4- to 7-membered heterocycloalkyl that is substituted with from 0 to 2 substituents independently chosen from halogen, hydroxy, amino, oxo, aminocarbonyl, aminosulfonyl, —COOH, $C_1$-$C_4$alkyl, $C_1$-$C_4$alkoxy, $C_1$-$C_4$hydroxyalkyl, $C_2$-$C_4$alkyl ether, $C_1$-$C_4$alkoxycarbonyl, $C_2$-$C_4$alkanoyl, $C_2$-$C_4$alkanoylamino, $C_1$-$C_4$alkylsulfonyl, and mono- and di-($C_1$-$C_4$alkyl)amino$C_0$-$C_2$alkyl.

In further embodiments, substituted biaryl piperazinyl-pyridine analogues of Formula I further satisfy Formula IV:

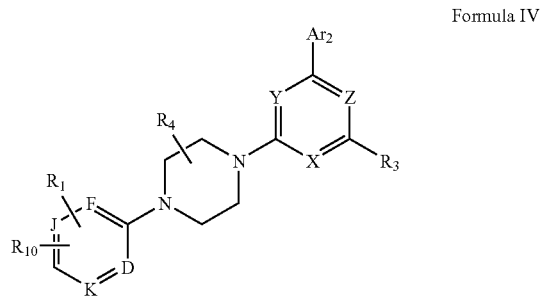

Formula IV wherein:

F is carbon substituted with a substituent represented by $R_1$ or $R_{10}$;

$R_{10}$ is as described for Formula III;

and the remaining variables are as described for Formula II.

Certain substituted biaryl piperazinyl-pyridine analogues of Formula IV further satisfy Formula IVa, in which variables are as described for Formula IV:

Formula IVa

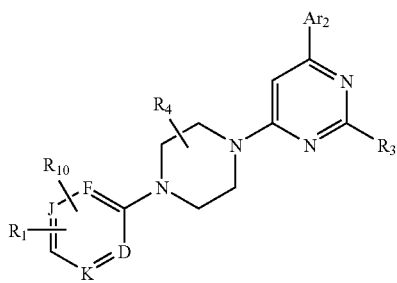

Certain substituted biaryl piperazinyl-pyridine analogues of Formula IV further satisfy Formula IVb or Formula IVc:

Formula IVb

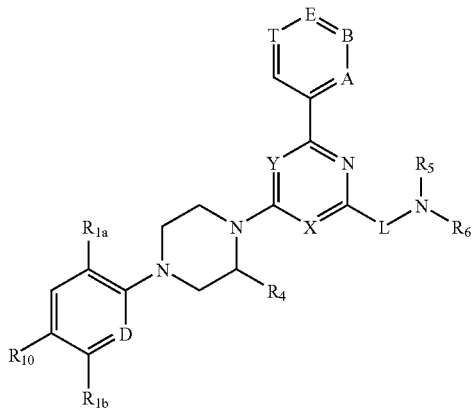

Formula IVc

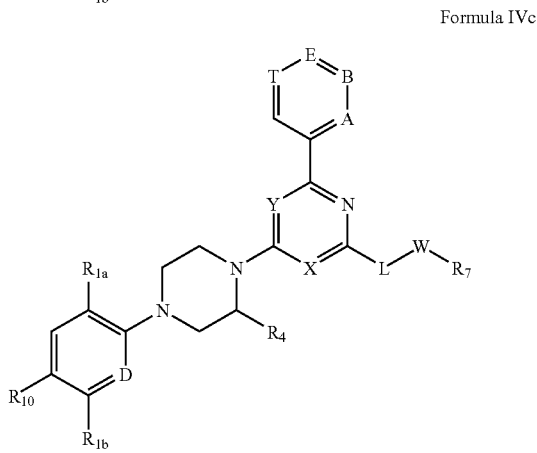

wherein:

A, B, E and T are independently nitrogen or $CR_{2a}$;

$R_{1a}$ is halogen, amino, cyano, $C_1$-$C_6$alkyl, $C_1$-$C_6$haloalkyl, $C_1$-$C_6$alkoxy, $C_1$-$C_6$alkylsulfonyl or mono- or di-($C_1$-$C_6$alkyl)aminosulfonyl;

$R_{1b}$ is hydrogen, halogen, amino, cyano, $C_1$-$C_6$alkyl, $C_1$-$C_6$haloalkyl, $C_1$-$C_6$alkoxy, $C_1$-$C_6$alkylsulfonyl, mono- or di-($C_1$-$C_6$alkyl)aminosulfonyl, ($C_3$-$C_8$cycloalkyl)aminocarbonyl or a group of the formula:

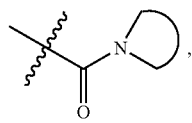

wherein

represents a 4- to 7-membered, N-linked heterocycloalkyl;

Each $R_{2a}$ is independently chosen from hydrogen, hydroxy, amino, cyano, halogen, aminosulfonyl, aminocarbonyl, —COOH, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_8$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)aminosulfonyl, such that at least one $R_{2a}$ is not hydrogen;

$R_4$ is hydrogen, methyl, ethyl or oxo;

$R_{10}$ is as described for Formula IIIe and Formula IIIf;

$R_x$ is independently selected at each occurrence from hydrogen, methyl, amino and cyano;

and the remaining variables are as described for Formula IV.

Within certain embodiments of Formula IVa and Formula IVb:

$R_{1a}$ is halogen, cyano, methyl or trifluoromethyl;

$R_{1b}$ is hydrogen, halogen, amino, $C_1$-$C_3$alkyl, $C_1$-$C_3$alkoxy, mono- or di-($C_1$-$C_4$alkyl)amino, mono- or di-($C_1$-$C_4$alkyl)aminocarbonyl, $C_1$-$C_3$alkylsulfonyl, or mono- or di-($C_1$-$C_4$alkyl)aminosulfonyl;

each $R_{2a}$ is independently chosen from hydrogen, halogen, cyano, amino, $C_1$-$C_4$alkyl, $C_1$-$C_4$alkoxy, and $C_1$-$C_4$haloalkyl; and $R_5$ and $R_6$ are independently chosen from:

(i) hydrogen; and (ii) $C_1$-$C_6$alkyl, $C_2$-$C_6$alkenyl, ($C_5$-$C_7$cycloalkyl)$C_0$-$C_2$alkyl and groups that are joined to L to form a 4- to 7-membered heterocycle; each of which is substituted with from 0 to 2 substituents independently chosen from halogen, hydroxy, oxo, —COOH, aminocarbonyl, aminosulfonyl, $C_1$-$C_4$alkyl, $C_1$-$C_4$haloalkyl, $C_1$-$C_4$alkoxy, $C_1$-$C_4$alkoxycarbonyl, $C_1$-$C_4$alkylsulfonyl and mono- and di-($C_1$-$C_6$alkyl)amino;

or $R_5$ and $R_6$, together with the N to which they are bound, form a 4- to 7-membered heterocycloalkyl that is substituted with from 0 to 2 substituents independently chosen from halogen, hydroxy, amino, oxo, aminocarbonyl, aminosulfonyl, —COOH, $C_1$-$C_4$alkyl, $C_1$-$C_4$alkoxy, $C_1$-$C_4$hydroxyalkyl, $C_2$-$C_4$alkyl ether, $C_1$-$C_4$alkoxycarbonyl, $C_2$-$C_4$alkanoyl, $C_2$-$C_4$alkanoylamino, $C_1$-$C_4$alkylsulfonyl, and mono- and di-($C_1$-$C_4$alkyl)amino$C_1$-$C_2$alkyl.

Further substituted biaryl piperazinyl-pyridine analogues of Formula I additionally satisfy one of Formulas V, VI, VII or VIII:

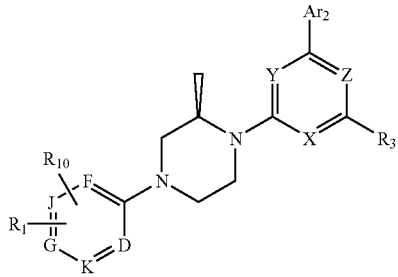
Formula V

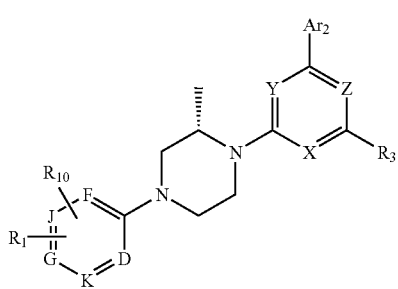
Formula VI

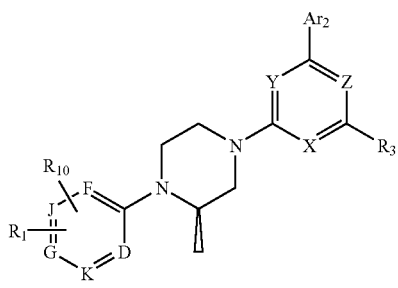
Formula VII

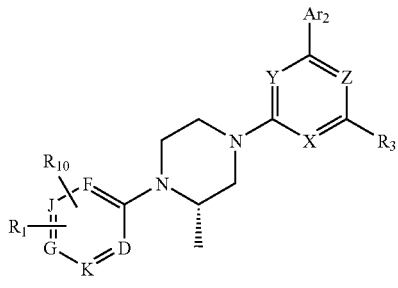
Formula VIII wherein:

D, K, G, J and F are independently N, CH or carbon substituted with a substituent represented by $R_1$ or $R_{10}$;

$R_1$ is as described for Formula II;

$R_{10}$ is as described for Formula III;

and the remaining variables are as described for Formula I.

Within certain embodiments of the above Formulas, variables are as follows:

$Ar_1$, $R_1$, $R_{1a}$, $R_{1b}$, $R_{1c}$ and $R_{10}$

Certain $Ar_1$ groups satisfy the formula:

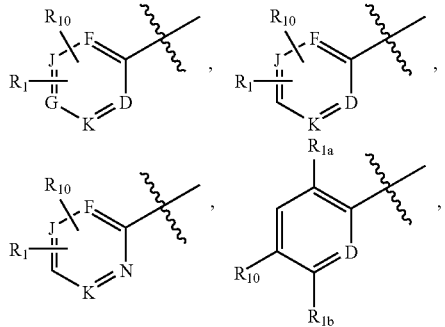

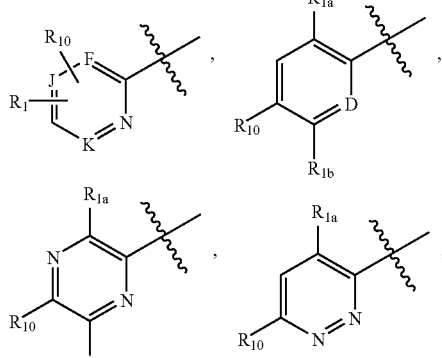

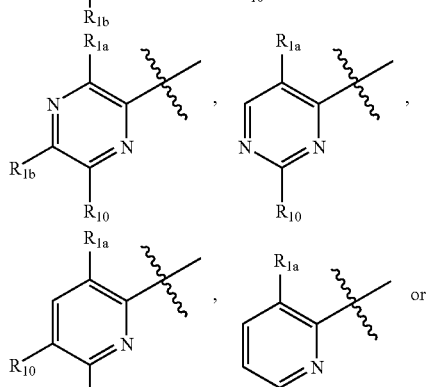

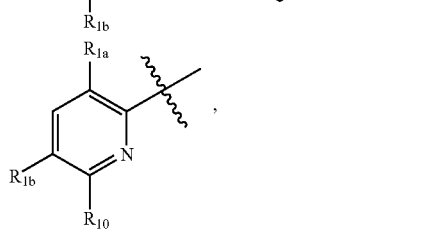

in which variables are as described above. In certain embodiments, D is N; in further embodiments, J, F, K and/or G are N; within still further embodiments, D and F are both N. Within other embodiments, K is N or both K and J are N. In stil further embodiments, J, F, K and/or G are optionally substituted carbon (e.g., J, F and K are optionally substituted carbon). Within certain compounds, F is substituted carbon (i.e., one substituent represented by $R_1$ or $R_{10}$ is located ortho to the point of attachment) and/or one substituent represented by $R_1$ or $R_{10}$ is located meta or para to the point of attachment, wherein the point of attachment refers to the attachment to the piperazinyl ring.

Certain substituents satisfy the formula Q-M-Ry. It will be apparent that if Q is $C_0$ and M is a single covalent bond, then $R_y$ is directly linked (via a single covalent bond) to the $Ar_1$ core ring.

$R_{10}$ in the above Formulas represents one substituent of $Ar_1$. In other words, a $R_{10}$ moiety, as defined above, is covalently bonded to any ring carbon atom of $Ar_1$, such as a carbon atom at the position designated D, K, G, J or F in certain formulas. Within certain compounds of Formula II and subformulas thereof, $R_{10}$ represents:

(a) —COOH, aminocarbonyl, imino, $C_1$-$C_6$alkoxycarbonyl or $C_2$-$C_6$alkanoyl;
(b) $C_1$-$C_6$alkyl, $C_2$-$C_6$alkyl ether, $C_1$-$C_6$alkoxy, $C_1$-$C_6$alkylamino or mono- or di-($C_{1\text{-}C4}$alkyl)aminocarbonyl, each of which is substituted with from 1 to 4 substituents independently chosen from:
  (i) halogen, hydroxy, —COOH, cyano, amino and aminocarbonyl; and
  (ii) $C_1$-$C_6$alkoxy, $C_3$-$C_8$cycloalkyl, $C_1$-$C_6$alkylsulfonyl, $C_1$-$C_6$alkoxycarbonyl, $C_2$-$C_4$alkanoyl, mono- and di-($C_1$-$C_8$alkyl)amino, 4- to 7-membered heterocycles and phenyl, each of which is substituted with from 0 to 4 substituents independently chosen from halogen, $C_1$-$C_4$alkyl and $C_1$-$C_6$alkoxy; or
(c) ($C_3$-$C_8$cycloalkyl)aminocarbonyl or a group of the formula:

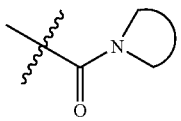

wherein

represents a 4- to 7-membered, N-linked heterocycloalkyl, each of which is substituted with from 0 to 4 substituents independently chosen from hydroxy, —COOH, cyano, amino, aminocarbonyl, $C_1$-$C_6$alkyl, $C_2$-$C_6$alkyl ether, $C_3$-$C_8$cycloalkyl, $C_1$-$C_6$alkoxy, $C_1$-$C_6$alkylsulfonyl, $C_1$-$C_6$alkoxycarbonyl, $C_2$-$C_4$alkanoyl, $C_2$-$C_4$alkanoylamino and mono- and di-($C_1$-$C_4$alkyl)amino.

Within certain compounds of the other Formulas, $R_{10}$ represents:

(a) nitro, —COOH, aminocarbonyl, imino, $C_1$-$C_6$alkoxycarbonyl or $C_2$-$C_6$alkanoyl;
(b) $C_1$-$C_6$alkyl, $C_2$-$C_6$alkyl ether, $C_1$-$C_6$alkoxy, $C_1$-$C_6$alkylamino or mono- or, di-($C_1$-$C_4$alkyl)aminocarbonyl, each of which is substituted with from 1 to 4 substituents independently chosen from:
  (i) halogen, hydroxy, —COOH, cyano, amino and aminocarbonyl; and
  (ii) $C_1$-$C_6$alkoxy, $C_3$-$C_8$cycloalkyl, $C_1$-$C_6$alkylsulfonyl, $C_1$-$C_6$alkoxycarbonyl, $C_2$-$C_4$alkanoyl, mono- and di-($C_1$-$C_8$alkyl)amino, 4- to 7-membered heterocycles and phenyl, each of which is substituted with from 0 to 4 substituents independently chosen from halogen, $C_1$-$C_4$alkyl and $C_1$-$C_6$alkoxy; or
(c) ($C_3$-$C_8$cycloalkyl)aminocarbonyl or a group of the formula:

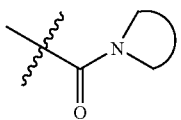

wherein

represents a 4- to 7-membered, N-linked heterocycloalkyl, each of which is substituted with from 0 to 4 substituents independently chosen from hydroxy, —COOH, cyano, amino, aminocarbonyl, $C_1$-$C_6$alkyl, $C_2$-$C_6$alkyl ether, $C_3$-$C_8$cycloalkyl, $C_1$-$C_6$alkoxy, $C_1$-$C_6$alkylsulfonyl, $C_1$-$C_6$alkoxycarbonyl, $C_2$-$C_4$alkanoyl, $C_2$-$C_4$alkanoylamino and mono- and di-($C_1$-$C_4$alkyl)amino.

Representative $R_{10}$ groups include, for example, nitro, aminocarbonyl, —COOH, $C_1$-$C_4$alkoxycarbonyl, hydroxy$C_1$-$C_4$alkyl (e.g., hydroxymethyl), amino$C_1$-$C_4$alkyl (e.g., aminomethyl), cyano$C_1$-$C_4$alkyl (e.g., cyanomethyl), carboxy$C_1$-$C_4$alkyl (e.g., carboxymethyl), mono- and di-($C_1$-$C_4$alkyl)amino$C_1$-$C_4$alkyl and mono- and di-($C_1$-$C_4$alkyl)amino$C_1$-$C_4$alkoxy. Other representative $R_{10}$ groups include ($C_3$-$C_8$cycloalkyl)aminocarbonyl groups and mono- and di-($C_1$-$C_4$alkyl)aminocarbonyl groups that are substituted with $C_1$-$C_4$alkoxy, $C_1$-$C_4$haloalkyl $C_2$-$C_6$alkyl ether, mono- or di-($C_1$-$C_4$alkyl)amino, optionally substituted 5- to 7-membered heterocycloalkyl groups (e.g., tetrahydrofuranyl or thiophenyl), and/or optionally substituted phenyl. Additional representative $R_{10}$ groups include groups of the formula:

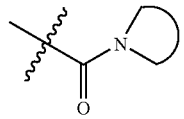

wherein

represents optionally substituted azetidinyl, pyrrolidinyl, piperidinyl piperazinyl, morpholinyl, thiomorpholinyl or azepanyl.

$R_1$ in the above Formulas represents up to three optional substituents of $Ar_1$ (in addition to $R_{10}$). In certain embodiments, $R_1$ represents one substituent (i.e., $Ar_1$ is di-substituted). Representative $R_1$ groups include, for example, halogen, nitro, cyano, methyl, $C_1$-$C_4$alkoxycarbonyl, trifluoromethyl and methylsulfonyl.

The variables $R_{1a}$ and $R_{1b}$, within Formulas that recite such variables, are generally as described above. Within certain compounds, $R_{1a}$ and $R_{1b}$ are independently hydrogen, halogen, amino, cyano, $C_1$-$C_6$alkyl, $C_1$-$C_6$haloalkyl, $C_1$-$C_6$alkoxy, $C_1$-$C_6$alkylsulfonyl, mono- or di-($C_1$-$C_6$alkyl)aminosulfonyl, ($C_3$-$C_8$cycloalkyl)aminocarbonyl or a group of the formula:

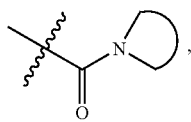

wherein

represents a 4- to 7-membered, N-linked heterocycloalkyl. In further embodiments, $R_{1a}$ is nitro, —COOH, halogen, cyano, methyl or trifluoromethyl; in further embodiments, $R_{1a}$ is halogen, cyano, methyl or trifluoromethyl.

$Ar_2$, $R_2$ and $R_{2a}$

In certain substituted biaryl piperazinyl-pyridine analogues of the above Formulas, $Ar_2$ is optionally substituted phenyl, pyridyl (i e., 2-pyridyl, 3-pyridyl or 4-pyridyl) or pyrimidyl. In other compounds, $Ar_2$ is a 9- to 12-membered bicyclic aryl or heteroaryl group that is optionally substituted as described above. In some embodiments, $Ar_2$ is unsubstituted phenyl or unsubstituted pyridyl. In other embodiments, $Ar_2$ is substituted with from 0 to 3 or from 1 to 3 substituents independently chosen from $R_2$ as described above. In certain such compounds, $Ar_2$ has at least one substituent ($R_2$) and each $R_2$ is independently chosen from amino, cyano, halogen, aminosulfonyl, $C_1$-$C_4$alkyl, $C_1$-$C_4$haloalkyl, $C_1$-$C_4$hydroxyalkyl, $C_1$-$C_4$aminoalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)aminosulfonyl. Representative substituents of $Ar_2$ include amino, cyano, halogen, $C_1$-$C_4$alkyl, $C_1$-$C_4$haloalkyl, $C_1$-$C_4$aminoalkyl, $C_1$-$C_4$alkoxy, $C_1$-$C_4$haloalkoxy, $C_1$-$C_4$alkylthio and mono- and di-($C_1$-$C_4$alkyl)amino$C_0$-$C_4$alkyl. In certain such compounds, $Ar_2$ is substituted meta and/or para to the point of attachment, wherein the point of attachment refers to the attachment to the core ring. In other words, if $Ar_2$ is phenyl, the phenyl is mono-substituted at the 3-position, mono-substituted at the 4-position, or di-substituted and the 3- and 4-positionsin such compounds. Representative $Ar_2$ groups include phenyl, pyridyl and pyrimidyl, each of which is substituted with from 0 to 3 or from 1 to 3 substituents as described herein.

Within certain $Ar_2$ groups, one $R_2$ is taken together with an adjacent $R_2$ to form a fused carbocycle or heterocycle. Representative such groups include, for example, the following bicyclic groups, optionally substituted as described herein:

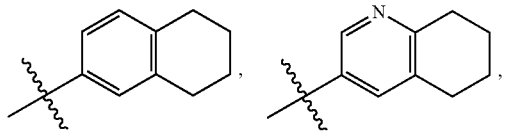

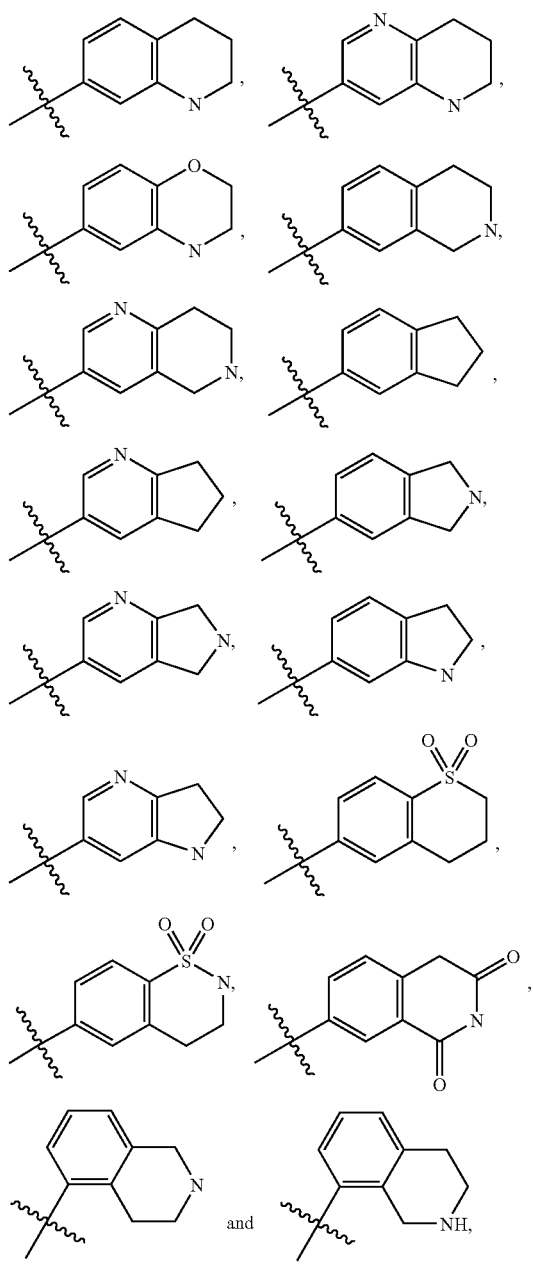

as well as variants of the foregoing in which the fused ring contains one or more additional double bonds, such as:

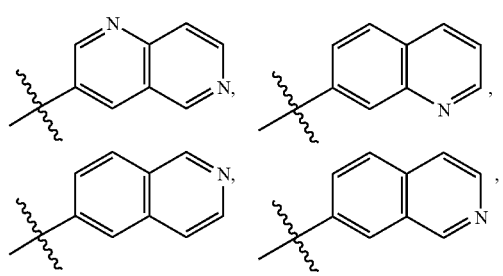

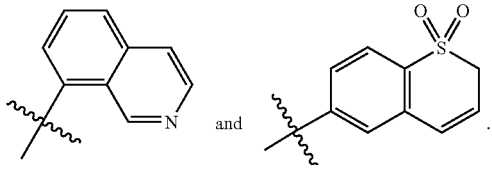

-continued

The variable $R_{2a}$, when present, is generally as described above; in certain embodiments, each $R_{2a}$ is independently chosen from hydrogen, hydroxyl, amino, cyano, halogen, aminosulfonyl, aminocarbonyl, —COOH, $C_1$-$C_4$alkyl, $C_1$-$C_4$haloalkyl, $C_1$-$C_4$hydroxy akyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)aminosulfonyl. In further such compounds, each $R_{2a}$ is independently chosen from hydrogen, halogen, cyano, amino, $C_1$-$C_4$alkyl, $C_1$-$C_4$haloalkyl and $C_1$-$C_4$alkoxy. In still further such compounds, A is CH or $CR_{2a}$, and each $R_{2a}$ is independently chosen from cyano, halogen, $C_1$-$C_4$alkyl, $C_1$-$C_4$haloalkyl, $C_1$-$C_4$alkoxy and mono- and di-($C_1$-$C_4$alkyl)amino$C_0$-$C_2$alkyl. In other such compounds, at least one of A, B, E and T is N. Certain $Ar_2$ groups have the formula:

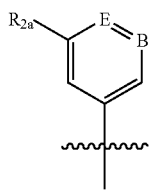

wherein B and E and $R_2$ are as described above.

$R_3$

In the definition of $R_3$, the variable "L" is defined as $C_0$-$C_6$alkylene or $C_1$-$C_6$alkylene that is taken together with $R_5$, $R_6$ or $R_7$ to form a 4- to 7-membered heterocycle. In any heterocycle so formed, at least one carbon atom present in L is also a ring atom, and is covalently bonded to a component atom of $R_5$, $R_6$ or $R_7$. The resulting heterocycle may be a heterocycloalkyl group (e.g., tetrahydrofuranyl, morpholinyl, piperidinyl or piperazinyl) or a heteroaryl group, such as pyridyl, or pyrimidyl. $R_3$ groups comprising such a heterocycle include, for example:

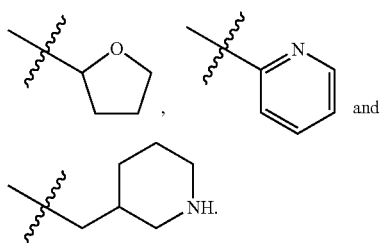

$R_3$, in certain embodiments of various Formulas provided herein, is a group of the formula:

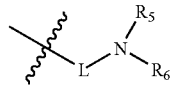

wherein:

L is $C_0$-$C_3$alkylene; and $R_5$ and $R_6$ are:

(a) independently chosen from hydrogen, $C_1$-$C_6$alkyl, $C_2$-$C_6$alkenyl, ($C_3$-$C_8$cycloalkyl)$C_0$-$C_4$alkyl, $C_2$-$C_4$alkanoyl and groups that are joined to L to form a 4- to 7-membered heterocycle; or (b) joined to form a 4- to 12-membered heterocycloalkyl;

wherein each alkyl, alkenyl, (cycloalkyl)alkyl, alkanoyl and heterocycloalkyl is substituted with from 0 to 4 substituents independently chosen from (i) halogen, hydroxy, amino, aminocarbonyl, oxo, —COOH and aminosulfonyl; and (ii) $C_1$-$C_4$alkyl, $C_5$-$C_7$cycloalkyl, $C_1$-$C_4$alkoxy, $C_2$-$C_4$alkanoyl, $C_1$-$C_4$haloalkyl, mono- and di-($C_1$-$C_4$alkyl)amino$C_0$-$C_2$alkyl, mono- and di-($C_1$-$C_4$alkyl)aminocarbonyl$C_0$-$C_2$alkyl, phenyl$C_0$-$C_4$alkyl and (4- to 7-membered heterocycle)$C_0$-$C_2$alkyl, each of which is substituted with from 0 to 4 secondary substituents independently chosen from halogen, hydroxy, cyano, $C_1$-$C_4$alkyl, $C_1$-$C_4$alkoxy and $C_1$-$C_4$haloalkyl.

Within certain such compounds, $R_5$ and $R_6$ are independently chosen from:

(i) hydrogen; and (ii) $C_1$-$C_6$alkyl, $C_2$-$C_6$alkenyl, ($C_5$-$C_7$cycloalkyl)$C_0$-$C_2$alkyl and groups that are joined to L to form a 4- to 7-membered heterocycle; each of which is substituted with from 0 to 2 substituents independently chosen from halogen, hydroxy, oxo, —COOH, aminocarbonyl, aminosulfonyl, $C_1$-$C_4$alkyl, $C_1$-$C_4$haloalkyl, $C_1$-$C_4$alkoxy, $C_1$-$C_4$alkoxycarbonyl, $C_1$-$C_4$alkylsulfonyl and mono- and di-($C_1$-$C_6$alkyl)amino;

or $R_5$ and $R_6$, together with the N to which they are bound, form a 4- to 7-membered heterocycloalkyl that is substituted with from 0 to 2 substituents independently chosen from halogen, hydroxy, amino, oxo, aminocarbonyl, aminosulfonyl, —COOH, $C_1$-$C_4$alkyl, $C_1$-$C_4$alkoxy, $C_1$-$C_4$hydroxyalkyl, $C_2$-$C_4$alkyl ether, $C_1$-$C_4$alkoxycarbonyl, $C_2$-$C_4$alkanoyl, $C_2$-$C_4$alkanoylamino, $C_1$-$C_4$alkylsulfonyl, and mono- and di-($C_1$-$C_4$alkyl)amino$C_0$-$C_2$alkyl Such $R_3$ groups include, for example, mono- and di-($C_1$-$C_4$alkyl)amino groups that are substituted with from 0 to 4 substituents independently chosen from halogen, hydroxy, amino, oxo, aminocarbonyl, —COOH, aminosulfonyl, $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino. Representative such groups include:

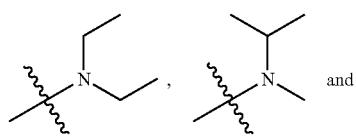

-continued

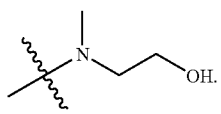

Within other $R_3$ groups, $R_5$ and $R_6$, together with the N to which they are bound, form a pyrrolidine, piperazine, piperidine, azetidine or morpholine ring, each of which is substituted with from 0 to 2 substituents independently chosen from $C_1$-$C_4$alkyl and $C_1$-$C_4$hydroxyalkyl.

Still further $R_3$ groups include phenyl and 4- to 7-membered heterocycles, each of which is substituted with from 0 to 4 substituents independently chosen from (a) halogen, hydroxy, amino, oxo, aminocarbonyl, aminosulfonyl and —COOH; and (b) $C_1$-$C_4$alkyl, $C_1$-$C_4$haloalkyl, $C_2$-$C_4$alkenyl, ($C_5$-$C_7$cycloalkyl)$C_0$-$C_2$alkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino, mono- and di-($C_1$-$C_4$alkyl)amino, mono- and di-($C_1$-$C_4$alkyl)aminocarbonyl, mono- or di-($C_1$-$C_4$alkyl)aminosulfonyl, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, —COOH, $C_1$-$C_4$alkyl and $C_1$-$C_4$haloalkyl. Certain such $R_3$ groups include azetidinyl, pyrrolidinyl, morpholinyl, thiomorpholinyl, piperidinyl, piperazinyl, tetrahydropyridyl and azepanyl, each of which is substituted with from 0 to 4 substituents independently chosen from: (a) halogen, hydroxy, amino, oxo, aminocarbonyl, aminosulfonyl and —COOH; and (b) $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino, each of which is substituted with from 0 to 4 secondary substituents independently chosen from hydroxy and halogen. Representative examples of such $R_3$ groups include the heterocycles:

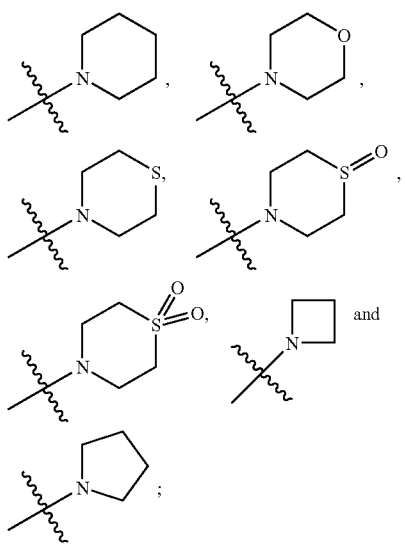

And substituted heterocycles, such as:

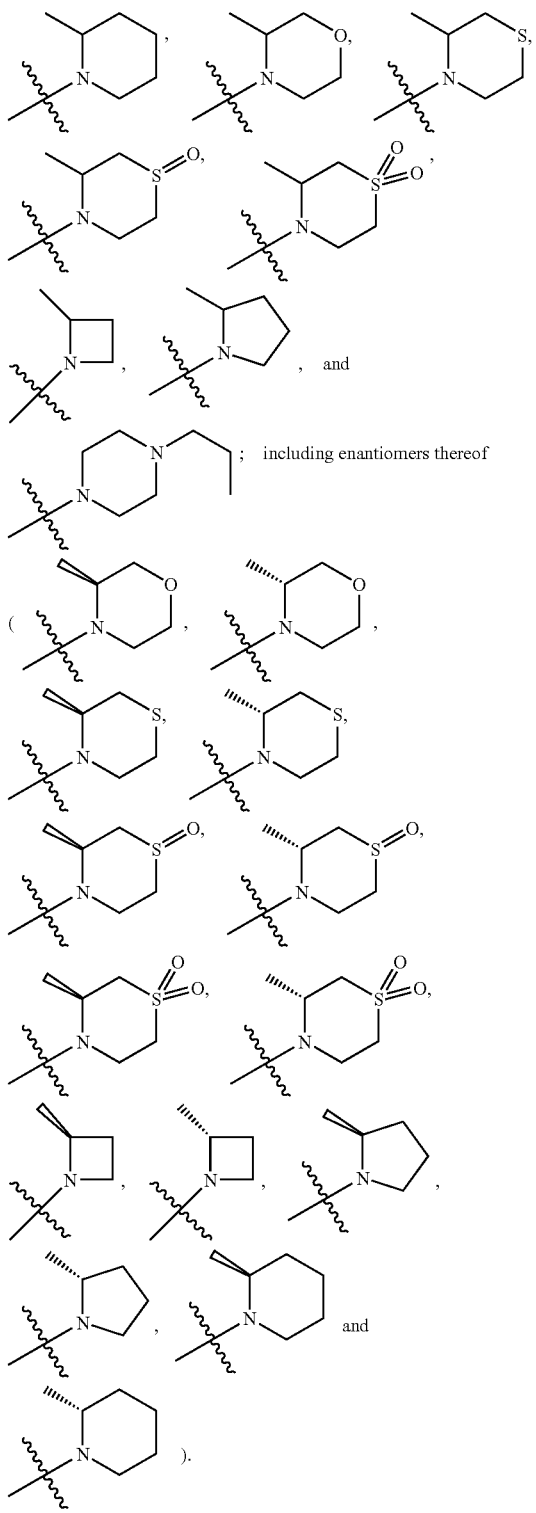

Other such $R_3$ groups include phenyl, pyridyl, pyrimidyl, pyrazinyl, pyridazinyl, imidazolyl, thienyl, oxazolyl and tetrahydrofuranyl, each of which is substituted with from 0 to 4 substituents independently chosen from halogen, hydroxy, amino, aminocarbonyl, aminosulfonyl, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino. In certain embodiments, $R_3$ is not —$NH_2$. In other words, if $R_3$ has the formula:

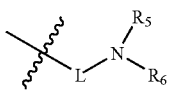

and L is a single covalent bond, then at least one of $R_5$ and $R_6$ is not hydrogen.

In further embodiments, $R_3$ is

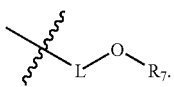

In certain such compounds, L is $C_0$-$C_3$alkylene; and $R_7$ is $C_1$-$C_6$alkyl, $C_2$-$C_6$alkenyl, ($C_5$-$C_7$cycloalkyl)$C_0$-$C_4$alkyl, $C_2$-$C_2$-$C_4$alkanoyl, phenyl$C_0$-$C_6$alkyl or (6-membered heteroaryl)$C_0$-$C_4$alkyl, each of which is substituted with from 0 to 4 substituents independently chosen from halogen, hydroxy, amino, aminocarbonyl, aminosulfonyl, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino. Such $R_3$ groups include, for example, benzyloxy and $C_1$-$C_6$alkoxy, each of which is optionally substituted with halogen, methyl, methoxy or trifluoromethyl.

Within still further embodiments, $R_3$ is hydrogen, $C_1$-$C_6$alkyl or a halogen.

Within further embodiments of the above Formulas, $R_3$ is $C_1$-$C_4$alkyl, $C_3$-$C_7$cycloalkyl or $C_1$-$C_4$haloalkyl, each of which is substituted with from 0 to 4 substituents independently chosen from halogen, hydroxy, cyano, oxo, aminocarbonyl, aminosulfonyl, —COOH, $C_3$-$C_7$cycloalkyl, phenyl and 4- to 7-membered heterocycle.

$R_4$ $R_4$, in certain substituted biaryl piperazinyl-pyridine analogues provided herein, represents zero substituents or one methyl, ethyl or oxo group; in certain embodiments such a substituent is located adjacent to the nitrogen atom that is bound to the core, as shown below:

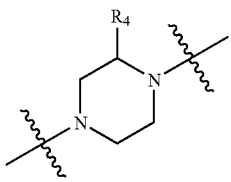

The carbon to which a methyl or ethyl group is attached is chiral in certain embodiments (e.g., as shown in Formula V, VI, VII or VIII), in which the group

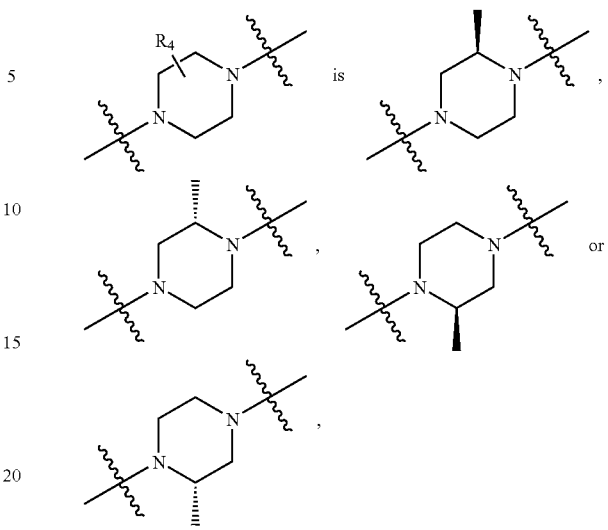

respectively.

In other embodiments, $R_4$ represents a single oxo substituent.

X, Y and Z

X, Y and Z, as noted above, are independently $CR_x$ or N, such that at least one of X, Y and Z is N. In certain embodiments, each $R_x$ is independently selected from hydrogen, fluoro, methyl, amino and cyano; each $R_x$ is independently selected from hydrogen, methyl, amino and cyano; each $R_x$ is independently chosen from hydrogen and methyl; or each $R_x$ is hydrogen. In certain representative compounds, Z is N (e.g., X and Y are CH). In other compounds provided herein, X is N (e.g., Y and Z are CH). In further compounds Z and X are N, X and Y are N or Z and Y are N. In still further compounds, X, Y and Z are each N.

Representative substituted biaryl piperazinyl-pyridine analogues provided herein include, but are not limited to, those specifically described in Examples 1-3. It will be apparent that the specific compounds recited herein are representative only, and are not intended to limit the scope of the present invention. Further, as noted above, all compounds provided herein may be present as a free base, a pharmaceutically acceptable salt or other form, such as a hydrate.

Within certain aspects of the present invention, substituted biaryl piperazinyl-pyridine analogues provided herein detectably alter (modulate) VR1 activity, as determined using an in vitro VR1 functional assay such as a calcium mobilization assay, dorsal root ganglion assay or in vivo pain relief assay. As an initial screen for such activity, a VR1 ligand binding assay may be used. References herein to a "VR1 ligand binding assay" are intended to refer to a standard in vitro receptor binding assay such as that provided in Example 5, and a "calcium mobilization assay" (also referred to herein as a "signal transduction assay") may be performed as described in Example 6. Briefly, to assess binding to VR1, a competition assay may be performed in which a VR1 preparation is incubated with labeled (e.g., $^{125}$I or $^{3}$H) compound that binds to VR1 (e.g., a capsaicin receptor agonist such as RTX) and unlabeled test compound. Within the assays provided herein, the VR1 used is preferably mammalian VR1, more preferably human or rat VR1. The receptor may be recombinantly expressed or naturally expressed. The VR1 preparation may be, for example, a membrane preparation from HEK293 or CHO cells that recombinantly express human VR1. Incubation with a compound that detectably modulates vanilloid ligand binding to VR1 results in a decrease or increase in the amount of label bound to the VR1 preparation, relative to the amount of label bound in the absence of the compound. This decrease or increase may be used to determine the $K_i$ at VR1 as described herein. In general, compounds that decrease the amount of label bound to the VR1 preparation within such an assay are preferred.

As noted above, certain substituted biaryl piperazinyl-pyridine analogues are VR1 antagonists. $IC_{50}$ values for such compounds may be determined using a standard in vitro VR1-mediated calcium mobilization assay, as provided in Example 6. Briefly, cells expressing capsaicin receptor are contacted with a compound of interest and with an indicator of intracellular calcium concentration (e.g., a membrane permeable calcium sensitivity dye such as Fluo-3 or Fura-2 (both of which are available, for example, from Molecular Probes, Eugene, Oreg.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 h). Cells are washed or filtered to remove excess dye and are then contacted with a vanilloid receptor agonist (e.g., capsaicin, RTX or olvanil), typically at a concentration equal to the $EC_{50}$ concentration, and a fluorescence response is measured. When agonist-contacted cells are contacted with a compound that is a VR1 antagonist the fluorescence response is generally reduced by at least 20%, preferably at least 50% and more preferably at least 80%, as compared to cells that are contacted with the agonist in the absence of test compound. The $IC_{50}$ for VR1 antagonists provided herein is preferably less than 1 micromolar, less than 100 nM, less than 10 nM or less than 1 nM. In certain embodiments, VR1 antagonists provided herein exhibit no detectable agonist activity an in vitro assay of capsaicin receptor agonism at a concentration of compound equal to the $IC_{50}$. Certain such antagonists exhibit no detectable agonist activity an in vitro assay of capsaicin receptor agonism at a concentration of compound that is 100-fold higher than the $IC_{50}$.

Other substituted biaryl piperazinyl-pyridine analogues may be capsaicin receptor agonists. Capsaicin receptor agonist activity may generally be determined as described in Example 6. When cells are contacted with 1 micromolar of a compound that is a VR1 agonist, the fluorescence response is generally increased by an amount that is at least 30% of the increase observed when cells are contacted with 100 nM capsaicin. The $EC_{50}$ for VR1 agonists provided herein is preferably less than 1 micromolar, less than 100 nM or less than 10 nM.

VR1 modulating activity may also, or alternatively, be assessed using a cultured dorsal root ganglion assay as provided in Example 9 and/or an in vivo pain relief assay as provided in Example 10. VR1 modulators provided herein preferably have a statistically significant specific effect on VR1 activity within one or more of the functional assays provided in Examples 6 and 10, herein.

Within certain embodiments, VR1 modulators provided herein do not substantially modulate ligand binding to other cell surface receptors, such as EGF receptor tyrosine kinase or the nicotinic acetylcholine receptor. In other words, such modulators do not substantially inhibit activity of a cell surface receptor such as the human epidermal growth factor (EGF) receptor tyrosine kinase or the nicotinic acetylcholine receptor (e.g., the $IC_{50}$ or $IC_{40}$ at such a receptor is preferably greater than 1 micromolar, and most preferably greater than 10 micromolar). Preferably, a modulator does not detectably inhibit EGF receptor activity or nicotinic acetylcholine receptor activity at a concentration of 0.5 micromolar, 1 micromolar or more preferably 10 micromolar. Assays for determining cell surface receptor activity are commercially available, and include the tyrosine kinase assay kits available from Panvera (Madison, Wis.).

In certain embodiments, preferred VR1 modulators are non-sedating. In other words, a dose of VR1 modulator that is twice the minimum dose sufficient to provide analgesia in an animal model for determining pain relief (such as a model provided in Example 10, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3):433-9). Preferably, a dose that is five times the minimum dose sufficient to provide analgesia does not produce statistically significant sedation. More preferably, a VR1 modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a therapeutically effective amount is administered to a subject), side effects (a preferred compound produces side effects comparable to placebo when a therapeutically effective amount of the compound is administered to a subject), serum protein binding and in vitro and in vivo half-life (a preferred compound exhibits an in vivo half-life allowing for Q.I.D. dosing, preferably T.I.D. dosing, more preferably B.I.D. dosing, and most preferably once-a-day dosing). In addition, differential penetration of the blood brain barrier may be desirable for VR1 modulators used to treat pain by modulating CNS VR1 activity such that total daily oral doses as described above provide such modulation to a therapeutically effective extent, while low brain levels of VR1 modulators used to treat peripheral nerve mediated pain may be preferred (i.e., such doses do not provide brain (e.g., CSF) levels of the compound sufficient to significantly modulate VR1 activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described within Example 7, herein.

As noted above, preferred compounds provided herein are nontoxic. In general, the term "nontoxic" shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 8, herein. In other words, cells treated as described in Example 8 with 100 μM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ at VR1 for the compound does not elevate serum levels of ALT, LDH or AST in laboratory rodents by more than 100% over matched mock-treated controls. In more highly preferred embodiments, such doses do not elevate such serum levels by more than 75% or 50% over matched controls. Alternatively, a compound does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ at VR1 for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred compounds do not induce sister chromatid exchange (e.g., in Chinese hamster ovary cells) at such concentrations.

For detection purposes, as discussed in more detail below, VR1 modulators provided herein may be isotopically-labeled or radiolabeled. For example, compounds may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Substituted Biaryl Piperazinyl-Pyridine Analogues

Substituted biaryl piperazinyl-pyridine analogues may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry. Each variable in the following schemes refers to any group consistent with the description of the compounds provided herein.

In the Schemes that follow the term "reduction" refers to the process of reducing a nitro functionality to an amino functionality, the process of transforming an ester functionality to an alcohol or the process of transforming an amide to an amino group. The reduction of a nitro group can be carried out in a number of ways well known to those skilled in the art of organic synthesis including, but not limited to, catalytic hydrogenation, reduction with $SnCl_2$ and reduction with titanium trichloride. The reduction of an ester group is typically performed using metal hydride reagents including, but not limited to, diisobutyl-aluminum hydride (DIBAL), lithium aluminum hydride (LAH), and sodium borohydride. The reduction of an amide can be carried out conveniently with reagents including, but not limited to, diborane as well as lithium aluminum hydride (LAH). For an overview of reduction methods see: Hudlicky, M. *Reductions in Organic Chemistry*, ACS Monograph 188, 1996.

In the Schemes that follow, the term "hydrolyze" refers to the reaction of a substrate or reactant with water. More specifically, "hydrolyze" refers to the conversion of an ester or nitrile functionality into a carboxylic acid. This process can be catalyzed by a variety of acids or bases well known to those skilled in the art of organic synthesis.

In the Schemes that follow, the term "catalyst" refers to a suitable transition metal catalyst such as, but not limited to, tetrakis(triphenylphosphine)palladium(0) or palladium(II) acetate. In addition, the catalytic systems may include ligands such as, but not limited to, 2-(Dicyclohexylphosphino)biphenyl and tri-tert-butylphosphine, and may also include a base such as $K_3PO_4$, $Na_2CO_3$ or sodium or potassium tert-butoxide. Transition metal-catalyzed reactions can be carried out at ambient or elevated temperatures using various inert solvents including, but not limited to, toluene, dioxane, DMF, N-methylpyrrolidinone, ethyleneglycol, dimethyl ether, diglyme and acetonitrile. When used in conjunction with suitable metallo-aryl reagents, transition metal-catalyzed (hetero)aryl/aryl coupling reactions can be used to prepare the compounds encompassed in general structures ID and IE (Scheme 1), and 2C (Scheme 2), 4E (Scheme 4), 5B (Scheme 5), 6-F (Scheme 6), 8B and 8D (Scheme 8), 9C (Scheme 9), and 10C (Scheme 10). Commonly employed reagent/catalyst pairs include aryl boronic acid/palladium(0) (Suzuki reaction; Miyaura and Suzuki (1995) *Chemical Reviews* 95:2457) and aryl trialkylstannane/palladium(0) (Stille reaction; T. N. Mitchell, (1992) *Synthesis* 9:803-815), arylzinc/palladium(0) and aryl Grignard/nickel(II). In addition, metal-catalyzed (hetero)aryl/amine coupling reactions (Buchwald-Hartwig cross-coupling reaction; J. F. Hartwig, *Angew. Chem. Int. Ed.* 37:2046-2067 (1998)) can be used to prepare the compounds encompassed in general structures 7F (Scheme 7), 9E (Scheme 9), and 10E (Scheme 10). The term "transmetalation," as used in Schemes 2, 8, and 13, refers to one or more fo the above referenced metal-catalyzed cross coupling reactions which is suitable for coupling of (hetero)aryl halides with alcohols or amines. Certain transmetalation reaction conditions include the Stille reaction and the Suzuki reaction.

In Schemes 11, 14 and 15, $R_8$ and $R_9$ are generally as described herein for $R_5$ and $R_6$ of Formula I. $R_{20}$, in Scheme 11, is any suitable leaving group, such as Br, Cl, I, OTf, mesylate or tosylate.

Certain definitions used in the following Schemes and elsewhere herein include:
BINAP (rac)-2,2'-Bis(diphenylphosphino)-1,1'-binaphthyl
$CDCl_3$ deuterated chloroform
δ chemical shift
DCE 1,2-dichloroethane
DCM dichloromethane or methylene chloride
DDQ 2,3-dichloro-5,6-dicyano-1,4-benzoquinone
DIBAL diisobutylaluminum hydride
DIEA N,N-diisopropylethylamine
DMA N,N-dimethylacetamide
DMF dimethylformamide
DMSO dimethylsulfoxide
DPPF 1,1'-bis(diphenylphosphino)ferrocene
$Et_3N$ triethylamine
EtOAc ethyl acetate
EtOH ethanol
h hour(s)
$^1H$ NMR proton nuclear magnetic resonance
HOAc acetic acid
HPLC high pressure liquid chromatography
Hz hertz
KOAc potassium acetate
LCMS liquid chromatography/mass spectrometry
MS mass spectrometry
(M+1) mass+1
m-CPBA m-chloroperbenzoic acid
MeOH methanol
min minute(s)
MsCl methanesulfonyl chloride
NaNHCN sodium cyanamide
n-BuLi n-butyl lithium
t-Bu tertiary butyl
Tf —$SO_2CF_3$
$Pd_2(dba)_3$ tris(dibenzylideneacetone)dipalladium(0)
$Pd(PPh_3)_4$ tetrakis(triphenylphosphine)palladium(0)
$PhNEt_2$ diethyl-phenyl-amine, also referred to as N,N-diethylaniline
$PPh_3$ triphenylphosphine
Selectfluor® 1-Chloromethyl-4-Fluoro-1,4-Diazoniabicyclo[2.2.2]OctaneBis (Tetrafluoroborate)
t-BuOK potassium tert-butoxide
TFA trifluoroacetic acid
THF tetrahydrofuran
TLC thin layer chromatography

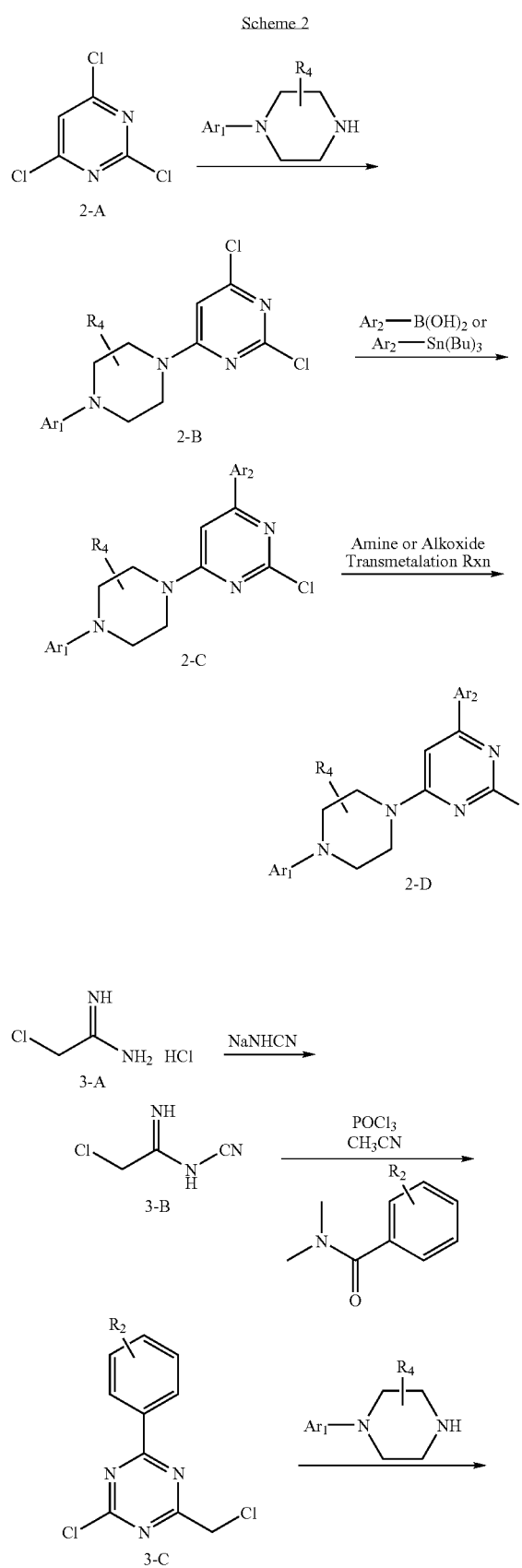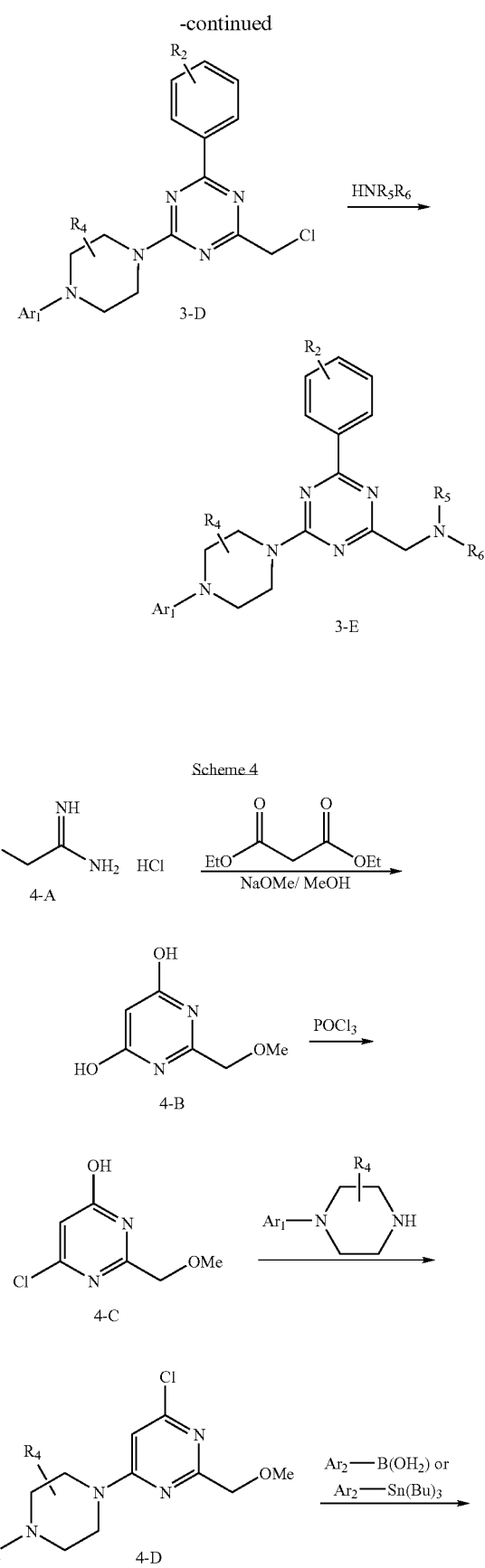

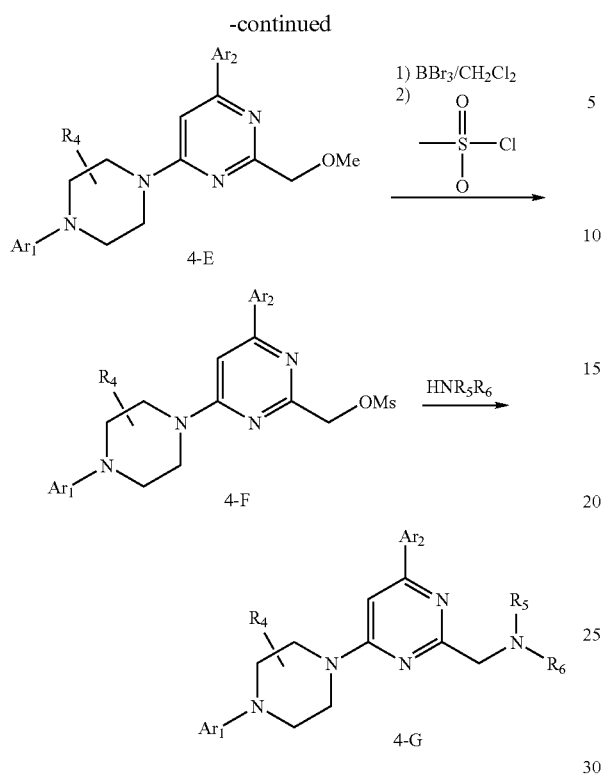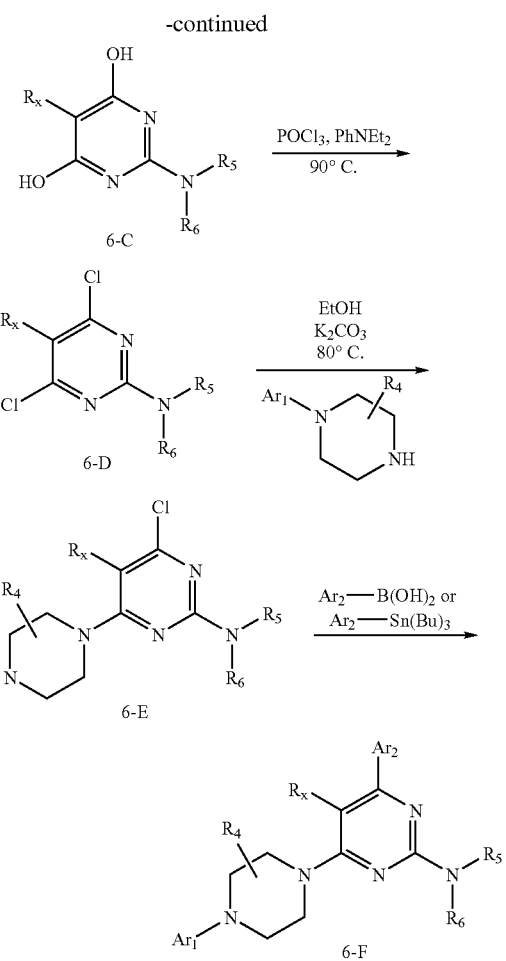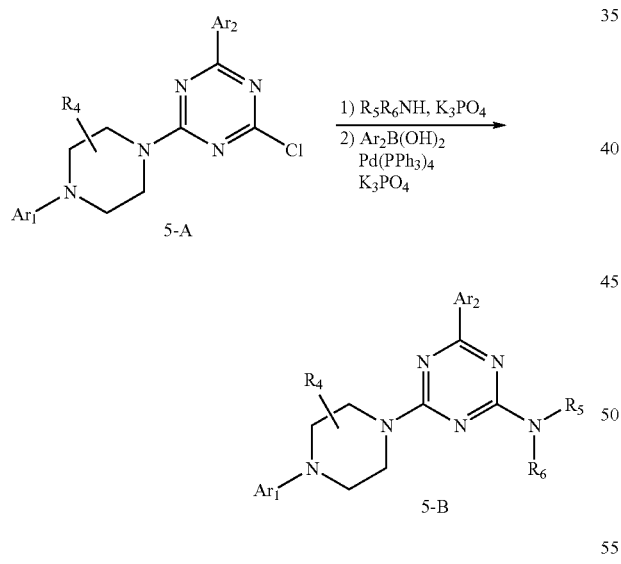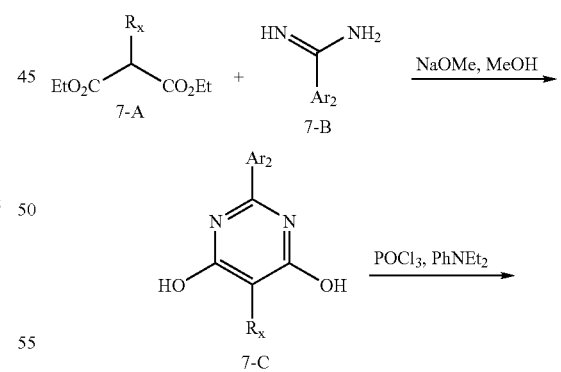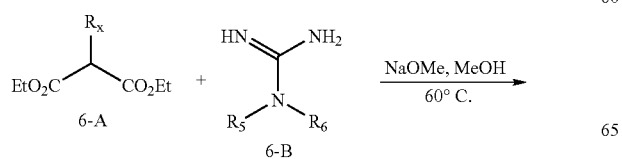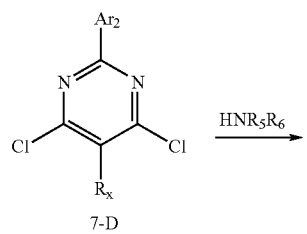

-continued
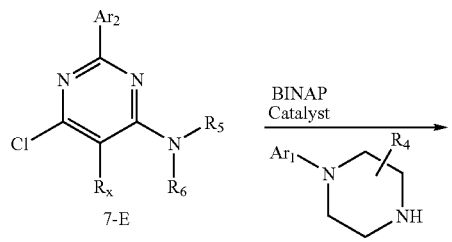
7-E
BINAP
Catalyst
→
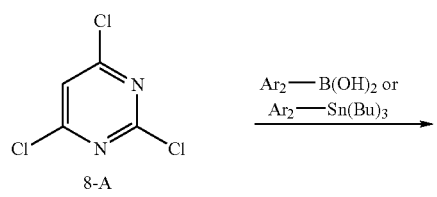
8-A
Ar₂—B(OH)₂ or
Ar₂—Sn(Bu)₃
→
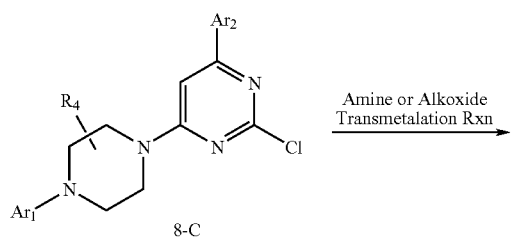
8-C
Amine or Alkoxide
Transmetalation Rxn
→
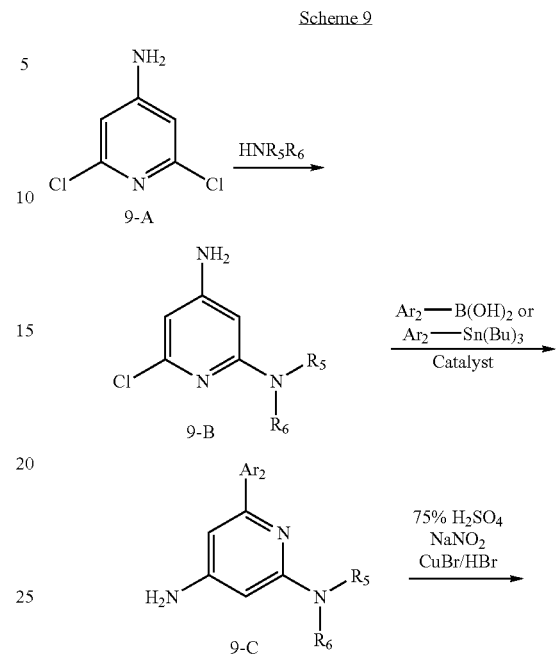
Scheme 9
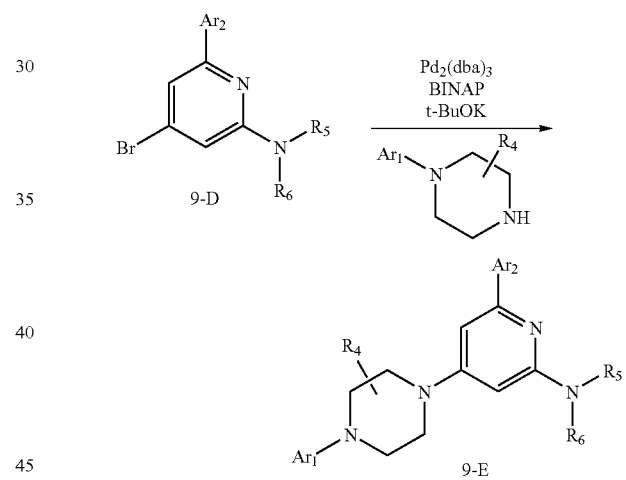
Scheme 10
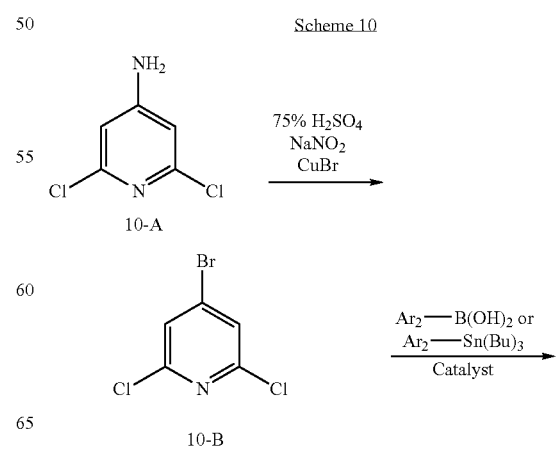

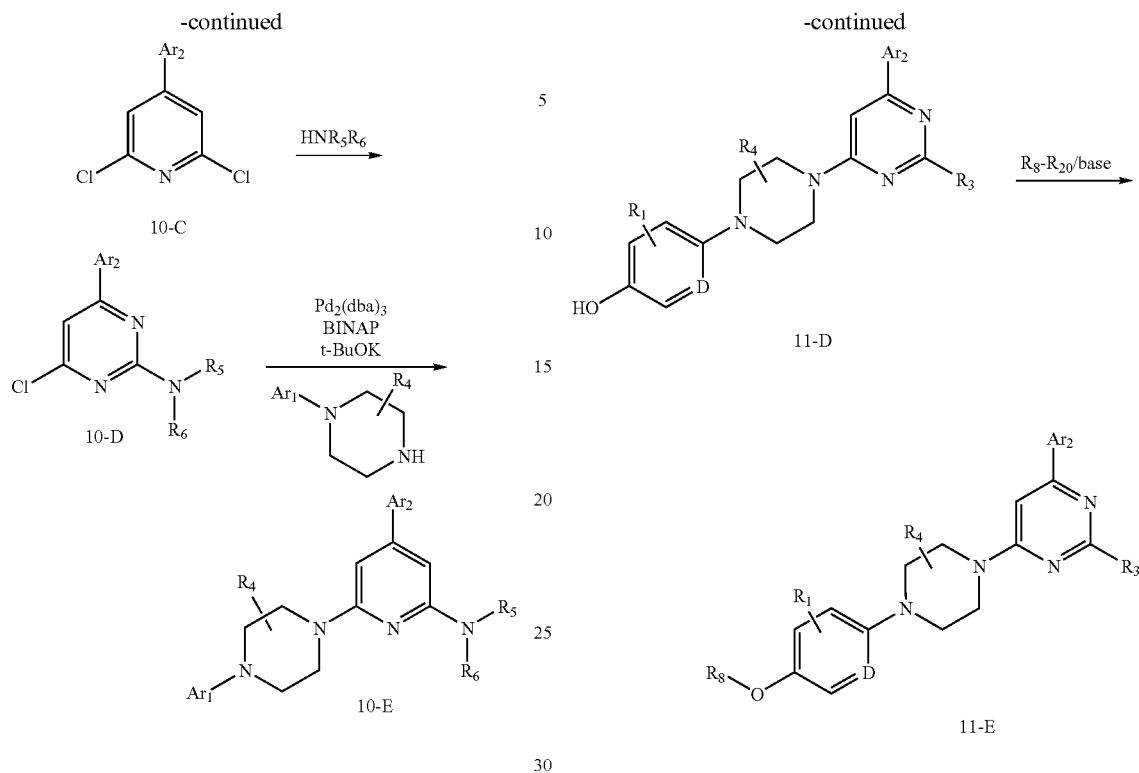
Scheme 11
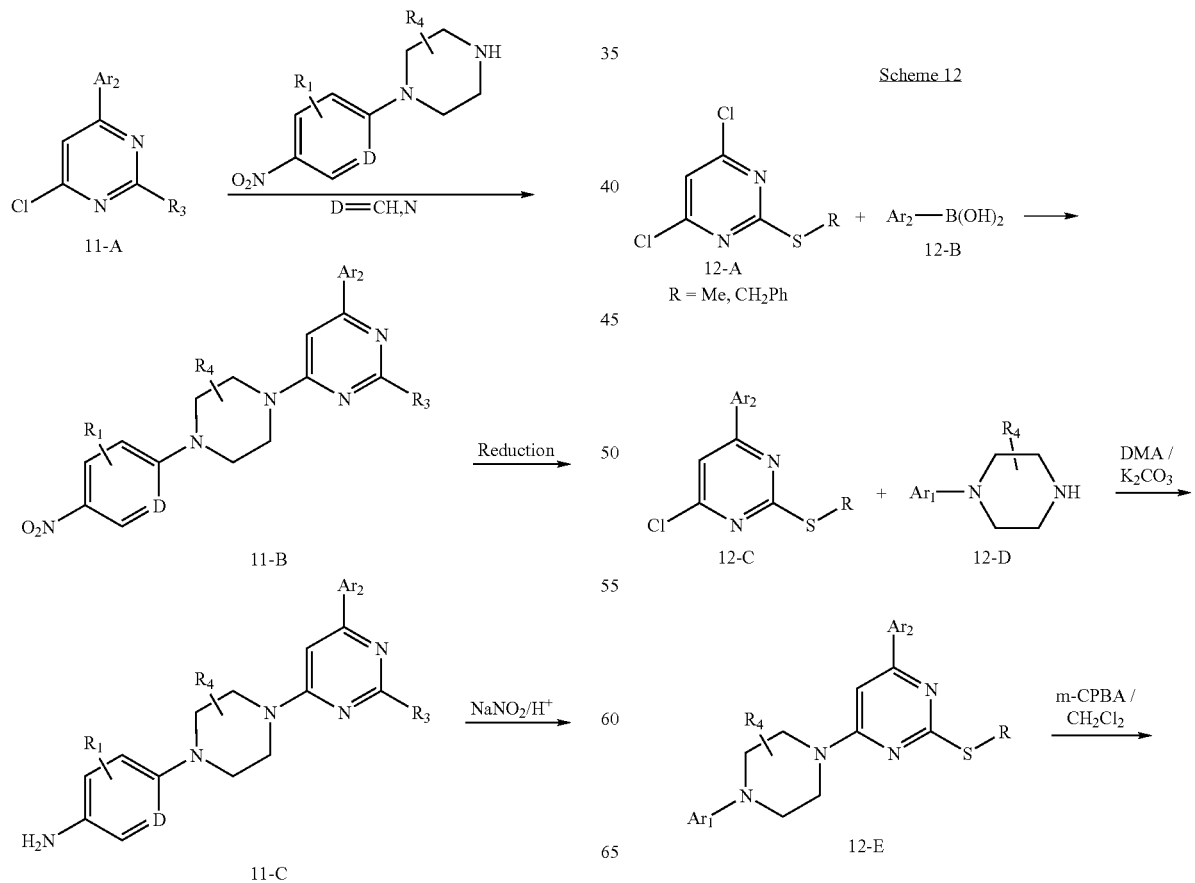
Scheme 12

-continued
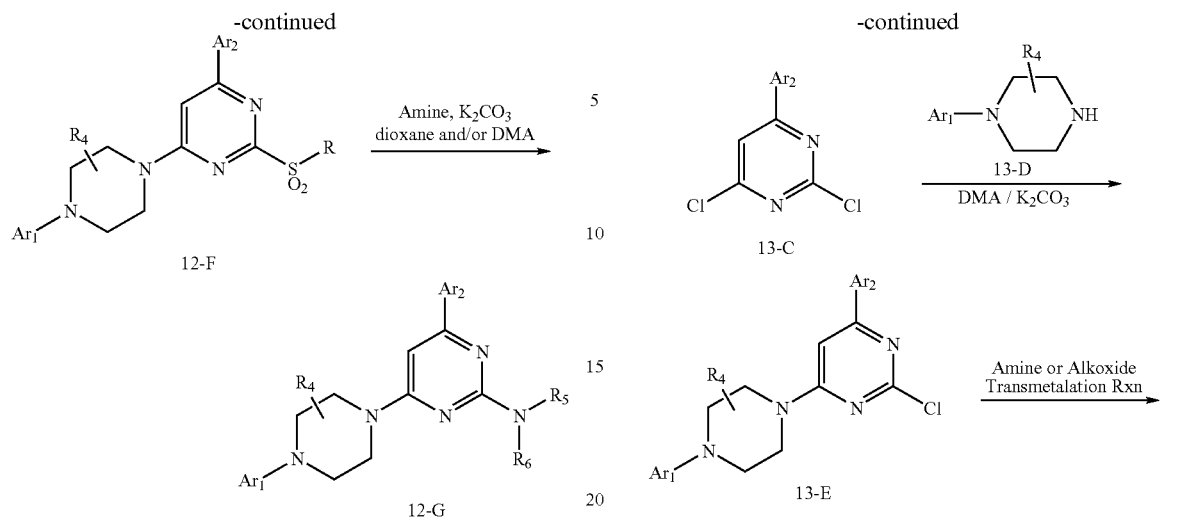
Scheme 13
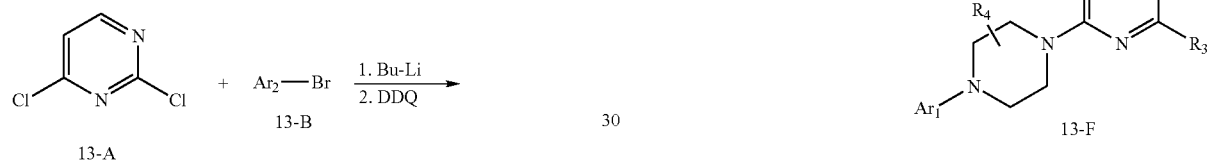
Scheme 14
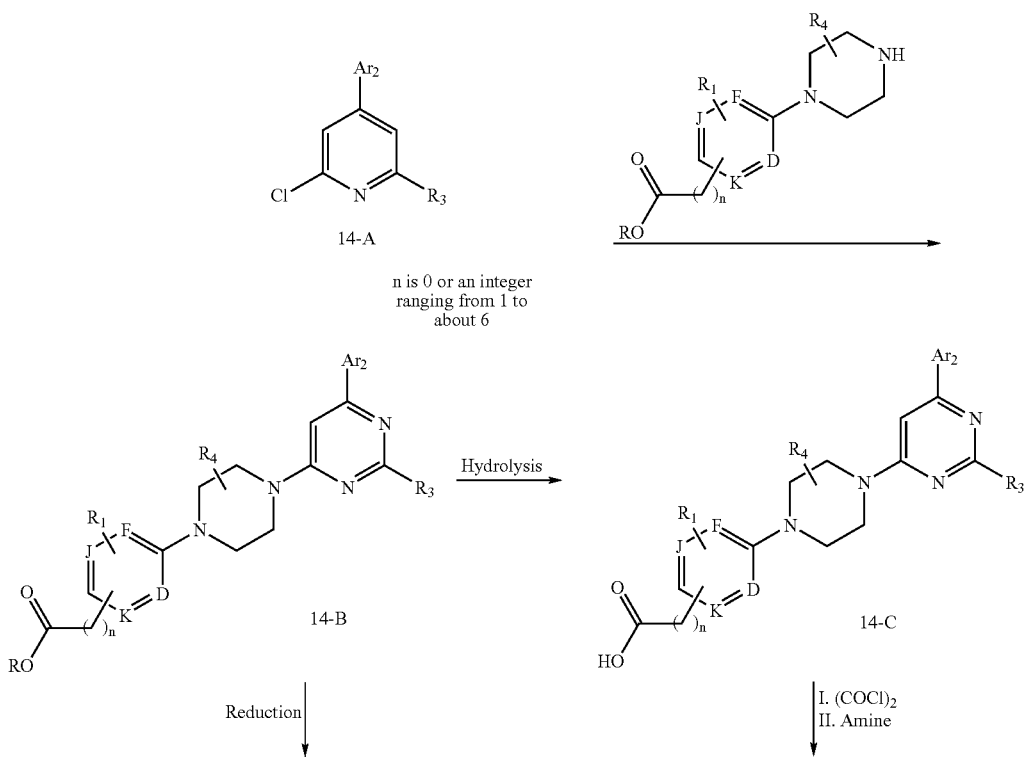

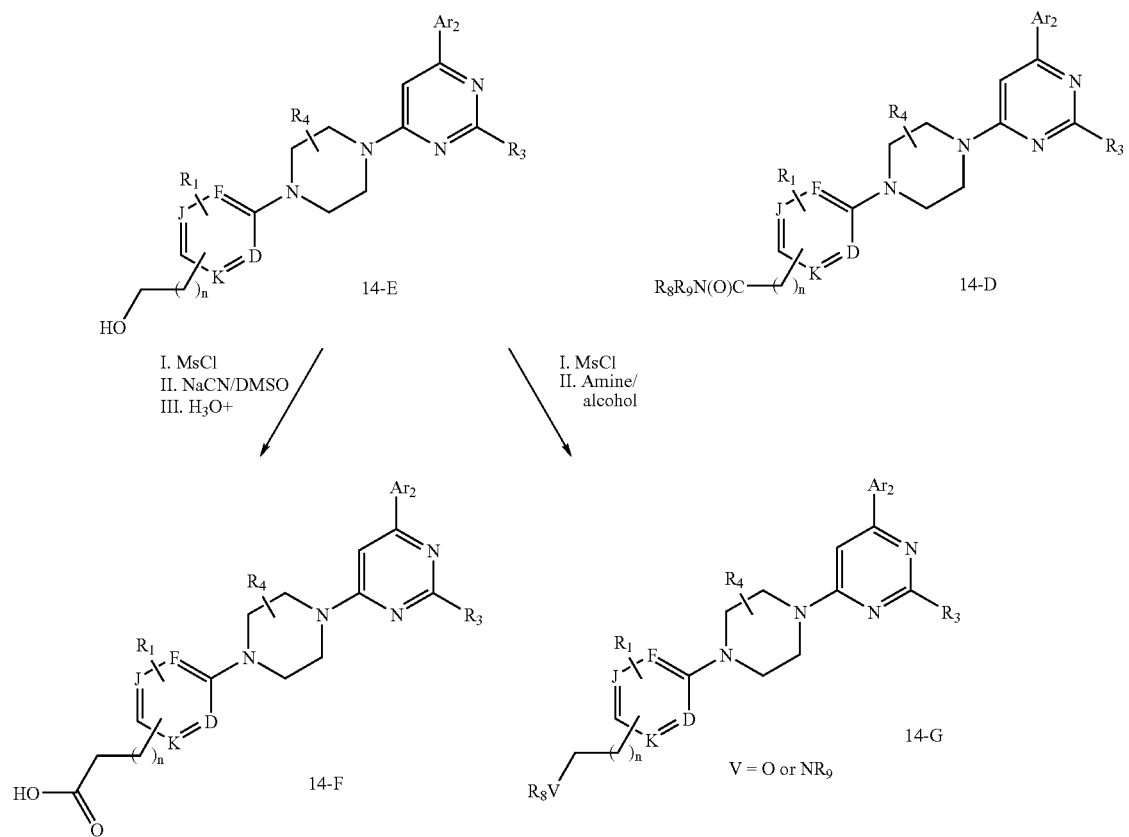
Scheme 15
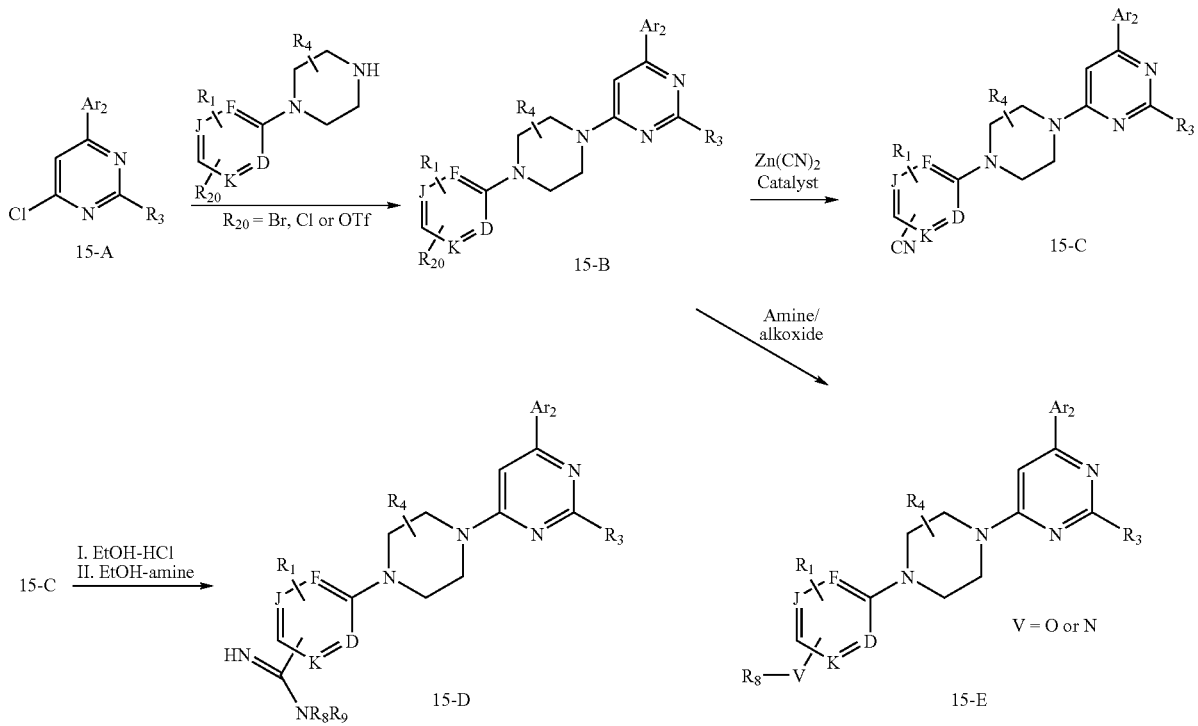

-continued
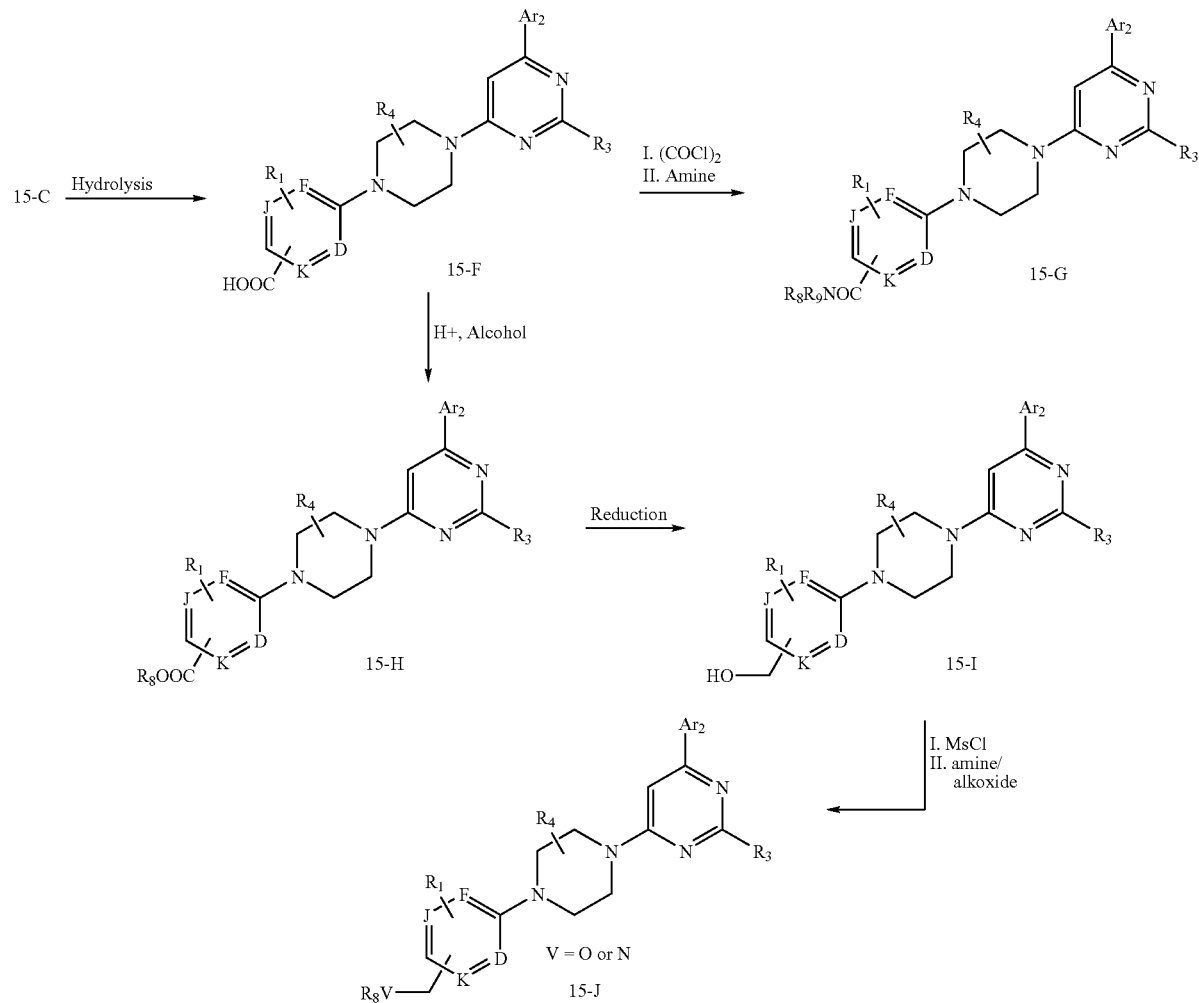
Scheme 16
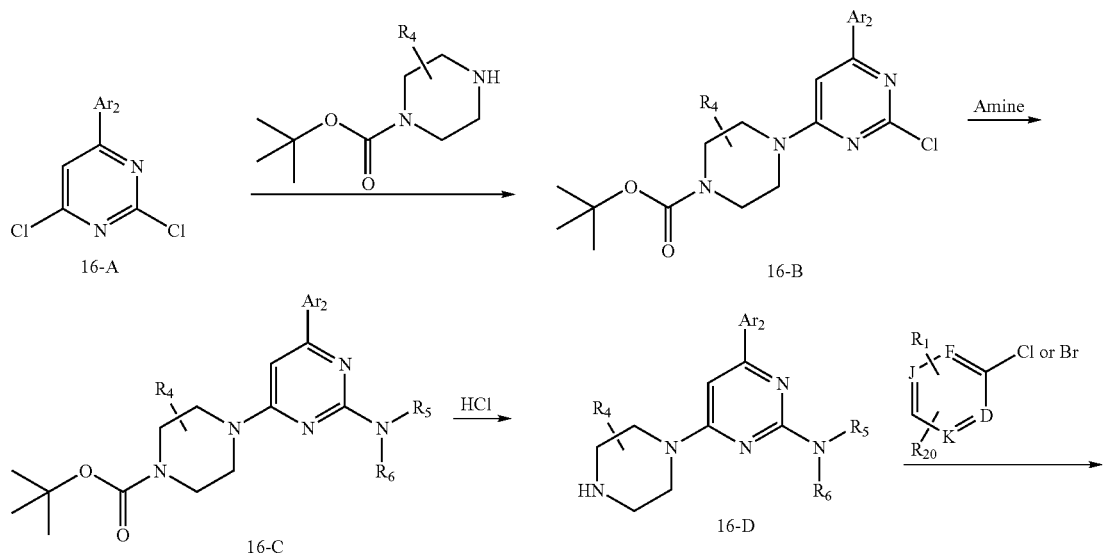

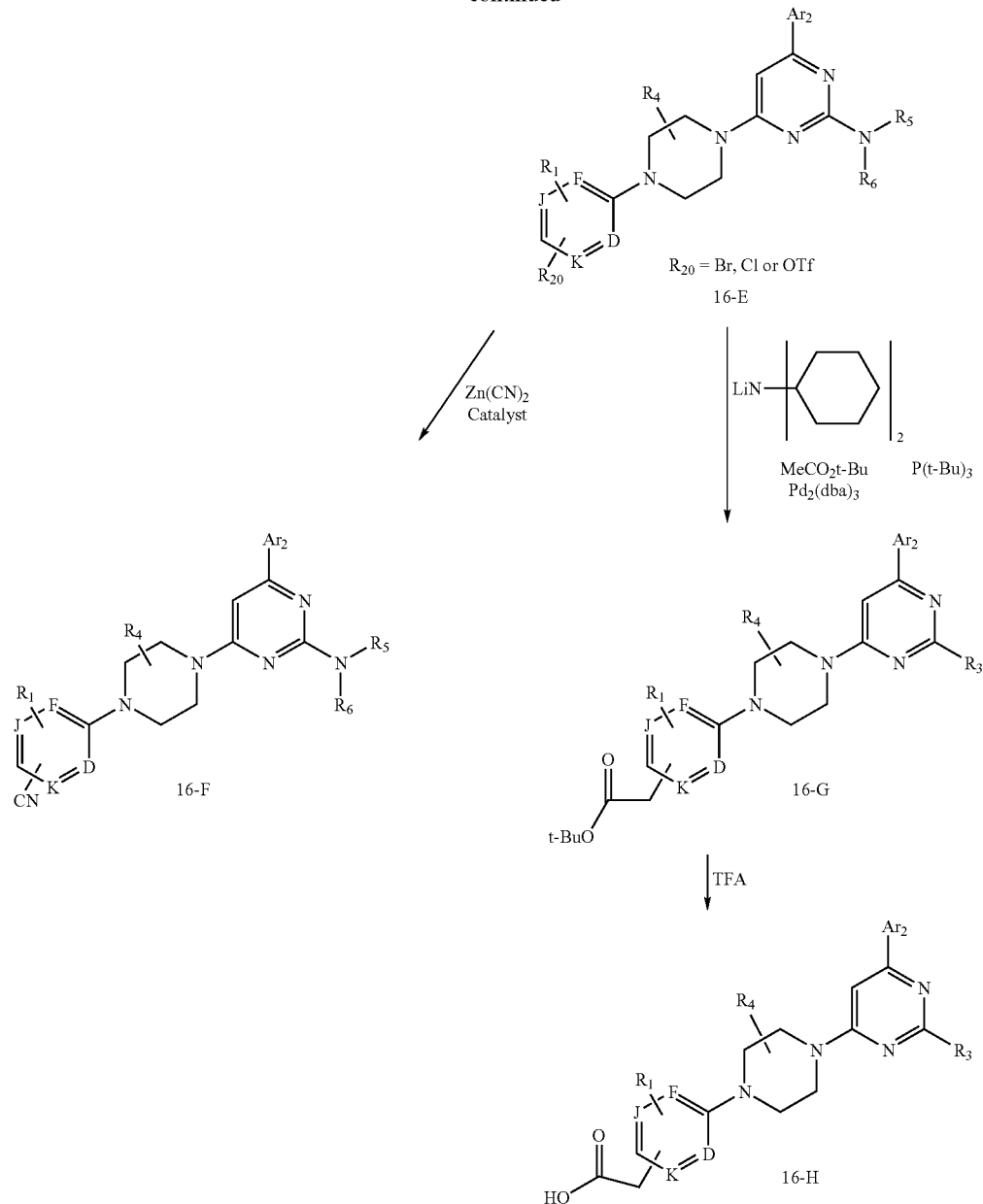
Scheme 17
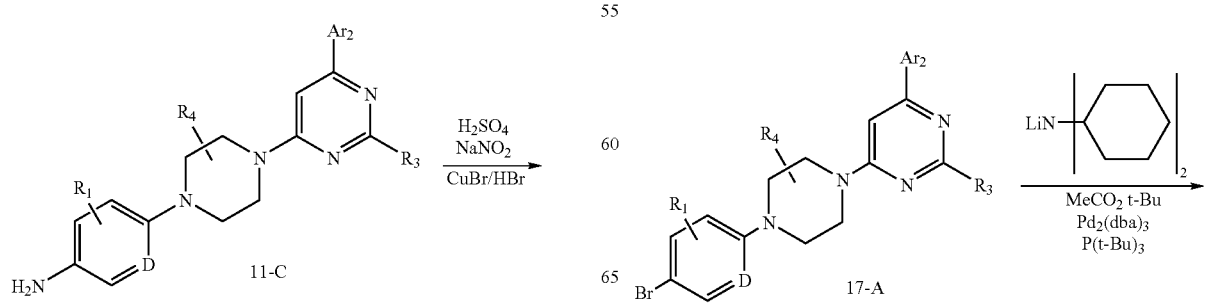

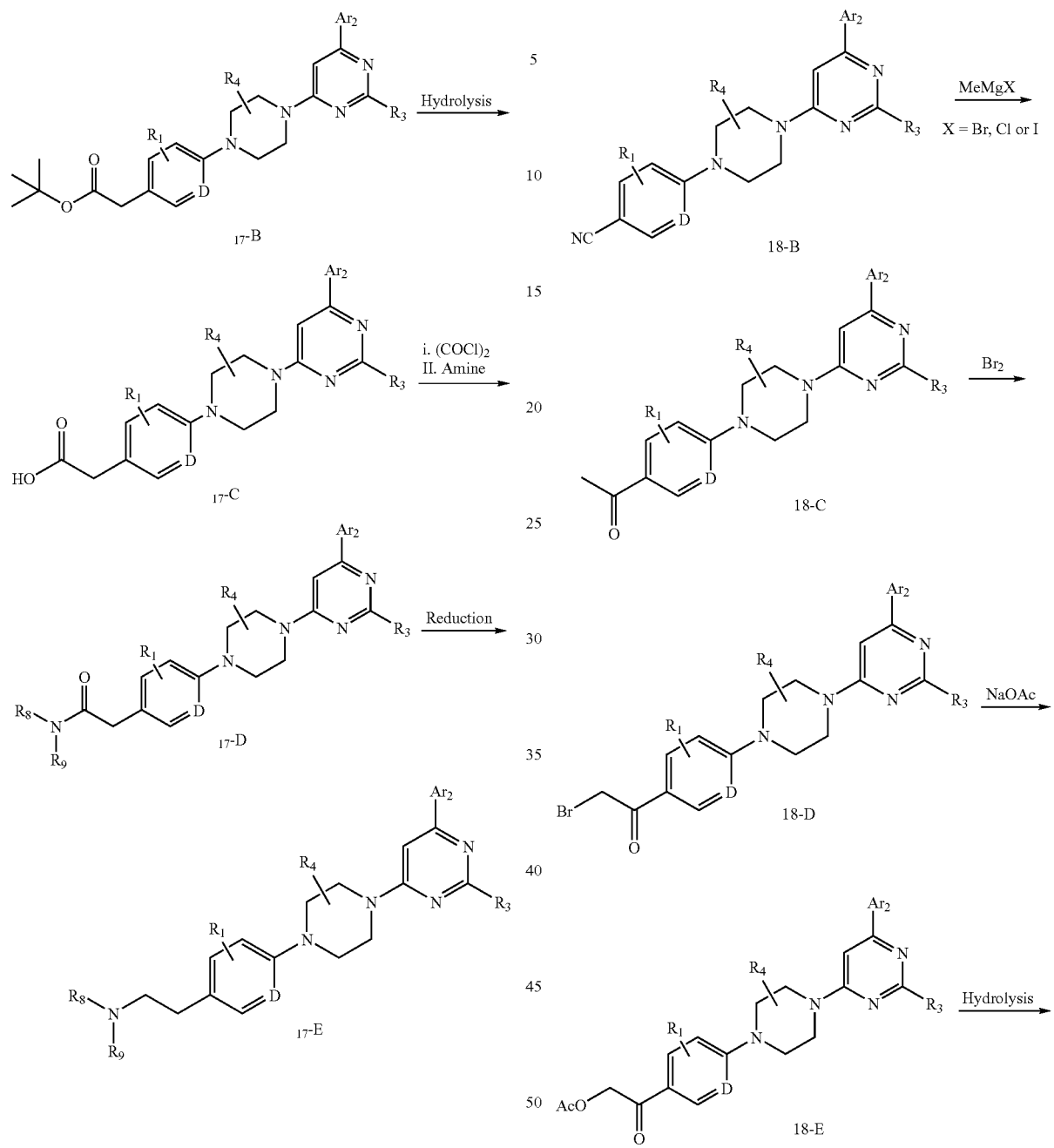
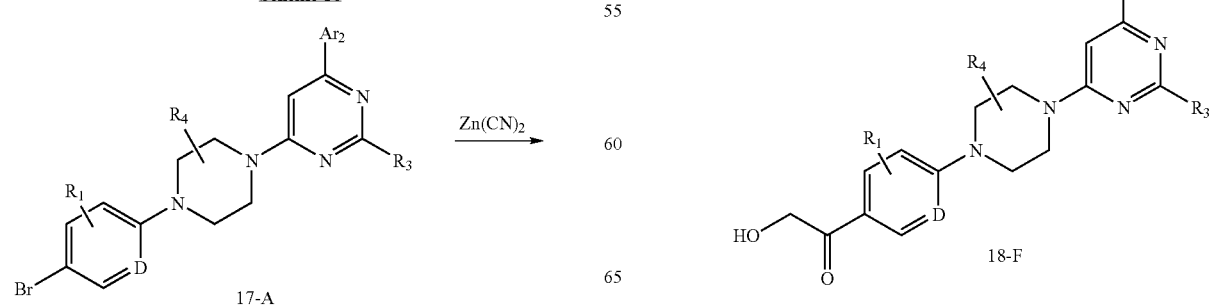

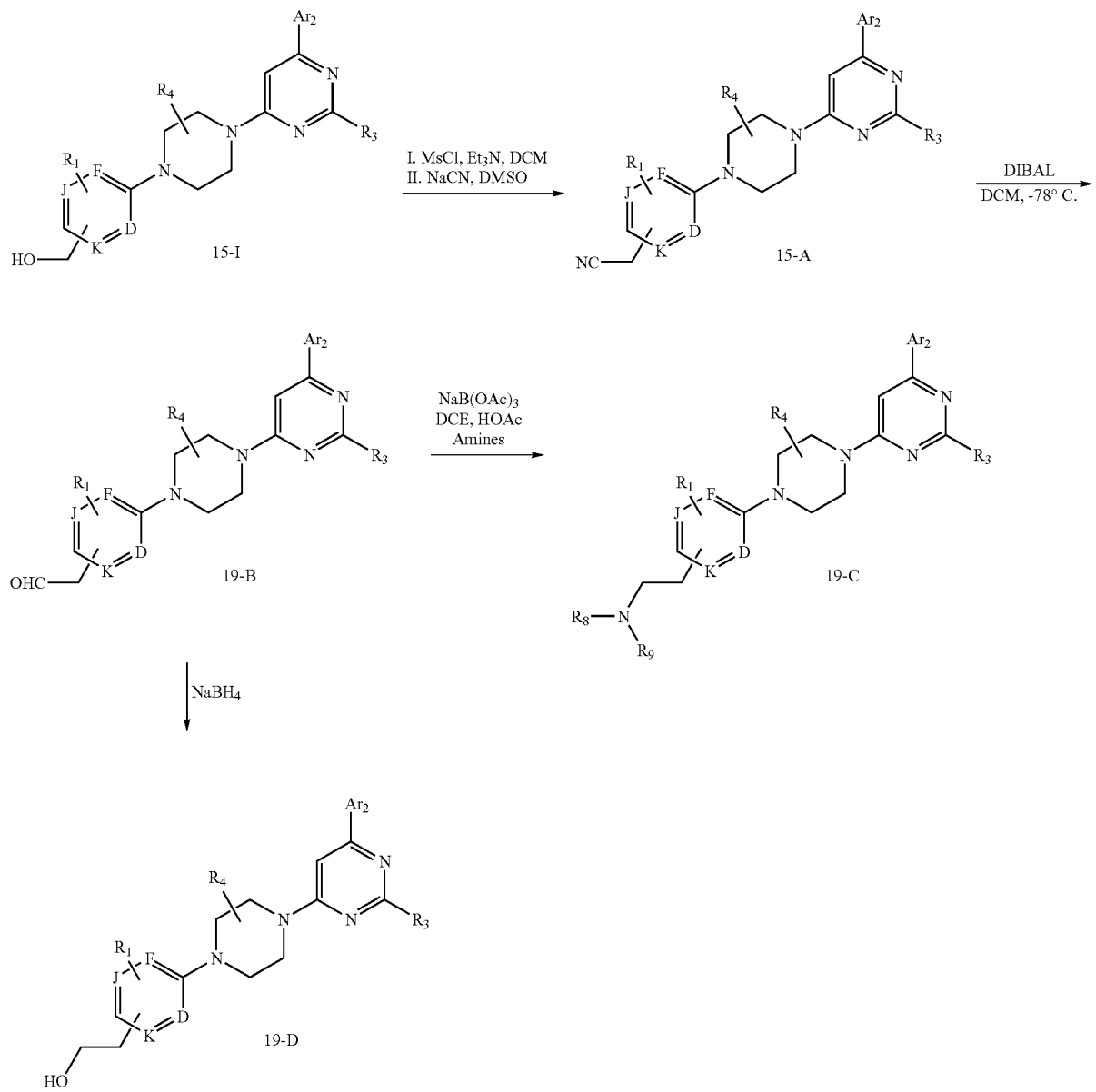
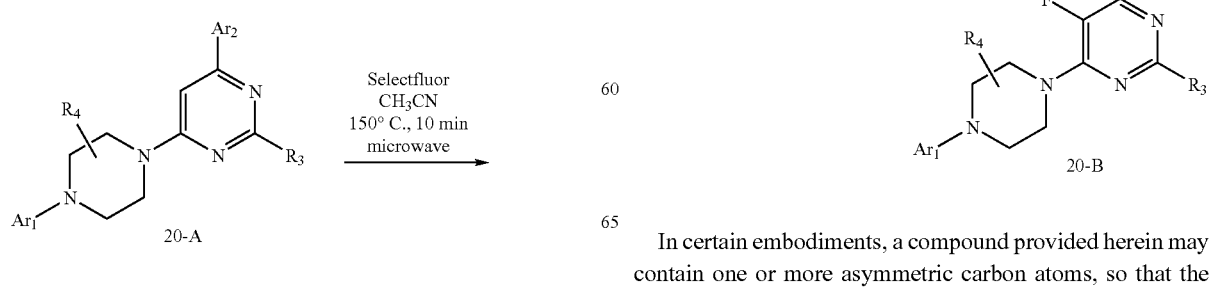
In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with suitable excipients, such as suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as, heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and/or one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g. ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in any of a variety of physical forms including, for example, solids, pastes, creams, foams, lotions, gels, powders, aqueous liquids and emulsions. The physical appearance and viscosity of such pharmaceutically acceptable forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and, other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectible aqueous or oleaginous suspension. The compound(s) provided herein, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release or controlled-release formulations (ie., a formulation such as a capsule that effects a slow release of modulator following administration). Such formulations may generally be prepared using well known technology and administered by, for example, oral, rectal or subcutaneous implantation, or by implantation at the desired targetsite. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds are generally administered in a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated and the particular mode of administration. Dosage units will generally contain from about 10 µg to about 500 mg of an active ingredient. Optimal dosages may be established using routine testing, and procedures that are well known in the art.

Pharmaceutical compositions may be packaged for treating conditions responsive to VR1 modulation (e.g. treatment of exposure to vanilloid ligand or other irritant, pain, itch, obesity on urinary incontinence). Packaged pharmaceutical compositions generally include (i) a container holding a pharmaceutical composition that comprises at least one VR1 modulator as described herein and (ii) instructions (e.g., labeling or a package insert) indicating that the contained composition is to be used for treating a condition responsive to VR1 modulation in the patient.

Methods of Use

VR1 modulators provided herein may be used to alter activity and/or activation of capsaicin receptors in a variety of contexts, both in vitro and in vivo. Within certain aspects, VR1 antagonists may be used to inhibit the binding of vanilloid ligand agonist (such as capsaicin and/or RTX) to capsaicin receptor in vitro or in vivo. In general, such methods comprise the step of contacting a capsaicin receptor with one or more VR1 modulators provided herein, in the presence of vanilloid ligand in aqueous solution and under conditions otherwise suitable for binding of the ligand to capsaicin receptor. The VR1 modulator(s) are generally present at a concentration that is sufficient to alter the binding of vanilloid ligand to VR1 in vitro (using the assay provided in Example 5) and/or VR1-mediated signal transduction (using an assay provided in Example 6). The capsaicin receptor may be present in solution or suspension (e.g., in an isolated membrane or cell preparation), or in a cultured or isolated cell. Within certain embodiments, the capsaicin receptor is expressed by a neuronal cell present in a patient, and the aqueous solution is a body fluid. Preferably, one or more VR1 modulators are administered to an animal in an amount such that the VR1 modulator is present in at least one body fluid of the animal at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a therapeutically effective dose that is less than 20 mg/kg body weight, preferably less than 5 mg/kg and, in some instances, less than 1 mg/kg.

Also provided herein are methods for modulating, preferably reducing, the signal-transducing activity (i.e., the calcium conductance) of a cellular capsaicin receptor. Such modulation may be achieved by contacting a capsaicin receptor (either in vitro or in vivo) with one or more VR1 modulators provided herein under conditions suitable for binding of the modulator(s) to the receptor. The VR1 modulator(s) are generally present at a concentration that is sufficient to alter the binding of vanilloid ligand to VR1 in vitro and/or VR1-mediated signal transduction as described herein. The receptor may be present in solution or suspension, in a cultured or isolated cell preparation or in a cell within a patient. For example, the cell may be a neuronal cell that is contacted in vivo in an animal. Alternatively, the cell may be an epithelial cell, such as a urinary bladder epithelial cell (urothelial cell) or an airway epithelial cell that is contacted in vivo in an animal. Modulation of signal tranducing activity may be assessed by detecting an effect on calcium ion conductance (also referred to as calcium mobilization or flux). Modulation of signal transducing activity may alternatively be assessed by detecting an alteration of a symptom (e.g., pain, burning sensation, broncho-constriction, inflammation, cough, hiccup, itch, urinary incontinence or overactive bladder) of a patient being treated with one or more VR1 modulators provided herein.

VR1 modulator(s) provided herein are preferably administered to a patient (e.g., a human) orally or topically, and are present within at least one body fluid of the animal while modulating VR1 signal-transducing activity. Preferred VR1 modulators for use in such methods modulate VR1 signal-transducing activity in vitro at a concentration of 1 nanomolar or less, preferably 100 picomolar or less, more preferably 20 picomolar or less, and in vivo at a concentration of 1 micromolar or less, 500 nanomolar or less, or 100 nanomolar or less in a body fluid such as blood.

The present invention further provides methods for treating conditions responsive to VR1 modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (ie., after the onset of symptoms, in order to reduce the severity and/or duration of symptoms). A condition is "responsive to VR1 modulation" if it is characterized by inappropriate activity of a capsaicin receptor, regardless of the amount of vanilloid ligand present locally, and/or if modulation of capsaicin receptor activity results in alleviation of the condition or a symptom thereof. Such conditions include, for example, symptoms resulting from exposure to VR1-activating stimuli, pain, respiratory disorders (such as cough, asthma, chronic obstructive pulmonary disease, chronic bronchitis, cystic fibrosis and rhinitis, including allergic rhinitis, such as seasonal an perennial rhinitis, and non-allergic rhinitis) itch, urinary incontinence, overactive bladder, hiccup and obesity, as described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated; however, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Patients experiencing symptoms resulting from exposure to capsaicin receptor-activating stimuli include individuals with burns caused by heat, light, tear gas or acid and those whose mucous membranes are exposed (e.g., via ingestion, inhalation or eye contact) to capsaicin (e.g., from hot peppers or in pepper spray) or a related irritant such as acid, tear gas, infectious agent(s) or air pollutant(s). The resulting symptoms (which may be treated using VR1 modulators, especially antagonists, provided herein) may include, for example, pain, broncho-constriction and inflammation.

Pain that may be treated using the VR1 modulators provided herein may be chronic or acute and includes, but is not limited to, peripheral nerve-mediated pain (especially neuropathic pain). Compounds provided herein may be used in the treatment of, for example, postmastectomy pain syndrome, stump pain, phantom limb pain, oral neuropathic pain, toothache (dental pain), denture pain, postherpetic neuralgia, diabetic neuropathy, chemotherapy-induced neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome and/or pain associated with nerve and root damage, including as pain associated with peripheral nerve disorders (e.g., nerve entrapment and brachial plexus avulsions, amputation, peripheral neuropathies including bilateral peripheral neuropathy, tic douloureux, atypical facial pain, nerve root damage, and arachnoiditis). Additional neuropathic pain conditions include causalgia (reflex sympathetic dystrophy—RSD, secondary to injury of a peripheral nerve), neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia), surgery-related pain, musculoskeletal pain, myofascial pain syndromes, AIDS-related neuropathy, MS-related neuropathy, central nervous system pain (e.g., pain due to brain stem damage, sciatica, and ankylosing spondylitis), and spinal pain, including spinal cord injury-related pain. Headache, including headaches involving peripheral nerve activity may also be treated as described herein. Such pain includes, for example, such as sinus, cluster (i.e., migranous neuralgia) and tension headaches, migraine, temporomandibular pain and maxillary sinus pain. For example, migraine headaches may be prevented by administration of a compound provided herein as soon as a pre-migrainous aura is experienced by the patient. Further conditions that can be treated as described herein include Charcot's pains, intestinal gas pains, ear pain, heart pain, muscle pain, eye pain, orofacial pain (e.g., odontalgia), abdominal pain, gynaecological pain (e.g., menstrual pain, dysmenorrhoea, pain associated with cystitis, labor pain, chronic pelvic pain, chronic prostitis and endometriosis), acute and chronic back pain (e.g., lower back pain), gout, scar pain, hemorrhoidal pain, dyspeptic pains; angina, nerve root pain, "non-painful" neuropathies, complex regional pain syndrome, homotopic pain and heterotopic pain—including pain associated with carcimnoma, often referred to as cancer pain (e.g., in patients with bone cancer), pain (and inflammation) associated with venom exposure (e.g., due to snake bite, spider bite, or insect sting) and trauma associated pain (e.g., post-surgical pain, episiotomy pain, pain from cuts, musculoskeletal pain, bruises and broken bones, and burn pain, especially primary hyperalgesia associated therewith). Additional pain conditions that may be treated as described herein include pain associated with respiratory disorders as described above, autoimmune diseases, immunodeficiency disorders, hot flashes, inflammatory bowel disease, irritable bowel syndrome and/or inflammatory bowel disease. VR1 modulators may also be used to treat depression and gastroesophageal reflux disease (GERD), including the pain associated with GERD.

Within certain aspects, VR1 modulators provided herein may be used for the treatment of mechanical pain. As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as post-surgical pain and pain from cuts, bruises and broken bones; toothache; denture pain; nerve root pain; osteoartiritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation.

Itching conditions that may be treated include psoriatic pruritus, itch due to hemodialysis, aguagenic pruritus, and itching associated with vulvar vestibulitis, contact dermatitis, insect bites and skin allergies. Urinary tract conditions that may be treated as described herein include urinary incontinence (including overflow incontinence, urge incontinence and stress incontinence), as well as overactive or unstable bladder conditions (including bladder detrusor hyper-reflexia, detrusor hyper-reflexia of spinal origin and bladder hypersensitivity). In certain such treatment methods, VR1 modulator is administered via a catheter or similar device, resulting in direct injection of VR1 modulator into the bladder. Compounds provided herein may also be used as antitussive agents (to prevent, relieve or suppress coughing) and for the treatment of hiccup, and to promote weight loss in an obese patient.

Within other aspects, VR1 modulators provided herein may be used within combination therapy for the treatment of conditions involving pain and/or inflammatory components. Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebo-vascular disease and certain infectious diseases.

Within such combination therapy, a VR1 modulator is administered to a patient along with an analgesic and/or anti-inflammatory agent. The VR1 modulator and analgesic and/ or anti-inflammatory agent may be present in the same pharmaceutical composition, or may be administered separately in either order. Anti-inflammatory agents include, for example, non-steroidal anti-inflammatory drugs (NSAIDs), non-specific and cyclooxygenase-2 (COX-2) specific cyclooxgenase enzyme inhibitors, gold compounds, corticosteroids, methotrexate, tumor necrosis factor (TNF) receptor antagonists, anti-TNF alpha antibodies, anti-C5 antibodies, and interleukin-1 (IL-1) receptor antagonists. Examples of NSAIDs include, but are not limited to ibuprofen (e.g., ADVIL™, MOTRIN™), flurbiprofen (ANSAID™), naproxen or naproxen sodium (e.g., NAPROSYN, ANAPROX, ALEVE™), diclofenac (e.g., CATAFLAM™, VOLTAREN™), combinations of diclofenac sodium and misoprostol (e.g., ARTHROTEC™), sulindac (CLINORIL™), oxaprozin (DAYPRO™), diflunisal (DOLOBID™), piroxicam (FELDENE™), indomethacin (INDOCIN™), etodolac (LODINE™), fenoprofen calcium (NALFON™), ketoprofen (e.g., ORUDIS™, ORUVAIL™), sodium nabumetone (RELAFEN™), sulfasalazine (AZULFIDINE™), tolmetin sodium (TOLECTIN™), andcehydroxychloroquine (PLAQUENIL™). One class of NSAIDs consists of compounds that inhibit cyclooxygenase (COX) enzymes. NSAIDs further include salicylates such as acetylsalicylic acid or aspirin, sodium salicylate, choline and magnesium salicylates (TRILISATE™), and salsalate (DISALCID™), as well as corticosteroids such as cortisone (CORTON™ acetate), dexamethasone (e.g., DECADRON™), methyl-prednisolone (MEDROL™) prednisolone (PRELONE™), prednisolone sodium phosphate (PEDIAPRED™), and prednisone (e.g., PREDNICEN-M™, DELTASONE™, STERA-PRED™). Further anti-inflammatoryr agents include meloxicam, rofecoxib, celecoxib, etoricoxib, parecoxib, valdecoxib and tilicoxib.

Suitable dosages for VR1 modulator within such combination therapy are generally as described above. Dosages and methods of administration of anti-inflammatory agents can be found, for example, in the manufacturer's instructions in the *Physician's Desk Reference*. In certain embodiments, the combination administration of a VR1 modulator with an anti-inflammatory agent results in a reduction of the dosage of the anti-inflammatory agent required to produce a therapeutic effect (ie., a decrease in the minimum therapeutically effective amount). Thus, preferably, the dosage of anti-inflammatory agent in a combination or combination treatment method of the invention is less than the maximum dose advised by the manufacturer for administration of the anti-inflammatory agent without combination administration of a VR1 antagonist. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a VR1 antagonist. It will be apparent that the dosage amount of VR1 antagonist component of the combination needed to achieve the desired effect may similarly be affected by the dosage amount and potency of the anti-inflammatory agent component of the combination.

In certain preferred embodiments, the combination administration of a VR1 modulator with an anti-inflammatory agent is accomplished by packaging one or more VR1 modulators and one or more anti-inflammatory agents in the same package, either in separate containers within the package or in the same contained as a mixture of one or more VR1 antagonists and one or more anti-inflammatory agents. Preferred mixtures are formulated for oral administration (e.g., as pills, capsules, tablets or the like). In certain embodiments, the package comprises a label bearing indicia indicating that the one or more VR1 modulators and one or more anti-inflammatory agents are to be taken together for the treatment of an inflammatory pain condition.

Within further aspects, VR1 modulators provided herein may be used in combination with one or more additional pain relief medications. Certain such medications are also anti-inflammatory agents, and are listed above. Other such medications are analgesic agents, including narcotic agents which typically act at one or more opioid receptor subtypes (e.g., $\mu$, $\kappa$ and/or $\delta$), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanil, alphaprodine, anileridine, bezitramide, buprenorphine, butorphanol, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, nalbuphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, sulfentanyl, thebaine and pharmaceutically acceptable salts and hydrates of the foregoing agents.

Other examples of narcotic analgesic agents include acetorphine, acetyldihydrocodeine, acetylmethadol, allyl-prodine, alphracetylmethadol, alphameprodine, alphameth-adol, benzethidine, benzylmorphine, betacetylmethadol, betameprodine, betamethadol, betaprodine, clonitazene, codeine methylbromide, codeine-N-oxide, cyprenorphine, desomorphine, dextromoramide, diampromide, diethylthi-ambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, frrethidine, hydromorphinol, hydroxypethidine, ketobemidone, levomoramide, levophenacylmorphan, methyldesorphine, methyldihydro-morphine, morpheridine, morphine methylpromide, morphine methylsulfonate, morphine-N-oxide, myrophin, naloxone, naltyhexone, nicocodeine, nicomorphine, noracymethadol, norlevorphanol, normnethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example acetaminophen (paracetamol); aspirin and other NSAIDs described above; NR2B antagonists; bradykinin antagonists; anti-migraine agents; anticonvulsants such as oxcarbazepine and carbamazepine; antidepressants (such as TCAs, SSRIs, SNRIs, substance P antagonists, etc.); spinal blocks; gabapentin; asthma treatments (such as $\beta_2$-adrenergic receptor agonists; leukotriene $D_4$ antagonists (e.g., montelukast); TALWIN® Nx and DEMEROL® (both available from Sanofi Winthrop Pharmaceuticals; New York, N.Y.); LEVO-DROMORAN®; BUPRENEX® (Reckitt & Coleman Pharmaceuticals, Inc.; Richmond, Va.); MSIR® (Purdue Pharma L.P.; Norwalk, Conn.); DILAUDID® (Knoll Pharmaceutical Co.; Mount Olive, N.J.); SUBLIMAZE®; SUFENTA® (Janssen Pharmaceutical Inc.; Titusville, N.J.); PERCOCET®, NUBAIN® and NUMORPHAN® (all available from Endo Pharmaceuticals Inc.; Chadds Ford, Pa.) HYDROSTAT® IR, MS/S and MS/L (all available from Richwood Pharmaceutical Co. Inc; Florence, Ky.), ORAMORPH® SR and ROXICODONE® (both available from Roxanne Laboratories; Columbus, Ohio) and STADOL® (Bristol-Myers Squibb; New York, N.Y.). Still further analgesic agents include CB2-receptor agonists, such as AM1241, and compounds that bind to the $\alpha 2\beta$ subunit, such as Neurontin (Gabapentin) and pregabalin.

Representative anti-migraine agents for use in combination with a VR1 modulator provided herein include CGRP antagonists, ergotamines and 5-$HT_1$ agonists, such as sumatripan, naratriptan, zolmatriptan and rizatriptan.

Within still further aspects, VR1 modulators provided herein may be used in combination with one or more leukotriene receptor antagonists (e.g., agents that inhibits the cysteinyl leukotriene $CysLT_1$ receptor). $CysLT_1$ antagonists include Montelukast (SINGULAIR®; Merck & Co., Inc.). Such combinations find use in the treatment of pulmonary disorders such as asthma.

For the treatment or prevention of cough, a VR1 modulator as provided herein may be used in combination with other medication designed to treat this condition, such as antibiotics, anti-inflammatory agents, cystinyl leukotrienes, histamine antagonists, corticosteroids, opioids, NMDA antagonists, proton pump inhibitors, nociceptin, neurokinin (NK1, NK2 and NK3) and bradykinin (BK1 and BK2) receptor antagonists, cannabinoids, blockers of Na+-dependent channels and large conductance $Ca^{+2}$-dependent $K^+$-channel activators. Specific agents include dexbrompheniramine plus pseudoephedrine, loratadine, oxymetazoline, ipratropium, albuterol, beclomethasone, morphine, codeine, pholcodeine and dextromethorphan.

The present invention further provides combination therapy for the treatment of urinary incontinence. Within such aspects, a VR1 modulator provided herein may be used in combination with other medication designed to treat this condition, such as estrogen replacement therapy, progesterone congeners, electrical stimulation, calcium channel blockers, antispasmodic agents, cholinergic antagonists, antimuscarinic drugs, tricyclic antidepressants, SNRIs, beta adrenoceptor agonists, phosphodiesterase inhibitors, potassium channel openers, nociceptin/orphanin FQ (OP4) agonists, neurokinin (NK1 and NK2) antagonists, P2X3 antagonists, musculotrophic drugs and sacral neuromodulation. Specific agents include oxybutinin, emepronium, tolterodine, flavoxate, flurbiprofen, dicyclomine, propiverine, propantheline, imipramine, doxepin, duloxetine, 1-deamino-8-D-arginine vasopressin, muscarinic receptor antagonists such as Tolterodine (DETROL®; Pharmacia Corporation) and anticholinergic agents such as Oxybutynin (DITROPAN®; Ortho-McNeil Pharmaceutical, Inc., Raritan, N.J.).

Suitable dosages for VR1 modulator within such combination therapy are generally as described above. Dosages and methods of administration of other pain relief medications can be found, for example, in the manufacturer's instructions in the *Physician's Desk Reference*. In certain embodiments, the combination administration of a VR1 modulator with one or more additional pain medications results in a reduction of the dosage of each therapeutic agent required to produce a therapeutic effect (e.g., the dosage or one or both agent may less than ¾, less than ½, less than ¼ or less than 10% of the maximum dose listed above or advised by the manufacturer).

For use in combination therapy, pharmaceutical compositions as described above may further comprise one or more additional medications as described above. In certain such compositions, the additional medication is an analgesic. Also provided herein are packaged pharmaceutical preparations comprising one or more VR1 modulators and one or more additional medications (e.g., analgesics) in the same package. Such packaged pharmaceutical preparations generally include (i) a container holding a pharmaceutical composition that comprises at least one VR1 modulator as described herein; (ii) a container holding a pharmaceutical composition that comprises at least one additional medication (such as a pain relief and/or anti-inflammatory medication) as described above and (iii) instructions (e.g., labeling or a package insert) indicating that the compositions are to be used simultaneously, separately or sequentially for treating or preventing a condition responsive to VR1 modulation in the patient (such as a condition in which pain and/or inflammation predominates).

Compounds that are VR1 agonists may further be used, for example, in crowd control (as a substitute for tear gas) or personal protection (e.g., in a spray formulation) or as pharmaceutical agents for the treatment of pain, itch, urinary incontinence or overactive bladder via capsaicin receptor desensitization. In general, compounds for use in crowd control or personal protection are formulated and used according to conventional tear gas or pepper spray technology.

Within separate aspects, the present invention provides a variety of non-pharmaceutical in vitro and in vivo uses for the compounds provided herein. For example, such compounds may be labeled and used as probes for the detection and localization of capsaicin receptor (in samples such as cell preparations or tissue sections, preparations or fractions thereof). In addition, compounds provided herein that comprise a suitable reactive group (such as an aryl carbonyl, nitro or azide group) may be used in photoaffinity labeling studies of receptor binding sites. In addition, compounds provided herein may be used as positive controls in assays for receptor activity, as standards for determining the ability of a candidate agent to bind to capsaicin receptor, or as radiotracers for positron emission tomography (PET) imaging or for single photon emission computerized tomography (SPECT). Such methods can be used to characterize capsaicin receptors in living subjects. For example, a VR1 modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of capsaicin receptor in the sample. Detection assays, including receptor autoradiography (receptor mapping) of capsaicin receptor in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well known cell separation methods. For example, modulators may be linked to the interior surface of a tissue culture plate or other support, for use as affinity ligands for immobilizing and thereby isolating, capsaicin receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

VR1 modulators provided herein may further be used within assays for the identification of other agents that bind to capsaicin receptor. In general, such assays are standard competition binding assays, in which bound, labeled VR1 modulator is displaced by a test compound. Briefly, such assays are performed by: (a) contacting capsaicin receptor with a radiolabeled VR1 modulator as described herein, under conditions that permit binding of the VR1 modulator to capsaicin receptor, thereby generating bound, labeled VR1 modulator; (b) detecting a signal that corresponds to the amount of bound, labeled VR1 modulator in the absence of test agent; (c) contacting the bound, labeled VR1 modulator with a test agent; (d) detecting a signal that corresponds to the amount of bound labeled VR1 modulator in the presence of test agent; and (e) detecting a decrease in signal detected in step (d), as compared to the signal detected in step (b).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass spectroscopy data in the following Examples is Electrospray MS, obtained in positive ion mode using a Micromass Time-of-Flight LCT (Micromass, Beverly Mass.), equipped with a Waters 600 pump (Waters Corp., Milford, Mass.), Waters 996 photodiode array detector, Gilson 215 autosampler (Gilson, Inc. Middleton, Wis.), and a Gilson 841 microinjector. MassLynx (Advanced Chemistry Development, Inc; Toronto, Canada) version 4.0 software with OpenLynx processing was used for data collection and analysis. MS conditions are as follows: capillary voltage=3.5 kV; cone voltage=30 V, desolvation and source temperature=350° C. and 120° C., respectively; mass range=181-750 with a scan time of 0.22 seconds and an interscan delay of 0.05 min.

Sample volume of 1 microliter is injected onto a 50×4.6 mm Chromolith SpeedROD RP-18e column (Merck KGaA, Darmstadt, Germany), and eluted using a 2-phase linear gradient at 6 ml/min flow rate. Sample is detected using total absorbance count over the 220-340 nm UV range. Elution conditions are: Mobile Phase A-95/5/0.05 Water/MeOH/TFA; Mobile Phase B-5/95/0.025 Water/MeOH/TFA. The following gradient is used (inject to inject cycle of 2.2 min):

| Gradient: | Time(min) | % B |
|---|---|---|
| | 0 | 10 |
| | 0.5 | 100 |
| | 1.2 | 100 |
| | 1.21 | 10 |

Example 1

Preparation of Representative Substituted Biaryl Piperazinyl-Pyridine Analogues

This Example illustrates the preparation of representative substituted biaryl piperazinyl-pyridine analogues.

A. (5-Chloro-6-{4-[6-(4-fluoro-phenyl)-2-(2-methyl-pyrrolidin-1-yl)-pyrimidin-4-yl]-piperazin-1-yl}-pyridin-3-yl)-acetic acid 1. (5-Chloro-6-{4-[6-(4-fluoro-phenyl)-2-(2-methyl-pyrrolidin-1-yl)-pyrimidin-4-yl]-piperazine-1-yl}-pyridin-3-yl)-acetonitrile

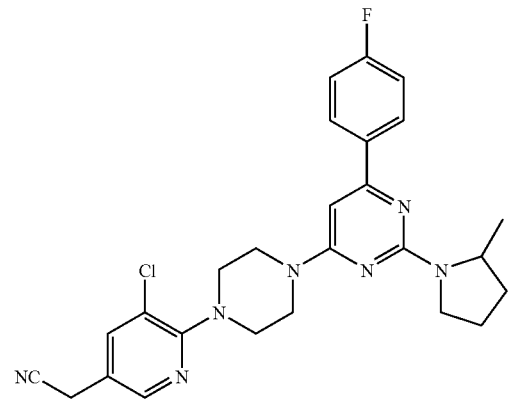

To an ice cooled solution of (5-chloro-6-{4-[6-(4-fluoro-phenyl)-2-(2-methyl-pyrrolidin-1-yl)pyrimidin-4-yl]-piperazin-1-yl}-pyridin-3-yl)-methanol (136 mg, 0.282 mmol) and Et$_3$N (79 μL, 0.564 mmol) in DCM, add MsCl (33 μL, 0.422 mmol) dropwise. Remove ice bath and stir for 1 h at room temperature. Dilute with 3 volumes of DCM, wash with brine, dry the organic layer (Na$_2$SO$_4$) and concentrate under reduced pressure. Dissolve the crude mesylate in DMSO, add 138 mg of NaCN and heat at 60° C. until no starting material remains as indicated by TLC. Dilute with water and extract the aqueous solution with EtOAc. Wash the organic extract with water (2×) followed by brine (1×), dry (Na$_2$SO$_4$) and concentrate under reduced pressure to give crude product. Purify using flash chromatography to give pure title compound.

2. (5-Chloro-6-{4-[6-(4-fluoro-phenyl)-2-(2-methyl-pyrrolidin-1-yl)-pyrimidin-4-yl]-piperazine-1-yl}-pyridin-3-yl)-acetic acid

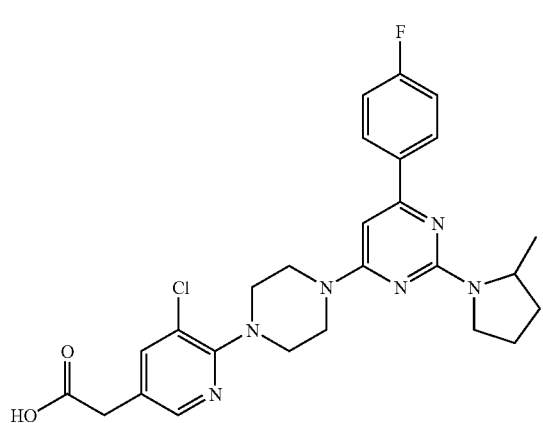

Heat a solution of (5-chloro-6-{4-[6-(4-fluoro-phenyl)-2-(2-methyl-pyrrolidin-1-yl)-pyrimidin-4-yl]-piperazin-1-yl}-pyridin-3-yl)-acetonitrile (50 mg, 0.098 mmol) in 12 M HCl for 4 h. Concentrate the mixture under reduced pressure and then place under vacuum to remove remaining HCl. Add a small amount of water and extract the resulting white precipitate with DCM. Dry the DCM (Na$_2$SO$_4$), and concentrate under reduced pressure. Triturate the resulting residue with ether to afford the title compound as a pale yellow solid.

B. 5-Chloro-6-{4-[6-(4-fluoro-phenyl)-2-(2-methyl-pyrrolidin-1-yl)-pyrimidin-4-yl]-piperazin-1-yl}-nicotinic acid

1. 4-(3-Chloro-5-ethoxycarbonyl-pyridin-2-yl)-piperazine-1-carboxylic acid tert-butyl ester

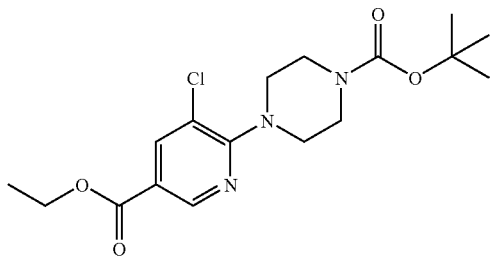

Heat a solution of 5,6-dichloro-nicotinic acid ethyl ester (TCI America) (4.43 g, 0.02 mol), piperazine-1-carboxylic acid tert-butyl ester (4.13 g, 0.022 mol) and DIEA (5.2 mL, 0.03 mol) in DMA at 110° C. for 5 h. Partition the reaction mixture between water and EtOAc. Wash the EtOAc layer with water (1×) and brine (1×), dry (Na$_2$SO$_4$) and concentrate under reduced pressure to give the title compound as an orange oil.

2. 5-Chloro-6-piperazin-1-yl-nicotinic acid ethyl ester

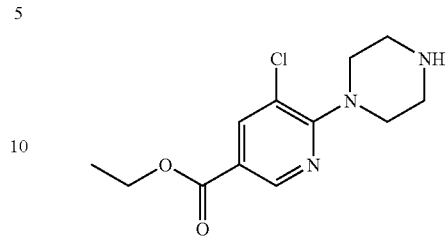

Dissolve a solution of 4-(3-chloro-5-ethoxycarbonyl-pyridin-2-yl)piperazine-1-carboxylic acid tert-butyl ester (7.78 g, 0.021 mol) in dioxane, and then add a solution of 4M HCl/dioxane (12 mL). Stir at 50° C. for 2 h, and then add additional 4M HCl/dioxane (5 mL) and stir for an additional 1 h. Cool the mixture in ice, collect the precipitate and wash with ether. Prepare the freebase by partitioning between EtOAc and 10% NaOH solution. Dry the organic layer (Na2SO$_4$) and concentrate under reduced pressure to give the title compound.

3. 2,4-dichloro-6-(4-fluorophenyl)pyrimidine

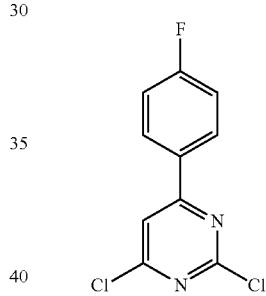

Dissolve 4-fluorobromobenzene (8.75 g, 0.05 moles) in anhydrous ether (80 mL) under nitrogen atmosphere and cool to −78° C. Add dropwise 1.6 M n-BuLi (34 mL, 0.055 moles) and stir at −78° C. for 45 min. Dissolve 2,4-dichloropyrimidine (7.45 g, 0.05 moles) in Et$_2$O (100 mL and add dropwise to the reaction mixture and warm the reaction mixture to −30° C. and stir at this temperature for 30 min followed by 0° C. for 30 min. Quench the reaction mixture with HOAc (3.15 mL, 0.055 moles) and water (0.5 mL, 0.027 moles) dissolved in THF (5.0 mL). Add dropwise a THF (40 mL) solution of DDQ (11.9 g, 0.053 moles) to the reaction mixture. Bring the reaction mixture to room temperature and stir at room temperature for 30 min. Cool the reaction mixture to 0° C. and add 3.0 N aq. NaOH (35 mL) and stir for 30 min. Decant the organic layer from the reaction mixture and wash the brown solid with Et$_2$O (3×100 mL). Combine the organic layers, wash several times with saturated NaCl solution and dry with MgSO$_4$. Filter and evaporate under vacuum to afford brown colored solid. Purify the crude by flash column chromatography using 5% EtOAc/hexane to afford the title product as white solid.

4. 5-Chloro-6-{4-[2-chloro-6-(4-fluoro-phenyl)-pyrimidin-4-yl]-piperazin-1-yl}-nicotinic acid ethyl ester

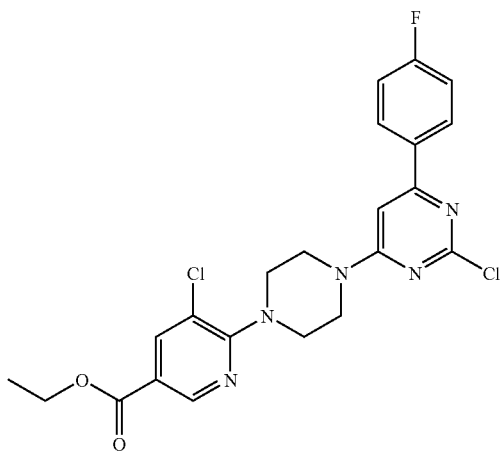

To a mixture of 2,4-dichloro-6-(4-fluoro-phenyl)-pyrimidine (2.82 g, 0.12 mol) and NaHCO$_3$ (1.95 g, 0.023 mol) in EtOH at 0° C., add 5-chloro-6-piperazin-1-yl-nicotinic acid ethyl ester (3.44 g, 0.013 mol). Remove the ice bath and stir at room temperature for 16 h. Concentrate under reduced pressure and partition between EtOAc and brine. Dry the organic layer (Na$_2$SO$_4$) and concentrate under reduced pressure to give the title compound.

5. 5-Chloro-6-{4-[6-(4-fluoro-phenyl)-2-(2-methyl-pyrrolidin-1-yl)-pyrimidin-4-yl]-piperazin-1-yl}-nicotinic acid ethyl ester

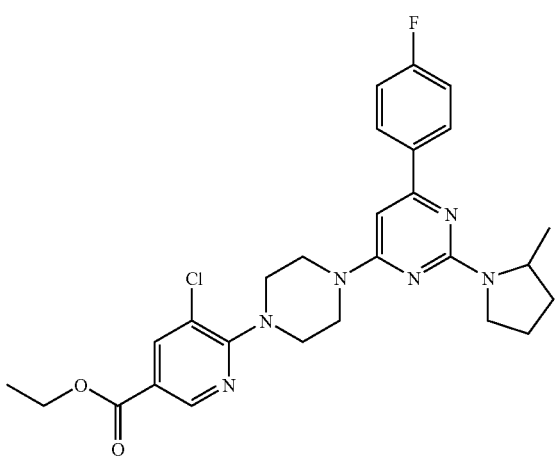

Heat a mixture of 5-chloro-6-{4-[2-chloro-6-(4-fluoro-phenyl)-pyrimidin-4-yl]-piperazin-1-yl}-nicotinic acid ethyl ester (1.19 g, 0.0025 mol) and 2-methylpyrrolidine (2.5 mL, 0.025 mol) in DMA at 120° C. for 14 h. Partition the reaction mixture between EtOAc and water. Wash the organic layer with water (1×) and brine (1×), then dry (Na$_2$SO$_4$) and concentrate under reduced pressure. Filter the crude product through a silica gel pad (2 inches deep×3 inches in diameter) eluting with 700 mL of 30% EtOAc/hexanes. Concentrate under reduced pressure to give the title compound as an off-white foam.

6. 5-Chloro-6-{4-[6-(4-fluoro-phenyl)-2-(2-methyl-pyrrolidin-1-yl)-pyrimidin-4-yl]-piperazin-1-yl}-nicotinic acid

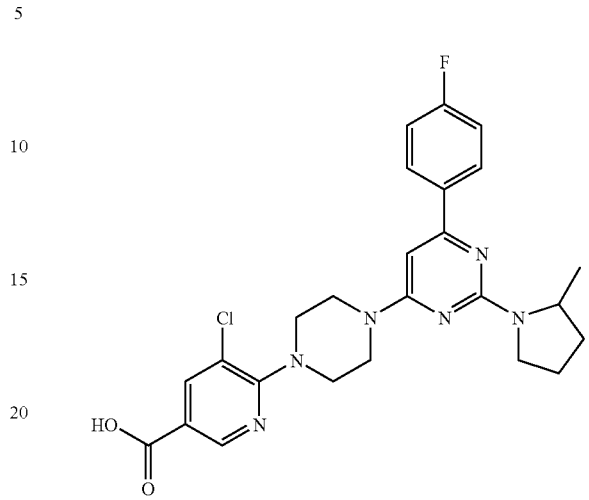

To a solution of 5-chloro-6-{4-[6-(4-fluoro-phenyl)2-(2-methyl-pyrrolidin-1-yl)-pyrimidin-4-yl]-piperazin-1-yl}-nicotinic acid ethyl ester (427 mg, 0.813 mmol) in THF, add water dropwise until the cloudiness almost persists. To this mixture add LiOH.H$_2$0 (350 mg, 8.13 mmol) followed by a small amount of EtOH. Heat the mixture at 55° C. for 2 h, and then concentrate under reduced pressure. Add a small amount of water to the residue, followed by 8.13 mmol of HCl (3M solution). Adjust the final pH to 4 and collect the off-white solid via filtration. Wash the solid with water and dry to afford the title compound.

C. (5-Chloro-6-{4-[6-(4-fluoro-phenyl)-2-(2-methyl-pyrrolidin-1-yl-pyrimidin-4-yl]-piperazin-1-yl}-pyridin-3-ylmethyl)-dimethyl-amine

1. (5-Chloro-6-{4-[6-(4-fluoro-phenyl)-2-(2-methyl-pyrrolidin-1-yl)-pyrimidin-4-yl]-piperazin-1-yl}-pyridin-3-yl)-methanol

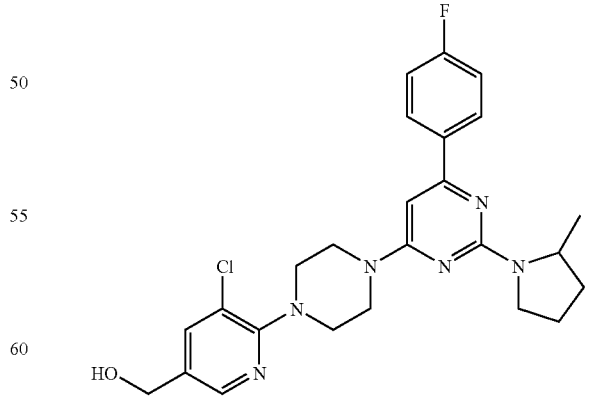

Dissolve 5-chloro-6-{4-[6-(4-fluoro-phenyl)-2-(2-methyl-pyrrolidin-1-yl)-pyrimidin-4-yl)pyrimidin-4-yl]-piperazin-1-yl}-nicotinic acid ethyl ester (595 mg, 1.13 mmol, prepared in Example 1-B, step 5, above) in DCM and cool to −78° C. using a dry ice/acetone bath. Add diisobutylaluminum hydride (4.53 mL, 1N in hexanes) dropwise and continue stirring for 1 h at −78° C. Add excess Na$_2$SO$_4$.10H$_2$O, stir at −78° C. for 5 min and then remove the cooling bath and allow to come to room temperature. Filter the mixture through celite washing with DCM then concentrate under reduced pressure. The resulting oil is purified using flash chromatography (30-50% EtOAc/hexanes eluent) to afford the title compound as a white foam.

2. Methanesulfonic acid 5-chloro-6-{4-[6-(4-fluoro-phenyl)-2-(2-methyl-pyrrolidin-1-yl)-pyrimidin-4-yl]-piperazin-1-yl}-pyridin-3-ylmethyl ester

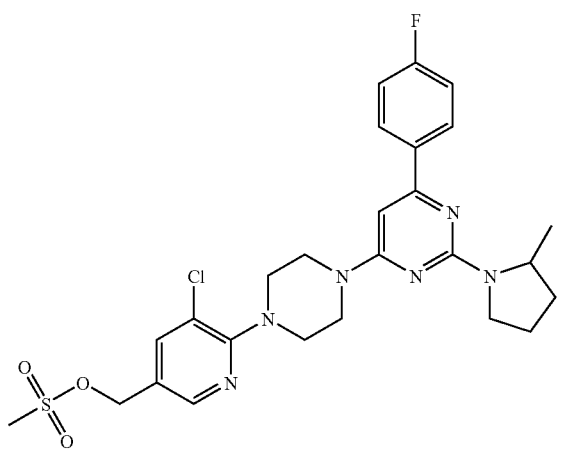

To an ice cooled solution of (5-chloro-6-{4-[6-(4-fluoro-phenyl)-2-(2-methyl-pyrrolidin-1-yl)-pyrimidin-4-yl]-piperazin-1-yl}-pyridin-3-yl)-methanol (136 mg, 0.282 mmol) and Et$_3$N (79 µL, 0.564 mmol) in DCM, add MsCl (33 µL, 0.422 mmol) dropwise. Remove ice bath and stir for 1 h at room temperature. Dilute with 3 volumes of DCM, wash with brine, dry the organic layer (Na$_2$SO$_4$) and concentrate under reduced pressure to give the title mesylate.

3. (5-Chloro-6-{4-[6-(4-fluoro-phenyl)-2-(2-methyl-pyrrolidin-1-yl)-pyrimidin-4-yl]-piperazin-1-yl}-pyridin-3-ylmethyl)-dimethyl-amine

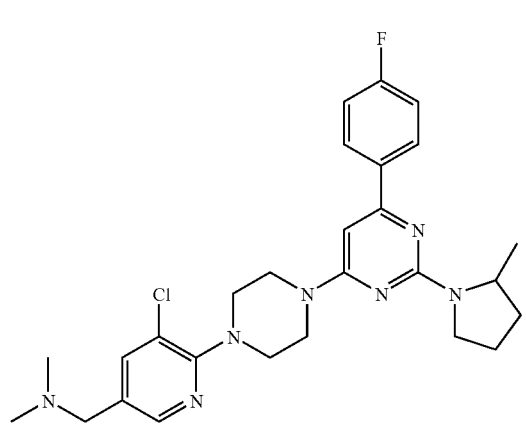

Heat a mixture of methanesulfonic acid 5-chloro-6-{4-[6-(4-fluoro-phenyl)-2-(2-methyl-pyrrolidin-1-yl)-pyrimidin-4-yl]-piperazin-1-yl}-pyridin-3-ylmethyl ester with an excess of dimethylamine (1M in THF) in a sealed tube at 80° C. for 2 h. Concentrate under reduced pressure then partition between EtOAc and 10% NaOH solution. Dry the organic layer (Na$_2$SO$_4$) and concentrate under reduced pressure. Purify the resulting residue using flash chromatography (10:90:1/MeOH:DCM:NH$_4$OH eluent) to give the title compound.

D. 6-{4-[6(4-Fluoro-phenyl)-2-(2-methyl-pyrrolidin-1-yl)-pyrimidin-4-yl]-3-(R)-methyl-piperazin-1-yl}-5-methyl-nicotinic acid 1. 4,6-Dichloro-2-(2-methylpyrrolidin-1-yl)pyrimidine

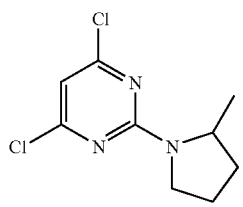

Dissolve 2,4,6-trichloropyrimidine (23.5 g, 0.13 mol) in anhydrous MeOH (220 mL), and add solid sodium bicarbonate (28.3 g, 0.33 mol). Cool to 0° C. and add 2-methylpyrrolidine (12 g, 0.14 mol), dropwise. Let stir at room temperature for 16 h. Filter off the excess sodium bicarbonate, and evaporate under reduced pressure. Purify by SiO$_2$ flash chromatography, using 50:1 hexanes:EtOAc, increasing to 30:1 hexanes:EtOAc, to provide the title compound as a white solid.

2. 4-Chloro-6-(4-fluorophenyl)-2-(2-methylpyrrolidin-1-yl)pyrimidine

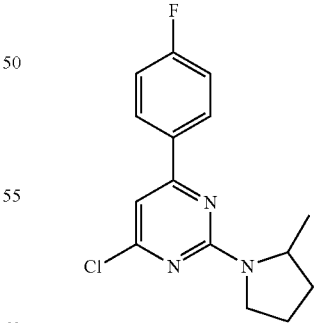

Heat a mixture of 4,6-dichloro-2-(2-methylpyrrolidin-1-yl)pyrimidine (2.25 g, 9.74 mmol), 4-fluorophenylboronic acid (10.23 mmol), Pd(PPh$_3$)$_4$ (562 mg, 0.487 mmol), and a 2M potassium phosphate solution (9.74 mL) in dioxane (35 mL) under nitrogen at 80° C. for 16 h. Evaporate the mixture

3. 1-(5-Bromo-3-methyl-pyridin-2-yl)-3-(R)-methyl-piperazine

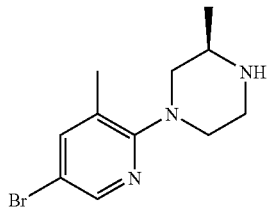

Heat a solution of 2,5-dibromo-3-methyl-pyridine (Chontech Inc.) (2.0 g, 7.97 mmol), (R)-2-methyl-piperazine (3.2 g, 31.9 mmol) in DMA at 130° C. for 16 h. Partition the reaction mixture between water and EtOAc. Wash the EtOAc layer with water (1×) and brine (1×), dry (Na$_2$SO$_4$) and concentrate under reduced pressure to give the title compound as a solid.

4. 4-[4-(5-Bromo-3-methyl-pyridin-2-yl)-2-(R)-methyl-piperazin-1-yl]-6-(4-fluoro-phenyl)-2-(2-methyl-pyrrolidin-1-yl)-pyrimidine

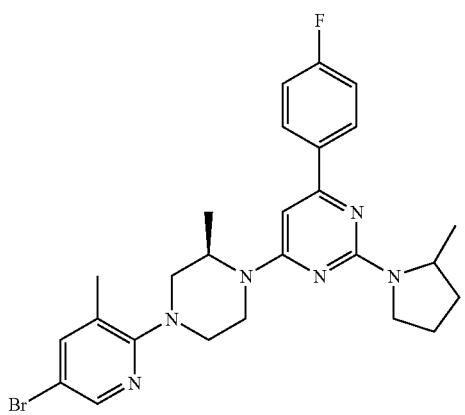

Heat a mixture of 4-chloro-6-(4-fluoro-phenyl)-2-(2-methyl-pyrrolidin-1-yl)-pyrimidine (1.30 g, 4.44 mmol), 1-(5-bromo-3-methyl-pyridin-2-yl)-3-(R)-methyl-piperazine (1.2 g, 4.44 mmol), and NaHCO$_3$ (0.71 g, 8.46 mmol) in EtOH at 50° C. for 20 h. Concentrate under reduced pressure and partition between EtOAc and brine. Dry the organic layer (Na$_2$SO$_4$) and concentrate under reduced pressure. Purify the residue by flash column chromatography eluting with EtOAc-hexanes (1:4) to afford the title compound as a white solid.

5. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinonitrile

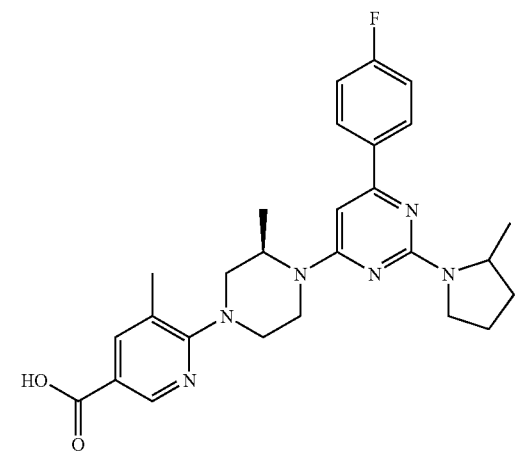

To a mixture of 4-[4-(5-bromo-3-methyl-pyridin-2-yl)-2-(R)-methyl-piperazin-1-yl]-6-(4-fluoro-phenyl)-2-(2-methyl-pyrrolidin-1-yl)pyrimidine (700 mg, 1.33 mmol) and Zn(CN)$_2$ (94 mg, 0.799 mmol) in DMF, add Pd(PPh$_3$)$_4$ (77 mg, 0.067 mmol). Purge the reaction mixture for 10 min with dry N$_2$. Heat the stirring reaction mixture overnight at 80° C., cool to room temperature and partition between water and EtOAc. Dry the solution (Na$_2$SO$_4$), concentrate under reduced pressure. Purify the residue by flash column eluting with EtOAc-Hexanes (1:1) to afford the title compound as a white solid.

6. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid Heat a solution of 6-{4-[6-(4-fluoro-phenyl)-2-(2-methyl-pyrrolidin-1-yl)-pyrimidin-4-yl]-3-(R)-methyl-piperazin-1-yl}-5-methyl-nicotinonitrile (100 mg, 0.212 mmol) in 12 M HCl for 4 h at 90° C. Concentrate the mixture under reduced pressure. Add a small amount of water, adjust the pH to 6-7, and collect the resulting white precipitate to afford the title compound as an off-white solid.

and add water (50 mL). Extract with EtOAc (3×50 mL), dry (Na$_2$SO$_4$), and evaporate. Purify by SiO$_2$ flash chromatography, eluting with 9:1 hexanes:EtOAc to provide the title compound as an oil.

E. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinamide

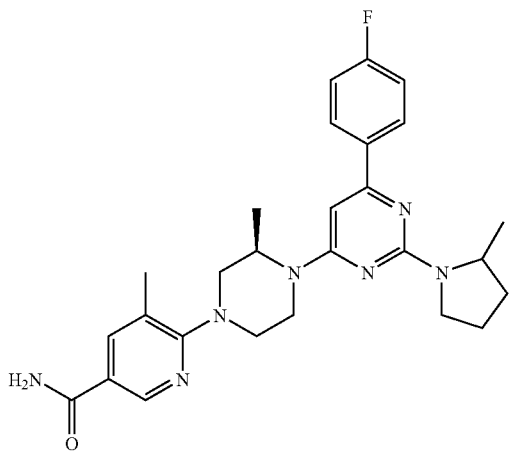

To a solution of 6-{4-[6-(4-fluoro-phenyl)-2-(2-methyl-pyrrolidin-1-yl)-pyrimidin-4-yl]-3-(R)-methyl-piperazin-1-yl}-5-methyl-nicotinic acid (70 mg, 0.142 mmol) in DCM, add oxalyl chloride (3 equivalents) and 1 drop of DMF. Stir the solution for 1 h at room temperature, concentrate, and dissolve in DCM. Cool the solution in an ice-bath, pass $NH_3$ through the solution for 15 min, and stir for 2 h at room temperature. Wash with water. Dry the solution ($Na_2SO_4$) and concentrate under reduced pressure. Purify the residue by flash column chromatography eluting with DCM-MeOH (9:1) to afford the title compound as an off white solid. $^1$H NMR (400 MHz, $CDCl_3$): δ 1.32 (m, 3H, CH($CH_3$)); 1.70 (m, 1H, $CH_2CH_2$); 1.91 (m, 1H, $CH_2CH_2$); 2.05 (m, 2H, $CH_2CH_2$); 2.39 (s, 3H, Ar—$CH_3$); 3.05 (m, 1H); 3.19 (m, 1H); 3.38 (m, 1H); 3.68 (m, 4H); 4.35 (m, 2H); 4.70 (m, 1H); 5.84 (br, 2H, $NH_2$); 6.24 (s, 1H, Ar—H); 7.10 (m, 2H); 7.90 (d, 1H, J=2.0 Hz); 8.01 (m, 2H); 8.52 (s, 1H).

F. (6-{4-[6-(4-Fluoro-phenyl)-2-(2-methyl-pyrrolidin-1-yl)pyrimidin-4-yl]-3-(R)-methyl-piperazin-1-yl}-5-methyl-pyridin-3-yl)-methanol

1. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid methyl ester

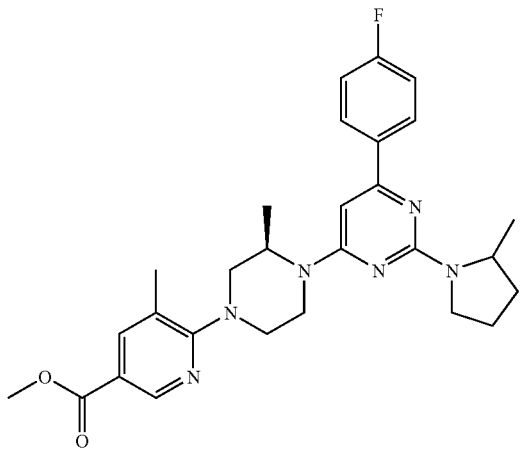

Reflux a solution of 6-{4-[6-(4-fluoro-phenyl)-2-(2-methyl-pyrrolidin-1-yl)-pyrimidin-4-yl]-3-(R)-methyl-piperazin-1-yl}-5-methyl-nicotinic acid (120 mg, 0.245 mmol) and 2 drops of concentrated $H_2SO_4$ in MeOH for 4 h. Cool to room temperature, concentrate, and partition between saturated $NaHCO_3$ and EtOAc. Dry the solution ($Na_2SO_4$), concentrate under reduced pressure. Purify the residue by flash column chromatography eluting with EtOAc-Hexanes (1:4) to afford the title ester as an oil.

2. (6-{4-[6-(4-Fluoro-phenyl)-2-(2-methyl-pyrrolidin-1-yl)-pyrimidin-4-yl]-3-(R)-methyl-piperazin-1-yl}-5-methyl-pyridin-3-yl)-methanol

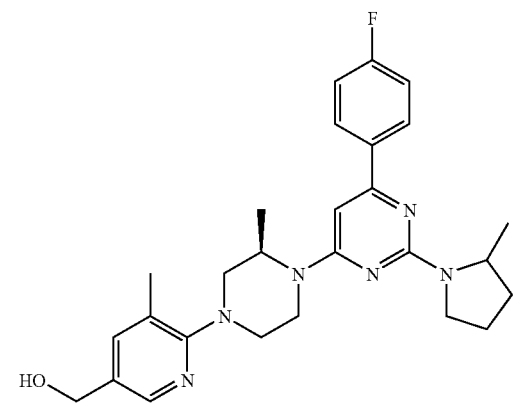

Dissolve 6-{4-[6-(4-fluoro-phenyl)-2-(2-methyl-pyrrolidin-1-yl)-pyrimidin-4-yl]-3-(R)-methyl-piperazin-1-yl}-5-methyl-nicotinic acid methyl ester (78 mg, 0.155 mmol) in DCM and cool to −78° C. using a dry ice/acetone bath. Add diisobutylaluminum hydride (0.619 mL, 1M in hexanes) dropwise and continue stirring for 1 h at −78° C. Add excess $Na_2SO_4 \cdot 10H_2O$ and stir at −78° C. for 5 min and then remove the cooling bath and allow to come to room temperature. Filter the mixture through celite washing with DCM, and then concentrate under reduced pressure. Purify the resulting oil using flash chromatography (30-50% EtOAc/hexanes eluent) to afford the title compound as a white foam. $^1$H NMR (400 MHz, $CDCl_3$): δ 1.32 (m, 3H, $CH_3$); 1.40 (m, 3H, $CH_3$); 1.69 (m, 1H, $CH_2CH_2$); 1.90 (m, 1H, $CH_2CH_2$); 2.05 (m, 2H, $CH_2CH_2$); 2.36 (s, 3H, Ar—$CH_3$); 3.00 (m, 1H); 3.08 (m, 1H); 3.37 (m, 2H); 3.48 (m, 1H); 3.68 (m, 2H); 4.34 (m, 2H); 4.69 (s, 2H, $CH_2OH$); 4.71 (m, 1H); 6.24 (s, 1H, Ar—H); 7.10 (m, 2H); 7.48 (d, 1H, J=2.0 Hz); 8.00 (m, 2H); 8.11 (s, 1H).

G. 6-{4-[6-(4-Fluoro-phenyl)-2-(2-methyl-pyrrolidin-1-yl)-pyrimidin-4-yl]-piperazin-1yl}-5-methyl-nicotinamidine

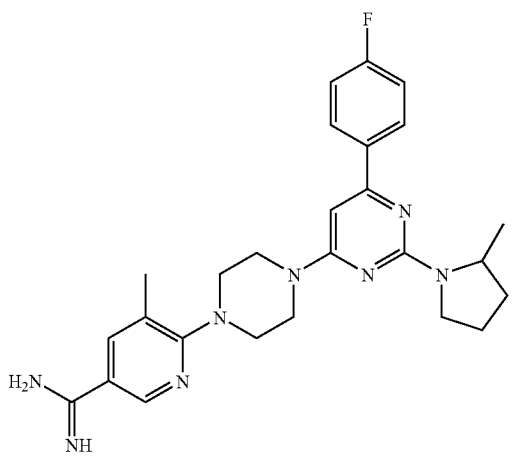

Pass HCl gas through a cooled solution of 6-{4-[6-(4-fluoro-phenyl)-2-(2-methyl-pyrrolidin-1-yl)-pyrimidin-4-yl]-piperazin-1-yl}-5-methyl-nicotinonitrile (100 mg, 0.219 mmol) in EtOH (30 ml) for 15 min. Keep the solution at 5° C. for 24 h and concentrate under reduce pressure. Add 30 ml of EtOH, cool to 0° C., and pass NH$_3$ gas through the solution for 20 min. Keep the reaction mixture at room temperature for 48 h. Concentrate under reduce pressure and purify the residue by silica gel plug eluting with DCM:MeOH:NH$_4$OH (90:10:1) to afford the title compound as off-white solid. $^1$H NMR (300 MHz, CDCl$_3$): δ 1.19-1.25 (m, 3H, CH(CH$_3$)); 1.58-1.62 (m, 1H, CH$_2$CH$_2$); 1.75-1.84 (m, 1H, CH$_2$CH$_2$); 1.93-2.01 (m, 2H, CH$_2$CH$_2$); 2.22 (s, 3H, Ar—CH$_3$); 3.26 (br, 4H, pip-H); 3.58 (br, 5H); 4.24 (br, 1H); 5.70 (m, 2H); 6.15 (s, 1H, Ar—H); 7.95 (m, 2H); 8.10 (s, 1H); 8.72 (s, 1H); 8.98 (br, 3H, C(=NH)NH$_2$).

Example 2

Synthesis of Additional Representative Substituted Biaryl Piperazinyl-Pyridine Analogues A. [2-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yloxy)-ethyl]-dimethyl-amine 1. 1-(3-Methyl-5-nitro-pyridin-2-yl)-piperazine

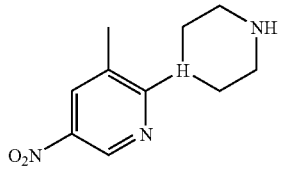

1-(3-Methyl-5-nitro-pyridin-2-yl)-piperazine is prepared by heating a solution of 1 g of 2-chloro-3-methyl-5-nitro-pyridine (Maybridge Chemical Company Ltd.) and piperazine (5 g) in DMA at 110° C. for 16 h. Partition between EtOAc and water and wash the organic layer with water (2×). Dry the organic layer with Na$_2$SO$_4$ and concentrate to give crude product. Purify via flash chromatography eluting with MeOH:DCM:NH$_4$OH (9:90:1) to give the title compound.

2. 4-(3-Chloro-4-fluoro-phenyl)-6-[4-(3-methyl-5-nitro-pyridin-2-yl)-piperazin-1-yl]-2-(2-methyl-pyrrolidin-1-yl)-pyrimidine

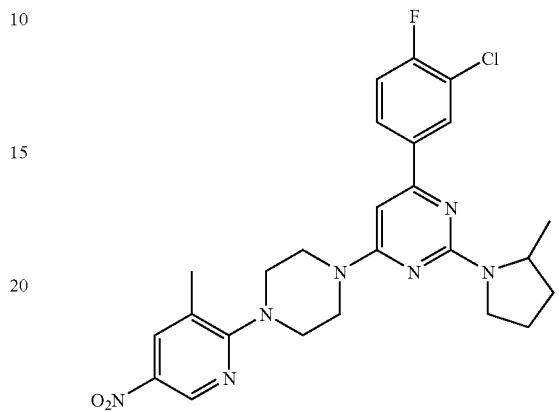

Heat a mixture of 4-chloro-6-(3-chloro-4-fluoro-phenyl)-2-(2-methyl-pyrrolidin-1-yl)-pyrimidine (210 mg), 1-(3-Methyl-5-nitro-pyridin-2-yl)-piperazine, and DIEA (185 mg, 1.44 mmol) in DMA at 120°C. for 16 h. Concentrate under reduced pressure and partition between EtOAc and brine. Dry the organic layer (Na$_2$SO$_4$) and concentrate under reduced pressure. Purify the residue by flash column eluting with EtOAc-Hexanes (1:4) to afford the title compound as a yellow solid.

3. 6-{4-[6-(3-Chloro-4-fluoro-phenyl)-2-(2-methyl-pyrrolidin-1-yl)-pyrimidin-4-yl]-piperazin-1-yl}-5-methyl-pyridin-3-ylamine

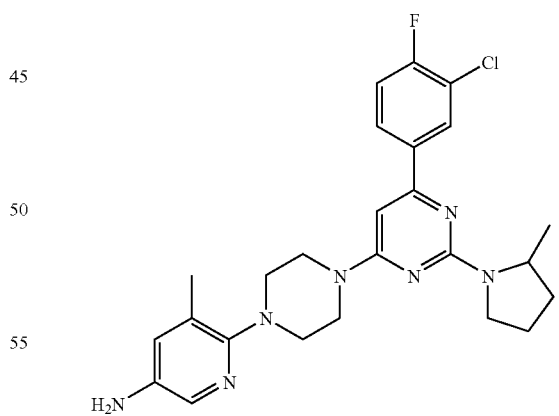

Heat a mixture of 4-(3-chloro-4-fluoro-phenyl)-6-[4-(3-methyl-5-nitro-pyridin-2-yl)-piperazin-1-yl]-2-(2-methyl-pyrrolidin-1-yl)-pyrimidine (300 mg, 0.59 mmol) and SnCl$_2$·2H$_2$O (529 mg, 2.95 mmol) in EtOAc at 80° C. for 16 h. Cool to room temperature and partition between EtOAc and 1N NaOH. Wash with water, dry the solution (Na$_2$SO$_4$), and concentrate under reduced pressure. Purify the residue by flash column eluting with EtOAc to afford the title compound as a light-yellow solid. $^1$H NMR (400 MHz, CDCl$_3$): δ 1.30 (t, 3H, J=6.4 Hz, CH$_3$); 1.69 (m, 1H, CH$_2$CH$_2$); 1.91 (m, 1H, CH$_2$CH$_2$); 2.06 (m, 2H, CH$_2$CH$_2$); 2.28 (s, 3H, Ar—CH$_3$); 3.10 (m, 4H); 3.47 (br, 2H, NH$_2$); 3.68 (m, 4H); 3.77 (m, 4H); 4.34 (m, 1H); 6.25 (s, 1H, Ar—H); 6.88 (d, J=2.0 Hz, 1H); 7.18 (m, 1H); 7.70 (d, 1H, J=3.2 Hz); 7.89 (m, 1H); 8.07 (m, 1H).

4. 6-{4-[6-(3-Chloro-4-fluoro-phenyl)-2-(2-methyl-pyrrolidin-1-yl)-pyrimidin-4-yl]-piperazin-1-yl}-5-methyl-pyridin-3-ol

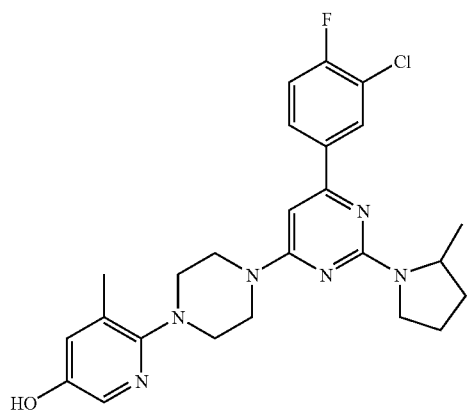

To a cooled solution (0° C.) of 6-{4-[6-(3-chloro-4-fluoro-phenyl)-2-(2-methyl-pyrrolidin-1-yl)-pyrimidin-4-yl]-piperazin-1-yl}-5-methyl-pyridin-3-ylamine (146 mg, 0.30 mmol) in 10% H$_2$SO$_4$, add a solution of NaNO$_2$ (22 mg, 0.32 mmol) in 3 mL H$_2$O and stir at 0° C. for 30 min. Warm up to room temperature and heat at 90° C. for 1 h. Cool to room temperature, adjust pH to 7, and extract with EtOAc. Wash with brine, dry the solution (Na$_2$SO$_4$), and concentrate under reduced pressure. Purify the residue by flash column chromatography eluting with EtOAc:hexanes (1:1) to afford the title compound.

5. [2-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yloxy)-ethyl]-dimethyl-amine

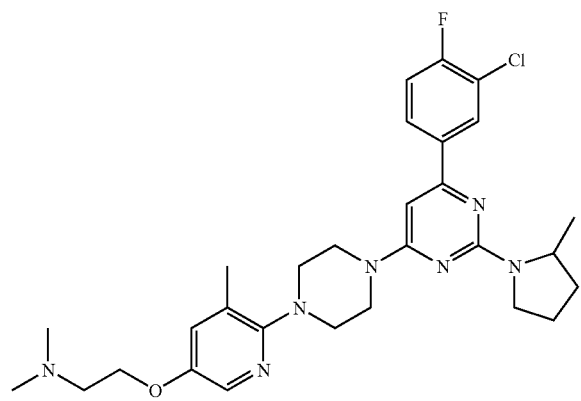

To a cooled mixture of (2-chloro-ethyl)-dimethyl-amine hydrochloride (116 mg, 0.81 mmol) in DMF, add Cs$_2$CO$_3$ (526 mg, 1.62 mmol) and stir at 0° C. for 30 min. Add 6-{4-[6-(3-chloro-4-fluoro-phenyl)-2-(2-methyl-pyrrolidin-1-yl)-pyrimidin-4-yl]-piperazin-1-yl}-5-pyridin-3-ol (78 mg, 0.16 mmol) and NaI (29 mg, 0.16 mmol). Stir the mixture at room temperature for 1 h and then for 2 h at 45° C. Partition between EtOAc and water. Wash with brine, dry the solution (Na$_2$SO$_4$), and concentrate under reduced pressure. Purify the residue by flash column chromatography eluting with DCM:MeOH:NH$_4$OH (90:10:1) to afford the title compound. $^1$H NMR (300 MHz, CDCl$_3$): δ1.29 (t, 3H, J=6.3 Hz, CH$_3$); 1.69 (m, 1H, CH$_2$CH$_2$); 1.91 (m, 1H, CH$_2$CH$_2$); 2.05 (m, 2H, CH$_2$CH$_2$); 2.32 (s, 3H, Ar—CH$_3$); 2.33 (s, 6H, N(CH$_3$)$_2$); 2.71 (t, J=5.7 Hz, 2H); 3.13 (m, 4H); 3.64 (m, 4H); 3.80 (m, 4H); 4.06 (t, J=5.7 Hz, 2H); 4.34 (m, 1H); 6.25 (s, 1H, Ar—B); 7.10 (d, J=2.7 Hz, 1H); 7.18 (m, 1H); 7.89 (m, 2H); 8.04 (m, 1H).

B. 5-Methyl-6-{4-[2-methylpyrrolidin-1-yl)-6-pyridin-4-yl-pyrimidin-4-yl]-piperazin-1-yl}-nicotinic acid ethyl ester 1. 4,6-Dichloro-2-(2-methylpyrrolidin-1-yl)pyrimidine

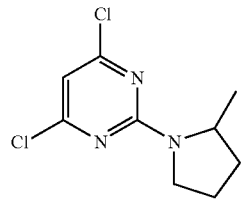

Dissolve 2,4,6-trichloropyrimidine (23.5 g, o.13 mol) in anhydrous MeOH (220 mL), and add solid sodium bicarbonate (28.3 g, 0.33 mol). Cool to 0° C. and add 2-methylpyrrolidine (12 g, 0.14 mol) dropwise. Let stir at room temperature for 16 h. Filter off the excess sodium bicarbonate, and evaporate under reduced pressure. Purify by SiO$_2$ liquid chromatography, using 50:1 hexanes:EtOAc, increasing to 30:1 hexanes:EtOAc, to provide the title compound as a white solid.

2. 4-(5-bromo-3-methyl-pyridin-2-yl)-piperazine-1-carboxylic acid tert-butyl ester

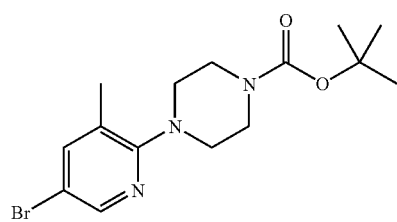

Heat a solution of 2,5-dibromo-3-methyl-pyridine (Chontech Inc.) (12.6 g, 50.3 mmol), piperazine-1-carboxylic acid tert-butyl ester (11.7 g, 62.9 mmol) and DIEA (13.3 g, 102.0 mmol) in DMA at 130° C. for 36 h. Partition the dark brown reaction mixture between water and EtOAc. Wash the EtOAc layer with water (1×) and brine (1×), dry (Na$_2$SO$_4$) and concentrate under reduced pressure to give the crude product.

Purify by flash chromatography, eluting with 9:1 hexanes:EtOAc, increasing to 3:1 hexanes:EtOAc to provide the title compound as a solid.

3. 4-(5-Cyano-3-methyl-pyridin-2-yl)-piperazine-1-carboxylic acid tert-butyl ester

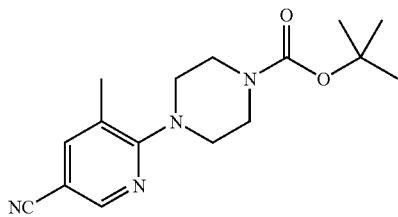

Heat a solution of 4-(5-bromo-3-methyl-pyridin-2-yl)-piperazine-1-carboxylic acid tert-butyl ester (5.0 g, 14.0 mmol), Zn(CN)$_2$ (989 mg, 8.4 mmol) and Pd(PPh$_3$)$_4$ (970 mg, 0.84 mmol), in dry DMF (50 mL) at 80° C. for 16 h under nitrogen in a sealed tube. Partition the reaction mixture between water and EtOAc. Wash the EtOAc layer with water (1×) and brine (1×), dry (Na$_2$SO$_4$) and concentrate under reduced pressure to give the title compound, and use immediately for the next reaction.

4. 5-Methyl-6-piperazine-1-yl-nicotinic acid

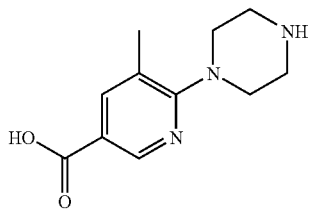

Treat a mixture of 4-(5-cyano-3-methyl-pyridin-2-yl)-piperazine-1-carboxylic acid tert-butyl ester (5 g) with concentrated HCl (75 mL). Let stir at room temperature for 5 min or until the outgassing has ceased, then heat in a sealed tube at 90° C. for 4 h. Evaporate the mixture, triturate with ether, and collect the solid 5-methyl-6-piperazine-1-yl-nicotinic acid.

5. 5-Methyl-6-piperazine-1-icotinic acid ethyl ester

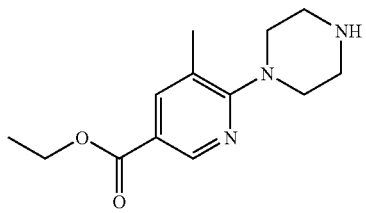

Place the carboxylic acid (5 g) in dry EtOH (100 mL) and bubble in HCl (g) for 10 min, then heat at 60° C. in a sealed tube for 16 h. Evaporate the mixture, add 1M NaOH (100 mL), and extract with EtOAc (3×50 mL). Dry (Na$_2$SO$_4$) and evaporate to furnish the title compound as a tan oil.

6. 6-{4-[6-chloro-2-(2-methylpyrrolidin-1-yl]-piperazin-1-yl}-5-methyl-nicotinic acid ethyl ester

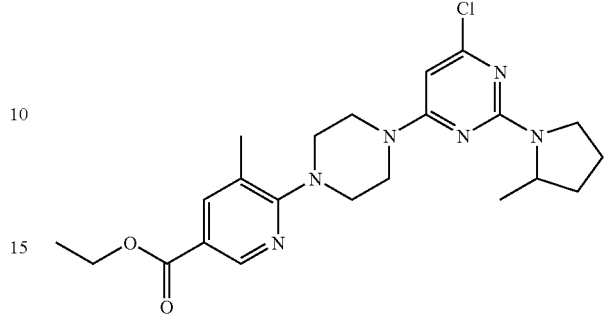

Heat a mixture of 5-methyl-6-piperazine-1-yl-nicotinic acid ethyl ester (2.0 g, 8.0 mmol), 4,6-dichloro-2-(2-methylpyrrolidin-1-yl)pyrimidine (1.9 g, 8.2 mmol), and sodium bicarbonate (1.4 g, 16.0 mmol) in EtOH (50 mL) for 16 h. Evaporate the mixture and place directly on a silica gel column. Elute with 3:1 hexanes:EtOAc to give the title compound as a white foamy solid.

7. 5-Methyl-6-{4-[2-methylpyrrolidin-1-yl)-6-pyridin-4-yl-pyrimidin-4-yl]-piperazin-1-yl}-nicotinic acid ethyl ester

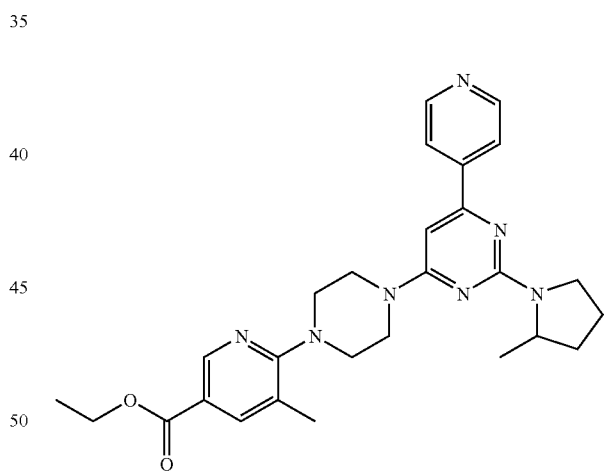

Heat a mixture of 6-{4-[6-chloro-2-(2-methylpyrrolidin-1-yl]-piperazin-1-yl}-5-methyl-nicotinic acid ethyl ester (300 mg, 0.7 mmol), 4-tri-n-butylstannylpyridine (526 mg, 1.4 mmol) and Pd(PPh$_3$)$_4$ (39 mg, 0.03 mol) in toluene (15 mL) at 110° C. for 16 h. Let cool to room temperature, filter off the catalyst, and add water (10 mL). Extract with EtOAc (3×10 mL), dry (Na$_2$SO$_4$) and evaporate. Purify using flash chromatography (9:1 hexanes/EtOAc) to give pure title compound.

$^1$H NMR (CDCl$_3$): 8.78 (s, 1H), 8.70 (d, 2H), 8.00 (s, 1H), 7.92 (d, 2H), 6.38 (s, 1H), 4.40 (quart, 2H), 3.81 (mult, 4H), 3.75 (mult, 1H), 3.41 (mult, 4H), 2.40 (s, 3H), 2.10 (m, 2H), 1.62 (m, 2H), 1.60 (m, 2H).

C. 6-{4-[6-(2-Isopropyl-pyridin-4-yl)-2-(2-methyl-pyrrolidin-1-yl)-pyrimidin-4-yl]-piperazin-1-yl}-5-methyl-nicotinic acid ethyl ester

1. 2-Isopropyl-4-trimethylstannanyl-pyridine

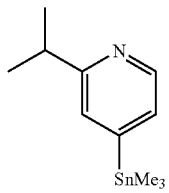

To a cold suspension (0° C.) of Na (25% in toluene, 10 g, 104 mmol) in DME (100 mL) add a solution of trimethyltin chloride (9.4 g, 47.4 mmol) in DME (20 mL) dropwise. Stir the mixture at 0° C. for 3 h followed by addition of the solution of cold (0° C.) 4-chloro-2-isopropyl-pyridine (Comins & Mantlo (1985) *J. Org. Chem.* 50:4410-4411) (4.9 g, 31.6 mmol) in DME (20 mL). Stir the mixture at 0° C. for 2 h and warm to room temperature. Filter, concentrate the filtrate, and dilute the residue with ether. Filter and concentrate the filtrate. Distil the residue (bp 75-80° C. at 1 mm Hg) to afford the title compound as a light oil.

2. 6-{4-[6-(2-Isopropyl-pyridin-4-yl)-2-(2-methyl-pyrrolidin-1-yl)-pyrimidin-4-yl]-piperazin-1-yl}-5-methyl-nicotinic acid ethyl ester

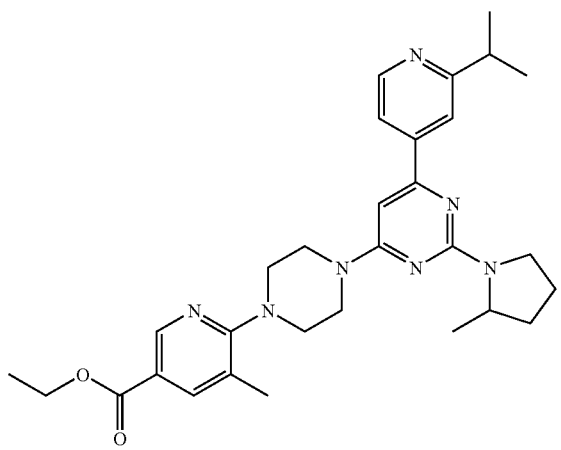

Using a procedure analogous to that used in Example 2-B step 7, 6-{4-[6-chloro-2-(2-methylpyrrolidin-1-yl]-piperazin-1-yl}-5-methyl-nicotinic acid ethyl ester is reacted with 2-isopropyl-4-trimethylstannanyl-pyridine to give the title compound.

D. 5-Chloro-6-{4-[2-(3-chloro-4-fluoro-phenyl)-6-morpholin-4-yl-pyridin-4yl]-piperazin-1-yl}-nicotinic acid ethyl ester

1. 2-chloro-6-morpholino-4-yl-pyridin-4-ylamine

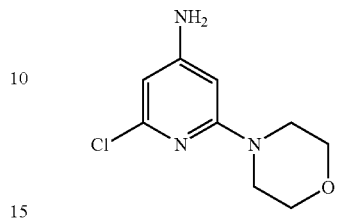

Stir a solution of 4-amino-2,6-dichloropyridine (3.3 g) in morpholine (15 mL) for 4 h at 150° C., concentrate, partition between H$_2$O and EtOAc, dry over Na$_2$SO$_4$, and concentrate under vacuum. Purify by flash chromatography (2:3 hexanes/EtOAc) to give the title compound.

2. 2-(3-chloro-4-fluoro-phenyl)-6-morpholino-4-yl-pyridin-4-ylamine

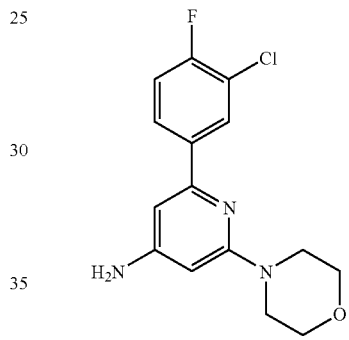

To a de-gassed mixture of 3-chloro-4-fluorophenylboronic acid (849 mg, 4.87 mmol), 2-chloro-6-morpholino-4-yl-pyridin-4-ylamine (800 mg, 3.74 mmol), and 2M K$_3$PO$_4$ (7.5 mmol) dioxane (15 mL) under nitrogen add Pd(PPh$_3$)$_4$ (0.23 mmol). Stir the mixture at 80° C. for 16 h, concentrate, extract with EtOAc. Dry over Na$_2$SO$_4$, concentrate under vacuum, and purify by flash chromatography (1:1 hexanes/EtOAc) to give the title compound.

3. 4-{4-bromo-6-(3-chloro-4-fluoro-phenyl)-pyridin-2yl}-morpholine

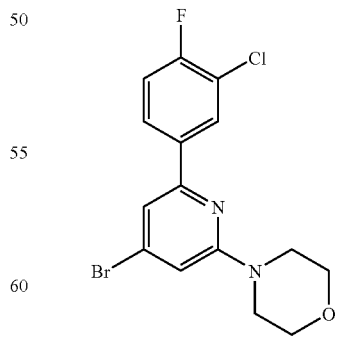

To an ice cooled solution of 2-(3-chloro-4-fluoro-phenyl)-6-morpholino-4-yl-pyridin-4-ylamine (250 mg, 0.81 mmol) in 75% H$_2$SO$_4$ (10 mL) add dropwise a solution of NaNO$_2$ (56 mg, 0.81 mmol) in 3 mL H$_2$O. Stir the mixture 30 min at 0° C.

Add CuBr (135 mg, 0.93 mmol) and 48% HBr (2 mL). Stir the mixture 15 min at 0° C. then 30 min at 60° C. Cool to room temperature, neutralize to pH 8, extract with EtOAc, dry over Na₂SO₄, and concentrate under vacuum. Purify by flash chromatography (3:1 hexanes/EtOAc) to give the title compound.

4. 5-Chloro-6-{4-[2-(3-chloro-4-fluoro-phenyl)-6-morpholin-4-yl-pyridin-4-yl]-piperazin-1-yl}-nicotinic acid ethyl ester

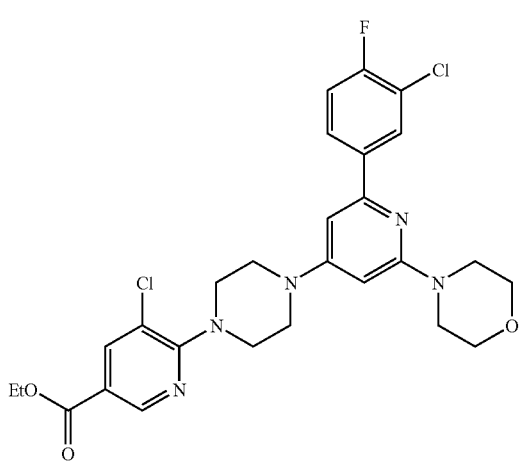

To a de-gassed mixture of 4-{4-bromo-6-(3-chloro-4-fluoro-phenyl)-pyridin-2yl}-morpholine (50 mg, 0.135 mmol), 5-chloro-6-piperazin-1-yl-nicotinic acid ethyl ester (0.162 mmol), and 1M (THF) t-BuOK (0.162 mmol), in toluene (3 mL) under nitrogen add Pd₂(dba)₃ (0.0054 mmol) and BINAP (0.0067 mmol). Stir the mixture at 80° C. for 16 h, concentrate, extract with EtOAc. Dry over Na₂SO₄, concentrate under vacuum, and purify by preparative TLC (3:1 hexanes/EtOAc) to give the title compound.

E. 5-Chloro-6-{4-[4-(3-chloro-4-fluoro-phenyl)-6-morpholin-4-yl-pyridin-2-yl]-piperazin-1-yl}-nicotinic acid ethyl ester

1. 2,3-dichloro-4-(3-chloro-4-fluoro-phenyl)-pyridine

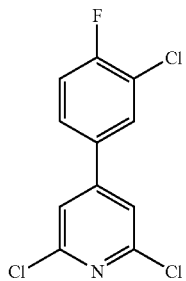

To a de-gassed mixture of 3-chloro-4-fluorophenylboronic acid (77 mg, 0.44 mmol)), 4-bromo-2,6-dichloro-pyridine (Talik and Plazek (1959) *Rocz. Chem.* 33:387-392) (100 mg, 0.44 mmol), and 2M Na₂CO₃ (0.55 mmol), in DME (4 mL) under nitrogen add Pd(PPh₃)₄ (0.026 mmol). Stir the mixture at 80° C. for 16 h, concentrate, extract with EtOAc. Dry over Na₂SO₄, concentrate under vacuum, and purify by preparative TLC (9:1 hexanes/EtOAc) to give the title compound.

2. 4-[6-chloro-4-(3-chloro-4-fluoro-phenyl)-pyridin-2-yl]-morpholine

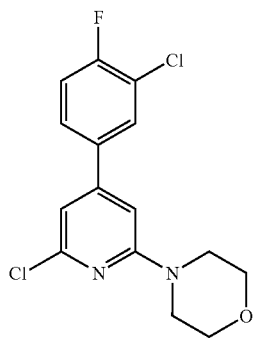

Stir a solution of 2,6-dichloro-4-(3-chloro-4-fluoro-phenyl)-pyridine (100 mg) in morpholine (2 mL) 3 h at 80° C., concentrate, partition between H₂O and EtOAc, dry over Na₂SO₄, and concentrate under vacuum. Purify by preparative TLC (3:1 hexanes/EtOAc) to give the title compound.

3. 5-Chloro-6-{4-[4-(3-chloro-4-fluoro-phenyl)-6-morpholin-4-yl-pyridin-2-yl]-piperazin-1-yl}-nicotinic acid ethyl ester

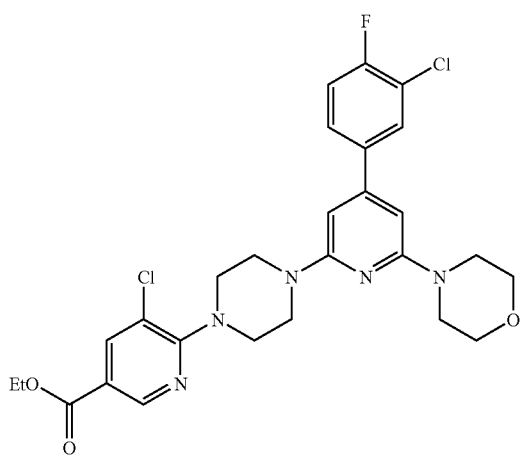

To a de-gassed mixture of 4-[6-chloro-4-(3-chloro-4-fluoro-phenyl)pyridin-2-yl]-morpholine (50 mg, 0.153 mmol)), 5-chloro-6-piperazin-1-yl-nicotinic acid ethyl ester (0.183 mmol), and 1M (THF) t-BuOK (0.183 mmol), in toluene (3 mL) under nitrogen add Pd₂(dba)₃ (0.006 mmol) and BINAP (0.008 mmol). Stir the mixture at 80° C. for 16 h, concentrate, and extract with EtOAc. Dry over Na₂SO₄, concentrate under vacuum, and purify by preparative TLC (3:1 hexanes/EtOAc) to give the title ester.

F. (6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridin-3-yl)-acetic acid 1. 4-[2-Chloro-6-(4-fluoro-phenyl)-pyrimidin-4-yl]-3-(R)-methyl-piperazine-1-carboxylic acid tert-butyl ester

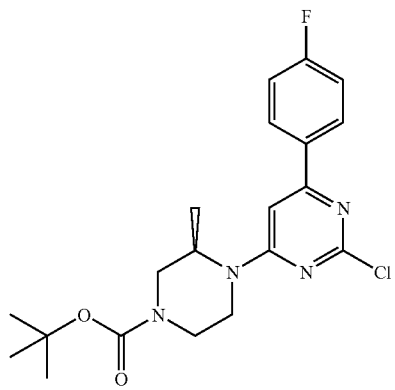

Heat a mixture of 2,4-dichloro-6-(4-fluoro-phenyl)-pyrimidine (2.8 g, 11.52 mmol), 3-(R)-methyl-piperazine-1-carboxylic acid tert-butyl ester (2.42 g, 12.1 mmol), and $K_2CO_3$ (3.2 g, 23.0 mmol) in DMA at 60° C. for 16 h. Dilute with water, extract with EtOAc, and wash with brine. Dry the organic layer ($Na_2SO_4$) and concentrate under reduced pressure. Purify the residue by flash column eluting with EtOAc-Hexanes (1:4) to afford the title compound as a white solid.

2. 4-[6-(4-Fluoro-phenyl)-2-(2-(R)-methyl-pyrrolidin-1-yl)-pyrimidin-4-yl]-3-(R)-methyl-piperazine-1-carboxylic acid tert-butyl ester

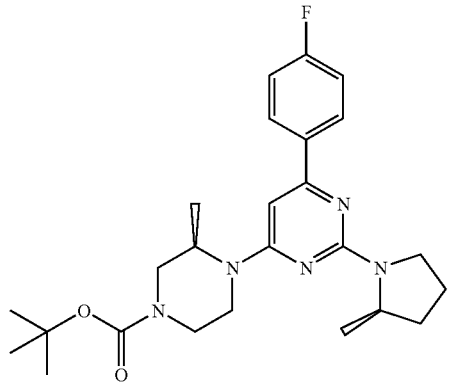

Heat a mixture of 4-[2-chloro-6-(4-fluoro-phenyl)-pyrimidin-4-yl]-3-(R)-methyl-piperazine-1-carboxylic acid tert-butyl ester (5.0 g, 12.3 mmol), 2-(R)-methyl-pyrrolidine hydrobromide (Nijhuis et. al. (1989) *J. Org. Chem.* 54:216-220) (3.0 g, 16.0 mmol), and $K_2CO_3$ (5.2 g, 37.8 mmol) in DMA at 120° C. for 16 h. Dilute with water, extract with EtOAc, and wash with brine. Dry the organic layer ($Na_2SO_4$) and concentrate under reduced pressure. Purify the residue by flash column eluting with EtOAc-Hexanes (1:4) to afford the title compound as a white solid.

3. 4-(4-Fluoro-phenyl)-6-(2-(R)-methyl-piperazin-1-yl)-2-(2-(R)-methyl-pyrrolidin-1-yl)-pyrimidine

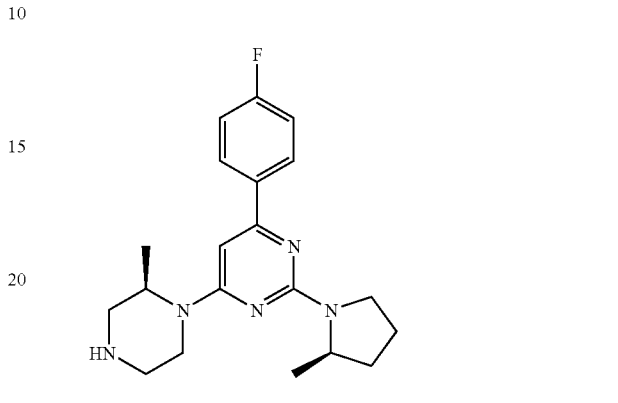

Stir 4-[6-(4-fluoro-phenyl)-2-(2-(R)-methyl-pyrrolidin-1-yl)-pyrimidin-4-yl]-3-(R)-methyl-piperazine-1-carboxylic acid tert-butyl ester (4.5 g, 9.88 mmol) in 4M HCl-dioxane (50 mL) for 40 min. Concentrate and partition between EtOAc and sat. $NaHCO_3$. Dry the organic layer ($Na_2SO_4$) and concentrate under reduced pressure to yield the title compound.

4. 4-[4-(5-bromo-3-methyl-pyridin-2-yl)-2-(R)-methyl-piperazin-1-yl]-6-(4-fluoro-phenyl)-2-(2-(R)-methyl-pyrrolidin-1-yl)-pyrimidine

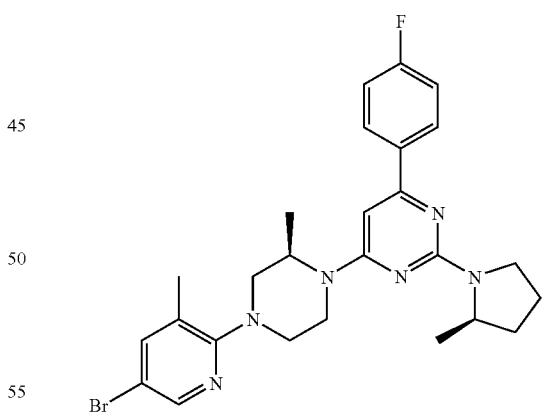

Heat a mixture of 4-(4-fluoro-phenyl)-6-(2-(R)-methyl-piperazin-1-yl)-2-(2-(R)-methyl-pyrrolidin-1-yl)-pyrimidine (400 mg, 1.13 mmol), 2,5-dibromo-3-methyl-pyridine (367 mg, 1.46 mmol), and DIEA (218 mg, 1.69 mmol) in DMA at 135° C. for 96 h. Dilute with water, extract with EtOAc, and wash with brine. Dry the organic layer ($Na_2SO_4$) and concentrate under reduced pressure. Purify the residue by flash column chromatography eluting with EtOAc-Hexanes (1:10) to afford the title compound as a white solid.

5. (6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridin-3-yl)-acetic acid tert-butyl ester

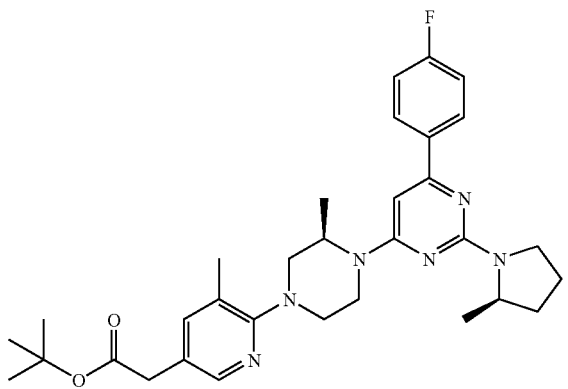

To lithium dicyclohexyl amide add a solution of acetic acid tert-butyl ester (62 μL, 0.46 mmol) in toluene (2 mL). Stir for 10 min at room temperature, and then add 4-[4-(5-bromo-3-methyl-pyridin-2-yl)-2-(R)-methyl-piperazin-1-yl]-6-(4-fluoro-phenyl)-2-(2-(R)-methyl-pyrrolidin-1-yl)-pyrimidine (200 mg, 0.38 mmol), $Pd_2(dba)_3$ (3.5 mg, 1%) and P(t-bu)$_3$ (0.8 mg, 1%). De-gas the suspension for 5 min and stir for 16 h at room temperature. Dilute with EtOAc, wash with brine, dry the organic layer ($Na_2SO_4$) and concentrate under reduced pressure. Purify using flash chromatography eluting with EtOAc-Hexanes (1:4) to give the title ester.

6. (6-4-[6-(4-Fluoro-phenyl)-2-(2-(R)-methyl-pyrrolidin-1-yl)-pyrimidin-4-yl]-3-(R)-methyl-piperazin-1-yl-5-methyl-pyridin-3-yl)-acetic acid

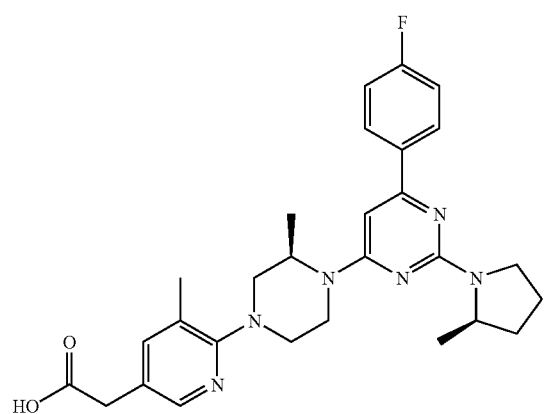

Stir a solution of (6-{4-[6-(4-fluoro-phenyl)-2-(2-(R)-methyl-pyrrolidin-1-yl)-pyrimidin-4-yl]-3-(R)-methyl-piperazin-1-yl}-5-methyl-pyridin-3-yl)-acetic acid tert-butyl ester (210 mg, 0.375 mmol) and 1 mL of TFA in DCM (10 mL) at room temperature for 16 h. Concentrate and partition between EtOAc and sat. $NaHCO_3$. Dry the organic layer ($Na_2SO_4$) and concentrate under reduced pressure. Purify using flash chromatography eluting with MeOH-DCM (1:19) to give the title compound.

G. 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid

1. 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid methyl ester

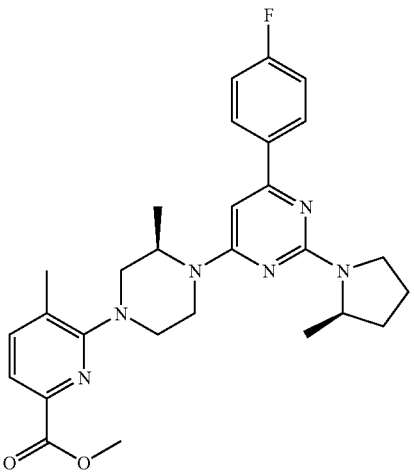

To a cold solution (0° C.) of 6-hydroxy-5-methyl-pyridine-2-carboxylic acid methyl ester (Adamczyk et. al. (2002) *Tetrahedron* 58:6951-6963) (167 mg, 1.0 mmol) in $CHCl_3$ (15 mL), add trifluoroacetic anhydride (423 mg, 1.5 mmol) dropwise followed by TEA (202 mg, 2.0 mmol). Stir the mixture for 1 h. Dilute with $CHCl_3$, wash with sat. $NaHCO_3$, dry the organic layer ($Na_2SO_4$) and concentrate under reduced pressure. Mix the residue with 4-(4-fluoro-phenyl)-6-(2-(R)-methyl-piperazin-1-yl)-2-(2-(R)-methyl-pyrrolidin-1-yl)-pyrimidine (426 mg, 1.2 mmol) and DIEA (129 mg, 1.0 mmol) in DMA. Heat the mixture at 100° C. for 16 h. Dilute with water, extract with EtOAc, and wash with brine. Dry the organic layer ($Na_2SO_4$) and concentrate under reduced pressure. Purify the residue by flash column eluting with EtOAc-Hexanes (1:5) to afford the title compound.

2. 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid

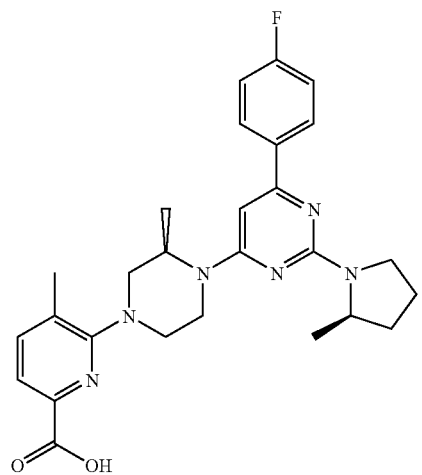

To a solution of 6-{4-[6-(4-fluoro-phenyl)-2-(2-(R)-methyl-pyrrolidin-1-y)-pyrimidin-4-yl]-3-(R)-methyl-piperazin-1-yl}-5-methyl-pyridine-2-carboxylic acid methyl ester (300 mg, 0.595 mmol) in THF, add water dropwise until the cloudiness almost persists. To this mixture add LiOH.H₂O (50 mg, 1.2 mmol). Heat the mixture at 50° C. for 2 h, and then concentrate under reduced pressure. Add a small amount of water to the residue. Adjust the final pH to 6 and collect the off-white solid via filtration. Wash the solid with water and dry to afford the title compound.

H. 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid amide

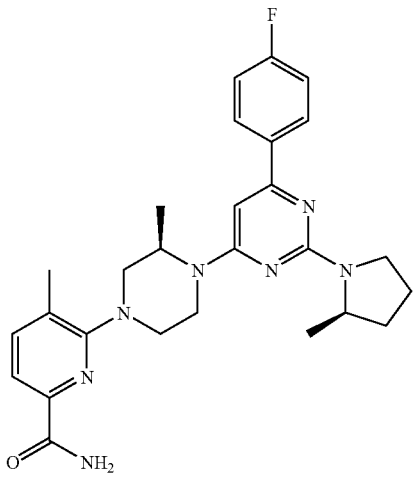

To a solution of 6-{4-[6-(4-fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid (84 mg, 0.142 mmol) in DCM, add oxalyl chloride (3 equivalents) and 1 drop of DMF. Stir the solution for 1 h at room temperature, concentrate, and dissolve in DCM. Cool the solution in an ice-bath, pass NH₃ through the solution for 15 min, and stir for 2 h at room temperature. Wash with water. Dry the solution (Na₂SO₄) and concentrate under reduced pressure. Purify the residue by flash column chromatography eluting with DCM-MeOH (9:1) to afford the title compound as an off white solid.

I. 5-Chloro-6-{4-[6-(3-chloro-4-fluoro-phenyl)-pyrimidin-4-yl]-3-(R)-methyl-piperazin-1-yl}-nicotinic acid ethyl ester 1. 5-Chloro-6-(3-(R)-methyl-piperazin-1-yl)-nicotinic acid ethyl ester

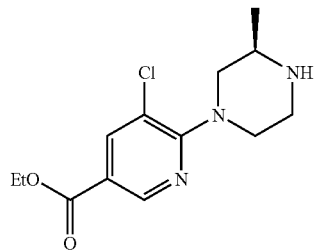

Heat a solution of (R)-2-methyl-piperazine (0.07 mol), 5,6-dichloro-nicotinic acid ethyl ester (TCI America) (10.1 g, 0.046 mol) and potassium carbonate (31.7 g, 0.23 mol) in DMA at 110° C. for 48 h. Cool the solution, and partition between EtOAc and brine. Separate the layers and extract the aqueous portion with EtOAc (1×). Wash the combined organic layers with 10% NaOH (4×), dry (Na₂SO₄), and concentrate under reduced pressure to give an oil which crystallizes on standing.

2. 5-Chloro-6-[4-(6-chloro-pyrimidin-4-yl)-3(R)-methyl-piperazin-1-yl]-nicotinic acid ethyl ester

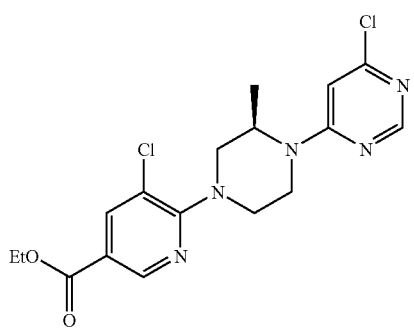

Heat a solution of 5-chloro-6-(3-(R)-methyl-piperazin-1-yl)-nicotinic acid ethyl ester (338 mg, 1.2 mmol), 4,6-dichloropyrimidine (179 mg, 1.2 mmol) and potassium carbonate (328 mg, 2.4 mmol) in DMA at 80° C. for 16 h. Partition between EtOAc and brine then separate layers and wash the organic layer with 10% NaOH (3×) followed by brine. Dry (Na₂SO₄) and concentrate under reduced pressure to give the title compound.

3. 5-Chloro-6-{4-[6-(3-chloro-4-fluoro-phenyl)-pyrimidin-4-yl]-3-(R)-methyl-piperazin-1-yl}-nicotinic acid ethyl ester

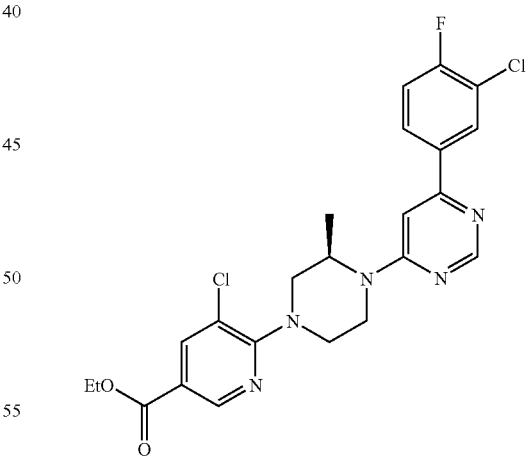

Bubble nitrogen through a mixture of 5-chloro-6-[4-(6-chloro-pyrimidin-4-yl)-3-(R)-methyl-piperazin-1-yl]-nicotinic acid ethyl ester (226 mg, 0.57 mmol), 3-chloro-4-fluorophenylboronic acid (99 mg, 0.57 mmol), K₃PO₄ (2M aqueous, 570 µL) and Pd(PPh₃)₄ (33 mg, 0.03 mmol) in dioxane for 10 mm. Heat the mixture to 80°C. for 16 h under a nitrogen atmosphere. Cool the mixture and partition between EtOAc and water. Dry (Na₂SO₄) the organic layer and concentrate under reduced pressure to yield the crude product. Purify the residue with preparative plate chromatography (2×2 mm thick) using 40% EtOAc/hexanes as the eluent to afford the title compound as a foam. ¹H NMR (400 MHz, CDCl₃): δ1.38 (m, 6H, 2 ×CH₃), 3.16 (m, 1H), 3.31 (dd, 1H, J=11 Hz), 3.51 (m, 1H), 4.12 (d, 1H, J=12.8 Hz), 4.21 (d, 1H, J=13 Hz), 4.39 (m, 3H), 4.77 (Br s, 1H), 6.82 (s, 1H), 7.25 (m, 1H), 7.89 (m, 1H), 8.07 (d, 1H, J=7 Hz), 8.18 (s, 1H), 8.71 (s, 1H), 8.79 (s, 1H).

J. 1'-[6-(3-Chloro-4-fluoro-phenyl)-2-(4-propyl-piperazin-1-yl)pyrimidin-4-yl]-3-methyl-5-nitro-1',2',3',4',5',6'-hexahydro-[2,4']bipyridinyl 1. 4-[2-Chloro-6-(3-chloro-4-fluoro-phenyl)-pyrimidin-4-yl]-piperazine-1-carboxylic acid tert-butyl ester

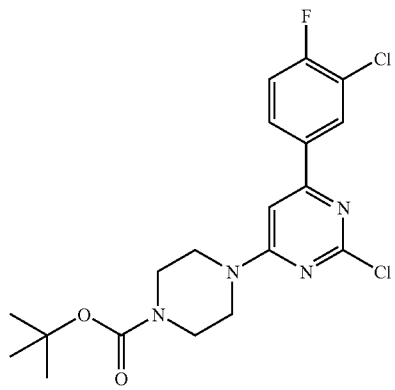

To a mixture of 2,4-dichloro-6-(3-chloro-4-fluoro-phenyl)-pyrimidine (0.12 mol) and NaHCO₃ (1.95 g, 0.023 mol) in EtOH at 0° C., add piperazine-1-carboxylic acid tert-butyl ester (0.013 mol). Remove the ice bath and stir at room temperature for 16 h. Concentrate under reduced pressure and partition between EtOAc and brine. Dry the organic layer (Na₂SO₄) and concentrate under reduced pressure to give the title compound.

2. 4-[6-(3-Chloro-4-fluoro-phenyl)-2-(4-propyl-piperazin-1-yl)-pyrimidin-4-yl]-piperazine-1-carboxylic acid tert-butyl ester

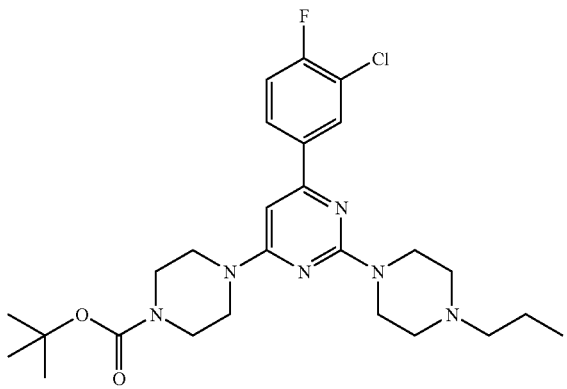

Heat a solution of 4-[2-chloro-6-(3-chloro-4-fluoro-phenyl)-pyrimidin-4-yl]-piperazine-1-carboxylic acid tert-butyl ester (2.5 g, 5.9 mmol), N-propylpiperazine (5.9 mmol) and DIEA (11.7 mmol) in DMA at 100° C. for 16 h. Cool, partition between 10% NaOH and EtOAc and wash the organic layer with additional NaOH solution (3×). Dry the organic layer (Na₂SO₄) and concentrate under reduced pressure to afford the title compound.

3. 4-(3-Chloro-4-fluoro-phenyl)-6-piperazin-1-yl-2-(4-propyl-piperazin-1-yl)-pyrimidine

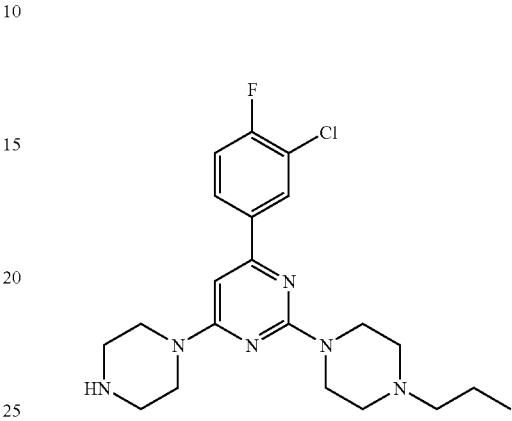

Dissolve 4-[6-(3-chloro-4-fluoro-phenyl)-2-(4-propyl-piperazin-1-yl)-pyrimidin-4-yl]-piperazine-1-carboxylic acid tert-butyl ester (2.0 g) in dioxane and then add a 4M solution of HCl in dioxane (15 mL). After the formation of precipitate stir the suspension vigorously for 2 h. Collect the solid and wash with ether and then freebase the material by partitioning between 10% NaOH solution and DCM. Separate the organic layer, dry (Na₂SO₄) and concentrate to give the title compound as an off-white solid.

4. 1'-[6-(3-Chloro-4-fluoro-phenyl)-2-(4-propyl-piperazin-1-yl)-pyrimidin-4-yl]-3-methyl-5-nitro-1',2',3',4',5',6'-hexahydro-[2,4']bipyridinyl

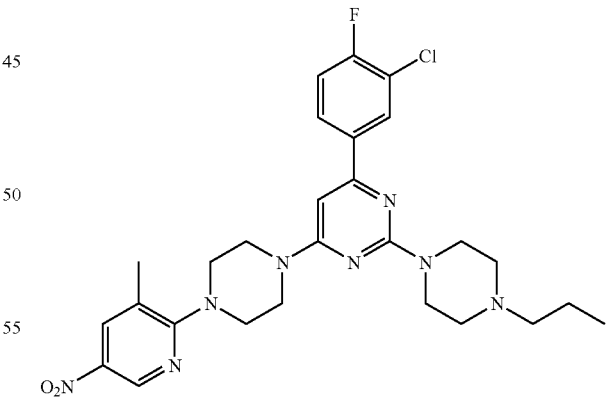

Heat a mixture of 4-(3-chloro-4-fluoro-phenyl)-6-piperazin-1-yl-2-(4-propyl-piperazin-1-yl)-pyrimidine (300 mg, 0.72 mmol), 2-chloro-3-methyl-5-nitro-pyridine (149 mg, 0.86 mmol) and DIEA (186 mg, 1.44 mmol) in DMA (4 mL) for 16 h at 110° C. Cool, partition between 10% NaOH and EtOAc and wash the organic layer with additional NaOH solution (3×). Dry the organic layer (Na₂SO₄) and concentrate under reduced pressure to afford the title compound.

K. 3'-Chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid 1. 4-[4-(4-Fluoro-phenyl)-6-(2-methyl-piperazin-1-yl)-pyrimidin-2-yl]-3-methyl-morpholine

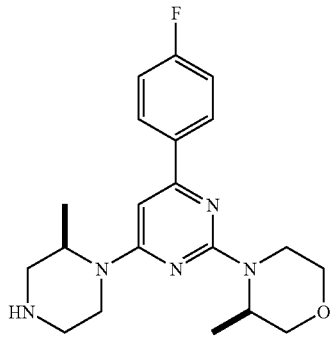

This compound is prepared using (R)-3-methylmorpholine (WO 02/064096) in a procedure analogous to that used for the preparation of 4-(4-fluoro-phenyl)-6-(2-methyl-piperazin-1-yl)-2-(2-methyl-pyrrolidin-1-yl)-pyrimidine in Example 2F step 3.

2. 6'-Amino-3'-chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid methyl ester

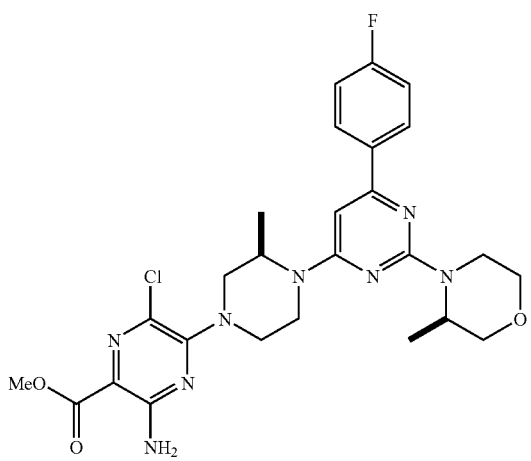

Heat a mixture of 4-[4-(4-fluoro-phenyl)-6-(2-methyl-piperazin-1-yl)-pyrimidin-2-yl]-3-(R)-methyl-morpholine with 1.1 equivalents of 3-amino-5,6-dichloro-pyrazine-2-carboxylic acid methyl ester (Cragoe et. al. *J. Med. Chem.*, 1967, 10, 66-75) in isopropanol at 85° C. for 12 h. Concentrate the mixture under reduced pressure, and then partition between 10% NaOH and EtOAc. Dry the organic layer (Na$_2$SO$_4$) and concentrate under reduced pressure to give the title compound.

3. 6'-Bromo-3'-chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid methyl ester

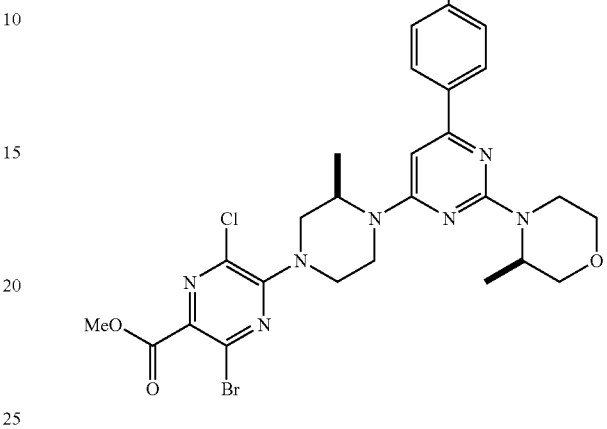

To a cooled (5° C.) and well stirred mixture of 6'-amino-3'-chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid methyl ester (10 g) in 48% HBr (75 mL) and glacial acetic acid (120 mL), add a solution (16 mL) of bromine in acetic acid (6:1) over a period of 45 min. To this mixture add a solution of NaNO$_2$ (8.3 g) in water (18 mL) while maintaining the temperature below 8° C. After the addition is complete, stir the mixture for 30 min and then destroy the excess bromine by adding 100 mL of 30% NaHSO$_3$. Neutralize the solution to pH 8 by the dropwise addition of 20% NaOH and then extract with EtOAc. Wash the organic extracts with dilute NH$_4$OH, dry (Na$_2$SO$_4$) and concentrate under reduced pressure to give the title compound.

4. 3'-Chloro-4-[6-(4-fluoro-phenyl)-2-(3-methyl-morpholin-4-yl)-pyrimidin-4-yl]-3-(R)-methyl-3,4,5,6-tetrahydro-2H-[1,2']bipyrazinyl-5'-carboxylic acid methyl ester

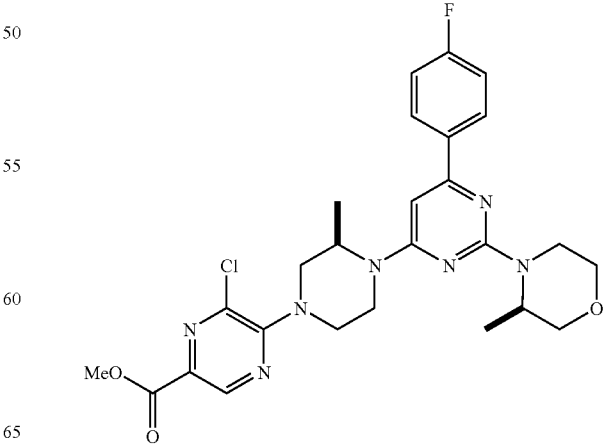

Stir a solution of 6'-bromo-3'-chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid methyl ester (3 g) in 100 mL of THF with 5% palladium on carbon (300 mg) under 1 atmosphere of hydrogen gas for several days. Filter the mixture through celite and concentrate under reduced pressure. Partition the residue between saturated NaHCO$_3$ solution and EtOAc. Dry (Na$_2$SO$_4$) the organic layer and concentrate under reduced pressure. Purify using flash column chromatography eluting with a gradient EtOAc/hexanes solvent system to give the title compound.

5. 3'-Chloro-4-[6-(4-fluoro-phenyl)-2-(3-methyl-morpholin-4-yl)-pyrimidin-4-yl]-3-(R)-methyl-3,4,5,6-tetrahydro-2H-[1,2']bipyrazinyl-5'-carboxylic acid

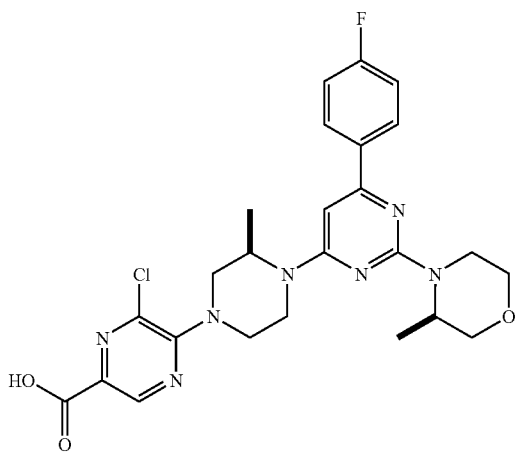

Stir a solution of 3'-chloro-4-[6-(4-fluoro-phenyl)-2-(3-(R)-methyl-morpholin-4-yl)-pyrimidin-4-yl]-3-methyl-3,4,5,6-tetrahydro-2H-[1,2']bipyrazinyl-5'-carboxylic acid methyl ester (500 mg) in a mixture of 10% NaOH (6 mL) and EtOH (20 mL) at room temperature for 16 h. Bring the mixture to pH 4 with 6 N HCl and extract the solution with EtOAc. Dry the organic layer (Na$_2$SO$_4$) and concentrate under reduced pressure to give the title compound.

L. 2-{4-[6-(3-Chloro-4-fluorophenyl-2-(2-methylpyrrolidin-1-yl)-pyrimidin-4-yl]-piperazin-1-yl}-pyrimidine-5-carboxylic acid amide 1. 2-{4-[6-(3-Chloro-4-fluorophenyl)-2-(2-methypyrrolidin-1-yl)-pyrimidin-4-yl]-piperazin-1-yl}-5-bromopyrimidine

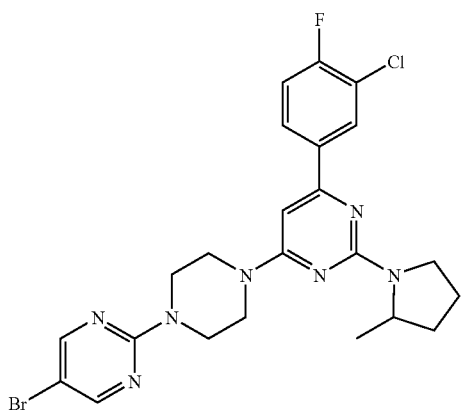

Heat a solution of 5-bromo-2-chloropyrimidine (Lancaster Chemicals, 565 mg), 4-(3-chloro-4-fluorophenyl)-2-(2-methylpyrrolidin-1-yl)-6-piperazin-1-yl-pyrimidine (1000 mg), DIEA (500 mg) and DMA (5 mL) at 110° C. for 3 h under nitrogen. Dilute with EtOAc (15 mL), wash with water (3×10 mL), dry (Na$_2$SO$_4$), and evaporate. Purify by silica gel chromatography, eluting with 1:1 hexanes:EtOAc to provide the title compound.

2. 2-{4-[6-(3-Chloro-4-fluorophenyl)-2-(2-methylpyrrolidin-1-yl)-pyrimidin-4-yl]-piperazin-1-yl}-pyrimidine-5-carbonitrile

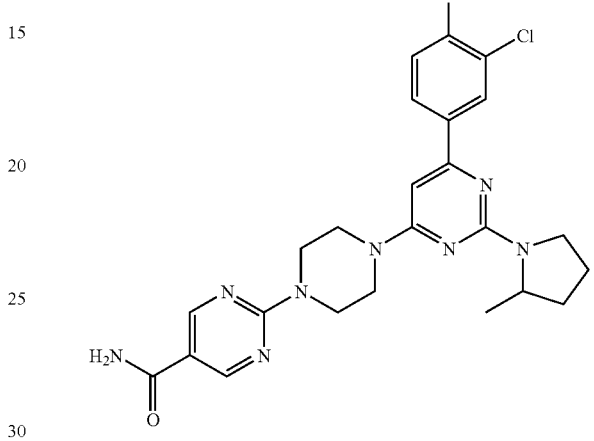

Heat a mixture of 2-{4-[6-(3-chloro-4-fluorophenyl)-2-(2-methylpyrrolidin-1-yl)-pyrimidin-4-yl]-piperazin-1-yl}-5-bromopyrimidine (478 mg) and CuCN (270 mg) in DMF at 150° C. for 16 h in a round bottom flask that is open to the air. Let cool, dilute with EtOAc (15 mL), wash with water (3×10 mL), dry (Na$_2$SO$_4$), and evaporate. Purify by silica gel chromatography, eluting with 3:1 hexanes:EtOAc to provide the title compound.

M. 6-{4-[6-(4-Fluoro-phenyl)-2-(2-(S)-methyl-pyrrolidin-1-yl)-pyrimidin-4-yl]-3-(R)-methyl-piperazin-1-yl}-5-chloro-nicotinic acid 1. 4,6-Dichloro-2-(2-(S)-methylpyrrolidin-1-yl)pyrimidine

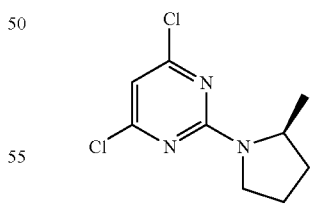

Dissolve 2,4,6-trichloropyrimidine (23.5 g, 0.13 mol) in anhydrous MeOH (220 mL), and add solid sodium bicarbonate (28.3 g, 0.33 mol). Cool to 0° C. and add 2-(S)-methylpyrrolidine (12 g, 0.14 mol) dropwise. Let stir at room temperature for 16 h. Filter off the excess sodium bicarbonate, and evaporate under reduced pressure. Purify by SiO$_2$ flash chromatography, using 50:1 hexanes:EtOAc, increasing to 30:1 hexanes:EtOAc, to provide the title compound as a white solid.

2. 4-Chloro-6-(4-fluorophenyl)-2-(2-(S)-methylpyrrolidin-1-yl)pyrimidine

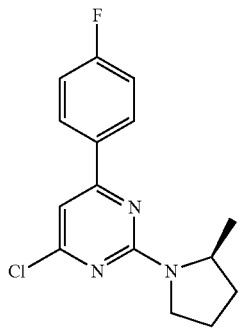

Heat a mixture of 4,6-dichloro-2-(2-(S)-methylpyrrolidin-1-yl)pyrimidine (2.25 g, 9.74 mmol), 4-fluorophenylboronic acid (10.23 mmol), Pd(PPh₃)₄ (562 mg, 0.487 mmol), and a 2M potassium phosphate solution (9.74 mL) in dioxane (35 mL) under nitrogen at 80° C. for 16 h. Evaporate the mixture and add water (50 mL). Extract with EtOAc (3×50 mL), dry (Na₂SO4), and evaporate. Purify by SiO₂ flash chromatography, eluting with 9:1 hexanes:EtOAc to provide the title compound as an oil.

3. 1-(5-Bromo-3-chloro-pyridin-2-yl)-3-(R)-methyl-piperazine

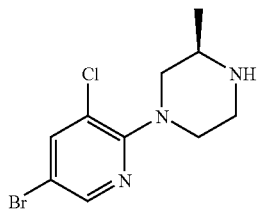

Heat a solution of 2,5-dibromo-3-chloro-pyridine (Chontech Inc.) (2.0 g) and (R)-2-methyl-piperazine (3.2 g, 31.9 mmol) in DMA at 130° C. for 16 h. Partition the reaction mixture between water and EtOAc. Wash the EtOAc layer with water (1×) and brine (1×), dry (Na₂SO₄) and concentrate under reduced pressure to give the title compound as a solid.

4. 4-[4-(5-Bromo-3-chloro-pyridin-2-yl)-2-(R)-methyl-piperazin-1-yl]-6-(4-fluoro-phenyl)-2-(2-(S)-methyl-pyrrolidin-1-yl)-pyrimidine

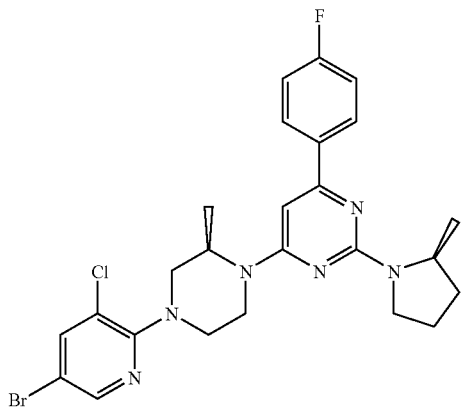

Heat a mixture of 4-chloro-6-(4-fluoro-phenyl)-2-(2-(S)-methyl-pyrrolidin-1-yl)-pyrimidine (1.30 g, 4.44 mmol), 1-(5-bromo-3-chloro-pyridin-2-yl)-3-(R)-methyl-piperazine (1.2 g), and NaHCO₃ (0.71 g, 8.46 mmol) in EtOH at 50° C. for 20 h. Concentrate under reduced pressure and partition between EtOAc and brine. Dry the organic layer (Na₂SO₄) and concentrate under reduced pressure. Purify the residue by flash column eluting with EtOAc-Hexanes (1:4) to afford the title compound as a white solid.

5. 6-{4-[6-(4-Fluoro-phenyl)-2-(2-(S)-methyl-pyrrolidin-1-yl)-pyrimidin-4-yl]-3-(R)-methyl-piperazin-1-yl}-5-chloro-nicotinonitrile

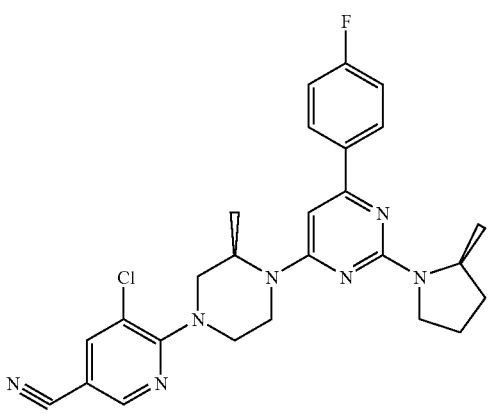

To a mixture of 4-[4-(5-bromo-3-chloro-pyridin-2-yl)-2-(R)-methyl-piperazin-1-y]-6-(4-fluoro-phenyl)-2-(2-(S)-methyl-pyrrolidin-1-yl)pyrimidine (700 mg) and Zn(CN)₂ (94 mg) in DMF, add Pd(PPh₃)₄ (77 mg, 0.067 mmol). Purge the reaction mixture for 10 min with dry N₂. Heat the stirring reaction mixture overnight at 80° C., cool to room temperature and partition between water and EtOAc. Dry the solution (Na₂SO₄), concentrate under reduced pressure. Purify the residue by flash column eluting with EtOAc-Hexanes (1:1) to afford the title compound as a white solid.

6. 6-{4-[6-(4-Fluoro-phenyl)-2-(2-(S)-methyl-pyrrolidin-1-yl)-pyrimidin-4-yl]-3-(R)-methyl-piperazin-1-yl}-5-chloro-nicotinic acid

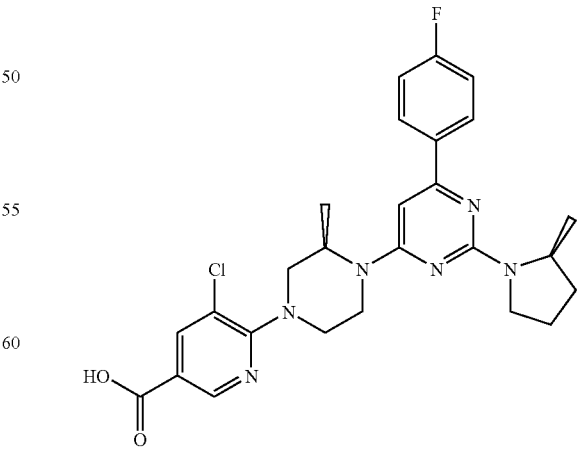

Heat a solution of 6-{4-[6-(4-fluoro-phenyl)-2-(2-(S)-methyl-pyrrolidin-1-yl)-pyrimidin-4-yl]-3-(R)-methyl-piperazin-1-yl}-5-chloro-nicotinonitrile (100 mg) in 12 M HCl for 4 h at 90° C. Concentrate the mixture under reduced pressure. Add a small amount of water, adjust the pH to 6-7, and collect the resulting white precipitate to afford the title compound as an off-white solid.

N. 2-(5-chloro-6-((R)-4-(6-(3-chloro-4-fluorophenyl)-2-((R)-2-methylpyrrolidin-1-yl)pyrimidin-4-yl)-3-methylpiperazin-1-yl)pyridin-3-yl)-N,N-dimethylethanamine 1. 2-(5-chloro-6-((R)-4-(6-(3-chloro-4-fluorophenyl)-2-((R)-2-methylpyrrolidin-1yl)pyrimidin-4-yl)-3-methylpiperazin-1-yl)pyridin-3-yl)acetonitrile

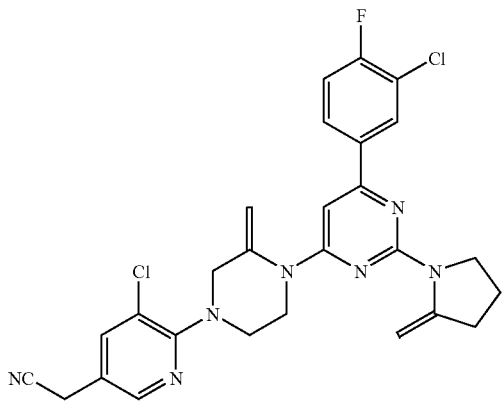

The title compound is prepared from (5-chloro-6-((R)-4-(6-(3-chloro-4-fluorophenyl)-2-((R)-2-methylpyrrolidin-1-yl)pyrimidin-4-yl)-3-methylpiperazin-1-yl)pyridin-3-yl)methanol using a procedure analogous to that used in Example 1-A1.

2. 2-(5-chloro-6-((R)-4-(6-(3-chloro-4-fluorophenyl)-2-((R)-2-methylpyrrolidin-1-yl)pyrimidin-4-yl)-3-methylpiperazin-1-yl)pyridin-3-yl)acetaldehyde

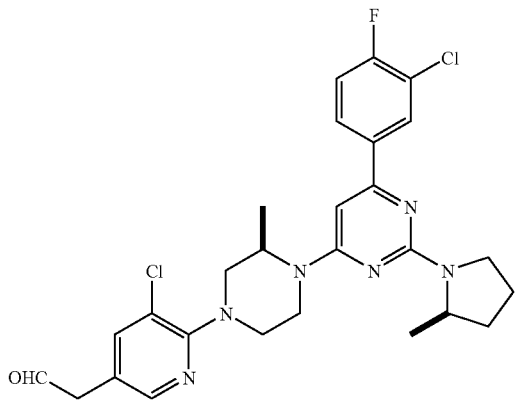

Add a solution of diisobutylaluminum hydride (1M in hexane, 333 μL) to a stirring solution of 2-(5-chloro-6-((R)-4-(6-(3-chloro-4-fluorophenyl)-2-((R)-2-methylpyrrolidin-1-yl)pyrimidin-4-yl)-3-methylpiperazin-1-yl)pyridin-3-yl)acetonitrile (120 mg, 0.22 mmol) in dichloromethane at −78° C. over a period of 10 min. When starting material is consumed, add an excess of Na$_2$SO$_4$.10H$_2$O and stir for 1 h while bringing the reaction mixture to ambient temperature. Filter the mixture through celite washing with DCM. Concentrate under reduced pressure and use without further purification.

3. 2-(5-chloro-6-((R)-4-(6-(3-chloro-4-fluorophenyl)-2-((R)-2-methylpyrrolidin-1-yl)pytimidin-4-yl)-3-methylpiperazin-1-yl)pyridin-3-yl)-N,N-dimethylethanamine

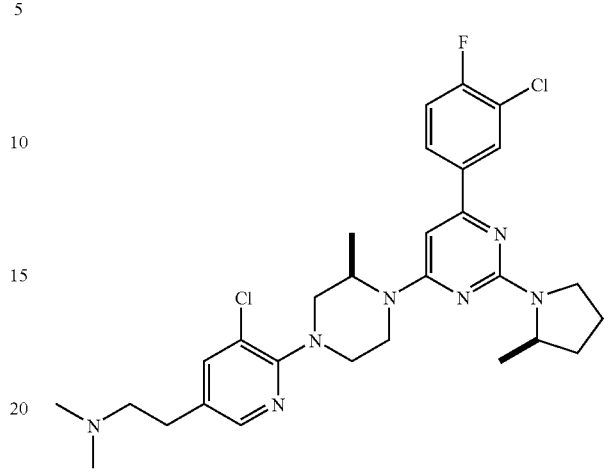

To a solution of 2-(5-chloro-6-((R)-4-(6-(3-chloro-4-fluorophenyl)-2-((R)-2-methylpyrrolidin-1-yl)pyrimidin-4-yl)-3-methylpiperazin-1-yl)pyridin-3-yl)acetaldehyde (64 mg, 0.118 mmol) in DCE, add dimethylamine (3.87M in THF, 40 μL) followed by 1 drop of HOAc. Stir the mixture overnight, and then dilute with DCM and wash (2×) with 10% NaOH solution. Concentrate under reduced pressure and add EtOAc, followed by a solution of HCl in ether. Concentrate and triturate the hydrochloride salt with fresh EtOAc to afford the title compound. $^1$H NMR (400 MHz, CDCl$_3$): δ1.31 (d, 3H, J=6.23 Hz, CH$_3$), 1.39 (d, 3H, J=6.6 Hz, CH3), 1.68 (m, 1H), 1.91 (m, 1H), 2.05 (m, 5H), 2.68 (s, 6H, N(CH$_3$)$_2$), 2.9-3.1 (m, 4H), 3.65 (m, 1H), 3.63-3.9 (m, 4H), 4.34 (m, 2H), 4.67 (br s, 1H), 6.20 (s, 1H), 7.18 (t, 1H), 7.55 (s, 1H), 7.88 (m, 1H), 8.06 (s, 2H).

4. 2-(5-chloro-6-((R)-4-(6-(3-chloro-4-fluorophenyl)-5-fluoro-2-((R)-2-methylpyrrolidin-1-yl)pyrimidin-4-yl)-3-methylpiperazin-1-yl)pyridin-3-yl)-N,N-dimethylethanamine

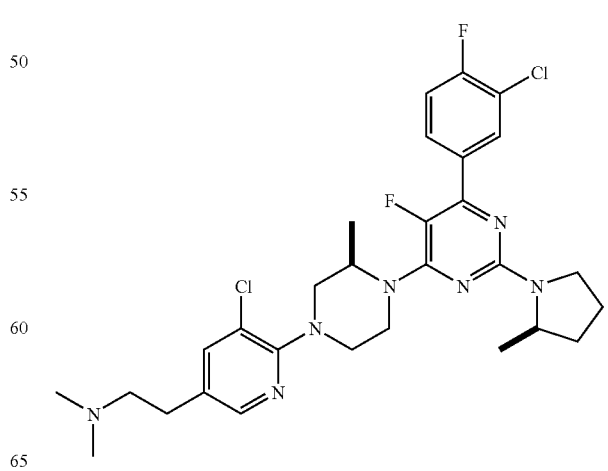

To a solution of 2-(5-chloro-6-((R)-4-(6-(3-chloro-4-fluorophenyl)-2-((R)-2-methylpyrrolidin-1-yl)pyrimidin-4-yl)-3-methylpiperazin-)1-yl)pyridin-3-yl)-N,N-dimethylethanamine (50 mg, 0.087 mmol) in acetonitrile, add SELECTFLUOR® (93 mg, 0.26 mmol). Heat the mixture at 150° C. for 10 min in microwave reactor, cool to room temperature, concentrate, and partition between EtOAc and saturated NaHCO₃ solution. Concentrate under reduced pressure and purify with flash chromatography to afford the title compound.

O. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid 1. 1-(5-Bromo-3-methyl-pyridin-2-yl)-3-(R)-methyl-piperazine

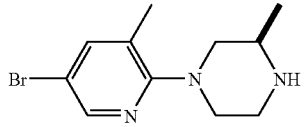

Heat a solution of 2,5-dibromo-3-methyl-pyridine (Chontech Inc., Waterford, Conn.) (2.0 g, 7.97 mmol), (R)-2-methyl-piperazine (ChemPacific Corp., Baltimore, Md.; 3.2 g, 31.9 mmol) in DMA at 130° C. for 16 h. Partition the reaction mixture between water and EtOAc. Wash the EtOAc layer with water (1×) and brine (1×), dry (Na₂SO₄) and concentrate under reduced pressure to give 1-(5-bromo-3-methyl-pyridin-2-yl)-3-(R)-methyl-piperazine as a solid.

2. 2,4-dichloro-6-(4-fluorophenyl)pyrimidine

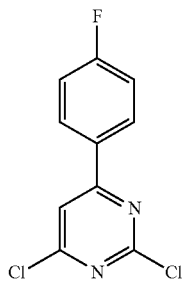

Dissolve 4-fluorobromobenzene (8.75 g, 0.05 moles) in anhydrous ether (80 mL) under nitrogen atmosphere and cool to −78° C. Add dropwise 1.6 M n-BuLi (34 mL, 0.055 moles) and stir at −78° C. for 45 min. Dissolve 2,4-dichloropyrimidine (7.45 g, 0.05 moles) in Et₂O (100 mL) and add dropwise to the reaction mixture. Warm the reaction mixture to −30° C. and stir at this temperature for 30 min followed by 0° C. for 30 min. Quench the reaction mixture with AcOH (3.15 mL, 0.055 moles) and water (0.5 mL, 0.027 moles) dissolved in THF (5.0 mL). Add dropwise a THF (40 mL) solution of DDQ (11.9 g, 0.053 moles) to the reaction mixture. Bring the reaction mixture to room temperature and stir at room temperature for 30 min. Cool the reaction mixture to 0° C., add 3.0 N aq. NaOH (35 mL) and stir for 30 min. Decant the organic layer from the reaction mixture and wash the brown solid with Et₂O (3×100 mL). Combine the organic layers, wash several times with saturated NaCl solution and dry with MgSO₄. Filter and evaporate under vacuum to afford a brown colored solid. Purify by flash column chromatography using 5% EtOAc/hexane to afford the title product as a white solid.

3. 4-[4-(5-Bromo-3-methyl-pyridin-2-yl)-2-(R)-methyl-piperazin-1-yl]-2-chloro-6-(4-fluoro-phenyl)-pyrimidine

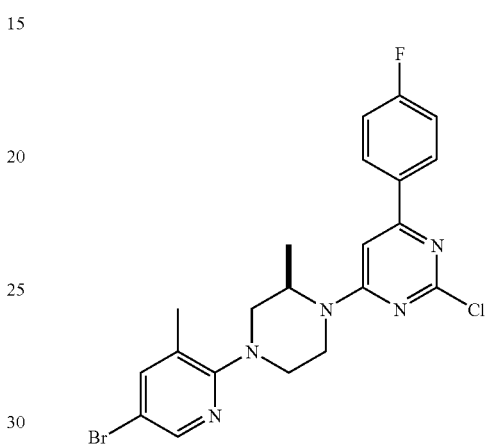

Heat a mixture of 2,4-dichloro-6-(4-fluoro-phenyl)-pyrimidine (6.0 g, 24.7 mmol), 1-(5-bromo-3-methyl-pyridin-2-yl)-3-(R)-methyl-piperazine (7.0 g, 25.9 mmol) and K₂CO₃ (6.8 g, 49.4 mmol) in DMA at 60° C. for 16 h. Partition the mixture between EtOAc and water, dry (Na₂SO₄) the organic layer and concentrate under reduced pressure. Purify with flash silica gel column eluting with 15% EtOAc/hexanes. Concentrate under reduced pressure to give the title compound.

4. 4-[4-(5-Bromo-3-methyl-pyridin-2-yl)-2-(R)-methyl-piperazin-1-yl]-6-(4-fluoro-phenyl)-2-(2-(R)-methyl-pyrrolidin-1-yl)-pyrimidine

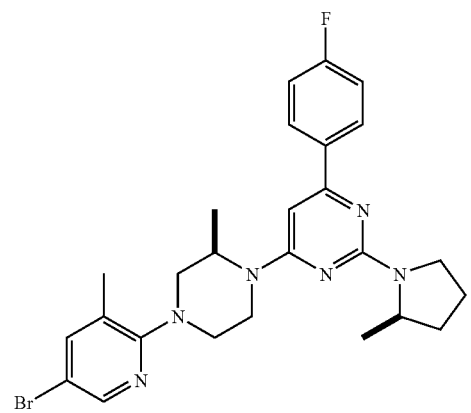

Heat a mixture of 4-[4-(5-bromo-3-methyl-pyridin-2-yl)-2-(R)-methyl-piperazin-1-yl]-2-chloro-6-(4-fluoro-phenyl)-pyrimidine (7.7 g, 16.2 mmol), (R)-2-methylpyrrolidine hydrobromide [prepared essentially as described by Nijhuis et. al. (1989) *J. Org. Chem.* 54(1):209] (3.5 g, 21.1 mmol) and K$_2$CO$_3$ (5.1 g, 37.3 mmol) in DMA at 110° C. for 16 h. Partition the mixture between EtOAc and water, dry (Na$_2$SO$_4$) the organic layer and concentrate under reduced pressure. Purify with flash silica gel column eluting with 10% EtOAc/hexanes. Concentrate under reduced pressure to give the title compound.

5. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinonitrile

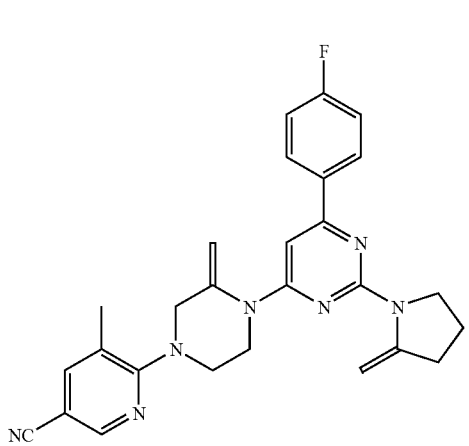

To a mixture of 4-[4-(5-bromo-3-methyl-pyridin-2-yl)-2-(R)-methyl-piperazin-1-yl]-6-(4-fluoro-phenyl)-2-(2-methyl-pyrrolidin-1-yl)-pyrimidine (700 mg, 1.33 mmol) and Zn(CN)$_2$ (94 mg, 0.799 mmol) in DMF, add Pd(PPh$_3$)$_4$ (77 mg, 0.067 mmol). Purge the reaction mixture for 10 min with dry N$_2$. Heat the stirring reaction mixture overnight at 80° C., cool to room temperature and partition between water and EtOAc. Dry the solution (Na$_2$SO$_4$), concentrate under reduced pressure. Purify the residue by flash column eluting with EtOAc-Hexanes (1:1) to afford the title compound as a white solid.

6. 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid

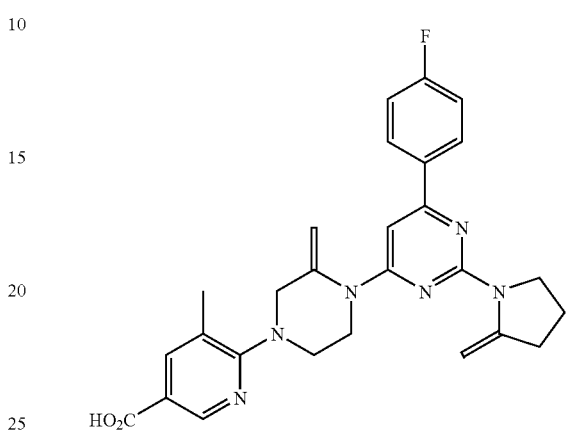

Heat a solution of 6-{4-[6-(4-fluoro-phenyl)-2-(2-methyl-pyrrolidin-1-yl)-pyrimidin-4-yl]-3-(R)-methyl-piperazin-1-yl}-5-methyl-nicotinonitrile (100 mg, 0.212 mmol) in 12 M HCl for 3 hours at 90° C. Concentrate the mixture under reduced pressure. Add a small amount of water, adjust the pH to 6-7, and collect the resulting white precipitate to afford the title compound as a off-white solid. $^1$H NMR (300 MHz, DMSO-d$_6$): δ 1.24 (m, 6H, 2×CH$_3$)); 1.61 (m, 1H,); 1.84 (m, 1H); 1.98 (m, 2H); 2.34 (s, 3H, Ar—CH$_3$); 2.91 (m, 1H); 3.08 (m, 1H); 3.26 (m, 2H); 3.56 (m, 2H); 3.74 (m, 1H); 4.21 (m, 1H); 4.35 (m, 1H); 4.74 (m, 1H); 6.57 (s, 1H); 7.26 (m, 2H); 7.91 (d, 1H, J=3 Hz); 8.15 (m, 2H); 8.60 (d, 1H, J=3 Hz).

Example 3

Additional Representative Substituted Biaryl Piperazinyl-Pyridine Analogues

Using routine modifications, the starting materials may be varied and additional steps employed to produce other compounds provided herein. Compounds listed in Tables I and II are prepared using such methods. A "*" in the column labeled "IC$_{50}$" in Table I indicates that the IC$_{50}$ determined as described in Example 6 is 1 micromolar or less. Mass spectroscopy data (column labeled "MS") in Table I is obtained as described above and is provided as M+1. Retention times are presented in min.

TABLE I

Representative Substituted Biaryl Piperazinyl-Pyridine Analogues

| Compound | Name | IC$_{50}$ | Ret. Time | MS (M + 1) |
|---|---|---|---|---|
| 1 | 2-{4-[6-(3-Chloro-4-fluoro-phenyl)-2-morpholin-4-yl-pyrimidin-4-yl]-piperazin-1-yl}-nicotinic acid ethyl ester | * | 1.27 | 527.30 |
| 2 | 2-{4-[6-(3-Chloro-4-fluoro-phenyl)-2-morpholin-4-yl-pyrimidin-4-yl]-piperazin-1-yl}-nicotinamide | * | 1.14 | 498.29 |
| 3 | 2-{4-[6-(3-Chloro-4-fluoro-phenyl)-2-morpholin-4-yl-pyrimidin-4-yl]-piperazin-1-yl}-nicotinic acid | * | 1.17 | 499.28 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 4 | 4-{4-(3-Chloro-4-fluoro-phenyl)-6-[4-(3-nitro-pyridin-2-yl)-piperazin-1-yl]-pyrimidin-2-yl}-morpholine | * | 1.26 | 500.27 |
| 5 | 4-(3-Chloro-4-fluoro-phenyl)-6-[4-(3-methyl-5-nitro-pyridin-2-yl)-piperazin-1-yl]-2-(2-methyl-pyrrolidin-1-yl)-pyrimidine | * | 1.26 | 512.36 |
| 6 | [2-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yloxy)-ethyl]-dimethyl-amine | * | 1.14 | 554.47 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 7 | 3-Chloro-2-{4-[6-(3-chloro-4-fluoro-phenyl)-2-(2-methyl-pyrrolidin-1-yl)-pyrimidin-4-yl]-piperazin-1-yl}-isonicotinic acid | * | 1.22 | 531.33 |
| 8 | 5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid methyl ester | * | 1.31 | 559.19 |
| 9 | 5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid | * | 1.27 | 545.17 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 10 | (5-Chloro-6-{4-[6-(3-chloro-4-fluoro-phenyl)-2-(2-methyl-pyrrolidin-1-yl)-pyrimidin-4-yl]-piperazin-1-yl}-pyridin-3-yl)-methanol | * | 1.23 | 517.18 |
| 11 | (5-Chloro-6-{4-[6-(3-chloro-4-fluoro-phenyl)-2-(2-methyl-pyrrolidin-1-yl)-pyrimidin-4-yl]-piperazin-1-yl}-pyridin-3-ylmethyl)-methyl-amine | * | 1.16 | 530.23 |
| 12 | C-{5-Chloro-6-{4-[6-(3-chloro-4-fluoro-phenyl)-2-(2-methyl-pyrrolidin-1-yl)-pyrimidin-4-yl]-piperazin-1-yl}-pyridin-3-yl)-methylamine | * | 1.15 | 516.20 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 13 | (5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-pyridin-3-yl)-methanol | * | 1.25 | 531.21 |
| 14 | 4-(3-Chloro-4-fluoro-phenyl)-6-[4-(3-methyl-5-nitro-pyridin-2-yl)-piperazin-1-yl]-2-(4-propyl-piperazin-1-yl)-pyrimidine | * | 1.26 | 555.26 |
| 15 | 5-Chloro-6-{4-[6-(3-chloro-4-fluoro-phenyl)-2-(2-methyl-pyrrolidin-1-yl)-pyrimidin-4-yl]-piperazin-1-yl}-nicotinamide | * | 1.22 | 530.19 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 16 | (5-Chloro-6-{4-[6-(3-chloro-4-fluoro-phenyl)-2-(4-propyl-piperazin-1-yl)-pyrimidin-4-yl]-piperazin-1-yl}-pyridin-3-yl)-methanol | * | 1.23 | 560.24 |
| 17 | 5-Chloro-6-{4-[6-(3-chloro-4-fluoro-phenyl)-2-(4-propyl-piperazin-1-yl)-pyrimidin-4-yl]-piperazin-1-yl}-nicotinic acid | * | 1.26 | 574.19 |
| 18 | 5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid ethyl ester | * | 1.33 | 573.22 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 19 | (5-Chloro-6-{4-[6-(3-chloro-4-fluoro-phenyl)-2-(2-methyl-pyrrolidin-1-yl)-pyrimidin-4-yl]-piperazin-1-yl}-pyridin-3-ylmethyl)-dimethyl-amine | * | 1.15 | 544.24 |
| 20 | 5-Chloro-6-{4-[6-(3-chloro-4-fluoro-phenyl)-2-(2-methyl-pyrrolidin-1-yl)-pyrimidin-4-yl]-piperazin-1-yl)-nicotinic acid methyl ester | * | 1.29 | 545.20 |
| 21 | 5-Chloro-6-{4-[6-(3-chloro-4-fluoro-phenyl)-2-(2-methyl-pyrrolidin-1-yl)-pyrimidin-4-yl]-piperazin-1-yl}-nicotinic acid | * | 1.26 | 531.21 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 22 | 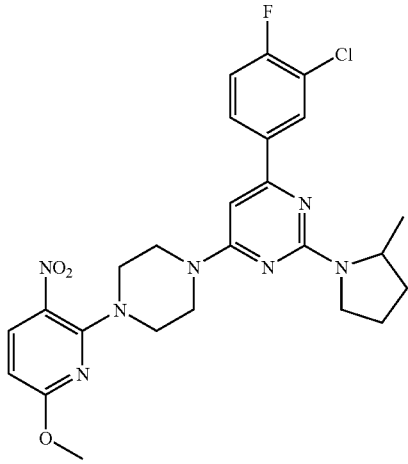 | 4-(3-Chloro-4-fluoro-phenyl)-6-[4-(6-methoxy-3-nitro-pyridin-2-yl)-piperazin-1-yl]-2-(2-methyl-pyrrolidin-1-yl)-pyrimidine | * | 1.26 | 528.21 |
| 23 | 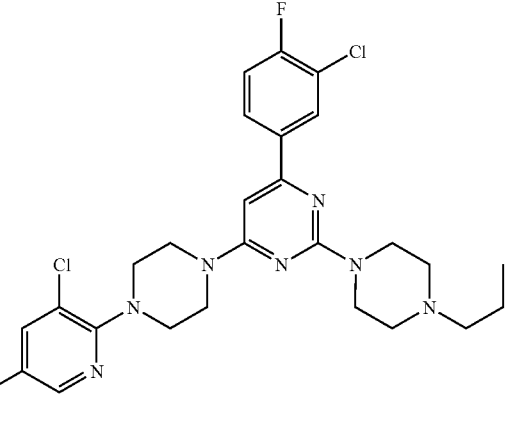 | 5-Chloro-6-{4-[6-(3-chloro-4-fluoro-phenyl)-2-(4-propyl-piperazin-1-yl)-pyrimidin-4-yl]-piperazin-1-yl}-nicotinic acid ethyl ester | * | 1.32 | 602.26 |
| 24 | 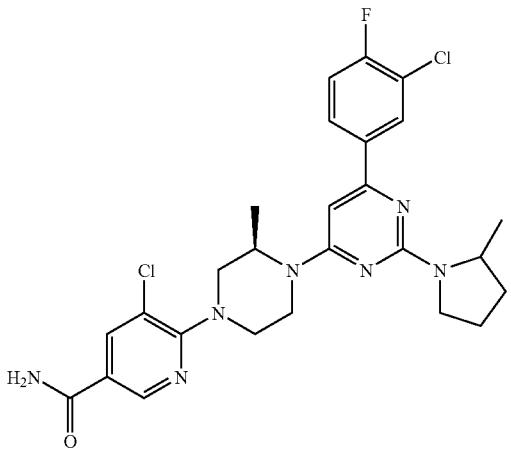 | 5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinamide | * | 1.24 | 544.19 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 25 | 5-Chloro-6-{4-[6-(4-fluoro-phenyl)-2-(2-methyl-pyrrolidin-1-yl)-pyrimidin-4-yl]-piperazin-1-yl}-nicotinic acid | * | 1.23 | 497.22 |
| 26 | (5-Chloro-6-{4-[6-(4-fluoro-phenyl)-2-(2-methyl-pyrrolidin-1-yl)-pyrimidin-4-yl]-piperazin-1-yl}-pyridin-3-yl)-methanol | * | 1.2 | 483.23 |
| 27 | 5-Chloro-6-{4-[6-(4-fluoro-phenyl)-2-(2-methyl-pyrrolidin-1-yl)-pyrimidin-4-yl]-3-(R)-methyl-piperazin-1-yl}-nicotinic acid ethyl ester | * | 1.28 | 539.30 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 28 | | 5-Chloro-6-{4-[6-(4-fluoro-phenyl)-2-pyrrolidin-1-yl-pyrimidin-4-yl]-3-(R)-methyl-piperazin-1-yl}-nicotinic acid ethyl ester | * | 1.28 | 525.27 |
| 29 | | 5-Chloro-6-{4-[6-(4-fluoro-phenyl)-2-(2-methyl-pyrrolidin-1-yl)-pyrimidin-4-yl]-3-(R)-methyl-piperazin-1-yl}-nicotinic acid | * | 1.23 | 511.27 |
| 30 | | 5-Chloro-6-{4-[6-(4-fluoro-phenyl)-2-pyrrolidin-1-yl-pyrimidin-4-yl]-3-(R)-methyl-piperazin-1-yl}-nicotinic acid | * | 1.22 | 497.25 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 31 | (5-Chloro-6-{4-[6-(4-fluoro-phenyl)-2-(2-methyl-pyrrolidin-1-yl)-pyrimidin-4-yl]-3-(R)-methyl-piperazin-1-yl}-pyridin-3-yl)-methanol | * | 1.21 | 497.28 |
| 32 | (5-Cloro-6-{4-[6-(4-fluoro-phenyl)-2-pyrrolidin-1-yl-pyrimidin-4-yl]-3-(R)-methyl-piperazin-1-yl}-pyridin-3-yl)-methanol | * | 1.19 | 483.26 |
| 33 | 5-Chloro-6-{4-{6-(4-fluoro-phenyl)-2-(2-methyl-pyrrolidin-1-yl)-pyrimidin-4-yl]-3-(R)-methyl-piperazin-1-yl}-nicotinamide | * | 1.2 | 510.28 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 34 | | 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid | * | 1.2 | 491.31 |
| 35 | | 5-Chloro-6-{4-[6-(4-fluoro-phenyl)-2-pyrrolidin-1-yl-pyrimidin-4-yl]-3-(R)-methyl-piperazin-1-yl}-nicotinamide | | | |
| 36 | | 6-{4-[6-(4-Fluoro-phenyl)-2-(2-methyl-pyrrolidin-1-yl)-pyrimidin-4-yl]-piperazin-1-yl}-5-methyl-nicotinic acid | * | 1.18 | 477.30 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 37 | (6-{4-[6-(4-Fluoro-phenyl)-2-(2-methyl-pyrrolidin-1-yl)-pyrimidin-4-yl]-3-(R)-methyl-piperazin-1-yl}-5-methyl-pyriddin-3-yl)-methanol | * | 1.13 | 477.34 |
| 39 | (5-Chloro-6-{4-[6-(4-fluoro-phenyl)-2-(2-methyl-pyrrolidin-1-yl)-pyrimidin-4-yl]-piperazin-1-yl}-pyridin-3-yl)-acetic acid | * | 1.21 | 511.26 |
| 40 | 5-Chloro-6-{4-[6-(4-fluoro-phenyl)-2-(2-methyl-pyrrolidin-1-yl)-pyrimidin-4-yl]-piperazin-1-yl}-nicotinamide | * | 1.18 | 496.26 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 41 | 5-Chloro-6-{3-(R)-methyl-4-[2-(2-methyl-pyrrolidin-1-yl)-6-phenyl-pyrimidin-4-yl]-piperazin-1-yl}-nicotinic acid ethyl ester | * | 1.31 | 521.31 |
| 42 | 5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-nicotinic acid ethyl ester | * | 1.34 | 556.28 |
| 43 | 5-Chloro-6-{4-[6-(2-isopropyl-pyridin-4-yl)-2-(2-methyl-pyrrolidin-1-yl)-pyrimidin-4-yl]-3-yl}-nicotinic acid ethyl ester | * | 1.34 | 564.36 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 44 | 6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinamide | * | 1.17 | 490.34 |
| 45 | 6-{4-[6-(4-Fluoro-phenyl)-2-(2-methyl-pyrrolidin-1-yl)-pyrimidin-4-yl]-piperazin-1-yl}-5-methyl-nicotinamide | * | 1.15 | 476.32 |
| 46 | 5-Chloro-6-{3-(R)-methyl-4-[2-(2-methyl-pyrrolidin-1-yl)-6-m-tolyl-pyrimidin-4-yl]-piperazin-1-yl}-nicotinic acid ethyl ester | * | 1.3 | 535.30 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 47 | 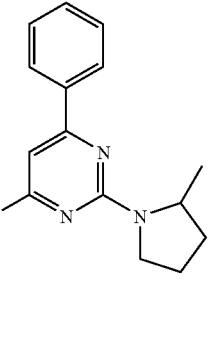 | (5-Chloro-6-{3-(R)-methyl-4-[2-(2-methyl-pyrrolidin-1-yl)-6-phenyl-pyrimidin-4-yl]-piperazin-1-yl}-pyridin-3-yl)-methanol | * | 1.23 | 479.26 |
| 48 | 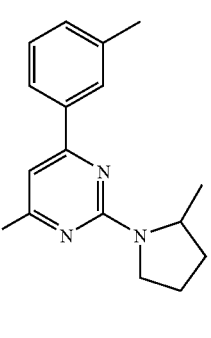 | (5-Chloro-6-{3-(R)-methyl-4-[2-(2-methyl-pyrrolidin-1-yl)-6-m-tolyl-pyrimidin-4-yl]-piperazin-1-yl}-pyridin-3-yl)-methanol | * | 1.25 | 493.27 |
| 49 | 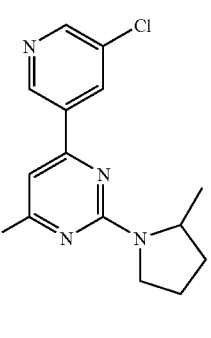 | (5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-pyridin-3-yl)-methanol | * | 1.24 | 514.22 |
| 50 | 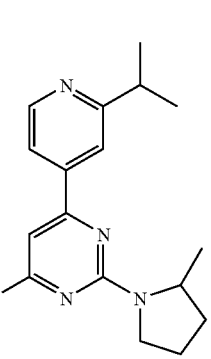 | (5-Chloro-6-{4-[6-(2-isopropyl-pyridin-4-yl)-2-(2-methyl-pyrrolidin-1-yl)-pyrimidin-4-yl]-3-(R)-methyl-piperazin-1-yl}-pyridin-3-yl)-methanol | * | 1.24 | 522.31 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 51 | 5-Chloro-6-{3-(R)-methyl-4-[2-(2-methyl-pyrrolidin-1-yl)-6-m-tolyl-pyrimidin-4-yl]-piperazin-1-yl}-nicotinic acid | * | 1.27 | 507.25 |
| 52 | 5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-nicotinic acid | * | 1.28 | 528.20 |
| 53 | 5-Chloro-6-{4-[6-(2-isopropyl-pyridin-4-yl)-2-(2-methyl-pyrrolidin-1-yl)-pyrimidin-4-yl]-3-(R)-methyl-piperazin-1-yl}-nicotinic acid | * | 1.28 | 536.28 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 54 | 5-Methyl-6-{4-[2-(2-methyl-pyrrolidin-1-yl)-6-phenyl-pyrimidin-4-yl]-piperazin-1-yl}-nicotinic acid ethyl ester | * | 1.26 | 487.30 |
| 55 | 5-Methyl-6-{4-[2-(2-methyl-pyrrolidin-1-yl)-6-m-tolyl-pyrimidin-4-yl]-piperazin-1-yl}-nicotinic acid ethyl ester | * | 1.28 | 501.31 |
| 56 | 5-Methyl-6-{4-[2-(2-methyl-pyrrolidin-1-yl)-6-pyridin-4-yl-pyrimidin-4-yl]-piperazin-1-yl}-nicotinic acid ethyl ester | * | 1.24 | 488.31 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 57 | | 6-{4-[6-(2-Isopropyl-pyridin-4-yl)-2-(2-methyl-pyrrolidin-1-yl)-pyrimidin-4-yl]-piperazin-1-yl}-5-methyl-nicotinic acid ethyl ester | * | 1.29 | 530.36 |
| 58 | | 5-Methyl-6-{3-(R)-methyl-4-[2-(2-methyl-pyrrolidin-1-yl)-6-phenyl-pyrimidin-4-yl]-piperazin-1-yl}-nicotinic acid ethyl ester | * | 1.27 | 501.31 |
| 59 | | 5-Methyl-6-{3-(R)-methyl-4-[2-(2-methyl-pyrrolidin-1-yl)-6-m-tolyl-pyrimidin-4-yl]-piperazin-1-yl}-nicotinic acid ethyl ester | * | 1.29 | 515.32 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 60 | 5-Methyl-6-{3-(R)-methyl-4-[2-(2-methyl-pyrrolidin-1-yl)-6-pyridin-4-yl-pyrimidin-4-yl]-piperazin-1-yl}-nicotinic acid ethyl ester | * | 1.26 | 502.32 |
| 61 | 6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-nicotinic acid ethyl ester | * | 1.3 | 544.36 |
| 62 | 6-{4-[2-Dimethylamino-6-(4-fluoro-phenyl)-pyrimidin-4-yl]-3-(R)-methyl-piperazin-1-yl}-5-methyl-nicotinic acid ethyl ester | * | 1.24 | 479.30 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 63 | | (5-Methyl-6-{3-(R)-methyl-4-[2-(2-methyl-pyrrolidin-1-yl)-6-phenyl-pyrimidin-4-yl]-piperazin-1-yl}-pyridin-3-yl)-methanol | * | 1.13 | 459.31 |
| 64 | | (5-Methyl-6-{3-(R)-methyl-4-[2-(2-methyl-pyrrolidin-1-yl)-6-m-tolyl-pyrimidin-4-yl]-piperazin-1-yl}-pyridin-3-yl)-methanol | * | 1.17 | 473.33 |
| 65 | | (5-Methyl-6-{3-(R)-methyl-4-[2-(2-methyl-pyrrolidin-1-yl)-6-pyridin-4-yl-pyrimidin-4-yl]-piperazin-1-yl}-pyridin-3-yl)-methanol | * | 1.1 | 460.32 |
| 66 | | (6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-pyridin-3-yl)-methanol | * | 1.16 | 502.34 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 67 | (6-{4-[2-Dimethylamino-6-(4-fluoro-phenyl)-pyrimidin-4-yl]-3-(R)-methyl-piperazin-1-yl}-5-methyl-pyridin-3-yl)-methanol | * | 1.09 | 437.28 |
| 68 | 5-Methyl-6-{3-(R)-methyl-4-[2-(2-methyl-pyrrolidin-1-yl)-6-phenyl-pyrimidin-4-yl]-piperazin-1-yl}-nicotinic acid | * | 1.22 | 473.30 |
| 69 | 5-Methyl-6-{3-(R)-methyl-4-[2-(2-methyl-pyrrolidin-1-yl)-6-m-tolyl-pyrimidin-4-yl]-piperazin-1-yl}-nicotinic acid | * | 1.24 | 487.32 |

TABLE I-continued

Representative Substituted Biaryl Piperazinyl-Pyridine Analogues

| | Compound | Name | IC$_{50}$ | Ret. Time | MS (M + 1) |
|---|---|---|---|---|---|
| 70 | | 5-Methyl-6-{3-(R)-methyl-4-[2-(2-methyl-pyrrolidin-1-yl)-6-pyridin-4-yl-pyrimidin-4-yl]-piperazin-1-yl}-nicotinic acid | * | 1.2 | 474.31 |
| 71 | | (5-Methyl-6-{4-[2-(2-methyl-pyrrolidin-1-yl)-6-phenyl-pyrimidin-4-yl]-piperazin-1-yl}-pyridin-3-yl)-methanol | * | 1.07 | 445.31 |
| 72 | | (5-Methyl-6-{4-[2-(2-methyl-pyrrolidin-1-yl)-6-m-tolyl-pyrimidin-4-yl]-piperazin-1-yl}-pyridin-3-yl)-methanol | * | 1.10 | 459.33 |
| 73 | | (5-Methyl-6-{4-[2-(2-methyl-pyrrolidin-1-yl)-6-pyridin-4-yl-pyrimidin-4-yl]-piperazin-1-yl}-pyridin-3-yl)-methanol | * | 1.03 | 446.32 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 74 | 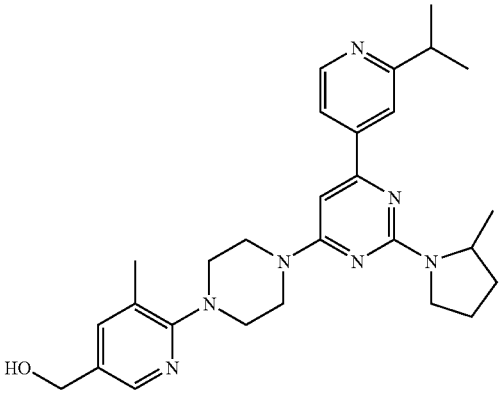 | (6-{4-[6-(2-Isopropyl-pyridin-4-yl)-2-(2-methyl-pyrrolidin-1-yl)-pyrimidin-4-yl]-piperazin-1-yl}-5-methyl-pyridin-3-yl)-methanol | * | 1.09 | 488.39 |
| 75 | 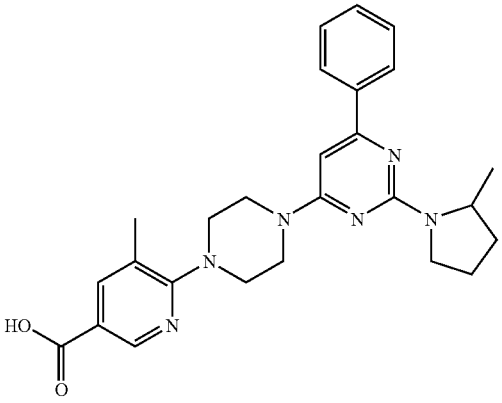 | 5-Methyl-6-{4-[2-(2-methyl-pyrrolidin-1-yl)-6-phenyl-pyrimidin-4-yl]-piperazin-1-yl}-nicotinic acid | * | 1.2 | 459.29 |
| 76 | 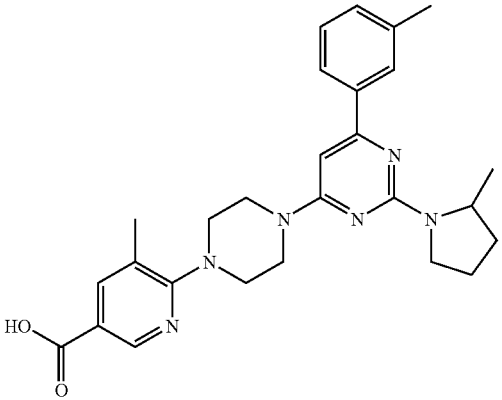 | 5-Methyl-6-{4-[2-(2-methyl-pyrrolidin-1-yl)-6-m-tolyl-pyrimidin-4-yl]-piperazin-1-yl}-nicotinic acid | * | 1.22 | 473.29 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 77 | | 5-Methyl-6-{4-[2-(2-methyl-pyrrolidin-1-yl)-6-pyridin-4-yl-pyrimidin-4-yl]-piperazin-1-yl}-nicotinic acid | * | 1.17 | 460.29 |
| 78 | | 6-{4-[6-(2-Isopropyl-pyridin-4-yl)-2-(2-methyl-pyrrolidin-1-yl)-pyrimidin-4-yl]-piperazin-1-yl}-5-methyl-nicotinic acid | * | 1.22 | 502.32 |
| 79 | | 5-Chloro-6-{4-[6-(3-chloro-4-fluoro-phenyl)-pyrimidin-4-yl]-3-(R)-methyl-piperazin-1-yl}-nicotinic acid ethyl ester | * | 1.34 | 490.17 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 80 | 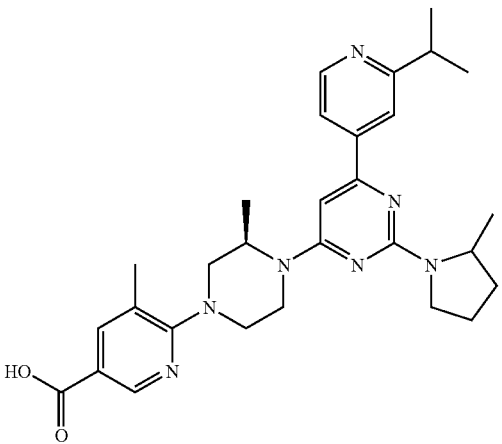 | 6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-nicotinic acid | * | 1.24 | 516.35 |
| 81 | 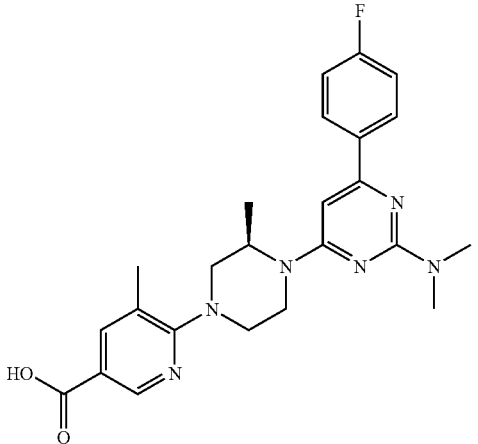 | 6-{4-[2-Dimethylamino-6-(4-fluoro-phenyl)-pyrimidin-4-yl]-3-(R)-methyl-piperazin-1-yl}-5-methyl-nicotinic acid | * | 1.18 | 451.27 |
| 82 | 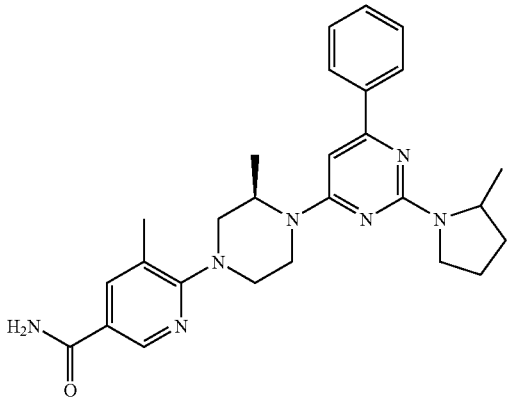 | 5-Methyl-6-{3-(R)-methyl-4-[2-(2-methyl-pyrrolidin-1-yl)-6-phenyl-pyrimidin-4-yl]-piperazin-1-yl}-nicotinamide | * | 1.18 | 472.30 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 83 | 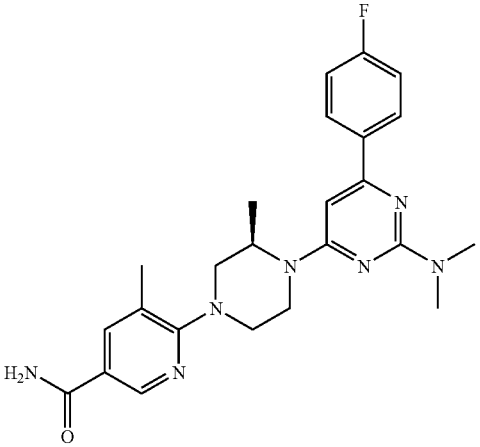 | 6-{4-[2-Dimethylamino-6-(4-fluoro-phenyl)-pyrimidin-4-yl]-3-(R)-methyl-piperazin-1-yl}-5-methyl-nicotinamide | * | 1.14 | 450.29 |
| 84 | 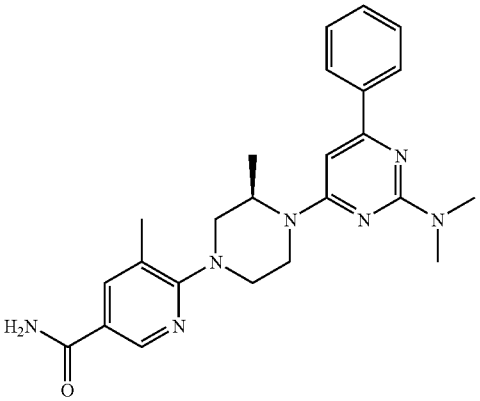 | 6-[4-(2-Dimethylamino-6-phenyl-pyrimidin-4-yl)-3-(R)-methyl-piperazin-1-yl]-5-methyl-nicotinamide | * | 1.13 | 432.25 |
| 85 | 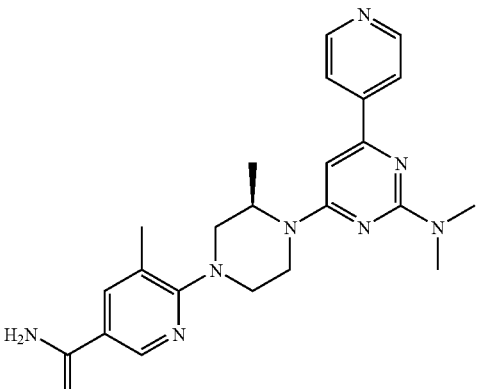 | 6-[4-(2-Dimethylamino-6-pyridin-4-yl-pyrimidin-4-yl)-3-(R)-methyl-piperazin-1-yl]-5-methyl-nicotinamide | * | 1.1 | 433.26 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 86 | 5-Chloro-6-{4-[6-(3-chloro-4-fluoro-phenyl)-pyrimidin-4-yl]-3-(R)-methyl-piperazin-1-yl}-nicotinamide | * | 1.22 | 461.11 |
| 87 | 5-Methyl-6-{4-[2-(2-methyl-pyrrolidin-1-yl)-6-phenyl-pyrimidin-4-yl]-piperazin-1-yl}-nicotinamide | * | 1.17 | 458.28 |
| 88 | 5-Methyl-6-{4-[2-(2-methyl-pyrrolidin-1-yl)-6-m-tolyl-pyrimidin-4-yl]-piperazin-1-yl}-nicotinamide | * | 1.19 | 472.30 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 89 | 5-Methyl-6-{4-[2-(2-methyl-pyrrolidin-1-yl)-6-pyridin-4-yl-pyrimidin-4-yl]-piperazin-1-yl)-nicotinamide | * | 1.14 | 459.30 |
| 90 | 6-{4-[6-(2-Isopropyl-pyridin-4-yl)-2-(2-methyl-pyrrolidin-1-yl)-pyrimidin-4-yl]-piperazin-1-yl}-5-methyl-nicotinamide | * | 1.19 | 501.33 |
| 91 | 6-{4-[6-(4-fluorophenyl)-2-(2-methylpyrrolidin-1-yl)pyrimidin-4-yl]piperazin-1-yl}-5-methylpyridine-3-carboximidamide | * | 1.12 | 238.15 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 92 | 5-Chloro-6-{4-[6-(4-fluoro-phenyl)-2-(2-(R)-methyl-pyrrolidin-1-yl)-pyrimidin-4-yl]-piperazin-1-yl}-nicotinic acid | * | 1.24 | 497.26 |
| 93 | (5-Chloro-6-{4-[6-(4-fluoro-phenyl)-2-(2-(R)-methyl-pyrrolidin-1-yl)-pyrimidin-4-yl]-piperazin-1-yl}-pyridin-3-yl)-acetic acid | * | 1.23 | 511.27 |
| 94 | 5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-nicotinic acid | * | 1.25 | 511.24 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 95 | 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-nicotinic acid | * | 1.21 | 491.29 |
| 96 | 5-Methyl-6-{3-(R)-methyl-4-[2-(2-(R)-methyl-pyrrolidin-1-yl)-6-phenyl-pyrimidin-4-yl]-piperazin-1-yl}-nicotinic acid | * | 1.21 | 473.29 |
| 97 | 2-{4-[6-(3-Chloro-4-fluoro-phenyl)-2-(2-methyl-pyrrolidin-1-yl)-pyrimidin-4-yl]-piperazin-1-yl}-pyrimidine-5-carboxylic acid amide | * | 1.22 | 497.26 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 98 | | (5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-methanol | * | 1.25 | 497.28 |
| 99 | | 6-{4-[6-(4-Fluoro-phenyl)-2-(2-(S)-methyl-pyrrolidin-1-yl)-pyrimidin-4-yl]-3-(R)-methyl-piperazin-1-yl}-5-methyl-nicotinic acid | * | 1.24 | 491.31 |
| 100 | | (5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-acetonitrile | * | 1.25 | 506.28 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 101 | (5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-acetic acid | * | 1.26 | 525.29 |
| 102 | 5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-nicotinamide | * | 1.27 | 544.29 |
| 103 | 5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-nicotinic acid | * | 1.27 | 545.22 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 104 | 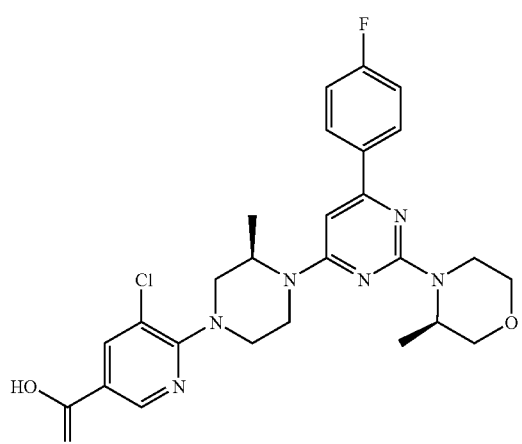 | 5-Chloro-6-{4-[6-(4-fluoro-phenyl)-2-(3-(R)-methyl-morpholin-4-yl)-pyrimidin-4-yl]-3-(R)-methyl-piperazin-1-yl}-nicotinic acid | * | 1.21 | 527.29 |
| 105 | 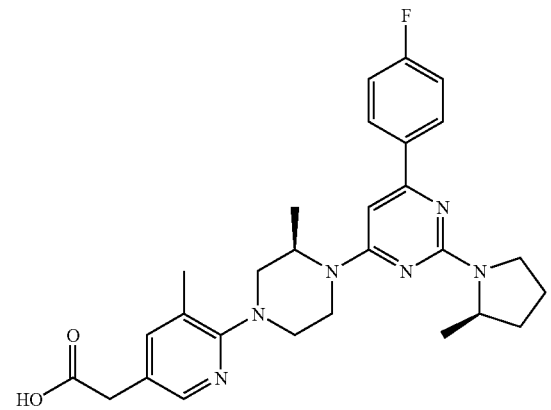 | (6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridin-3-yl)-acetic acid | * | 1.12 | 505.35 |
| 106 | 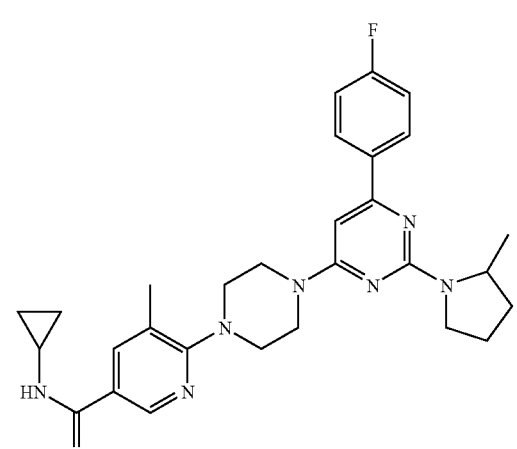 | N-Cyclopropyl-6-{4-[6-(4-fluoro-phenyl)-2-(2-methyl-pyrrolidin-1-yl)-pyrimidin-4-yl]-piperazin-1-yl}-5-methyl-nicotinamide | * | 1.17 | 516.38 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 107 | 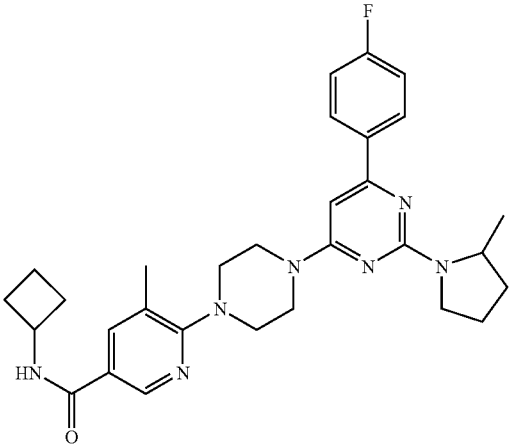 | N-cyclobutyl-6-{4-[6-(4-fluorophenyl)-2-(2-methylpyrrolidin-1-yl)pyrimidin-4-yl]piperazin-1-yl}-5-methylnicotinamide | * | 1.2 | 530.39 |
| 108 | 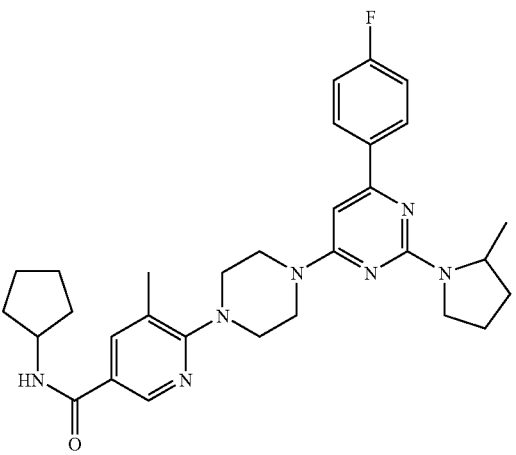 | N-Cyclopentyl-6-{4-[6-(4-fluoro-phenyl)-2-(2-methyl-pyrrolidin-1-yl)-pyrimidin-4-yl]-piperazin-1-yl}-5-methyl-nicotinamide | * | 1.22 | 544.41 |
| 109 | 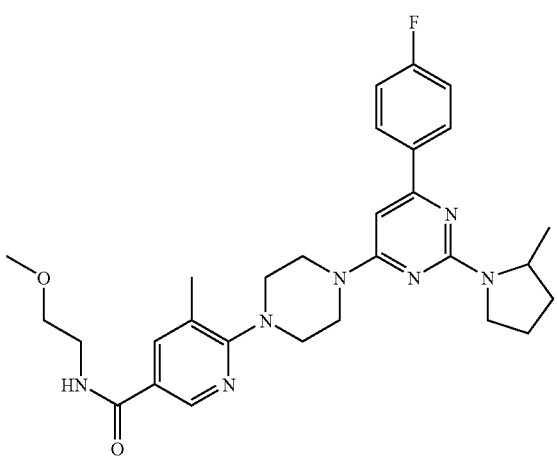 | 6-{4-[6-(4-fluorophenyl)-2-(2-methylpyrrolidin-1-yl)pyrimidin-4-yl]piperazin-1-yl}-N-(2-methoxyethyl)-5-methylnicotinamide | * | 1.17 | 534.39 |

TABLE I-continued

Representative Substituted Biaryl Piperazinyl-Pyridine Analogues

| Compound | | Name | IC$_{50}$ | Ret. Time | MS (M + 1) |
|---|---|---|---|---|---|
| 109 | | 6-{4-[6-(4-fluorophenyl)-2-(2-methylpyrrolidin-1-yl)pyrimidin-4-yl]piperazin-1-yl}-N-(2-methoxyethyl)-5-methylnicotinamide | * | 1.17 | 534.39 |
| 110 | | 6-{4-[6-(4-fluorophenyl)-2-(2-methylpyrrolidin-1-yl)pyrimidin-4-yl]piperazin-1-yl}-N-(3-methoxypropyl)-5-methylnicotinamide | * | 1.18 | 548.40 |
| 111 | | 6-{4-[6-(4-fluorophenyl)-2-(2-methylpyrrolidin-1-yl)pyrimidin-4-yl]piperazin-1-yl}-5-methyl-N-(tetrahydrofuran-2-ylmethyl)nicotinamide | * | 1.18 | 560.41 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 112 | N-(3-ethoxypropyl)-6-{4-[6-(4-fluorophenyl)-2-(2-methylpyrrolidin-1-yl)pyrimidin-4-yl]piperazin-1-yl}-5-methylnicotinamide | * | 1.2 | 562.43 |
| 113 | N-benzyl-6-{4-[6-(4-fluorophenyl)-2-(2-methylpyrrolidin-1-yl)pyrimidin-4-yl]piperazin-1-yl}-5-methylnicotinamide | * | 1.22 | 566.40 |
| 114 | N-(4-fluorobenzyl)-6-{4-[6-(4-fluorophenyl)-2-(2-methylpyrrolidin-1-yl)pyrimidin-4-yl]piperazin-1-yl}-5-methylnicotinamide | * | 1.22 | 584.40 |

TABLE I-continued

Representative Substituted Biaryl Piperazinyl-Pyridine Analogues

| Compound | Name | IC$_{50}$ | Ret. Time | MS (M + 1) |
|---|---|---|---|---|
| 115 | 6-{4-[6-(4-fluorophenyl)-2-(2-methylpyrrolidin-1-yl)pyrimidin-4-yl]piperazin-1-yl}-N-(4-methoxybenzyl)-5-methylnicotinamide | * | 1.22 | 596.42 |
| 116 | N-[3-(dimethylamino)-propyl]-6-{4-[6-(4-fluorophenyl)-2-(2-methylpyrrolidin-1-yl)pyrimidin-4-yl]piperazin-1-yl}-5-methylnicotinamide | * | 1.11 | 561.46 |
| 117 | 6-{4-[6-(4-fluorophenyl)-2-(2-methylpyrrolidin-1-yl)pyrimidin-4-yl]piperazin-1-yl}-N-(2-methoxy-1-methylethyl)-5-methylnicotinamide | * | 1.18 | 548.41 |

| Compound | | Name | IC$_{50}$ | Ret. Time | MS (M + 1) |
|---|---|---|---|---|---|
| 118 | | 6-{4-[6-(4-fluorophenyl)-2-(2-methylpyrrolidin-1-yl)pyrimidin-4-yl]piperazin-1-yl}-5-methyl-N-(2-thienylmethyl)nicotinamide | * | 1.21 | 572.37 |
| 119 | | N-(2-ethoxyethyl)-6-{4-[6-(4-fluorophenyl)-2-(2-methylpyrrolidin-1-yl)pyrimidin-4-yl]piperazin-1-yl}-5-methylnicotinamide | * | 1.18 | 548.41 |
| 120 | | 6-{4-[6-(4-fluorophenyl)-2-(2-methylpyrrolidin-1-yl)pyrimidin-4-yl]piperazin-1-yl}-5-methyl-N-(2,2,2-trifluoroethyl)nicotinamide | * | 1.2 | 558.36 |
| 121 | | N-benzyl-6-{4-[6-(4-fluorophenyl)-2-(2-methylpyrrolidin-1-yl)pyrimidin-4-yl]piperazin-1-yl}-N,5-dimethylnicotinamide | * | 1.22 | 580.43 |

-continued

| Compound | | Name | IC$_{50}$ | Ret. Time | MS (M + 1) |
|---|---|---|---|---|---|
| 122 | | 4-(4-fluorophenyl)-2-(2-methylpyrrolidin-1-yl)-6-{4-[3-methyl-5-(pyrrolidin-1-ylcarbonyl)-pyridin-2-yl]piperazin-1-yl}pyrimidine | * | 1.18 | 530.40 |
| 123 | | 4-(4-fluorophenyl)-6-{4-[3-methyl-5-(piperidin-1-ylcarbonyl)pyridin-2-yl]piperazin-1-yl}-2-(2-methylpyrrolidin-1-yl)pyrimidine | * | 1.2 | 544.42 |
| 124 | | 4-[(6-{4-[6-(4-fluorophenyl)-2-(2-methylpyrrolidin-1-yl)pyrimidin-4-yl]piperazin-1-yl}-5-methylpyridin-3-yl)carbonyl]morpholine | * | 1.16 | 546.40 |
| 125 | | 4-(4-fluorophenyl)-6-(4-{3-methyl-5-[(4-methylpiperidin-1-yl)carbonyl]pyridin-2-yl}piperazin-1-yl)-2-(2-methylpyrrolidin-1-yl)pyrimidine | * | 1.23 | 558.44 |

-continued

| Compound | | Name | IC$_{50}$ | Ret. Time | MS (M + 1) |
|---|---|---|---|---|---|
| 126 | 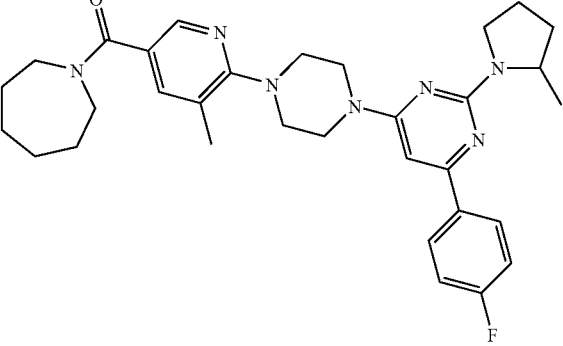 | 1-[(6-{4-[6-(4-fluorophenyl)-2-(2-methylpyrrolidin-1-yl)pyrimidin-4-yl]piperazin-1-yl}-5-methylpyridin-3-yl)carbonyl]azepane | * | 1.22 | 558.44 |
| 127 | 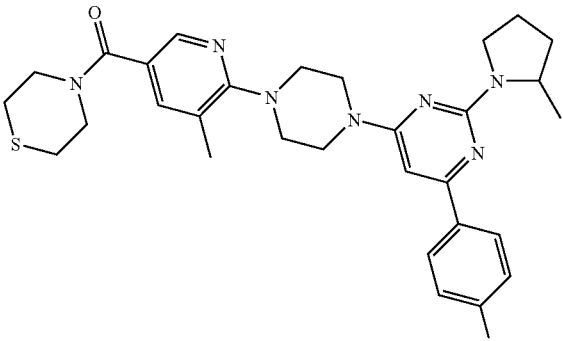 | 4-[(6-{4-[6-(4-fluorophenyl)-2-(2-methylpyrrolidin-1-yl)pyrimidin-4-yl]piperazin-1-yl}-5-methylpyridin-3-yl)carbonyl]thiomorpholine | * | 1.19 | 562.38 |
| 128 | 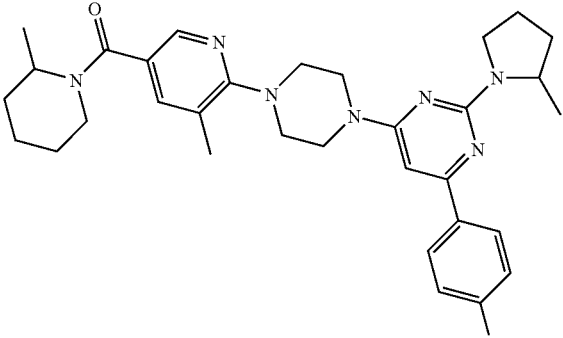 | 4-(4-fluorophenyl)-6-(4-{3-methyl-5-[(2-methylpiperidin-1-yl)carbonyl]pyridin-2-yl}piperazin-1-yl)-2-(2-methylpyrrolidin-1-yl)pyrimidine | * | 1.22 | 558.44 |
| 129 | 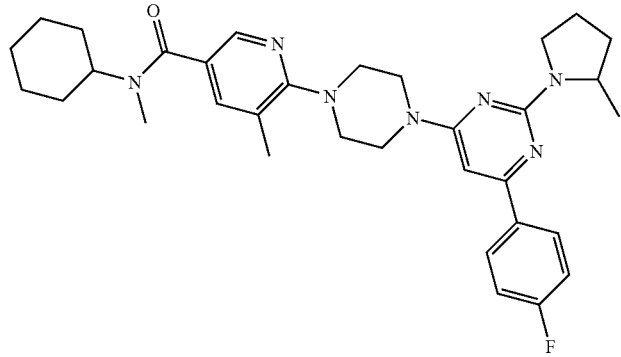 | N-cyclohexyl-6-{4-[6-(4-fluorophenyl)-2-(2-methylpyrrolidin-1-yl)pyrimidin-4-yl]piperazin-1-yl}-N,5-dimethylnicotinamide | * | 1.24 | 572.45 |

-continued

| Compound | | Name | IC$_{50}$ | Ret. Time | MS (M + 1) |
|---|---|---|---|---|---|
| 130 | | 4-(4-fluorophenyl)-6-(4-{3-methyl-5-[(4-phenylpiperidin-1-yl)carbonyl]pyridin-2-yl}piperazin-1-yl)-2-(2-methylpyrrolidin-1-yl)pyrimidine | * | 1.26 | 620.48 |
| 131 | | 4-(4-fluorophenyl)-6-(4-{3-methyl-5-[(4-methylpiperazin-1-yl)carbonyl]pyridin-2-yl}piperazin-1-yl)-2-(2-methylpyrrolidin-1-yl)pyrimidine | * | 1.1 | 559.44 |
| 132 | | 4-(4-fluorophenyl)-6-[4-(5-{[4-(2-methoxyethyl)-piperazin-1-yl]carbonyl}-3-methylpyridin-2-yl)piperazin-1-yl]-2-(2-methylpyrrolidin-1-yl)pyrimidine | * | 1.11 | 603.48 |
| 133 | | 4-(4-{5-[(4-cyclopentyl-piperazin-1-yl)carbonyl]-3-methylpyridin-2-yl}piperazin-1-yl)-6-(4-fluorophenyl)-2-(2-methylpyrrolidin-1-yl)pyrimidine | * | 1.12 | 613.51 |

-continued

| | Compound | Name | IC$_{50}$ | Ret. Time | MS (M + 1) |
|---|---|---|---|---|---|
| 134 | | 4-(4-{5-[(4-acetyl-piperazin-1-yl)carbonyl]-3-methylpyridin-2-yl}piperazin-1-yl)-6-(4-fluorophenyl)-2-(2-methylpyrrolidin-1-yl)pyrimidine | * | 1.14 | 587.44 |
| 135 | | 4-(4-fluorophenyl)-6-(4-{3-methyl-5-[(2-methylpyrrolidin-1-yl)carbonyl]pyridin-2-yl}piperazin-1-yl)-2-(2-methylpyrrolidin-1-yl)pyrimidine | * | 1.2 | 544.42 |
| 136 | | N-[2-(dimethylamino)-ethyl]-6-{4-[6-(4-fluorophenyl)-2-(2-methyl-pyrrolidin-1-yl)pyrimidin-4-yl]piperazin-1-yl}-N,5-dimethylnicotinamide | * | 1.1 | 561.46 |
| 137 | | N-[3-(dimethylamino)-propyl]-6-{4-[6-(4-fluorophenyl)-2-(2-methyl-pyrrolidin-1-yl)pyrimidin-4-yl]piperazin-1-yl}-N,5-dimethylnicotinamide | * | 1.11 | 575.48 |

-continued

| Compound | | Name | IC$_{50}$ | Ret. Time | MS (M + 1) |
|---|---|---|---|---|---|
| 138 | | 6-{4-[6-(4-fluorophenyl)-2-(2-methylpyrrolidin-1-yl)pyrimidin-4-yl]piperazin-1-yl}-N,5-dimethyl-N-(1-methylpyrrolidin-3-yl)nicotinamide | * | 1.11 | 573.47 |
| 139 | | 1-[(6-{4-[6-(4-fluorophenyl)-2-(2-methylpyrrolidin-1-yl)pyrimidin-4-yl]piperazin-1-yl}-5-methylpyridin-3-yl)carbonyl]-N,N-dimethylpyrrolidin-3-amine | * | 1.1 | 573.47 |
| 140 | | N-{1-[(6-{4-[6-(4-fluorophenyl)-2-(2-methylpyrrolidin-1-yl)pyrimidin-4-yl]piperazin-1-yl}-5-methylpyridin-3-yl)carbonyl]pyrrolidin-3-yl}acetamide | * | 1.15 | 587.45 |

-continued

| Compound | | Name | IC$_{50}$ | Ret. Time | MS (M + 1) |
|---|---|---|---|---|---|
| 141 | | 4-(4-fluorophenyl)-6-(4-{5-[(4-methoxypiperidin-1-yl)carbonyl]-3-methylpyridin-2-yl}piperazin-1-yl)-2-(2-methylpyrrolidin-1-yl)pyrimidine | * | 1.18 | 574.45 |
| 142 | | 4-(4-{5-[(4,4-difluoro-piperidin-1-yl)carbonyl]-3-methylpyridin-2-yl}piperazin-1-yl)-6-(4-fluorophenyl)-2-(2-methylpyrrolidin-1-yl)pyrimidine | * | 1.2 | 580.41 |
| 143 | | 5-Chloro-6-{4-[6-(4-fluoro-phenyl)-2-(3-(R)-methyl-morpholin-4-yl)-pyrimidin-4-yl]-3-(R)-methyl-piperazin-1-yl}-nicotinamide | * | 1.17 | 526.39 |

| Compound | Name | IC$_{50}$ | Ret. Time | MS (M + 1) |
|---|---|---|---|---|
| 144 | 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid | * | 1.18 | 491.40 |
| 145 | 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid amide | * | 1.23 | 490.22 |
| 146 | (5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-pyridin-3-yl)-methanol | * | 1.29 | 531.15 |

-continued

| Compound | Name | IC$_{50}$ | Ret. Time | MS (M + 1) |
|---|---|---|---|---|
| 147 | 2-(5-Chloro-6-{4-[6-(4-fluoro-phenyl)-2-(2-methyl-pyrrolidin-1-yl)-pyrimidin-4-yl]-piperazin-1-yl}-pyridin-3-yl)-propan-2-ol | * | 1.28 | 511.26 |
| 148 | 1-(5-Chloro-6-{4-[6-(4-fluoro-phenyl)-2-(2-methyl-pyrrolidin-1-yl)-pyrimidin-4-yl]-piperazin-1-yl}-pyridin-3-yl)-ethanol | * | 1.26 | 497.23 |
| 149 | 5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-N-(2-hydroxy-ethyl)-nicotinamide | * | 1.28 | 588.24 |

-continued

| Compound | | Name | IC$_{50}$ | Ret. Time | MS (M + 1) |
|---|---|---|---|---|---|
| 150 | | 6-{4-[6-(4-Fluoro-phenyl)-2-(3-(R)-methyl-morpholin-4-yl)-pyrimidin-4-yl]-3-(R)-methyl-piperazin-1-yl}-5-methyl-nicotinic acid | * | 1.25 | 507.28 |
| 151 | | 6-{4-[6-(4-Fluoro-phenyl)-2-(2-(S)-hydroxymethyl-pyrrolidin-1-yl)-pyrimidin-4-yl]-3-(R)-methyl-piperazin-1-yl}-5-methyl-nicotinic acid | * | 1.23 | 507.27 |
| 152 | | 2-(5-Chloro-6-{4-[6-(4-fluoro-phenyl)-2-(2-methyl-pyrrolidin-1-yl)-pyrimidin-4-yl]-piperazin-1-yl}-pyridin-3-yl)-acetamide | * | 1.22 | 510.16 |

-continued

| Compound | Name | IC$_{50}$ | Ret. Time | MS (M + 1) |
|---|---|---|---|---|
| 153 | 6-{4-[6-(4-Fluoro-phenyl)-2-(isopropyl-methyl-amino)-pyrimidin-4-yl]-3-(R)-methyl-piperazin-1-yl}-5-methyl-nicotinic acid | * | 1.25 | 479.21 |
| 154 | 6-{4-[6-(3-Chloro-4-fluoro-phenyl)-2-(2-(R)-methyl-pyrrolidin-1-yl)-pyrimidin-4-yl]-3-(R)-methyl-piperazin-1-yl}-5-methyl-nicotinic acid | * | 1.29 | 525.17 |
| 155 | (5-Chloro-6-{4-[6-(4-fluoro-phenyl)-2-(2-(S)-hydroxymethyl-pyrrolidin-1-yl)-pyrimidin-4-yl]-3-(R)-methyl-piperazin-1-yl}-pyridin-3-yl)-(2-(S)-hydroxymethyl-pyrrolidin-1-yl)-methanone | * | 1.24 | 610.24 |

-continued

| Compound | | Name | IC$_{50}$ | Ret. Time | MS (M + 1) |
|---|---|---|---|---|---|
| 156 | | 5-Chloro-6-{4-[6-(4-fluoro-phenyl)-2-(2-(S)-hydroxymethyl-pyrrolidin-1-yl)-pyrimidin-4-yl]-3-(R)-methyl-piperazin-1-yl)-nicotinic acid | * | 1.27 | 527.16 |
| 157 | | 5-Chloro-6-{4-[6-(4-fluoro-phenyl)-2-(isopropyl-methyl-amino)-pyrimidin-4-yl]-3-(R)-methyl-piperazin-1-yl}-nicotinic acid | * | 1.28 | 499.16 |
| 158 | | 5-Chloro-6-{4-[6-(4-fluoro-phenyl)-2-(2-(S)-hydroxymethyl-pyrrolidin-1-yl)-pyrimidin-4-yl]-piperazin-1-yl}-nicotinic acid | * | 1.25 | 513.19 |

-continued

| Compound | Name | IC$_{50}$ | Ret. Time | MS (M + 1) |
|---|---|---|---|---|
| 159 | 5-Chloro-6-{4-[6-(4-fluoro-phenyl)-2-(3-(R)-methyl-morpholin-4-yl)-pyrimidin-4-yl]-piperazin-1-yl}-nicotinic acid | * | 1.28 | 513.17 |
| 160 | 5-Chloro-6-{4-[6-(4-fluoro-phenyl)-2-(isopropyl-methyl-amino)-pyrimidin-4-yl]-piperazin-1-yl}-nicotinic acid | * | 1.26 | 485.19 |
| 161 | 6-{4-[6-(3-Chloro-4-fluoro-phenyl)-2-(isopropyl-methyl-amino)-pyrimidin-4-yl]-piperazin-1-yl}-5-methyl-nicotinic acid | * | 1.28 | 499.21 |

-continued

| Compound | | Name | IC$_{50}$ | Ret. Time | MS (M + 1) |
|---|---|---|---|---|---|
| 162 | | 4-(4-Fluoro-phenyl)-6-[2-(R)-methyl-4-(3-methyl-5-oxazol-2-yl-pyridin-2-yl)-piperazin-1-yl]-2-(2-(R)-methyl-pyrrolidin-1-yl)-pyrimidine | * | 1.28 | 514.27 |
| 163 | | 5-Chloro-6-{4-[2-(2-(S)-hydroxymethyl-pyrrolidin-1-yl)-6-phenyl-pyrimidin-4-yl]-3-(R)-methyl-piperazin-1-yl}-nicotinic acid | * | 1.26 | 509.21 |
| 164 | | 4-(4-Fluoro-phenyl)-6-{2-(R)-methyl-4-[3-methyl-5-(1H-tetrazol-5-yl)-pyridin-2-yl]-piperazin-1-yl}-2-(2-(R)-methyl-pyrrolidin-1-yl)-pyrimidine | * | 1.24 | 515.27 |

-continued

| Compound | Name | IC$_{50}$ | Ret. Time | MS (M + 1) |
|---|---|---|---|---|
| 165 | 5-Chloro-6-{4-[2-(2-(S)-hydroxymethyl-pyrrolidin-1-yl)-6-phenyl-pyrimidin-4-yl]-3-(R)-methyl-piperazin-1-yl}-nicotinamide | * | 1.23 | 508.22 |
| 166 | 5-Chloro-N-(2-hydroxy-ethyl)-6-{4-[2-(2-(S)-hydroxymethyl-pyrrolidin-1-yl)-6-phenyl-pyrimidin-4-yl]-3-(R)-methyl-piperazin-1-yl}-nicotinamide | * | 1.23 | 552.26 |
| 167 | 5-Chloro-N-(2-hydroxy-ethyl)-6-{3-(R)-methyl-4-[2-(2-(R)-methyl-pyrrolidin-1-yl)-6-phenyl-pyrimidin-4-yl]-piperazin-1-yl}-nicotinamide | * | 1.25 | 536.29 |

-continued

| Compound | Name | IC$_{50}$ | Ret. Time | MS (M + 1) |
|---|---|---|---|---|
| 168 | 5-Methyl-6-{3-(R)-methyl-4-[2-(2-methyl-pyrrolidin-1-yl)-6-p-tolyl-pyrimidin-4-yl]-piperazin-1-yl}-nicotinic acid | * | 1.22 | 488.30 |
| 169 | 4-(4-Fluoro-phenyl)-6-{4-[5-(1H-imidazol-2-yl)-3-methyl-pyridin-2-yl]-2-(R)-methyl-piperazin-1-yl}-2-(2-(R)-methyl-pyrrolidin-1-yl)-pyrimidine | * | 1.18 | 257.14 |
| 170 | 6-{4-[6-(4-Fluoro-phenyl)-2-(2-(R)-methyl-pyrrolidin-1-yl)-pyrimidin-4-yl]-3-(S)-methyl-piperazin-1-yl}-5-methyl-nicotinic acid | * | 1.17 | 491.36 |

-continued

| Compound | Name | IC$_{50}$ | Ret. Time | MS (M + 1) |
|---|---|---|---|---|
| 171 | N-(2-Hydroxy-ethyl)-5-methyl-6-{3-(R)-methyl-4-[6-(6-methyl-pyridin-3-yl)-2-(2-methyl-pyrrolidin-1-yl)-pyrimidin-4-yl]-piperazin-1-yl}-nicotinamide | * | 1.1 | 531.42 |
| 172 | 6-{4-[2-(4-Fluoro-phenyl)-6-(2-(R)-methyl-pyrrolidin-1-yl)-pyridin-4-yl]-3-(R)-methyl-piperazin-1-yl}-5-methyl-nicotinic acid | * | 1.16 | 490.39 |
| 173 | (5-Chloro-6-{4-[6-(3-chloro-4-fluoro-phenyl)-2-piperidin-1-yl-pyrimidin-4-yl]-3-(R)-methyl-piperazin-1-yl}-pyridin-3-yl)-methanol | * | 1.24 | 531.23 |

-continued

| Compound | Name | IC$_{50}$ | Ret. Time | MS (M + 1) |
|---|---|---|---|---|
| 174 | 5-Chloro-6-{4-[6-(3-chloro-4-fluoro-phenyl)-2-(2-(R)-methyl-pyrrolidin-1-yl)-pyrimidin-4-yl]-2-(R)-methyl-piperazin-1-yl}-nicotinic acid ethyl ester | * | 1.29 | 573.22 |
| 175 | 6-{4-[2-(3-Chloro-phenyl)-6-(2-(R)-methyl-pyrrolidin-1-yl)-pyridin-4-yl]-3-(R)-methyl-piperazin-1-yl}-5-methyl-nicotinic acid | * | 1.2 | 506.25 |
| 176 | 6-{4-[2-(4-Fluoro-3-methyl-phenyl)-6-(2-(R)-methyl-pyrrolidin-1-yl)-pyridin-4-yl]-3-(R)-methyl-piperazin-1-yl}-5-methyl-nicotinic acid | * | 1.2 | 504.32 |

| Compound | Name | IC$_{50}$ | Ret. Time | MS (M + 1) |
|---|---|---|---|---|
| 177 | 6-{4-[6-(4-Fluoro-phenyl)-2-(2-(R)-methyl-pyrrolidin-1-yl)-pyrimidin-4-yl]-piperazin-1-yl}-5-trifluoromethyl-nicotinic acid | * | 1.21 | 531.21 |
| 178 | 6-{4-[2-(3-Chloro-4-fluoro-phenyl)-6-(2-(R)-methyl-pyrrolidin-1-yl)-pyridin-4-yl]-3-(R)-methyl-piperazin-1-yl}-5-methyl-nicotinic acid | * | 1.19 | 524.24 |
| 179 | 6-{4-[6-(4-Fluoro-phenyl)-2-(2-(R)-methyl-pyrrolidin-1-yl)-pyrimidin-4-yl]-3-(R)-methyl-piperazin-1-yl}-5-trifluoromethyl-nicotinic acid | * | 1.22 | 545.24 |

-continued

| Compound | Name | IC$_{50}$ | Ret. Time | MS (M + 1) |
|---|---|---|---|---|
| 180 | 6-{4-[5'-Chloro-6-(2-(R)-methyl-pyrrolidin-1-yl)-[2,3']bipyridinyl-4-yl]-3-(R)-methyl-piperazin-1-yl}-5-methyl-nicotinic acid | * | 1.14 | 507.20 |
| 181 | 2-[6-((3R)-4-{6-(4-fluorophenyl)-2-[(2R)-2-methyl-1-pyrrolidinyl]-4-piperazinyl)-5-methyl-3-pyridinyl]ethanol | * | 1.19 | 491.24 |
| 182 | 2-{[6-((3R)-4-{6-(3-chloro-4-fluorophenyl)-2-[(2R)-2-methyl-1-pyrrolidinyl]-4-pyrimidinyl}-3-methyl-1-piperazinyl)-5-methyl-3-pyridinyl]oxy}ethanol | * | 1.25 | 541.21 |

-continued

| Compound | Name | IC$_{50}$ | Ret. Time | MS (M + 1) |
|---|---|---|---|---|
| 183 | 2-{[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)-pyridin-3-yl]oxy}ethanol | * | 1.29 | 561.16 |
| 184 | 2-{[6-((3R)-4-{6-(4-fluorophenyl)-2-[(2S)-2-(hydroxymethyl)pyrrolidin-1-yl]pyrimidin-4-yl}-3-methylpiperazin-1-yl)-5-methylpyridin-3-yl]oxy}ethanol | * | 1.2 | 523.40 |
| 185 | 2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]ethanol | * | 1.2 | 545.23 |

| Compound | Name | IC$_{50}$ | Ret. Time | MS (M + 1) |
|---|---|---|---|---|
| 186 | 2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]-N,N-dimethylethanamine | * | 1.13 | 572.27 |
| 187 | 2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]-N-methylethanamine | * | 1.23 | 558.48 |
| 188 | 6-((3R)-4-{6-(4-fluorophenyl)-2-[(2R)-2-methyl-1-pyrrolidinyl]-4-pyrimidinyl}-3-methyl-1-piperazinyl)-5-methylnicotinonitrile | | 1.26 | 471.33 |

-continued

| Compound | Name | IC$_{50}$ | Ret. Time | MS (M + 1) |
|---|---|---|---|---|
| 189 | 5-fluoro-4-(4-fluoro-phenyl)-6-[(2R)-2-methyl-4-(3-methylpyridin-2-yl)piperazin-1-yl]-2-[(2R)-2-methylpyrrolidin-1-yl]pyrimidine | * | 1.26 | 465.34 |
| 190 | tert-butyl rel-{6-[(3R)-4-{6-(4-fluorophenyl)-2-[(2R)-2-methylpyrrolidin-1-yl]pyrimidin-4-yl}-3-methylpiperazin-1-yl]-5-methylpyridin-3-yl}acetate | * | 1.22 | 561.30 |
| 191 | rel-(2E)-3-{5-chloro-6-[(3R)-4-{6-(3-chloro-4-fluorophenyl)-2-[(2R)-2-methylpyrrolidin-1-yl]-pyrimidin-4-yl}-3-methylpiperazin-1-yl]-pyridin-3-yl}prop-2-en-1-ol | * | 1.23 | 557.18 |

-continued

| Compound | | Name | IC$_{50}$ | Ret. Time | MS (M + 1) |
|---|---|---|---|---|---|
| 192 | 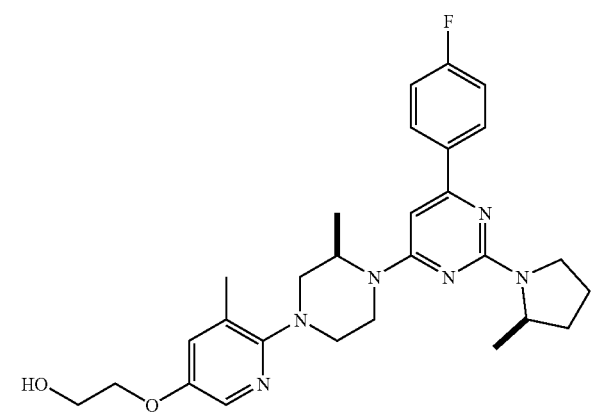 | rel-2-({6-[(3R)-4-{6-(4-fluorophenyl)-2-[(2R)-2-methylpyrrolidin-1-yl]pyrimidin-4-yl}-3-methylpiperazin-1-yl]-5-methylpyridin-3-yl}oxy)ethanol | * | 1.15 | 507.26 |
| 193 | 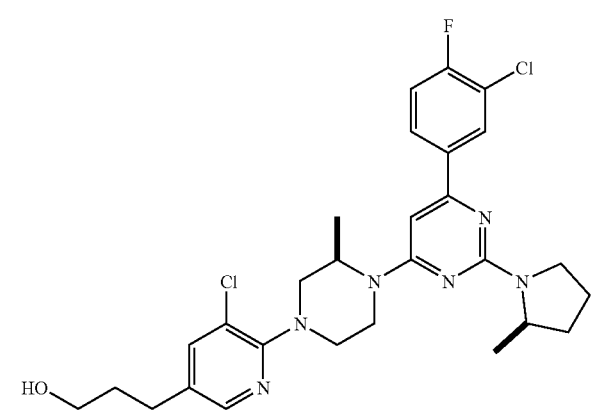 | rel-3-{5-chloro-6-[(3R)-4-{6-(3-chloro-4-fluorophenyl)-2-[(2R)-2-methylpyrrolidin-1-yl]pyrimidin-4-yl}-3-methylpiperazin-1-yl]-pyridin-3-yl}propan-1-ol | * | 1.32 | 559.41 |

TABLE II

Additional Representative Substituted Biaryl Piperazinyl-Pyridine Analogues

| Compound | Name |
|---|---|
| 194 | 5-Chloro-6-{4-[6-(4-fluoro-phenyl)-2-(2-(S)-methyl-pyrrolidin-1-yl)-pyrimidin-4-yl]-3-(R)-methyl-piperazin-1-yl}-nicotinic acid |

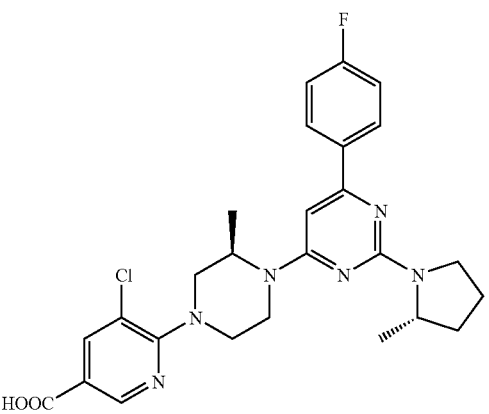

TABLE II-continued

Additional Representative Substituted Biaryl Piperazinyl-Pyridine Analogues

| Compound | Name |
| --- | --- |
| 195 | 5-Chloro-6-{4-[6-(3-chloro-4-fluoro-phenyl)-2-(2-(S)-methyl-piperidin-1-yl)-pyrimidin-4-yl]-3-(R)-methyl-piperazin-1-yl}-nicotinic acid |
| 196 | 5-Chloro-6-{4-[6-(4-fluoro-phenyl)-2-(3-(S)-methyl-morpholin-4-yl)-pyrimidin-4-yl]-3-(R)-methyl-piperazin-1-yl}-nicotinic acid |
| 197 | 5-Chloro-6-{4-[6-(4-fluoro-phenyl)-2-(2-(S)-methyl-pyrrolidin-1-yl)-pyrimidin-4-yl]-3-(S)-methyl-piperazin-1-yl}-nicotinic acid |

TABLE II-continued

Additional Representative Substituted Biaryl Piperazinyl-Pyridine Analogues

| Compound | Name |
| --- | --- |
| 198 | 5-Chloro-6-{4-[6-(4-fluoro-phenyl)-2-(3-(R)-methyl-morpholin-4-yl)-pyrimidin-4-yl]-3-(S)-methyl-piperazin-1-yl}-nicotinic acid |
| 199 | 5-Chloro-6-{4-[6-(4-fluoro-phenyl)-2-(3-(R)-methyl-morpholin-4-yl)-pyrimidin-4-yl]-3-(R)-methyl-piperazin-1-yl}-nicotinic acid |
| 200 | 5-Chloro-6-{4-[6-(4-fluoro-phenyl)-2-(2-(S)-methyl-pyrrolidin-1-yl)-pyrimidin-4-yl]-3-(R)-methyl-piperazin-1-yl}-nicotinamide |

TABLE II-continued

Additional Representative Substituted Biaryl Piperazinyl-Pyridine Analogues

| Compound | Name |
| --- | --- |
| 201 | 5-Chloro-6-{4-[6-(3-chloro-4-fluoro-phenyl)-2-(2-(S)-methyl-piperidin-1-yl)-pyrimidin-4-yl]-3-(R)-methyl-piperazin-1-yl}-nicotinamide |
| 202 | 5-Chloro-6-{4-[6-(4-cyano-phenyl)-2-(3-(S)-methyl-morpholin-4-yl)-pyrimidin-4-yl]-3-(R)-methyl-piperazin-1-yl}-nicotinamide |
| 203 | 5-Chloro-6-{4-[6-(4-chloro-phenyl)-2-(3-(R)-methyl-morpholin-4-yl)-pyrimidin-4-yl]-3-(R)-methyl-piperazin-1-yl}-nicotinamide |

TABLE II-continued

Additional Representative Substituted Biaryl Piperazinyl-Pyridine Analogues

| Compound | Name |
|---|---|
| 204 | 5-Chloro-6-{4-[6-(3,4-difluoro-phenyl)-2-(2-(S)-methyl-pyrrolidin-1-yl)-pyrimidin-4-yl]-3-(S)-methyl-piperazin-1-yl}-nicotinamide |
| 205 | 5-Chloro-6-{4-[6-(4-fluoro-3-methyl-phenyl)-2-(3-(R)-methyl-morpholin-4-yl)-pyrimidin-4-yl]-3-(S)-methyl-piperazin-1-yl}-nicotinamide |
| 206 | 5-Chloro-6-{3-(S)-methyl-4-[6-(5-methyl-pyridin-3-yl)-2-(2-(S)-methyl-pyrrolidin-1-yl)-pyrimidin-4-yl]-piperazin-1-yl}-nicotinamide |

TABLE II-continued

Additional Representative Substituted Biaryl Piperazinyl-Pyridine Analogues

| Compound | Name |
| --- | --- |
| 207 | 5-Chloro-6-{4-[6-(2-isopropyl-pyridin-4-yl)-2-(2-(S)-methyl-pyrrolidin-1-yl)-pyrimidin-4-yl]-3-(R)-methyl-piperazin-1-yl}-nicotinamide |
| 208 | (6-{4-[6-(4-Fluoro-phenyl)-2-(2-(S)-methyl-pyrrolidin-1-yl)-pyrimidin-4-yl]-3-(R)-methyl-piperazin-1-yl}-5-trifluoromethyl-pyridin-3-yl)-methanol |
| 209 | (6-{4-[6-(3-Chloro-4-fluoro-phenyl)-2-(2-(S)-methyl-piperidin-1-yl)-pyrimidin-4-yl]-3-(R)-methyl-piperazin-1-yl}-5-trifluoromethyl-pyridin-3-yl)-methanol |

TABLE II-continued

Additional Representative Substituted Biaryl Piperazinyl-Pyridine Analogues

| Compound | Name |
|---|---|
| 210 | 4-[6-[4-(5-Hydroxymethyl-3-trifluoromethyl-pyridin-2-yl)-2-(R)-methyl-piperazin-1-yl]-2-(3-(S)-methyl-morpholin-4-yl)-pyrimidin-4-yl]-benzonitrile |
| 211 | (6-{4-[6-(4-Chloro-phenyl)-2-(3-(R)-methyl-morpholin-4-yl)-pyrimidin-4-yl]-3-(R)-methyl-piperazin-1-yl}-5-trifluoromethyl-pyridin-3-yl)-methanol |
| 212 | (6-{4-[6-(3,4-Difluoro-phenyl)-2-(2-(S)-methyl-pyrrolidin-1-yl)-pyrimidin-4-yl]-3-(S)-methyl-piperazin-1-yl}-5-trifluoromethyl-pyridin-3-yl)-methanol |

TABLE II-continued

Additional Representative Substituted Biaryl Piperazinyl-Pyridine Analogues

| Compound | | Name |
|---|---|---|
| 213 | | (6-{4-[6-(4-Fluoro-3-methyl-phenyl)-2-(3-(R)-methyl-morpholin-4-yl)-pyrimidin-4-yl]-3-(S)-methyl-piperazin-1-yl}-5-trifluoromethyl-pyridin-3-yl)-methanol |
| 214 | | (6-{4-[6-(5-Chloro-pyridin-3-yl)-2-(2-(S)-methyl-pyrrolidin-1-yl)-pyrimidin-4-yl]-3-(S)-methyl-piperazin-1-yl}-5-trifluoromethyl-pyridin-3-yl)-metbanol |
| 215 | | (6-{4-[6-(2-Isopropyl-pyridin-4-yl)-2-(2-(S)-methyl-pyrrolidin-1-yl)-pyrimidin-4-yl]-3-(R)-methyl-piperazin-1-yl}-5-trifluoromethyl-pyridin-3-yl)-methanol |

TABLE II-continued

Additional Representative Substituted Biaryl Piperazinyl-Pyridine Analogues

| Compound | | Name |
|---|---|---|
| 216 | | (6-{4-[6-(4-Fluoro-phenyl)-2-(2-(S)-methyl-pyrrolidin-1-yl)-pyrimidin-4-yl]-3-(R)-methyl-piperazin-1-yl}-5-trifluorometbyl-pyridin-3-yl)-acetic acid |
| 217 | | (6-{4-[6-(3-Chloro-4-fluoro-phenyl)-2-(2-(S)-methyl-piperidin-1-yl)-pyrimidin-4-yl]-3-(R)-methyl-piperazin-1-yl}-5-trifluoromethyl-pyridin-3-yl)-acetic acid |
| 218 | | (6-{4-[6-(4-Cyano-phenyl)-2-(3-(S)-methyl-morpholin-4-yl)-pyrimidin-4-yl]-3-(R)-methyl-piperazin-1-yl}-5-trifluoromethyl-pyridin-3-yl)-acetic acid |

TABLE II-continued

Additional Representative Substituted Biaryl Piperazinyl-Pyridine Analogues

| Compound | Name |
| --- | --- |
| 219 | (5-Chloro-6-{4-[6-(4-chloro-phenyl)-2-(3-(R)-methyl-morpholin-4-yl)-pyrimidin-4-yl]-3-(R)-methyl-piperazin-1-yl}-pyridin-3-yl)-acetic acid |
| 220 | (6-{4-[6-(3,4-Difluoro-phenyl)-2-(2-(S)-methyl-pyrrolidin-1-yl)-pyrimidin-4-yl]-3-(S)-methyl-piperazin-1-yl}-5-trifluoromethyl-pyridin-3-yl)-acetic acid |
| 221 | (5-Chloro-6-{4-[6-(4-fluoro-phenyl)-2-(3-(R)-methyl-morpholin-4-yl)-pyrimidin-4-yl]-3-(S)-methyl-piperazin-1-yl}-pyridin-3-yl)-acetic acid |

TABLE II-continued

Additional Representative Substituted Biaryl Piperazinyl-Pyridine Analogues

| Compound | | Name |
|---|---|---|
| 222 | | (6-{4-[6-(5-Chloro-pyridin-3-yl)-2-(2-(S)-methyl-pyrrolidin-1-yl)-pyrimidin-4-yl]-3-(S)-methyl-piperazin-1-yl}-5-trifluoromethyl-pyridin-3-yl)-acetic acid |
| 223 | | (5-Chloro-6-{4-[6-(2-isopropyl-pyridin-4-yl)-2-(2-(S)-methyl-pyrrolidin-1-yl)-pyrimidin-4-yl]-3-(R)-methyl-piperazin-1-yl}-pyridin-3-yl)-acetic acid |
| 224 | | 5-Chloro-6-{4-[6-(4-fluoro-phenyl)-2-(azetidin-1-yl)-pyrimidin-4-yl]-3-(R)-methyl-piperazin-1-yl}-nicotinic acid |

TABLE II-continued

Additional Representative Substituted Biaryl Piperazinyl-Pyridine Analogues

| Compound | Name |
|---|---|
| 225 | 5-Chloro-6-{4-[6-(4-chloro-phenyl)-2-(2-(S)-methyl-azetidin-1-yl)-pyrimidin-4-yl]-3-(R)-methyl-piperazin-1-yl}-nicotinic acid |
| 226 | 5-Chloro-6-{4-[6-(3,4-difluoro-phenyl)-2-(2-(R)-methyl-azetidin-1-yl)-pyrimidin-4-yl]-3-(R)-methyl-piperazin-1-yl}-nicotinic acid |
| 227 | 6-{4-[2-Azetidin-1-yl-6-(4-chloro-phenyl)-pyrimidin-4-yl]-3-(S)-methyl-piperazin-1-yl}-5-trifluoromethyl-nicotinamide |

TABLE II-continued

Additional Representative Substituted Biaryl Piperazinyl-Pyridine Analogues

| Compound | Name |
|---|---|
| 228 | (6-{4-[6-(4-Fluoro-phenyl)-2-(2-(R)-methyl-azetidin-1-yl)-pyrimidin-4-yl]-3-(S)-methyl-piperazin-1-yl}-5-trifluorometbyl-pyridin-3-yl)-methanol |
| 229 | (6-{4-[6-(2-Isopropyl-pyridin-4-yl)-2-(2-(S)-methyl-azetidin-1-yl)-pyrimidin-4-yl]-3-(S)-methyl-piperazin-1-yl}-5-trifluoromethyl-pyridin-3-yl)-methanol |

Example 4

VR1-Transfected Cells and Membrane Preparations

This Example illustrates the preparation of VR1-transfected cells and VR1-containing membrane preparations for use in capsaicin binding assays (Example 5).

A cDNA encoding full length human capsaicin receptor (SEQ ID NO:1, 2 or 3 of U.S. Pat. No. 6,482,611) is subcloned in the plasmid pBK-CMV (Stratagene, La Jolla, Calif.) for recombinant expression in mammalian cells.

Human embryonic kidney (HEK293) cells are transfected with the pBK-CMV expression construct encoding the full length human capsaicin receptor using standard methods. The transfected cells are selected for two weeks in media containing G418 (400 μg/ml) to obtain a pool of stably transfected cells. Independent clones are isolated from this pool by limiting dilution to obtain clonal stable cell lines for use in subsequent experiments.

For radioligand binding experiments, cells were seeded in T175 cell culture flasks in media without antibiotics and grown to approximately 90% confluency. The flasks were then washed with PBS and harvested in PBS containing 5 mM EDTA. The cells were pelleted by gentle centrifugation and stored at −80° C. until assayed.

Previously frozen cells are disrupted with the aid of a tissue homogenizer in ice-cold HEPES homogenization buffer (5 mM KCl 5, 5.8 mM NaCl, 0.75 mM $CaCl_2$, 2 mM $MgCl_2$, 320 mM sucrose, and 10 mM HEPES pH 7.4). Tissue homogenates are first centrifuged for 10 min at 1000×g (4° C.) to remove the nuclear fraction and debris, and then the supernatant from the first centrifugation is further centrifuged for 30 min at 35,000×g (4° C.) to obtain a partially purified membrane fraction. Membranes are resuspended in the HEPES homogenization buffer prior to the assay. An aliquot of this membrane homogenate is used to determine protein concentration via the Bradford method (BIO-RAD Protein Assay Kit, #500-0001, BIO-RAD, Hercules, Calif.).

Example 5

Capsaicin Receptor Binding Assay

This Example illustrates a representative assay of capsaicin receptor binding that may be used to determine the binding affinity of compounds for the capsaicin (VR1) receptor.

Binding studies with [$^3$H] Resiniferatoxin (RTX) are carried out essentially as described by Szallasi and Blumberg (1992) *J. Pharmacol. Exp. Ter.* 262:883-888. In this protocol, non-specific RTX binding is reduced by adding bovine alpha, acid glycoprotein (100 μg per tube) after the binding reaction has been terminated.

[$^3$H] RTX (37 Ci/mmol) is synthesized by and obtained from the Chemical Synthesis and Analysis Laboratory, National Cancer Institute-Frederick Cancer Research and Development Center, Frederick, Md. [$^3$H] RTX may also be obtained from commercial vendors (e.g, Amersham Pharmacia Biotech, Inc.; Piscataway, N.J.).

The membrane homogenate of Example 4 is centrifuged as before and resuspended to a protein concentration of 333 μg/ml in homogenization buffer. Binding assay mixtures are set up on ice and contain [$^3$H]RTX (specific activity 2200 mCi/ml), 2 μl non-radioactive test compound, 0.25 mg/ml bovine serum albumin (Cohn fraction V), and $5\times10^4$–$1\times10^5$ VR1-transfected cells. The final volume is adjusted to 500 μl (for competition binding assays) or 1,000 μl (for saturation binding assays) with the ice-cold HEPES homogenization buffer solution (pH 7.4) described above. Non-specific binding is defined as that occurring in the presence of 1 μM non-radioactive RTX (Alexis Corp.; San Diego, Calif.). For saturation binding, [$^3$H]RTX is added in the concentration range of 7-1,000 pM, using 1 to 2 dilutions. Typically 11 concentration points are collected per saturation binding curve.

Competition binding assays are performed in the presence of 60 pM [$^3$H]RTX and various concentrations of test compound. The binding reactions are initiated by transferring the assay mixtures into a 37° C. water bath and are terminated following a 60 minute incubation period by cooling the tubes on ice. Membrane-bound RTX is separated from free, as well as any alpha$_1$-acid glycoprotein-bound RTX, by filtration onto WALLAC glass fiber filters (PERKIN-ELMER, Gaithersburg, Md.) which were pre-soaked with 1.0% PEI (polyethyleneimine) for 2 h prior to use. Filters are allowed to dry overnight then counted in a WALLAC 1205 BETA PLATE counter after addition of WALLAC BETA SCINT scintillation fluid.

Equilibrium binding parameters are determined by fitting the allosteric Hill equation to the measured values with the aid of the computer program FIT P (Biosoft, Ferguson, Mo.) as described by Szallasi, et al. (1993) *J. Pharmacol. Exp. Ther.* 266:678-683. Compounds provided herein generally exhibit $K_i$ values for capsaicin receptor of less than 1 μM, 100 nM, 50 nM, 25 nM, 10 nM, or 1 nM in this assay.

Example 6

Calcium Mobilization Assay

This Example illustrates representative calcium mobilization assays for use in evaluating test compounds for agonist and antagonist activity.

Cells transfected with expression plasmids (as described in Example 4) and thereby expressing human capsaicin receptor are seeded and grown to 70-90% confluency in FALCON black-walled, clear-bottomed 96-well plates (#3904, BECTON-DICKINSON, Franklin Lakes, N.J.). The culture medium is emptied from the 96 well plates and FLUO-3 AM calcium sensitive dye (Molecular Probes, Eugene, Oreg.) is added to each well (dye solution: 1 mg FLUO-3 AM, 440 μL DMSO and 440 μl 20% pluronic acid in DMSO, diluted 1:250 in Krebs-Ringer HEPES (KRH) buffer (25 mM HEPES, 5 mM KCl, 0.96 mM NaH$_2$PO$_4$, 1 mM MgSO$_4$, 2 mM CaCl$_2$, 5 mM glucose, 1 mM probenecid, pH 7.4), 50 μl diluted solution per well). Plates are covered with aluminum foil and incubated at 37° C. for 1-2 h in an environment containing 5% CO$_2$. After the incubation, the dye is emptied from the plates, and the cells are washed once with KRH buffer, and resuspended in KRH buffer.

Determination of Capsaicin EC$_{50}$

To measure the ability of a test compound to agonize or antagonize a calcium mobilization response in cells expressing capsaicin receptors to capsaicin or other vanilloid agonist, the EC$_{50}$ of the agonist capsaicin is first determined. An additional 20 μl of KRH buffer and 1 μl DMSO is added to each well of cells, prepared as described above. 100 μl capsaicin in KRH buffer is automatically transferred by the FLIPR instrument to each well. Capsaicin-induced calcium mobilization is monitored using either FLUOROSKAN ASCENT (Labsystems; Franklin, Mass.) or FLIPR (fluorometric imaging plate reader system; Molecular Devices, Sunnyvale, Calif.) instruments. Data obtained between 30 and 60 seconds after agonist application are used to generate an 8-point concentration response curve, with final capsaicin concentrations of 1 nM to 3 μM. KALEIDAGRAPH software (Synergy Software, Reading, Pa.) is used to fit the data to the equation:

$$y=a*(1/(1+(b/x)^c))$$

to determine the 50% excitatory concentration (EC$_{50}$) for the response. In this equation, y is the maximum fluorescence signal, x is the concentration of the agonist or antagonist (in this case, capsaicin), a is the $E_{max}$, b corresponds to the EC$_{50}$ value and c is the Hill coefficient.

Determination of Agonist Activity

Test compounds are dissolved in DMSO, diluted in KRH buffer, and immediately added to cells prepared as described above. 100 nM capsaicin (an approximate EC$_{50}$ concentration) is also added to cells in the same 96-well plate as a positive control. The final concentration of test compounds in the assay wells is between 0.1 nM and 5 μM.

The ability of a test compound to act as an agonist of the capsaicin receptor is determined by measuring the fluorescence response of cells expressing capsaicin receptors elicited by the compound as function of compound concentration. This data is fit as described above to obtain the EC$_{50}$, which is generally less than 1 micromolar, preferably less than 100 nM, and more preferably less than 10 nM. The extent of efficacy of each test compound is also determined by calculating the response elicited by a concentration of test compound (typically 1 μM) relative to the response elicited by 100 nM capsaicin. This value, called Percent of Signal (POS), is calculated by the following equation:

POS=100*test compound response/100 nM capsaicin response

This analysis provides quantitative assessment of both the potency and efficacy of test compounds as human capsaicin receptor agonists. Agonists of the human capsaicin receptor generally elicit detectable responses at concentrations less than 100 μM, or preferably at concentrations less than 1 μM, or most preferably at concentrations less than 10 nM. Extent of efficacy at human capsaicin receptor is preferably greater than 30 POS, more preferably greater than 80 POS at a concentration of 1 μM. Certain agonists are essentially free of antagonist activity as demonstrated by the absence of detectable antagonist activity in the assay described below at compound concentrations below 4 nM, more preferably at concentrations below 10 μM and most preferably at concentrations less than or equal to 100 μM.

Determination of Antagonist Activity

Test compounds are dissolved in DMSO, diluted in 20 μl KRH buffer so that the final concentration of test compounds in the assay well is between 1 μM and 5 μM, and added to cells prepared as described above. The 96 well plates containing prepared cells and test compounds are incubated in the dark, at room temperature for 0.5 to 6 h. It is important that the incubation not continue beyond 6 h. Just prior to determining the fluorescence response, 100 µl capsaicin in KRH buffer at twice the $EC_{50}$ concentration determined as described above is automatically added by the FLIPR instrument to each well of the 96 well plate for a final sample volume of 200 µl and a final capsaicin concentration equal to the $EC_{50}$. The final concentration of test compounds in the assay wells is between 1 µM and 5 µM. Antagonists of the capsaicin receptor decrease this response by at least about 20%, preferably by at least about 50%, and most preferably by at least 80%, as compared to matched control (i.e., cells treated with capsaicin at twice the $EC_{50}$ concentration in the absence of test compound), at a concentration of 10 micromolar or less, preferably 1 micromolar or less. The concentration of antagonist required to provide a 50% decrease, relative to the response observed in the presence of capsaicin and without antagonist, is the $IC_{50}$ for the antagonist, and is preferably below 1 micromolar, 100 nanomolar, 10 nanomolar or 1 nanomolar.

Certain preferred VR1 modulators are antagonists that are essentially free of agonist activity as demonstrated by the absence of detectable agonist activity in the assay described above at compound concentrations below 4 nM, more preferably at concentrations below 10 µM and most preferably at concentrations less than or equal to 100 µM.

Example 7

Microsomal in vitro Half-life

This Example illustrates the evaluation of compound half-life values ($t_{1/2}$ values) using a representative liver microsomal half-life assay.

Pooled human liver microsomes are obtained from Xeno-Tech LLC (Kansas City, Kans.). Such liver microsomes may also be obtained from In Vitro Technologies (Baltimore, Md.) or Tissue Transformation Technologies (Edison, N.J.). Six test reactions are prepared, each containing 25 µl microsomes, 5 µl of a 100 µM solution of test compound, and 399 µl 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 µl microsomes, 399 µl 0.1 M phosphate buffer, and 5 µl of a 100 µM solution of a compound with known metabolic properties (e.g., DIAZEPAM or CLOZAPINE). Reactions are preincubated at 39° C. for 10 min.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 µl glucose-6-phosphate dehydrogenase suspension (Roche Molecular Biochemicals; Indianapolis, Ind.) into 1285.7 µl distilled water. 71 µl Starting Reaction Mixture (3 mL CoFactor Mixture; 1.2 mL Glucose-6-phosphate dehydrogenase solution) is added to 5 of the 6 test reactions and to the positive control. 71 µl 100 mM $MgCl_2$ is added to the sixth test reaction, which is used as a negative control. At each time point (0, 1, 3, 5, and 10 min), 75 µl of each reaction mix is pipetted into a well of a 96-well deep-well plate containing 75 µl ice-cold acetonitrile. Samples are vortexed and centrifuged 10 min at 3500 rpm (Sorval T 6000D centrifuge, H1000B rotor). 75 µl of supernatant from each reaction is transferred to a well of a 96-well plate containing 150 µl of a 0.5 µM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds provided herein exhibit in vitro $t_{1/2}$ values of greater than 10 min and less than 4 h, preferably between 30 min and 1 h, in human liver microsomes.

Example 8

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog #30-2003). 100 µl of diluted cells is added to each well, except for five standard curve control wells that contain 100 µl of warm medium without cells. The plate is then incubated at 37° C. under 95% $O_2$, 5% $CO_2$ for 2 h with constant shaking. After incubation, 50 µL of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 min.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 min. A white PACKARD sticker is attached to the bottom of each plate and samples are dark adapted by wrapping plates in foil and placing in the dark for 10 min. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

Example 9

Dorsal Root Ganglion Cell Assay

This Example illustrates a representative dorsal root ganglian cell assay for evaluating VR1 antagonist or agonist activity of a compound.

DRG are dissected from neonatal rats, dissociated and cultured using standard methods (Aguayo and White (1992) *Brain Research* 570:61-67). After 48 h incubation, cells are washed once and incubated for 30-60 min with the calcium sensitive dye Fluo 4 AM (2.5-10 µg/ml; Teffabs, Austin, Tex.). Cells are then washed once. Addition of capsaicin to the cells results in a VR1-dependent increase in intracellular calcium levels which is monitored by a change in Fluo-4 fluorescence with a fluorometer. Data are collected for 60-180 seconds to determine the maximum fluorescent signal.

For antagonist assays, various concentrations of compound are added to the cells. Fluorescent signal is then plotted as a function of compound concentration to identify the concentration required to achieve a 50% inhibition of the capsaicin-activated response, or $IC_{50}$. Antagonists of the capsaicin receptor preferably have an $IC_{50}$ below 1 micromolar, 100 nanomolar, 10 nanomolar or 1 nanomolar.

For agonist assays, various concentrations of compound are added to the cells without the addition of capsaicin. Compounds that are capsaicin receptor agonists result in a VR1-dependent increase in intracellular calcium levels which is monitored by a change in Fluo-4 fluorescence with a fluorometer. The $EC_{50}$, or concentration required to achieve 50% of the maximum signal for a capsaicin-activated response, is preferably below 1 micromolar, below 100 nanomolar or below 10 nanomolar.

Example 10

Animal Models for Determining Pain Relief

This Example illustrates representative methods for assessing the degree of pain relief provided by a compound.

A. Pain Relief Testing

The following methods may be used to assess pain relief.

Mechanical Allodynia

Mechanical allodynia (an abnormal response to an innocuous stimulus) is assessed essentially as described by Chaplan et al. (1994) *J. Neurosci. Methods* 53:55-63 and Tal and Eliav (1998) *Pain* 64(3):511-518. A series of von Frey filaments of varying rigidity (typically 8-14 filaments in a series) are applied to the plantar surface of the hind paw with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Compounds are effective in reversing or preventing mechanical allodynia-like symptoms if rats treated with such compounds require stimulation with a Von Frey filament of higher rigidity strength to provoke a positive allodynic response as compared to control untreated or vehicle treated rats. Alternatively, or in addition, testing of an animal in chronic pain may be done before and after compound administration. In such an assay, an effective compound results in an increase in the rigidity of the filament needed to induce a response after treatment, as compared to the filament that induces a response before treatment or in an animal that is also in chronic pain but is left untreated or is treated with vehicle. Test compounds are administered before or after onset of pain. When a test compound is administered after pain onset, testing is performed 10 min to 3 h after administration.

Mechanical Hyperalgesia

Mechanical hyperalgesia (an exaggerated response to painful stimulus) is tested essentially as described by Koch et al. (1996) *Analgesia* 2(3):157-164. Rats are placed in individual compartments of a cage with a warmed, perforated metal floor. Hind paw withdrawal duration (i.e., the amount of time for which the animal holds its paw up before placing it back on the floor) is measured after a mild pinprick to the plantar surface of either hind paw.

Compounds produce a reduction in mechanical hyperalgesia if there is a statistically significant decrease in the duration of hindpaw withdrawal. Test compound may be administered before or after onset of pain. For compounds administered after pain onset, testing is performed 10 min to 3 h after administration.

Thermal Hyperalgesia

Thermal hyperalgesia (an exaggerated response to noxious thermal stimulus) is measured essentially as described by Hargreaves et al. (1988) *Pain*. 32(1):77-88. Briefly, a constant radiant heat source is applied the animals' plantar surface of either hind paw. The time to withdrawal (i.e., the amount of time that heat is applied before the animal moves its paw), otherwise described as thermal threshold or latency, determines the animal's hind paw sensitivity to heat.

Compounds produce a reduction in thermal hyperalgesia if there is a statistically significant increase in the time to hindpaw withdrawal (i.e., the thermal threshold to response or latency is increased). Test compound may be administered before or after onset of pain. For compounds administered after pain onset, testing is performed 10 min to 3 h after administration.

B. Pain Models

Pain may be induced using any of the following methods, to allow testing of analgesic efficacy of a compound. In general, compounds provided herein result in a statistically significant reduction in pain as determined by at least one of the previously described testing methods, using male SD rats and at least one of the following models.

Acute Inflammatory Pain Model

Acute inflammatory pain is induced using the carrageenan model essentially as described by Field et al. (1997) *Br. J. Pharmacol.* 121(8):1513-1522. 100-200 µl of 1-2% carrageenan solution is injected into the rats' hind paw. Three to four hours following injection, the animals' sensitivity to thermal and mechanical stimuli is tested using the methods described above. A test compound (0.01 to 50 mg/kg) is administered to the animal, prior to testing, or prior to injection of carrageenan. The compound can be administered orally or through any parenteral route, or topically on the paw. Compounds that relieve pain in this model result in a statistically significant reduction in mechanical allodynia and/or thermal hyperalgesia.

Chronic Inflammatory Pain Model

Chronic inflammatory pain is induced using one of the following protocols:

1. Essentially as described by Bertorelli et al. (1999) *Br. J. Pharmacol.* 128(6):1252-1258, and Stein et al. (1998) *Pharmacol. Biochem. Behav.* 31(2):455-51, 200 µl Complete Freund's Adjuvant (0.1 mg heat killed and dried *M. Tuberculosis*) is injected to the rats' hind paw: 100 µl into the dorsal surface and 100 µl into the plantar surface.
2. Essentially as described by Abbadie et al. (1994) *J Neurosci.* 14(10):5865-5871 rats are injected with 150 µl of CFA (1.5 mg) in the tibio-tarsal joint.

Prior to injection with CFA in either protocol, an individual baseline sensitivity to mechanical and thermal stimulation of the animals' hind paws is obtained for each experimental animal.

Following injection of CFA, rats are tested for thermal hyperalgesia, mechanical allodynia and mechanical hyperalgesia as described above. To verify the development of symptoms, rats are tested on days 5, 6, and 7 following CFA injection. On day 7, animals are treated with a test compound, morphine or vehicle. An oral dose of morphine of 1-5 mg/kg is suitable as positive control. Typically, a dose of 0.01-50 mg/kg of test compound is used. Compounds can be administered as a single bolus prior to testing or once or twice or three times daily, for several days prior to testing. Drugs are administered orally or through any parenteral route, or applied topically to the animal.

Results are expressed as Percent Maximum Potential Efficacy (MPE). 0% MPE is defined as analgesic effect of vehicle, 100% MPE is defined as an animal's return to pre-CFA baseline sensitivity. Compounds that relieve pain in this model result in a MPE of at least 30%.

Chronic Neuropathic Pain Model

Chronic neuropathic pain is induced using the chronic constriction injury (CCI) to the rat's sciatic nerve essentially as described by Bennett and Xie (1988) *Pain* 33:87-107. Rats are anesthetized (e.g. with an intraperitoneal dose of 50-65 mg/kg pentobarbital with additional doses administered as needed). The lateral aspect of each hind limb is shaved and disinfected. Using aseptic technique, an incision is made on the lateral aspect of the hind limb at the mid thigh level. The biceps femoris is bluntly dissected and the sciatic nerve is exposed. On one hind limb of each animal, four loosely tied ligatures are made around the sciatic nerve approximately 1-2 mm apart. On the other side the sciatic nerve is not ligated and is not manipulated. The muscle is closed with continuous pattern and the skin is closed with wound clips or sutures. Rats are assessed for mechanical allodynia, mechanical hyperalgesia and thermal hyperalgesia as described above.

Compounds that relieve pain in this model result in a statistically significant reduction in mechanical allodynia, mechanical hyperalgesia and/or thermal hyperalgesia when administered (0.01-50 mg/kg, orally, parenterally or topically) immediately prior to testing as a single bolus, or for several days: once or twice or three times daily prior to testing.

What is claimed is:

1. A compound or salt selected from the group consisting of:

2-{4-[6-(3-Chloro-4-fluoro-phenyl)-2-morpholin-4-yl-pyrimidin-4-yl]-piperazin-1-yl}-nicotinic acid ethyl ester;

2-{4-[6-(3-Chloro-4-fluoro-phenyl)-2-morpholin-4-yl-pyrimidin-4-yl]-piperazin-1-yl}-nicotinamide;

2-{4-[6-(3-Chloro-4-fluoro-phenyl)-2-morpholin-4-yl-pyrimidin-4-yl]-piperazin-1-yl}-nicotinic acid;

[2-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yloxy)-ethyl]-dimethyl-amine;

3-Chloro-2-{4-[6-(3-chloro-4-fluoro-phenyl)-2-(2-methyl-pyrrolidin-1-yl)-pyrimidin-4-yl]-piperazin-1-yl}-isonicotinic acid;

5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid methyl ester;

5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid;

(5-Chloro-6-{4-[6-(3-chloro-4-fluoro-phenyl)-2-(2-methyl-pyrrolidin-1-yl)-pyrimidin-4-yl]-piperazin-1-yl}-pyridin-3-yl)-methanol;

(5-Chloro-6-{4-[6-(3-chloro-4-fluoro-phenyl)-2-(2-methyl-pyrrolidin-1-yl)-pyrimidin-4-yl]-piperazin-1-yl}-pyridin-3-ylmethyl)-methyl-amine;

C-(5-Chloro-6-{4-[6-(3-chloro-4-fluoro-phenyl)-2-(2-methyl-pyrrolidin-1-yl)-pyrimidin-4-yl]-piperazin-1-yl}-pyridin-3-yl)-methylamine;

(5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-pyridin-3-yl)-methanol;

5-Chloro-6-{4-[6-(3-chloro-4-fluoro-phenyl)-2-(2-methyl-pyrrolidin-1-yl)-pyrimidin-4-yl]-piperazin-1-yl}-nicotinamide;

(5-Chloro-6-{4-[6-(3-chloro-4-fluoro-phenyl)-2-(4-propyl-piperazin-1-yl)-pyrimidin-4-yl]-piperazin-1-yl}-pyridin-3-yl)-methanol;

5-Chloro-6-{4-[6-(3-chloro-4-fluoro-phenyl)-2-(4-propyl-piperazin-1-yl)-pyrimidin-4-yl]-piperazin-1-yl}-nicotinic acid;

5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinic acid ethyl ester;

(5-Chloro-6-{4-[6-(3-chloro-4-fluoro-phenyl)-2-(2-methyl-pyrrolidin-1-yl)-pyrimidin-4-yl]-piperazin-1-yl}-pyridin-3-ylmethyl)-dimethyl-amine;

5-Chloro-6-{4-[6-(3-chloro-4-fluoro-phenyl)-2-(2-methyl-pyrrolidin-1-yl)-pyrimidin-4-yl]-piperazin-1-yl}-nicotinic acid methyl ester;

5-Chloro-6-{4-[6-(3-chloro-4-fluoro-phenyl)-2-(2-methyl-pyrrolidin-1-yl)-pyrimidin-4-yl]-piperazin-1-yl}-nicotinic acid;

5-Chloro-6-{4-[6-(3-chloro-4-fluoro-phenyl)-2-(4-propyl-piperazin-1-yl)-pyrimidin-4-yl]-piperazin-1-yl}-nicotinic acid ethyl ester;

5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-nicotinamide;

5-Chloro-6-{4-[6-(4-fluoro-phenyl)-2-methyl-pyrrolidin-1-yl)-pyrimidin-4-yl]-piperazin-1-yl}-nicotinic acid;

(5-Chloro-6-{4-[6-(4-fluoro-phenyl)-2-(2-methyl-pyrrolidin-1-yl)-pyrimidin-4-yl]-piperazin-1-yl}-pyridin-3-yl)-methanol;

5-Chloro-6-{4-[6-(4-fluoro-phenyl)-2-(2-methyl-pyrrolidin-1-yl)-pyrimidin-4-yl]-3-(R)-methyl-piperazin-1-yl}-nicotinic acid ethyl ester;

5-Chloro-6-{4-[6-(4-fluoro-phenyl)-2-pyrrolidin-1-yl-pyrimidin-4-yl]-3-(R)-methyl-piperazin-1-yl}-nicotinic acid ethyl ester;

5-Chloro-6-{4-[6-(4-fluoro-phenyl)-2-(2-methyl-pyrrolidin-1-yl)-pyrimidin-4-yl]-3-(R)-methyl-piperazin-1-yl}-nicotinic acid;

5-Chloro-6-{4-[6-(4-fluoro-phenyl)-2-pyrrolidin-1-yl-pyrimidin-4-yl]-3-(R)-methyl-piperazin-1-yl}-nicotinic acid;

(5-Chloro-6-{4-[6-(4-fluoro-phenyl)-2-(2-methyl-pyrrolidin-1-yl)-pyrimidin-4-yl]-3-(R)-methyl-piperazin-1-yl}-pyridin-3-yl)-methanol;

(5-Chloro-6-{4-[6-(4-fluoro-phenyl)-2-pyrrolidin-1-yl-pyrimidin-4-yl]-3-(R)-methyl-piperazin-1-yl}-pyridin-3-yl)-methanol;

5-Chloro-6-{4-[6-(4-fluoro-phenyl)-2-(2-methyl-pyrrolidin-1-yl)-pyrimidin-4-yl]-3-(R)-methyl-piperazin-1-yl}-nicotinamide;

6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinic acid;

5-Chloro-6-{4-[6-(4-fluoro-phenyl)-2-pyrrolidin-1-yl-pyrimidin-4-yl]-3-(R)-methyl-piperazin-1-yl}-nicotinamide;

6-{4-[6-(4-Fluoro-phenyl)-2-(2-methyl-pyrrolidin-1-yl)-pyrimidin-4-yl]-piperazin-1-yl}-5-methyl-nicotinic acid;

(6-{4-[6-(4-Fluoro-phenyl)-2-(2-methyl-pyrrolidin-1-yl)-pyrimidin-4-yl]-3-(R)-methyl-piperazin-1-yl}-5-methyl-pyridin-3-yl)-methanol;

(6-{4-[6-(4-Fluoro-phenyl)-2-(2-methyl-pyrrolidin-1-yl)-pyrimidin-4-yl]-piperazin-1-yl}-5-methyl-pyridin-3-yl)-methanol;

(5-Chloro-6-{4-[6-(4-fluoro-phenyl)-2-(2-methyl-pyrrolidin-1-yl)-pyrimidin-4-yl]-piperazin-1-yl}-pyridin-3-yl)-acetic acid;

5-Chloro-6-{4-[6-(4-fluoro-phenyl)-2-(2-methyl-pyrrolidin-1-yl)-pyrimidin-4-yl]-piperazin-1-yl}-nicotinamide;

5-Chloro-6-{3-(R)-methyl-4-[2-(2-methyl-pyrrolidin-1-yl)-6-phenyl-pyrimidin-4-yl]-piperazin-1-yl}-nicotinic acid ethyl ester;

5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-nicotinic acid ethyl ester;

5-Chloro-6-{4-[6-(2-isopropyl-pyridin-4-yl)-2-(2-methyl-pyrrolidin-1-yl)-pyrimidin-4-yl]-3-(R)-methyl-piperazin-1-yl}-nicotinic acid ethyl ester;

6-{4-[6-(4-Fluoro-phenyl)-2-(2-methyl-pyrrolidin-1-yl)-pyrimidin-4-yl]-3-(R)-methyl-piperazin-1-yl}-5-methyl-nicotinamide;

6-{4-[6-(4-Fluoro-phenyl)-2-(2-methyl-pyrrolidin-1-yl)-pyrimidin-4-yl]-piperazin-1-yl}-5-methyl-nicotinamide;

5-Chloro-6-{3-(R)-methyl-4-[2-(2-methyl-pyrrolidin-1-yl)-6-m-tolyl-pyrimidin-4-yl]-piperazin-1-yl}-nicotinic acid ethyl ester;

(5-Chloro-6-{3-(R)-methyl-4-[2-(2-methyl-pyrrolidin-1-yl)-6-phenyl-pyrimidin-4-yl]-piperazin-1-yl}-pyridin-3-yl)-methanol;

(5-Chloro-6-{3-(R)-methyl-4-[2-(2-methyl-pyrrolidin-1-yl)-6-m-tolyl-pyrimidin-4-yl]-piperazin-1-yl}-pyridin-3-yl)-methanol;

(5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-pyridin-3-yl)-methanol;

(5-Chloro-6-{4-[6-(2-isopropyl-pyridin-4-yl)-2-(2-methyl-pyrrolidin-1-yl)-pyrimidin-4-yl]-3-(R)-methyl-piperazin-1-yl}-pyridin-3-yl)-methanol;

5-Chloro-6-{3-(R)-methyl-4-[2-(2-methyl-pyrrolidin-1-yl)-6-m-tolyl-pyrimidin-4-yl]-piperazin-1-yl}-nicotinic acid;

5-Chloro-6-{4-[6-(5-chloro-pyridin-3-yl)-2-(2-methyl-pyrrolidin-1-yl)-pyrimidin-4-yl]-3-(R)-methyl-piperazin-1-yl}-nicotinic acid; 5-Chloro-6-{4-[6-(2-isopropyl-pyridin-4-yl)-2-(2-methyl-pyrrolidin-1-yl)-pyrimidin-4-yl]-3-(R)-methyl-piperazin-1-yl}-nicotinic acid;

5-Methyl-6-{4-[2-(2-methyl-pyrrolidin-1-yl)-6-phenyl-pyrimidin-4-yl]-piperazin-1-yl}-nicotinic acid ethyl ester;

5-Methyl-6-{4-[2-(2-methyl-pyrrolidin-1-yl)-6-m-tolyl-pyrimidin-4-yl]-piperazin-1-yl}-nicotinic acid ethyl ester;

5-Methyl-6-{4-[2-(2-methyl-pyrrolidin-1-yl)-6-pyridin-4-yl-pyrimidin-4-yl]-piperazin-1-yl}-nicotinic acid ethyl ester;

6-{4-[6-(2-Isopropyl-pyridin-4-yl)-2-(2-methyl-pyrrolidin-1-yl)-pyrimidin-4-yl]-piperazin-1-yl}-5-methyl-nicotinic acid ethyl ester;

5-Methyl-6-{3-(R)-methyl-4-[2-(2-methyl-pyrrolidin-1-yl)-6-phenyl-pyrimidin-4-yl]-piperazin-1-yl}-nicotinic acid ethyl ester;

5-Methyl-6-{3-(R)-methyl-4-[2-(2-methyl-pyrrolidin-1-yl)-6-m-tolyl-pyrimidin-4-yl]-piperazin-1-yl}-nicotinic acid ethyl ester;

5-Methyl-6-{3-(R)-methyl-4-[2-(2-methyl-pyrrolidin-1-yl)-6-pyridin-4-yl-pyrimidin-4-yl]-piperazin-1-yl}-nicotinic acid ethyl ester;

6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-nicotinic acid ethyl ester;

6-{4-[2-Dimethylamino-6-(4-fluoro-phenyl)-pyrimidin-4-yl]-3-(R)-methyl-piperazin-1-yl}-5-methyl-nicotinic acid ethyl ester;

(5-Methyl-6-{3-(R)-methyl-4-[2-(2-methyl-pyrrolidin-1-yl)-6-phenyl-pyrimidin-4-yl]-piperazin-1-yl}-pyridin-3-yl)-methanol;

(5-Methyl-6-{3-(R)-methyl-4-[2-(2-methyl-pyrrolidin-1-yl)-6-m-tolyl-pyrimidin-4-yl]-piperazin-1-yl}-pyridin-3-yl)-methanol;

(5-Methyl-6-{3-(R)-methyl-4-[2-(2-methyl-pyrrolidin-1-yl)-6-pyridin-4-yl-pyrimidin-4-yl]-piperazin-1-yl}-pyridin-3-yl)-methanol;

(6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-pyridin-3-yl)-methanol;

(6-{4-[2-Dimethylamino-6-(4-fluoro-phenyl)-pyrimidin-4-yl]-3-(R)-methyl-piperazin-1-yl}-5-methyl-pyridin-3-yl)-methanol;

5-Methyl-6-{3-(R)-methyl-4-[2-(2-methyl-pyrrolidin-1-yl)-6-phenyl-pyrimidin-4-yl]-piperazin-1-yl}-nicotinic acid;

5-Methyl-6-{3-(R)-methyl-4-[2-(2-methyl-pyrrolidin-1-yl)-6-m-tolyl-pyrimidin-4-yl]-piperazin-1-yl}-nicotinic acid;

5-Methyl-6-{3-(R)-methyl-4-[2-(2-methyl-pyrrolidin-1-yl)-6-pyridin-4-yl-pyrimidin-4-yl]-piperazin-1-yl}-nicotinic acid;

(5-Methyl-6-{4-[2-(2-methyl-pyrrolidin-1-yl)-6-phenyl-pyrimidin-4-yl]-piperazin-1-yl}-pyridin-3-yl)-methanol;

(5-Methyl-6-{4-[2-(2-methyl-pyrrolidin-1-yl)-6-m-tolyl-pyrimidin-4-yl]-piperazin-1-yl}-pyridin-3-yl)-methanol;

(5-Methyl-6-{4-[2-(2-methyl-pyrrolidin-1-yl)-6-pyridin-4-yl-pyrimidin-4-yl]-piperazin-1-yl}-pyridin-3-yl)-methanol;

(6-{4-[6-(2-Isopropyl-pyridin-4-yl)-2-(2-methyl-pyrrolidin-1-yl)-pyrimidin-4-yl]-piperazin-1-yl}-5-methyl-pyridin-3-yl)-methanol;

5-Methyl-6-{4-[2-(2-methyl-pyrrolidin-1-yl)-6-phenyl-pyrimidin-4-yl]-piperazin-1-yl}-nicotinic acid;

5-Methyl-6-{4-[2-(2-methyl-pyrrolidin-1-yl)-6-m-tolyl-pyrimidin-4-yl]-piperazin-1-yl}-nicotinic acid;

5-Methyl-6-{4-[2-(2-methyl-pyrrolidin-1-yl)-6-pyridin-4-yl-pyrimidin-4-yl]-piperazin-1-yl}-nicotinic acid;

6-{4-[6-(2-Isopropyl-pyridin-4-yl)-2-(2-methyl-pyrrolidin-1-yl)-pyrimidin-4-yl]-piperazin-1-yl}-5-methyl-nicotinic acid;

5-Chloro-6-{4-[6-(3-chloro-4-fluoro-phenyl)-pyrimidin-4-yl]-3-(R)-methyl-piperazin-1-yl}-nicotinic acid ethyl ester;

6-{4-[6-(2-Isopropyl-pyridin-4-yl)-2-(2-methyl-pyrrolidin-1-yl)-pyrimidin-4-yl]-3-(R)-methyl-piperazin-1-yl}-5-methyl-nicotinic acid;

6-{4-[2-Dimethylamino-6-(4-fluoro-phenyl)-pyrimidin-4-yl]-3-(R)-methyl-piperazin-1-yl}-5-methyl-nicotinic acid;

5-Methyl-6-{3-(R)-methyl-4-[2-(2-methyl-pyrrolidin-1-yl)-6-phenyl-pyrimidin-4-yl]-piperazin-1-yl}-nicotinamide;

6-{4-[2-Dimethylamino-6-(4-fluoro-phenyl)-pyrimidin-4-yl]-3-(R)-methyl-piperazin-1-yl}-5-methyl-nicotinamide;

6-[4-(2-Dimethylamino-6-phenyl-pyrimidin-4-yl)-3-(R)-methyl-piperazin-1-yl]-5-methyl-nicotinamide;

6-[4-(2-Dimethylamino-6-pyridin-4-yl-pyrimidin-4-yl)-3-(R)-methyl-piperazin-1-yl]-5-methyl-nicotinamide;

5-Chloro-6-{4-[6-(3-chloro-4-fluoro-phenyl)-pyrimidin-4-yl]-3-(R)-methyl-piperazin-1-yl}-nicotinamide;

5-Methyl-6-{4-[2-(2-methyl-pyrrolidin-1-yl)-6-phenyl-pyrimidin-4-yl]-piperazin-1-yl}-nicotinamide;

5-Methyl-6-{4-[2-(2-methyl-pyrrolidin-1-yl)-6-m-tolyl-pyrimidin-4-yl]-piperazin-1-yl}-nicotinamide;

5-Methyl-6-{4-[2-(2-methyl-pyrrolidin-1-yl)-6-pyridin-4-yl-pyrimidin-4-yl]-piperazin-1-yl}-nicotinamide;

6-{4-[6-(2-Isopropyl-pyridin-4-yl)-2-(2-methyl-pyrrolidin-1-yl)-pyrimidin-4-yl]-piperazin-1-yl}-5-methyl-nicotinamide;

6-{4-[6-(4-fluorophenyl)-2-(2-methylpyrrolidin-1-yl)pyrimidin-4-yl]piperazin-1-yl}-5-methylpyridine-3-carboximidamide;

5-Chloro-6-{4-[6-(4-fluoro-phenyl)-2-(2-(R)-methyl-pyrrolidin-1-yl)-pyrimidin-4-yl]-piperazin-1-yl}-nicotinic acid;

(5-Chloro-6-{4-[6-(4-fluoro-phenyl)-2-(2-(R)-methyl-pyrrolidin-1-yl)-pyrimidin-4-yl]-piperazin-1-yl}-pyridin-3-yl)-acetic acid;

5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-nicotinic acid;

6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-nicotinic acid;

5-Methyl-6-{3-(R)-methyl-4-[2-(2-(R)-methyl-pyrrolidin-1-yl)-6-phenyl-pyrimidin-4-yl]-piperazin-1-yl}-nicotinic acid;

2-{4-[6-(3-Chloro-4-fluoro-phenyl)-2-(2-methyl-pyrrolidin-1-yl)-pyrimidin-4-yl]-piperazin-1-yl}-pyrimidine-5-carboxylic acid amide;

(5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-methanol;

6-{4-[6-(4-Fluoro-phenyl)-2-(2-(S)-methyl-pyrrolidin-1-yl)-pyrimidin-4-yl]-3-(R)-methyl-piperazin-1-yl}-5-methyl-nicotinic acid;

(5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-acetonitrile;

(5-Chloro-6-{4-[6-(4-fluoro-phenyl)-2-(2-(R)-methyl-pyrrolidin-1-yl)-pyrimidin-4-yl]-3-(R)-methyl-piperazin-1-yl}-pyridin-3-yl)-acetic acid;

5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-nicotinamide;

5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-nicotinic acid;

5-Chloro-6-{4-[6-(4-fluoro-phenyl)-2-(3-(R)-methyl-morpholin-4-yl)-pyrimidin-4-yl]-3-(R)-methyl-piperazin-1-yl}-nicotinic acid;

(6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridin-3-yl)-acetic acid;

N-Cyclopropyl-6-{4-[6-(4-fluoro-phenyl)-2-(2-methyl-pyrrolidin-1-yl)-pyrimidin-4-yl]-piperazin-1-yl}-5-methyl-nicotinamide;

N-cyclobutyl-6-{4-[6-(4-fluorophenyl)-2-(2-methylpyrrolidin-1-yl)pyrimidin-4-yl]piperazin-1-yl}-5-methylnicotinamide;

N-Cyclopentyl-6-{4-[6-(4-fluoro-phenyl)-2-(2-methyl-pyrrolidin-1-yl)-pyrimidin-4-yl]-piperazin-1-yl}-5-methyl-nicotinamide;

6-{4-[6-(4-fluorophenyl)-2-(2-methylpyrrolidin-1-yl)pyrimidin-4-yl]piperazin-1-yl}-N-(2-methoxyethyl)-5-methylnicotinamide;

6-{4-[6-(4-fluorophenyl)-2-(2-methylpyrrolidin-1-yl)pyrimidin-4-yl]piperazin-1-yl}-N-(3-methoxypropyl)-5-methylnicotinamide;

6-{4-[6-(4-fluorophenyl)-2-(2-methylpyrrolidin-1-yl)pyrimidin-4-yl]piperazin-1-yl}-5-methyl-N-(tetrahydrofuran-2-ylmethyl)nicotinamide;

N-(3-ethoxypropyl)-6-{4-[6-(4-fluorophenyl)-2-(2-methylpyrrolidin-1-yl)pyrimidin-4-yl]piperazin-1-yl}-5-methylnicotinamide;

N-benzyl-6-{4-[6-(4-fluorophenyl)-2-(2-methylpyrrolidin-1-yl)pyrimidin-4-yl]piperazin-1-yl}-5-methylnicotinamide;

N-(4-fluorobenzyl)-6-{4-[6-(4-fluorophenyl)-2-(2-methylpyrrolidin-1-yl)pyrimidin-4-yl]piperazin-1-yl}-5-methylnicotinamide;

6-{4-[6-(4-fluorophenyl)-2-(2-methylpyrrolidin-1-yl)pyrimidin-4-yl]piperazin-1-yl}-N-(4-methoxybenzyl)-5-methylnicotinamide;

N-[3-(dimethylamino)propyl]-6-{4-[6-(4-fluorophenyl)-2-(2-methylpyrrolidin-1-yl)pyrimidin-4-yl]piperazin-1-yl}-5-methylnicotinamide;

6-{4-[6-(4-fluorophenyl)-2-(2-methylpyrrolidin-1-yl)pyrimidin-4-yl]piperazin-1-yl}-N-(2-methoxy-1-methylethyl)-5-methylnicotinamide;

6-{4-[6-(4-fluorophenyl)-2-(2-methylpyrrolidin-1-yl)pyrimidin-4-yl]piperazin-1-yl}-5-methyl-N-(2-thienylmethyl)nicotinamide;

N-(2-ethoxyethyl)-6-{4-[6-(4-fluorophenyl)-2-(2-methylpyrrolidin-1-yl)pyrimidin-4-yl]piperazin-1-yl}-5-methylnicotinamide;

6-{4-[6-(4-fluorophenyl)-2-(2-methylpyrrolidin-1-yl)pyrimidin-4-yl]piperazin-1-yl}-5-methyl-N-(2,2,2-trifluoroethyl)nicotinamide;

N-benzyl-6-{4-[6-(4-fluorophenyl)-2-(2-methylpyrrolidin-1-yl)pyrimidin-4-yl]piperazin-1-yl}-N,5-dimethylnicotinamide;

4-(4-fluorophenyl)-2-(2-methylpyrrolidin-1-yl)-6-{4-[3-methyl-5-(pyrrolidin-1-ylcarbonyl)pyridin-2-yl]piperazin-1-yl}pyrimidine;

4-(4-fluorophenyl)-6-{4-[3-methyl-5-(piperidin-1-ylcarbonyl)pyridin-2-yl]piperazin-1-yl}-2-(2-methylpyrrolidin-1-yl)pyrimidine;

4-[(6-{4-[6-(4-fluorophenyl)-2-(2-methylpyrrolidin-1-yl)pyrimidin-4-yl]piperazin-1-yl}-5-methylpyridin-3-yl)carbonyl]morpholine;

4-(4-fluorophenyl)-6-(4-{3-methyl-5-[(4-methylpiperidin-1-yl)carbonyl]pyridin-2-yl}piperazin-1-yl)-2-(2-methylpyrrolidin-1-yl)pyrimidine;

1-[(6-{4-[6-(4-fluorophenyl)-2-(2-methylpyrrolidin-1-yl)pyrimidin-4-yl]piperazin-1-yl}-5-methylpyridin-3-yl)carbonyl]azepane;

4-[(6-{4-[6-(4-fluorophenyl)-2-(2-methylpyrrolidin-1-yl)pyrimidin-4-yl]piperazin-1-yl}-5-methylpyridin-3-yl)carbonyl]thiomorpholine;

4-(4-fluorophenyl)-6-(4-{3-methyl-5-[(2-methylpiperidin-1-yl)carbonyl]pyridin-2-yl}piperazin-1-yl)-2-(2-methylpyrrolidin-1-yl)pyrimidine;

N-cyclohexyl-6-{4-[6-(4-fluorophenyl)-2-(2-methylpyrrolidin-1-yl)pyrimidin-4-yl]piperazin-1-yl}-N,5-dimethylnicotinamide;

4-(4-fluorophenyl)-6-(4-{3-methyl-5-[(4-phenylpiperidin-1-yl)carbonyl]pyridin-2-yl}piperazin-1-yl)-2-(2-methylpyrrolidin-1-yl)pyrimidine;

4-(4-fluorophenyl)-6-(4-{3-methyl-5-[(4-methylpiperazin-1-yl)carbonyl]pyridin-2-yl}piperazin-1-yl)-2-(2-methylpyrrolidin-1-yl)pyrimidine;

4-(4-fluorophenyl)-6-[4-(5-{[4-(2-methoxyethyl)piperazin-1-yl]carbonyl}-3-methylpyridin-2-yl)piperazin-1-yl]-2-(2-methylpyrrolidin-1-yl)pyrimidine;

4-(4-{5-[(4-cyclopentylpiperazin-1-yl)carbonyl]-3-methylpyridin-2-yl}piperazin-1-yl)-6-(4-fluorophenyl)-2-(2-methylpyrrolidin-1-yl)pyrimidine;

4-(4-{5-[(4-acetylpiperazin-1-yl)carbonyl]-3-methylpyridin-2-yl}piperazin-1-yl)-6-(4-fluorophenyl)-2-(2-methylpyrrolidin-1-yl)pyrimidine;

4-(4-fluorophenyl)-6-(4-{3-methyl-5-[(2-methylpyrrolidin-1-yl)carbonyl]pyridin-2-yl}piperazin-1-yl)-2-(2-methylpyrrolidin-1-yl)pyrimidine;

N-[2-(dimethylamino)ethyl]-6-{4-[6-(4-fluorophenyl)-2-(2-methylpyrrolidin-1-yl)pyrimidin-4-yl]piperazin-1-yl}-N,5-dimethylnicotinamide;

N-[3-(dimethylamino)propyl]-6-{4-[6-(4-fluorophenyl)-2-(2-methylpyrrolidin-1-yl)pyrimidin-4-yl]piperazin-1-yl}-N,5-dimethylnicotinamide;

6-{4-[6-(4-fluorophenyl)-2-(2-methylpyrrolidin-1-yl)pyrimidin-4-yl]piperazin-1-yl}-N,5-dimethyl-N-(1-methylpyrrolidin-3-yl)nicotinamide;

1-[(6-{4-[6-(4-fluorophenyl)-2-(2-methylpyrrolidin-1-yl)pyrimidin-4-yl]piperazin-1-yl}-5-methylpyridin-3-yl)carbonyl]-N,N-dimethylpyrrolidin-3-amine;

N-{1-[(6-{4-[6-(4-fluorophenyl)-2-(2-methylpyrrolidin-1-yl)pyrimidin-4-yl]piperazin-1-yl}-5-methylpyridin-3-yl)carbonyl]pyrrolidin-3-yl}acetamide;

4-(4-fluorophenyl)-6-(4-{5-[(4-methoxypiperidin-1-yl)carbonyl]-3-methylpyridin-2-yl}piperazin-1-yl)-2-(2-methylpyrrolidin-1-yl)pyrimidine;

4-(4-{5-[(4,4-difluoropiperidin-1-yl)carbonyl]-3-methylpyridin-2-yl}piperazin-1-yl)-6-(4-fluorophenyl)-2-(2-methylpyrrolidin-1-yl)pyrimidine;

5-Chloro-6-{4-[6-(4-fluoro-phenyl)-2-(3-(R)-methyl-morpholin-4-yl)-pyrimidin-4-yl]-3-(R)-methyl-piperazin-1-yl}-nicotinamide;

6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid;

6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-pyridine-2-carboxylic acid amide;

(5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-pyridin-3-yl)-methanol;

2-(5-Chloro-6-{4-[6-(4-fluoro-phenyl)-2-(2-methyl-pyrrolidin-1-yl)-pyrimidin-4-yl]-piperazin-1-yl}-pyridin-3-yl)-propan-2-ol;

1-(5-Chloro-6-{4-[6-(4-fluoro-phenyl)-2-(2-methyl-pyrrolidin-1-yl)-pyrimidin-4-yl]-piperazin-1-yl}-pyridin-3-yl)-ethanol;

5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-N-(2-hydroxy-ethyl)-nicotinamide;

6-{4-[6-(4-Fluoro-phenyl)-2-(3-(R)-methyl-morpholin-4-yl)-pyrimidin-4-yl]-3-(R)-methyl-piperazin-1-yl}-5-methyl-nicotinic acid;

6-{4-[6-(4-Fluoro-phenyl)-2-(2-(S)-hydroxymethyl-pyrrolidin-1-yl)-pyrimidin-4-yl]-3-(R)-methyl-piperazin-1-yl}-5-methyl-nicotinic acid;

2-(5-Chloro-6-{4-[6-(4-fluoro-phenyl)-2-(2-methyl-pyrrolidin-1-yl)-pyrimidin-4-yl]-piperazin-1-yl}-pyridin-3-yl)-acetamide;

6-{4-[6-(4-Fluoro-phenyl)-2-(isopropyl-methyl-amino)-pyrimidin-4-yl]-3-(R)-methyl-piperazin-1-yl}-5-methyl-nicotinic acid;

6-{4-[6-(3-Chloro-4-fluoro-phenyl)-2-(2-(R)-methyl-pyrrolidin-1-yl)-pyrimidin-4-yl]-3-(R)-methyl-piperazin-1-yl}-5-methyl-nicotinic acid;

(5-Chloro-6-{4-[6-(4-fluoro-phenyl)-2-(2-(S)-hydroxymethyl-pyrrolidin-1-yl)-pyrimidin-4-yl]-3-(R)-methyl-piperazin-1-yl}-pyridin-3-yl)-(2-(S)-hydroxymethyl-pyrrolidin-1-yl)-methanone;

5-Chloro-6-{4-[6-(4-fluoro-phenyl)-2-(2-(S)-hydroxymethyl-pyrrolidin-1-yl)-pyrimidin-4-yl]-3-(R)-methyl-piperazin-1-yl}-nicotinic acid;

5-Chloro-6-{4-[6-(4-fluoro-phenyl)-2-(isopropyl-methyl-amino)-pyrimidin-4-yl]-3-(R)-methyl-piperazin-1-yl}-nicotinic acid;

5-Chloro-6-{4-[6-(4-fluoro-phenyl)-2-(2-(S)-hydroxymethyl-pyrrolidin-1-yl)-pyrimidin-4-yl]-piperazin-1-yl}-nicotinic acid;

5-Chloro-6-{4-[6-(4-fluoro-phenyl)-2-(3-(R)-methyl-morpholin-4-yl)-pyrimidin-4-yl]-piperazin-1-yl}-nicotinic acid;

5-Chloro-6-{4-[6-(4-fluoro-phenyl)-2-(isopropyl-methyl-amino)-pyrimidin-4-yl]-piperazin-1-yl}-nicotinic acid;

6-{4-[6-(3-Chloro-4-fluoro-phenyl)-2-(isopropyl-methyl-amino)-pyrimidin-4-yl]-piperazin-1-yl}-5-methyl-nicotinic acid;

4-(4-Fluoro-phenyl)-6-[2-(R)-methyl-4-(3-methyl-5-oxazol-2-yl-pyridin-2-yl)-piperazin-1-yl]-2-(2-(R)-methyl-pyrrolidin-1-yl)-pyrimidine;

5-Chloro-6-{4-[2-(2-(S)-hydroxymethyl-pyrrolidin-1-yl)-6-phenyl-pyrimidin-4-yl]-3-(R)-methyl-piperazin-1-yl}-nicotinic acid;

4-(4-Fluoro-phenyl)-6-{2-(R)-methyl-4-[3-methyl-5-(1H-tetrazol-5-yl)-pyridin-2-yl]-piperazin-1-yl}-2-(2-(R)-methyl-pyrrolidin-1-yl)-pyrimidine;

5-Chloro-6-{4-[2-(2-(S)-hydroxymethyl-pyrrolidin-1-yl)-6-phenyl-pyrimidin-4-yl]-3-(R)-methyl-piperazin-1-yl}-nicotinamide;

5-Chloro-N-(2-hydroxy-ethyl)-6-{4-[2-(2-(S)-hydroxymethyl-pyrrolidin-1-yl)-6-phenyl-pyrimidin-4-yl]-3-(R)-methyl-piperazin-1-yl}-nicotinamide;

5-Chloro-N-(2-hydroxy-ethyl)-6-{3-(R)-methyl-4-[2-(2-(R)-methyl-pyrrolidin-1-yl)-6-phenyl-pyrimidin-4-yl]-piperazin-1-yl}-nicotinamide;

5-Methyl-6-{3-(R)-methyl-4-[2-(2-methyl-pyrrolidin-1-yl)-6-p-tolyl-pyrimidin-4-yl]-piperazin-1-yl}-nicotinic acid;

4-(4-Fluoro-phenyl)-6-{4-[5-(1H-imidazol-2-yl)-3-methyl-pyridin-2-yl]-2-(R)-methyl-piperazin-1-yl}-2-(2-(R)-methyl-pyrrolidin-1-yl)-pyrimidine;

6-{4-[6-(4-Fluoro-phenyl)-2-(2-(R)-methyl-pyrrolidin-1-yl)-pyrimidin-4-yl]-3-(S)-methyl-piperazin-1-yl}-5-methyl-nicotinic acid;

N-(2-Hydroxy-ethyl)-5-methyl-6-{3-(R)-methyl-4-[6-(6-methyl-pyridin-3-yl)-2-(2-methyl-pyrrolidin-1-yl)-pyrimidin-4-yl]-piperazin-1-yl}-nicotinamide;

(5-Chloro-6-{4-[6-(3-chloro-4-fluoro-phenyl)-2-piperidin-1-yl-pyrimidin-4-yl]-3-(R)-methyl-piperazin-1-yl}-pyridin-3-yl)-methanol;

5-Chloro-6-{4-[6-(3-chloro-4-fluoro-phenyl)-2-(2-(R)-methyl-pyrrolidin-1-yl)-pyrimidin-4-yl]-2-(R)-methyl-piperazin-1-yl}-nicotinic acid ethyl ester; methyl nicotinic acid;

6-{4-[6-(4-Fluoro-phenyl)-2-(2-(R)-methyl-pyrrolidin-1-yl)-pyrimidin-4-yl]-piperazin-1-yl}-5-trifluoromethyl-nicotinic acid;

6-{4-[6-(4-Fluoro-phenyl)-2-(2-(R)-methyl-pyrrolidin-1-yl)-pyrimidin-4-yl]-3-(R)-methyl-piperazin-1-yl}-5-trifluoromethyl-nicotinic acid;

2-[6-((3R)-4-{6-(4-fluorophenyl)-2-[(2R)-2-methyl-1-pyrrolidinyl]-4-pyrimidinyl}-3-methyl-1-piperazinyl)-5-methyl-3-pyridinyl]ethanol;

2-{[6-((3R)-4-{6-(3-chloro-4-fluorophenyl)-2-[(2R)-2-methyl-1-pyrrolidinyl]-4-pyrimidinyl}-3-methyl-1-piperazinyl)-5-methyl-3-pyridinyl]oxy}ethanol;

2-{[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]oxy}ethanol;

2-{[6-((3R)-4-{6-(4-fluorophenyl)-2-[(2S)-2-(hydroxymethyl)pyrrolidin-1-yl]pyrimidin-4-yl}-3-methylpiperazin-1-yl)-5-methylpyridin-3-yl]oxy}ethanol;

2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]ethanol;

2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]-N,N-dimethylethanamine; and 2-[5-chloro-6-((3R)-4-{6-(3-chloro-4-fluorophenyl)-2-[(2R)-2-methylpyrrolidin-1-yl]pyrimidin-4-yl}-3-methylpiperazin-1-yl)pyridin-3-yl]-N-methylethanamine;

and pharmaceutically acceptable salts thereof.

2. The compound or salt of claim 1, wherein the compound or salt is (5-Chloro-6-{4-[6-(3-chloro-4-fluoro-phenyl)-2-(2-methyl-pyrrolidin-1-yl)-pyrimidin-4-yl]-3-(R)-methyl-piperazin-1-yl}-pyridin-3-yl)-methanol or a pharmaceutically acceptable salt thereof.

3. The compound or salt of claim 1, wherein the compound or salt is 6-{4-[6-(4-Fluoro-phenyl)-2-(2-(R)-methyl-pyrrolidin-1-yl)-pyrimidin-4-yl]-3-(R)-methyl-piperazin-1-yl}-5-methyl-nicotinic acid or a pharmaceutically acceptable salt thereof.

4. The compound or salt of claim 1, wherein the compound or salt is (5-Chloro-6-{4-[6-(3-chloro-4-fluoro-phenyl)-2-(2-(R)-methyl-pyrrolidin-1-yl)-pyrimidin-4-yl]-3-(R)-methyl-piperazin-1-yl}-pyridin-3-yl)-methanol or a pharmaceutically acceptable salt thereof.

5. The compound or salt of claim 1, wherein the compound or salt is 6-{4-[6-(4-Fluoro-phenyl)-2-(2-(R)-methyl-pyrrolidin-1-yl)-pyrimidin-4-yl]-3-(S)-methyl-piperazin-1-yl}-5-methyl-nicotinic acid or a pharmaceutically acceptable salt thereof.

6. The compound or salt of claim 1, wherein the compound or salt is 2-{[6-((3R)-4-{6-(3-chloro-4-fluorophenyl)-2-[(2R)-2-methyl-1-pyrrolidinyl]-4-pyrimidinyl}-3-methyl-1-piperazinyl)-5-methyl-3-pyridinyl]oxy}ethanol or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,662,830 B2 | Page 1 of 1 |
| APPLICATION NO. | : 11/204202 | |
| DATED | : February 16, 2010 | |
| INVENTOR(S) | : Charles A. Blum | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 658 days.

Signed and Sealed this

Fifteenth Day of March, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,830 B2 | Page 1 of 1 |
| APPLICATION NO. | : 11/204202 | |
| DATED | : February 16, 2010 | |
| INVENTOR(S) | : Charles A. Blum | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 779 days.

Signed and Sealed this
Twenty-seventh Day of March, 2012

David J. Kappos
*Director of the United States Patent and Trademark Office*